United States Patent
Burckert et al.

(10) Patent No.: US 12,291,579 B2
(45) Date of Patent: May 6, 2025

(54) ANTI-PHOSPHOCHOLINE ANTIBODIES AND METHODS OF USE THEREOF

(71) Applicant: Oxitope Pharma B.V., Naarden (NL)

(72) Inventors: Jean-Philippe Burckert, South San Francisco, CA (US); Katherine Vousden, Saffron Walden (GB)

(73) Assignee: Oxitope Pharma B.V. (NL)

( * ) Notice: Subject to any disclaimer, the term of this patent is extended or adjusted under 35 U.S.C. 154(b) by 0 days.

(21) Appl. No.: 18/920,412

(22) Filed: Oct. 18, 2024

(65) Prior Publication Data

US 2025/0034283 A1    Jan. 30, 2025

Related U.S. Application Data

(63) Continuation of application No. PCT/IB2024/000127, filed on Mar. 18, 2024.

(60) Provisional application No. 63/452,798, filed on Mar. 17, 2023.

(51) Int. Cl.
 *C07K 16/44* (2006.01)
 *A61K 47/68* (2017.01)

(52) U.S. Cl.
 CPC .......... *C07K 16/44* (2013.01); *C07K 2317/52* (2013.01); *C07K 2317/565* (2013.01); *C07K 2317/622* (2013.01)

(58) Field of Classification Search
 None
 See application file for complete search history.

(56) References Cited

U.S. PATENT DOCUMENTS

| | | | |
|---|---|---|---|
| 5,900,359 A | 5/1999 | Matsuura et al. | |
| 6,225,070 B1 | 5/2001 | Witztum et al. | |
| 6,271,199 B2 | 8/2001 | Brand et al. | |
| 6,375,925 B1 | 4/2002 | Tsimikas et al. | |
| 6,379,699 B1 | 4/2002 | Virtanen et al. | |
| 6,814,951 B1 | 11/2004 | Thiele et al. | |
| 7,166,469 B2 | 1/2007 | Holvoet et al. | |
| 7,229,775 B2 | 6/2007 | Holvoet et al. | |
| 7,229,776 B2 | 6/2007 | Holvoet et al. | |
| 7,390,627 B2 | 6/2008 | Holvoet et al. | |
| 7,422,864 B2 | 9/2008 | Matsuura | |
| 7,556,927 B2 | 7/2009 | Witztum et al. | |
| 7,575,873 B2 | 8/2009 | Witztum et al. | |
| 7,939,287 B2 | 5/2011 | Tsimikas et al. | |
| 7,993,642 B2 | 8/2011 | Tsunoda et al. | |
| 8,012,483 B2 * | 9/2011 | De Faire | C07K 16/44 424/152.1 |
| 8,025,876 B2 | 9/2011 | Nilsson et al. | |
| 8,034,336 B2 | 10/2011 | Nilsson et al. | |
| 8,124,080 B2 | 2/2012 | Vollmers | |
| 8,129,123 B2 | 3/2012 | Tsimikas et al. | |
| 8,163,504 B2 | 4/2012 | Mallat et al. | |
| 8,318,161 B2 | 11/2012 | Esue | |
| 8,361,732 B2 | 1/2013 | Mallat et al. | |
| 8,383,355 B2 | 2/2013 | Mallat et al. | |
| 8,410,251 B2 | 4/2013 | Matsuura et al. | |
| 8,575,314 B2 | 11/2013 | Matsuura et al. | |
| 8,729,240 B2 | 5/2014 | Chiba et al. | |
| 8,883,428 B2 | 11/2014 | Witztum et al. | |
| 9,075,050 B2 | 7/2015 | Tsimikas et al. | |
| 9,273,125 B2 | 3/2016 | Vollmers | |
| 9,347,959 B2 | 5/2016 | Tsimikas et al. | |
| 9,393,303 B2 | 7/2016 | Sverdlov et al. | |
| 9,568,487 B2 | 2/2017 | Cipolla | |
| 9,738,722 B2 | 8/2017 | Moore et al. | |
| 9,796,786 B2 | 10/2017 | Pettersson et al. | |
| 9,803,028 B2 | 10/2017 | Pettersson et al. | |
| 10,222,382 B2 | 3/2019 | De Faire et al. | |
| 10,434,141 B2 | 10/2019 | Nilsson et al. | |
| 10,669,332 B2 | 6/2020 | Frostegård | |
| 10,752,680 B2 | 8/2020 | Frostegård | |
| 10,858,422 B2 | 12/2020 | Nilsson et al. | |
| 11,008,381 B2 | 5/2021 | Witztum et al. | |
| 11,008,382 B2 | 5/2021 | Witztum et al. | |
| 11,168,148 B2 | 11/2021 | Tsimikas et al. | |
| 11,530,259 B2 | 12/2022 | Witztum et al. | |
| 11,655,288 B2 | 5/2023 | Witztum et al. | |
| 11,690,912 B2 | 7/2023 | Liang et al. | |
| 2003/0077668 A1 | 4/2003 | Uchida et al. | |
| 2006/0194270 A1 | 8/2006 | Matsuura | |
| 2007/0087002 A1 | 4/2007 | Green | |
| 2009/0130776 A1 | 5/2009 | Imamura et al. | |

(Continued)

FOREIGN PATENT DOCUMENTS

| | | | |
|---|---|---|---|
| EP | 1046652 A1 | 10/2000 | |
| EP | 968230 B1 | 10/2006 | |

(Continued)

OTHER PUBLICATIONS

Shaw Peter X et al., "Natutal antibodies with the T15 idiotype may act in atherosclerosis, apoptotic clearance, and protective immunity," J Clin Invest. 2000;105(12):1731-1740.

Abe et al., "Gene expression profiling of the effect of high-dose intravenous Ig in patients with Kawasaki disease," J Immunol. 2005;174(9):5837-45.

Binder et al., "Innate sensing of oxidation-specific epitopes in health and disease," Nat Rev Immunol. 2016;16(8):485-97.

Byun et al., "Oxidized Phospholipids on Apolipoprotein B-100 and Recurrent Ischemic Events Following Stroke or Transient Ischemic Attack," J Am Coll Cardiol. 2017;69(2):147-158.

(Continued)

*Primary Examiner* — Phuong Huynh
(74) *Attorney, Agent, or Firm* — Dechert LLP; Andrew T. Wilkins; David M. Lee

(57) ABSTRACT

The present disclosure provides polypeptides that specifically bind to phosphocholine (PC). Also provided are pharmaceutical compositions comprising these polypeptides, nucleic acids encoding these polypeptides, expression vectors and host cells for making these polypeptides, and methods of treating a subject using these polypeptides.

20 Claims, No Drawings
Specification includes a Sequence Listing.

(56) References Cited

U.S. PATENT DOCUMENTS

| | | |
|---|---|---|
| 2010/0004430 A1 | 1/2010 | Nilsson et al. |
| 2012/0058906 A1 | 3/2012 | Smider et al. |
| 2012/0141466 A9 | 6/2012 | Heffernan et al. |
| 2012/0149596 A1 | 6/2012 | Tsimikas et al. |
| 2012/0189631 A1 | 7/2012 | Shimohata et al. |
| 2012/0230911 A1 | 9/2012 | Hsieh et al. |
| 2014/0154705 A1 | 6/2014 | Manneh |
| 2014/0193413 A1 | 7/2014 | Pettersson et al. |
| 2015/0056209 A1 | 2/2015 | Witztum et al. |
| 2015/0196663 A1 | 7/2015 | Shusta et al. |
| 2015/0266947 A1 | 9/2015 | Sierks et al. |
| 2015/0376268 A1 | 12/2015 | Witztum et al. |
| 2016/0145350 A1 | 5/2016 | Lonberg et al. |
| 2016/0251426 A1 | 9/2016 | Frostegård |
| 2016/0251427 A1 | 9/2016 | Frostegård |
| 2017/0340702 A1 | 11/2017 | Carvlin et al. |
| 2017/0355756 A1 | 12/2017 | Julien et al. |
| 2018/0148502 A9 | 5/2018 | Frostegård |
| 2018/0186870 A9 | 7/2018 | Frostegård |
| 2018/0265576 A1 | 9/2018 | Witztum et al. |
| 2019/0225709 A1 | 7/2019 | Tsimikas et al. |
| 2020/0262906 A1 | 8/2020 | Frostegård |
| 2021/0032359 A1 | 2/2021 | Frostegård |
| 2021/0155679 A1 | 5/2021 | Witztum et al. |
| 2021/0221916 A1 | 7/2021 | Tsimikas et al. |
| 2023/0167198 A1 | 6/2023 | Tsimikas et al. |

FOREIGN PATENT DOCUMENTS

| | | |
|---|---|---|
| EP | 1021728 B8 | 4/2008 |
| EP | 1596198 B1 | 4/2010 |
| EP | 1797893 B1 | 4/2010 |
| EP | 1928913 B1 | 6/2013 |
| EP | 2789629 A1 | 10/2014 |
| EP | 2319869 B1 | 8/2016 |
| EP | 2678356 B1 | 11/2016 |
| EP | 3176179 A1 | 6/2017 |
| EP | 3510046 A1 | 7/2019 |
| EP | 3746478 A1 | 12/2020 |
| EP | 2542580 B1 | 8/2021 |
| EP | 4143225 A2 | 3/2023 |
| JP | 2016025863 A | 2/2016 |
| RU | 2577228 C2 | 3/2016 |
| WO | WO-1997015599 A1 | 5/1997 |
| WO | WO-2001038395 A1 | 5/2001 |
| WO | WO-2001088547 A2 | 11/2001 |
| WO | WO-2004091520 A2 | 10/2004 |
| WO | WO-2005100405 A2 | 10/2005 |
| WO | WO-2007026972 A2 | 3/2007 |
| WO | WO-2008068048 A2 | 6/2008 |
| WO | WO-2008104194 A1 | 9/2008 |
| WO | WO-2009019260 A2 | 2/2009 |
| WO | WO-2010005389 A1 | 1/2010 |
| WO | WO-2010038104 A1 | 4/2010 |
| WO | WO-2011025978 A2 | 3/2011 |
| WO | WO-2011031460 A2 | 3/2011 |
| WO | WO-2011038786 A1 | 4/2011 |
| WO | WO-2011107291 A1 | 9/2011 |
| WO | WO-2011159000 A1 | 12/2011 |
| WO | WO-2011160845 A2 | 12/2011 |
| WO | WO-2012113783 A1 | 8/2012 |
| WO | WO-2012125582 A1 | 9/2012 |
| WO | WO-2013020995 A1 | 2/2013 |
| WO | WO-2013022968 A1 | 2/2013 |
| WO | WO-2013104918 A2 | 7/2013 |
| WO | WO-2013152325 A1 | 10/2013 |
| WO | WO-2013158841 A1 | 10/2013 |
| WO | WO-2014113510 A1 | 7/2014 |
| WO | WO-2014116880 A1 | 7/2014 |
| WO | WO-2014131034 A2 | 8/2014 |
| WO | WO-2018049083 A1 | 3/2018 |
| WO | WO-2018079658 A1 | 5/2018 |
| WO | WO-2018079674 A1 | 5/2018 |
| WO | WO-2018220224 A1 | 12/2018 |
| WO | WO-2019084460 A1 | 5/2019 |
| WO | WO-2019148204 A1 | 8/2019 |
| WO | WO-2019215300 A1 | 11/2019 |
| WO | WO-2019232070 A1 | 12/2019 |
| WO | WO-2019232081 A1 | 12/2019 |
| WO | WO-2020010024 A1 | 1/2020 |
| WO | WO-2020092928 A1 | 5/2020 |
| WO | WO-2020185598 A1 | 9/2020 |
| WO | WO-2021030450 A1 | 2/2021 |
| WO | WO-2021064076 A1 | 4/2021 |
| WO | WO-2021097146 A1 | 5/2021 |
| WO | WO-2021097379 A1 | 5/2021 |
| WO | WO-2021146562 A1 | 7/2021 |
| WO | WO-2021204998 A1 | 10/2021 |
| WO | WO-2021222181 A2 | 11/2021 |
| WO | WO-2022072244 A1 | 4/2022 |
| WO | WO-2022076459 A1 | 4/2022 |
| WO | WO-2022229368 A1 | 11/2022 |
| WO | WO-2022262764 A1 | 12/2022 |
| WO | WO-2023057588 A1 | 4/2023 |
| WO | WO-2024194685 A2 | 9/2024 |
| WO | WO-2024194686 A2 | 9/2024 |

OTHER PUBLICATIONS

Carson et al., "Antibodies against malondialdehyde-acetaldehyde adducts can help identify patients with abdominal aortic aneurysm," J Vasc Surg. 2016;63(2):477-84.

Casset et al., "A peptide mimetic of an anti-CD4 monoclonal antibody by rational design," Biochem Biophys Res Commun. 2003;307(1):198-205.

Cedar et al., "Researchers Link Kawasaki Disease in Childhood with Increased Risk of Adult Heart Disease," accessed from cedars-sinai.org on Dec. 15, 2021.

Chen et al., "Enhancement and destruction of antibody function by somatic mutation: unequal occurrence is controlled by V gene combinatorial associations," EMBO J. 199515;14(12):2784-2794.

Chen et al., "Selection and analysis of an optimized anti-VEGF antibody: crystal structure of an affinity-matured Fab in complex with antigen," J Mol Biol. 1999;293(4):865-81.

De Pascalis et al., "Grafting of "abbreviated" complementarity-determining regions containing specificity-determining residues essential for ligand contact to engineer a less immunogenic humanized monoclonal antibody," J Immunol. 2002;169(6):3076-84.

Freigang, "The regulation of inflammation by oxidized phospholipids," Eur J Immunol. 2016;46(8):1818-25.

Fruhwirth et al., "Oxidized phospholipids: from molecular properties to disease," Biochim Biophys Acta. 2007;1772(7):718-36.

Goel et al., "Plasticity within the antigen-combining site may manifest as molecular mimicry in the humoral immune response," J Immunol. 2004;173(12):7358-67.

Hartvigsen et al., "Anti-inflammatory and Antiatherogenic Properties of 5 Monoclonal Malondialdehyde-Modified LDL-Specific IgM," ATVB Abstracts. 2009;29(7):Abstract P275.

Hausenloy and Yellon, "Myocardial ischemia-reperfusion injury: a neglected therapeutic target," J Clin Invest. 2013;123(1):92-100.

Jaffe et al., "Prevention and treatment of microvascular obstruction-related myocardial injury and coronary no-reflow following percutaneous coronary intervention: a systematic approach," JACC Cardiovasc Interv. 2010;3(7):695-704.

Kadl et al., "Oxidized phospholipid-induced inflammation is mediated by Toll-like receptor 2," Free Radic Biol Med. 2011;51(10):1903-9.

Khan and Salunke, "Adjustable locks and flexible keys: plasticity of epitope-paratope interactions in germline antibodies," J Immunol. 2014;192(11):5398-405.

Kumar and Cannon, :Acute coronary syndromes: diagnosis and management, part I, Mayo Clin Proc. 2009;84(10):917-38.

Kussie et al., "A single engineered amino acid substitution changes antibody fine specificity," J Immunol. 1994;152(1):146-52.

Kwok et al., "TLR2 ligation induces the production of IL-23/IL-17 via IL-6, STAT3 and NF-kB pathway in patients with primary Sjogren's syndrome," Arthritis Res Ther. 2012;14(2):R64.

(56) References Cited

OTHER PUBLICATIONS

Lamminmaki and Kankare, "Crystal structure of a recombinant anti-estradiol Fab fragment in complex with 17beta-estradiol," J Biol Chem. 2001;276(39):36687-94.

Leitinger, "Oxidized phospholipids as triggers of inflammation in atherosclerosis," Mol Nutr Food Res. 2005;49(11):1063-71.

Liu et al., "Increased expression of TLR2 in CD4(+) T cells from SLE patients enhances immune reactivity and promotes IL-17 expression through histone modifications," Eur J Immunol. 2015;45(9):2683-93.

MacCallum et al., "Antibody-antigen interactions: contact analysis and binding site topography," J Mol Biol. 1996;262(5):732-45.

Mariuzza et al., "The structural basis of antigen-antibody recognition," Annu Rev Biophys Biophys Chem. 1987;16:139-59.

Matsuzaki et al., "Drug Delivery System, a Promising Therapeutic Strategy for Acute Myocardial Infarction," Drug Delivery System. 2015;30(4):276-285.

Mikuls et al., "Enrichment of malondialdehyde-acetaldehyde antibody in the rheumatoid arthritis joint," Rheumatology (Oxford). 2017;56(10):1794-1803.

Mortazavi et al., "Down-regulation of TLR2, 3, 9 and Signaling Mediators, MyD88 and TRIF, Gene Transcript Levels in Patients with Kawasaki Disease Treated with IVIG," Iran J Allergy Asthma Immunol. 2015;14(2):188-97.

Padlan et al., "Structure of an antibody-antigen complex: crystal structure of the HyHEL-10 Fab-lysozyme complex," Proc Natl Acad Sci U S A. 1989;86(15):5938-42.

PCT Internation Search Report and Written Opinion from PCT/US2017/050566, dated Jan. 9, 2018.

PCT International Preliminary Report on Patentability from PCT/US2014/018402, dated Aug. 25, 2015.

PCT International Preliminary Report on Patentability from PCT/US2017/050566, dated Mar. 21, 2019.

PCT International Preliminary Report on Patentability from PCT/US2018/057793, dated Apr. 28, 2020.

PCT International Preliminary Report on Patentability from PCT/US2019/015723, dated Aug. 13, 2020.

PCT International Search Report and Written Opinion from PCT/US2014/018402, dated Aug. 11, 2014.

PCT International Search Report and Written Opinion from PCT/US2018/057793, dated Mar. 7, 2019.

PCT International Search Report and Written Opinion from PCT/US2019/015723, dated Jun. 24, 2019.

PCT International Search Report and Wrriten Opinion from PCT/IB2024/000126, dated Sep. 27, 2024.

Peng et al., "Increased Toll-Like Receptors Activity and TLR Ligands in Patients with Autoimmune Thyroid Diseases," Front Immunol. 2016;7:578.

Poosarla et al., "Computational de novo design of antibodies binding to a peptide with high affinity," Biotechnol Bioeng. 2017;114(6):1331-1342.

Que et al., "IGHV1-69-Encoded Antibodies Expressed in Chronic Lymphocytic Leukemia React with Malondialdehyde-Acetaldehyde Adduct, an Immunodominant Oxidation-Specific Epitope," PLoS One. 2013;8(6):e65203.

Rossi et al., "Tumor necrosis factor is elevated in progressive multiple sclerosis and causes excitotoxic neurodegeneration," Mult Scler. 2014;20(3):304-12.

Rudikoff et al., "Single amino acid substitution altering antigen-binding specificity," Proc Natl Acad Sci U S A. 1982;79(6):1979-83.

Scherler et al., "Acute phase of Kawasaki disease: a review of national guideline recommendations," Eur J Pediatr. 2022;181(7):2563-2573.

Seimon et al., "Atherogenic lipids and lipoproteins trigger CD36-TLR2-dependent apoptosis in macrophages undergoing endoplasmic reticulum stress," Cell Metab. 2010;12(5):467-82.

Shaw et al., "Natural antibodies with the T15 idiotype may act in atherosclerosis, apoptotic clearance, and protective immunity," J Clin Invest. 2000;105(12):1731-40.

Shimomoto et al., "A purified MAA-based ELISA is a useful tool for determining anti-MAA antibody titer with high sensitivity," PLoS One. 2017;12(2):e0172172.

Sousa et al., "Primary PCI in ST-elevation myocardial infarction: Mode of referral and time to PCI," Revista Portuguesa de Cardiologia. 2012;31(10):641-646.

Sun et al., "Neutralization of Oxidized Phospholipids Ameliorates Non-alcoholic Steatohepatitis," Cell Metab. 2020;31(1):189-206.

Tsimikas et al., "Oxidation-specific biomarkers, prospective 15-year cardiovascular and stroke outcomes, and net reclassification of cardiovascular events," J Am Coll Cardiol. 2012;60(21):2218-29.

Vajdos et al., "Comprehensive functional maps of the antigen-binding site of an anti-ErbB2 antibody obtained with shotgun scanning mutagenesis," J Mol Biol. 2002;320(2):415-28.

Verma et al., "Fundamentals of reperfusion injury for the clinical cardiologist," Circulation. 2002;105(20):2332-6.

Wei et al., "The Relation between the Timing of Percutaneous Coronary Intervention and Outcomes in Patients with Acute Coronary Syndrome with Routine Invasive Strategy—Data from Taiwan Acute Coronary Syndrome Full Spectrum Data Registry," Acta Cardiol Sin. 2016;32(1):39-48.

Wikipedia, "Single-Chain variable fragment," accessed from Wikipedia.org on Dec. 15, 2021.

Wu et al., "Humanization of a murine monoclonal antibody by simultaneous optimization of framework and CDR residues," J Mol Biol. 1999;294(1):151-62.

Yamada, "[Series: knowledge of emergency required for internist; acute coronary syndrome: ACS],", Nihon Naika Gakkai Zasshi. 2011;100(8):2295-301.

PCT International Search Report and Written Opinion from PCT/IB2024/000127, dated Nov. 18, 2024.

* cited by examiner

ANTI-PHOSPHOCHOLINE ANTIBODIES AND METHODS OF USE THEREOF

CROSS-REFERENCE TO RELATED APPLICATIONS

This application is a continuation of International Application Serial No. PCT/IB2024/000127, filed Mar. 18, 2024, which claims priority to U.S. Provisional Patent Application Ser. No. 63/452,798, filed Mar. 17, 2023, the entire disclosures of which are hereby incorporated herein by reference.

REFERENCE TO SEQUENCE LISTING

This application contains a sequence listing which has been submitted electronically in ST.26 format and is hereby incorporated by reference in its entirety. Said ST.26 copy, created on Oct. 7, 2024, is named "212225_seqlist.xml" and is 644,762 bytes in size.

FIELD

The present disclosure relates to antibodies that are specific for phosphocholine (PC), and methods of use thereof.

BACKGROUND

Phospholipids that contain polyunsaturated fatty acids are highly susceptible to modification by reactive oxygen species (ROS) and non-radical oxidizing agents. Oxidized lipids in cell membranes and in circulation can have both advantageous and harmful effects on the human body. Endogenous oxidized phospholipids (OxPL) have been shown to function as stress signals, causing phagocytes such as macrophages to respond by triggering inflammatory programs and eliminating the source of stress. However, excessive amounts of oxidized phospholipid products have been linked to chronic inflammation and the pathogenesis of various cardiopulmonary disorders, such as atherosclerosis and thrombosis, acute lung injury, and neurodegenerative processes.

Oxidized low-density lipoprotein (OxLDL) contains a number of OxPL species and is found in atherosclerotic lesions and detected at high concentration in sera from patients with hyperlipidemia, diabetes mellitus, and liver disease. The phosphocholine (PC) headgroup of OxPLs has been shown to be important for phospholipid binding to integral membrane proteins such as CD36 and the innate defense molecule C-reactive protein (CRP) (Boullier et al., *J Lipid Res.* 2005 May; 46 (5): 969-76; Gershov et al., *J Exp Med.* 2000 Nov. 6; 192 (9): 1353-64).

Thus, there is a need for therapies, including antibodies, that bind PC for targeting OxPL across a wide range of diseases.

SUMMARY

The present disclosure provides polypeptides (e.g., antibodies) that specifically bind to PC. Also provided are pharmaceutical compositions comprising these antibodies, nucleic acids encoding these antibodies, expression vectors and host cells for making these antibodies, and methods of treating a subject using these antibodies. The polypeptides provided herein are particularly advantageous because they bind PC with high affinity, display favorable stability, stress resistance, and immunogenicity profiles, and can be produced at high yields. The polypeptides provided herein are particularly useful for treating an inflammatory disorder or degenerative disease in a subject.

Accordingly, in one aspect, the present disclosure provides an antibody that specifically binds phosphocholine (PC), the antibody comprising: a VH comprising the CDRH1, CDRH2, and CDRH3 amino acid sequences of any one of the VH amino acid sequences set forth in SEQ ID NOs: 1-180; and a VL comprising the CDRL1, CDRL2, and CDRL3 amino acid sequences of any one of the VL amino acid sequences set forth in SEQ ID NOs: 181-368.

In an embodiment, the antibody comprises the CDRH1, CDRH2, CDRH3, CDRL1, CDRL2, and CDRL3 amino acid sequences of the VH and VL amino acid sequences, respectively, set forth in SEQ ID NOs: 1 and 181; 2 and 182; 3 and 183; 4 and 184; 5 and 185; 1 and 184; 6 and 184; 1 and 186; 7 and 187; 8 and 188; 9 and 189; 10 and 190; 4 and 191; 11 and 192; 12 and 193; 13 and 194; 14 and 195; 15 and 196; 16 and 184; 17 and 197; 18 and 198; 1 and 199; 19 and 200; 20 and 201; 21 and 202; 22 and 203; 23 and 204; 24 and 205; 25 and 184; 4 and 206; 26 and 207; 27 and 208; 28 and 209; 9 and 210; 29 and 211; 30 and 212; 31 and 213; 32 and 214; 33 and 215; 34 and 216; 17 and 217; 1 and 218; 35 and 184; 36 and 184; 35 and 219; 35 and 220; 37 and 184; 38 and 221; 39 and 222; 9 and 223; 9 and 224; 40 and 184; 41 and 225; 8 and 226; 42 and 227; 35 and 228; 43 and 229; 4 and 230; 9 and 231; 8 and 232; 1 and 233; 8 and 234; 44 and 184; 1 and 235; 45 and 236; 30 and 237; 46 and 184; 47 and 238; 48 and 239; 1 and 230; 49 and 190; 44 and 240; 50 and 184; 51 and 241; 52 and 242; 53 and 243; 54 and 184; 55 and 244; 56 and 245; 57 and 246; 58 and 247; 59 and 248; 60 and 249; 8 and 250; 61 and 184; 35 and 251; 62 and 252; 1 and 253; 63 and 254; 64 and 181; 65 and 255; 66 and 256; 67 and 257; 68 and 198; 35 and 258; 69 and 259; 70 and 260; 71 and 261; 72 and 262; 73 and 263; 74 and 264; 75 and 265; 76 and 266; 77 and 267; 4 and 205; 78 and 268; 1 and 269; 27 and 269; 79 and 269; 80 and 270; 81 and 269; 22 and 269; 82 and 269; 83 and 271; 84 and 272; 1 and 273; 8 and 274; 8 and 275; 22 and 276; 8 and 277; 85 and 278; 86 and 279; 87 and 269; 88 and 280; 89 and 269; 60 and 281; 90 and 269; 91 and 282; 22 and 283; 92 and 269; 93 and 284; 94 and 285; 95 and 286; 96 and 269; 73 and 287; 97 and 288; 68 and 289; 98 and 269; 99 and 290; 100 and 291; 4 and 292; 4 and 289; 101 and 284; 66 and 289; 89 and 293; 102 and 294; 103 and 269; 22 and 295; 104 and 296; 105 and 297; 106 and 270; 107 and 269; 67 and 269; 62 and 298; 66 and 269; 108 and 299; 109 and 300; 110 and 301; 111 and 302; 112 and 269; 113 and 303; 1 and 304; 72 and 305; 114 and 306; 115 and 307; 116 and 269; 117 and 308; 118 and 269; 110 and 309; 119 and 310; 120 and 311; 121 and 269; 122 and 312; 123 and 289; 9 and 313; 124 and 314; 120 and 289; 125 and 315; 110 and 316; 126 and 317; 127 and 318; 49 and 319; 128 and 320; 9 and 321; 22 and 322; 129 and 323; 130 and 269; 131 and 324; 132 and 325; 133 and 326; 134 and 327; 53 and 328; 135 and 272; 136 and 329; 4 and 301; 137 and 330; 138 and 269; 1 and 284; 22 and 331; 139 and 269; 140 and 332; 141 and 269; 142 and 333; 143 and 334; 144 and 335; 101 and 298; 1 and 336; 145 and 269; 146 and 337; 147 and 269; 17 and 338; 22 and 320; 4 and 339; 148 and 340; 149 and 341; 150 and 342; 151 and 343; 152 and 344; 94 and 289; 153 and 345; 154 and 346; 155 and 347; 22 and 348; 89 and 282; 156 and 349; 157 and 296; 158 and 350; 159 and 329; 24 and 351; 160 and 352; 161 and 269; 162 and 353; 163 and 269; 1 and 354; 164 and 355; 165 and 269; 1 and 356; 166 and 357; 167 and 358; 110 and 334; 87 and 359; 168 and 360; 169 and 269; 170 and 269; 171 and 269; 172 and 361; 8 and 362; 173 and 304; 174 and 269; 1 and 363; 175 and 364; 176 and 365; 177 and 269; 178 and 366; 179 and 269; 180 and 367; or 89 and 368.

In an embodiment, the antibody comprises the CDRH1, CDRH2, and CDRH3 amino acid sequences, respectively, set forth in SEQ ID NOs: 369, 428, and 484; 370, 429, and 485; 371, 428, and 486; 372, 428, and 484; 373, 429, and 484; 374, 430, and 484; 375, 428, and 487; 376, 428, and 484; 377, 428, and 484; 378, 428, and 484; 379, 428, and 484; 372, 428, and 488; 376, 431, and 484; 380, 432, and 484; 372, 428, and 489; 381, 428, and 490; 382, 428, and 484; 381, 428, and 491; 377, 428, and 492; 376, 433, and 484; 383, 434, and 484; 383, 428, and 484; 384, 435, and 484; 369, 436, and 484; 372, 437, and 487; 385, 428, and 493; 386, 428, and 484; 372, 437, and 484; 387, 428, and 484; 385, 428, and 484; 372, 438, and 484; 388, 428, and 494; 369, 439, and 484; 389, 428, and 484; 381, 428, and 484; 376, 440, and 495; 390, 441, and 484; 370, 442, and 484; 391, 428, and 484; 392, 432, and 484; 377, 443, and 484; 393, 428, and 484; 383, 444, and 489; 394, 428, and 484; 383, 444, and 496; 376, 434, and 484; 395, 445, and 497; 396, 446, and 487; 392, 428, and 484; 393, 428, and 498; 376, 428, and 495; 369, 440, and 484; 397, 428, and 484; 389, 447, and 484; 398, 448, and 492; 373, 449, and 490; 399, 428, and 484; 400, 450, and 484; 401, 428, and 484; 390, 428, and 484; 400, 428, and 499; 384, 429, and 484; 402, 436, and 484; 381, 451, and 484; 403, 428, and 484; 369, 429, and 484; 404, 429, and 484; 372, 429, and 484; 388, 428, and 484; 405, 451, and 484; 406, 428, and 484; 400, 428, and 484; 404, 428, and 484; 384, 432, and 500; 376, 452, and 501; 407, 428, and 484; 375, 428, and 484; 408, 428, and 484; 369, 428, and 497; 403, 453, and 484; 402, 454, and 484; 383, 434, and 500; 376, 455, and 502; 383, 435, and 484; 376, 428, and 490; 369, 428, and 503; 409, 428, and 484; 383, 428, and 504; 369, 434, and 484; 369, 456, and 484; 370, 457, and 484; 404, 458, and 499; 410, 428, and 484; 383, 459, and 484; 407, 428, and 489; 374, 434, and 484; 411, 460, and 505; 383, 428, and 485; 386, 460, and 490; 412, 455, and 493; 383, 461, and 484; 376, 437, and 484; 383, 462, and 500; 400, 463, and 484; 376, 464, and 484; 400, 434, and 506; 369, 436, and 507; 377, 465, and 484; 413, 459, and 484; 369, 452, and 484; 414, 466, and 484; 373, 428, and 484; 415, 428, and 489; 369, 428, and 491; 403, 458, and 508; 392, 467, and 484; 369, 452, and 509; 388, 468, and 490; 377, 440, and 484; 370, 428, and 484; 384, 467, and 487; 392, 469, and 510; 378, 464, and 484; 416, 434, and 484; 370, 428, and 511; 376, 428, and 502; 417, 428, and 484; 376, 428, and 512; 381, 428, and 493; 383, 470, and 501; 404, 471, and 484; 418, 428, and 484; 383, 472, and 513; 419, 428, and 484; 372, 473, and 484; 383, 474, and 484; 420, 434, and 484; 370, 428, and 514; 369, 475, and 484; 421, 436, and 484; 378, 452, and 484; 376, 476, and 515; 376, 428, and 504; 422, 469, and 484; 369, 428, and 516; 405, 460, and 484; 413, 431, and 484; 406, 429, and 484; 383, 428, and 517; 377, 437, and 518; 369, 477, and 487; 403, 464, and 484; 369, 454, and 484; 372, 478, and 519; 423, 429, and 484; 382, 434, and 484; 424, 479, and 484; 376, 429, and 484; 425, 428, and 484; 403, 428, and 520; 417, 460, and 484; 409, 460, and 484; 404, 452, and 484; 383, 428, and 521; 372, 480, and 493; 369, 477, and 484; 369, 481, and 484; 384, 452, and 484; 377, 482, and 484; 410, 483, and 484; 384, 428, and 484; 489; 426, 429, and 484; 427, 428, and 484; 373, 452, and 506; 369, 429, and 521; 405, 428, and 522; 376, 428, and 510; 384, 428, and 484; 410, 429, and 484; or 400, 452, and 484.

In an embodiment, the antibody comprises the CDRL1, CDRL2, and CDRL3 amino acid sequences, respectively, set forth in SEQ ID NOs: 523, 591, and 656; 523, 592, and 657; 523, 593, and 658; 523, 591, and 659; 523, 594, and 659; 523, 595, and 660; 523, 596, and 659; 524, 591, and 659; 523, 591, and 661; 523, 591, and 662; 523, 597, and 658; 523, 598, and 662; 525, 599, and 659; 523, 600, and 663; 523, 591, and 664; 523, 601, and 659; 526, 597, and 665; 523, 602, and 659; 527, 591, and 661; 528, 591, and 662; 529, 603, and 662; 523, 604, and 666; 523, 605, and 667; 530, 606, and 659; 523, 607, and 659; 523, 608, and 659; 523, 609, and 662; 531, 591, and 663; 523, 608, and 661; 523, 610, and 659; 523, 611, and 668; 523, 611, and 658; 523, 596, and 662; 523, 612, and 667; 523, 613, and 668; 523, 591, and 669; 523, 591, and 663; 523, 614, and 659; 532, 615, and 662; 523, 616, and 670; 523, 591, and 668; 523, 617, and 671; 533, 595, and 659; 523, 618, and 659; 534, 619, and 662; 535, 620, and 659; 536, 621, and 659; 537, 603, and 671; 523, 622, and 659; 523, 617, and 659; 523, 623, and 659; 538, 607, and 672; 523, 616, and 671; 523, 624, and 659; 523, 620, and 659; 523, 625, and 660; 523, 602, and 671; 523, 611, and 663; 523, 626, and 670; 523, 606, and 673; 523, 627, and 671; 523, 628, and 671; 539, 591, and 662; 523, 591, and 670; 523, 611, and 659; 537, 613, and 671; 540, 598, and 659; 541, 591, and 659; 542, 629, and 659; 523, 591, and 671; 523, 630, and 667; 543, 631, and 659; 523, 632, and 664; 523, 597, and 661; 523, 633, and 659; 544, 607, and 659; 523, 630, and 659; 523, 591, and 665; 523, 610, and 674; 523, 634, and 671; 545, 591, and 661; 523, 635, and 667; 546, 591, and 659; 523, 636, and 664; 547, 591, and 663; 548, 619, and 659; 523, 637, and 659; 523, 638, and 659; 549, 591, and 659; 550, 591, and 675; 551, 591, and 659; 552, 591, and 659; 553, 591, and 676; 554, 591, and 659; 523, 591, and 676; 555, 606, and 659; 556, 591, and 659; 523, 637, and 677; 557, 591, and 659; 558, 591, and 659; 523, 591, and 677; 553, 639, and 659; 549, 591, and 667; 559, 617, and 666; 523, 591, and 672; 523, 606, and 659; 523, 592, and 670; 560, 591, and 667; 530, 591, and 659; 561, 603, and 666; 562, 591, and 659; 523, 616, and 660; 523, 602, and 677; 523, 616, and 659; 523, 630, and 660; 563, 591, and 659; 523, 640, and 659; 564, 591, and 659; 523, 641, and 677; 565, 591, and 662; 523, 642, and 664; 566, 643, and 659; 523, 644, and 667; 567, 606, and 659; 568, 591, and 659; 523, 569, 645, and 659; 523, 603, and 659; 570, 628, and 678; 571, 630, and 663; 572, 591, and 664; 573, 591, and 670; 523, 646, and 659; 574, 591, and 670; 523, 647, and 667; 575, 591, and 659; 537, 591, and 659; 523, 635, and 670; 576, 591, and 659; 577, 606, and 659; 523, 648, and 679; 523, 592, and 659; 523, 595, and 659; 523, 600, and 659; 523, 649, and 664; 578, 641, and 659; 523, 591, and 667; 523, 606, and 660; 523, 650, and 656; 579, 621, and 671; 580, 591, and 660; 527, 591, and 659; 581, 595, and 659; 582, 640, and 664; 583, 651, and 659; 534, 591, and 659; 584, 591, and 671; 523, 591, and 680; 523, 591, and 681; 585, 591, and 659; 523, 649, and 659; 586, 591, and 666; 587, 652, and 659; 588, 638, and 659; 523, 623, and 664; 523, 591, and 682; 553, 653, and 659; 523, 654, and 659; 523, 648, and 659; 560, 591, and 659; 580, 606, and 659; 589, 593, and 661; 523, 637, and 676; 590, 622, and 659; 555, 591, and 661; 523, 615, and 672; 523, 626, and 668; 523, 655, and 659; or 523, 606, and 680.

In an embodiment, the antibody comprises the CDRH1, CDRH2, CDRH3, CDRL1, CDRL2, and CDRL3 amino acid sequences, set forth in SEQ ID NOs: 369, 428, 484, 523, 591, and 656; 370, 429, 485, 523, 592, and 657; 371, 428, 486, 523, 593, and 658; 372, 428, 484, 523, 591, and 659; 373, 429, 484, 523, 594, and 659; 369, 428, 484, 523, 591, and 659; 374, 430, 484, 523, 591, and 659; 369, 428, 484, 523, 595, and 660; 375, 428, 487, 523, 596, and 659; 376, 428, 484, 524, 591, and 659; 377, 428, 484, 523, 591, and 661; 378, 428, 484, 523, 591, and 662; 372, 428, 484, 523, 597, and 658; 379, 428, 484, 523, 598, and 662; 372, 428, 488, 525, 599, and 659; 376, 431, 484, 523, 600, and 663; 380, 432, 484, 523, 591, and 664; 372, 428, 489, 523, 601, and 659; 381, 428, 490, 523, 591, and 659; 382, 428, 484, 526, 597, and 665; 381, 428, 491, 523, 602, and 659; 369, 428, 484, 527, 591, and 661; 377, 428, 492, 528, 591, and 662; 376, 433, 484, 529, 603, and 662; 383, 434, 484, 523, 604, and 666; 383, 428, 484, 523, 605, and 667; 384, 435, 484, 530, 606, and 659; 369, 436, 484, 523, 607, and 659; 372, 437, 487, 523, 591, and 659; 372, 428, 484, 523, 608, and 659; 385, 428, 493, 523, 609, and 662; 386, 428, 484, 531, 591, and 663; 372, 437, 484, 523, 608, and 661; 377, 428, 484, 523, 610, and 659; 387, 428, 484, 523, 611, and 668; 385, 428, 484, 523, 611, and 658; 372, 438, 484, 523, 596, and 662; 388, 428, 494, 523, 612, and 667; 369, 439, 484, 523, 613, and 668; 389, 428, 484, 523, 591, and 669; 382, 428, 484, 523, 591, and 663; 369, 428, 484, 523, 614, and 659; 381, 428, 484, 523, 591, and 659; 376, 440, 495, 523, 591, and 659; 381, 428, 484, 532, 615, and 662; 381, 428, 484, 523, 616, and 670; 390, 441, 484, 523, 591, and 659; 370, 442, 484, 523, 591, and 668; 391, 428, 484, 523, 617, and 671; 377, 428, 484, 533, 595, and 659; 377, 428, 484, 523, 618, and 659; 392, 432, 484, 523, 591, and 659; 377, 443, 484, 534, 619, and 662; 376, 428, 484, 535, 620, and 659; 393, 428, 484, 536, 621, and 659; 381, 428, 484, 537, 603, and 671; 383, 444, 489, 523, 622, and 59; 372, 428, 484, 523, 617, and 659; 377, 428, 484, 523, 623, and 659; 376, 428, 484, 538, 607, and 672; 369, 428, 484, 523, 616, and 671; 376, 428, 484, 523, 624, and 659; 394, 428, 484, 523, 591, and 659; 369, 428, 484, 523, 620, and 659; 383, 444, 496, 523, 625, and 660; 385, 428, 484, 523, 602, and 671; 376, 434, 484, 523, 591, and 659; 395, 445, 497, 523, 611, and 663; 396, 446, 487, 523, 626, and 670; 369, 428, 484, 523, 617, and 659; 392, 428, 484, 523, 591, and 662; 394, 428, 484, 523, 606, and 673; 393, 428, 498, 523, 591, and 659; 376, 428, 495, 523, 627, and 671; 369, 440, 484, 523, 628, and 671; 397, 428, 484, 539, 591, and 662; 389, 447, 484, 523, 591, and 659; 398, 448, 492, 523, 591, and 670; 373, 449, 490, 523, 611, and 659; 399, 428, 484, 537, 613, and 671; 400, 450, 484, 540, 598, and 659; 401, 428, 484, 541, 591, and 659; 390, 428, 484, 542, 629, and 659; 376, 428, 484, 523, 591, and 671; 400, 428, 499, 523, 591, and 659; 381, 428, 484, 523, 630, and 667; 384, 429, 484, 543, 631, and 659; 369, 428, 484, 523, 632, and 664; 402, 436, 484, 523, 597, and 661; 381, 451, 484, 523, 591, and 656; 403, 428, 484, 523, 633, and 659; 369, 429, 484, 544, 607, and 659; 404, 429, 484, 523, 630, and 659; 372, 429, 484, 523, 602, and 659; 381, 428, 484, 523, 591, and 665; 388, 428, 484, 523, 610, and 674; 405, 451, 484, 523, 634, and 671; 406, 428, 484, 545, 591, and 661; 400, 428, 484, 523, 635, and 667; 404, 428, 484, 546, 591, and 659; 384, 432, 500, 523, 636, and 664; 376, 452, 501, 547, 591, and 663; 407, 428, 484, 548, 619, and 659; 375, 428, 484, 523, 637, and 659; 372, 428, 484, 523, 607, and 659; 408, 428, 484, 523, 638, and 659; 386, 428, 484, 523, 591, and 659; 369, 428, 497, 523, 591, and 659; 403, 453, 484, 549, 591, and 659; 402, 454, 484, 523, 591, and 659; 383, 428, 484, 523, 591, and 659; 383, 434, 500, 523, 591, and 659; 376, 455, 502, 550, 591, and 675; 383, 435, 484, 523, 591, and 664; 369, 428, 484, 523, 602, and 659; 376, 428, 484, 551, 591, and 659; 376, 428, 484, 552, 591, and 659; 383, 428, 484, 553, 591, and 676; 376, 428, 484, 554, 591, and 659; 376, 428, 490, 523, 591, and 676; 369, 428, 503, 555, 606, and 659; 409, 428, 484, 523, 591, and 659; 383, 428, 504, 556, 591, and 659; 369, 434, 484, 523, 591, and 659; 390, 428, 484, 523, 637, and 677; 369, 456, 484, 523, 591, and 659; 370, 457, 484, 557, 591, and 659; 383, 428, 484, 558, 591, and 659; 404, 458, 499, 523, 591, and 659; 410, 428, 484, 523, 591, and 677; 383, 459, 484, 553, 639, and 659; 407, 428, 489, 549, 591, and 667; 374, 434, 484, 523, 591, and 659; 404, 428, 484, 559, 617, and 666; 411, 460, 505, 523, 591, and 672; 372, 429, 484, 523, 606, and 659; 383, 428, 485, 523, 591, and 659; 386, 460, 490, 523, 601, and 659; 412, 455, 493, 523, 592, and 670; 372, 428, 484, 560, 591, and 667; 372, 428, 484, 523, 606, and 659; 383, 461, 484, 523, 591, and 677; 369, 429, 484, 523, 606, and 659; 369, 434, 484, 530, 591, and 659; 376, 437, 484, 561, 603, and 666; 383, 462, 500, 523, 591, and 659; 383, 428, 484, 562, 591, and 659; 400, 463, 484, 523, 616, and 660; 376, 464, 484, 523, 602, and 677; 400, 434, 506, 549, 591, and 659; 369, 436, 507, 523, 591, and 659; 404, 429, 484, 523, 591, and 659; 384, 429, 484, 523, 616, and 659; 369, 429, 484, 523, 591, and 659; 377, 465, 484, 523, 630, and 660; 413, 459, 484, 563, 591, and 659; 369, 452, 484, 523, 591, and 663; 414, 466, 484, 523, 640, and 659; 373, 428, 484, 523, 591, and 659; 415, 428, 489, 564, 591, and 659; 369, 428, 484, 523, 591, and 671; 400, 428, 484, 641, and 677; 369, 428, 491, 565, 591, and 662; 403, 458, 508, 523, 642, and 664; 392, 467, 484, 523, 591, and 659; 369, 452, 509, 566, 643, and 659; 388, 468, 490, 523, 591, and 659; 369, 452, 484, 523, 644, and 667; 377, 440, 484, 567, 606, and 659; 370, 428, 484, 523, 591, and 656; 384, 467, 487, 523, 591, and 659; 392, 469, 510, 568, 591, and 659; 378, 464, 484, 523, 606, and 659; 377, 428, 484, 569, 645, and 659; 416, 434, 484, 523, 603, and 659; 370, 428, 484, 523, 606, and 659; 370, 428, 511, 570, 628, and 678; 369, 452, 484, 571, 630, and 663; 376, 428, 502, 572, 591, and 664; 417, 428, 484, 523, 591, and 665; 392, 428, 484, 573, 591, and 670; 376, 428, 512, 523, 646, and 659; 377, 428, 484, 574, 591, and 670; 383, 428, 484, 523, 647, and 667; 381, 428, 493, 575, 591, and 659; 383, 470, 501, 523, 591, and 659; 404, 471, 484, 537, 591, and 659; 418, 428, 484, 523, 635, and 670; 383, 472, 513, 576, 591, and 659; 419, 428, 484, 577, 606, and 659; 397, 428, 484, 523, 648, and 679; 372, 473, 484, 523, 591, and 664; 383, 474, 484, 523, 592, and 659; 372, 428, 484, 523, 591, and 663; 420, 434, 484, 523, 595, and 659; 370, 428, 514, 523, 591, and 659; 369, 428, 484, 523, 591, and 677; 383, 428, 484, 523, 600, and 659; 369, 475, 484, 523, 591, and 659; 421, 436, 484, 523, 649, and 664; 378, 452, 484, 523, 591, and 659; 376, 476, 515, 578, 641, and 659; 376, 428, 504, 523, 591, and 667; 422, 469, 484, 523, 606, and 660; 383, 461, 484, 523, 616, and 659; 369, 428, 484, 523, 650, and 656; 369, 428, 516, 523, 591, and 659; 405, 460, 484, 523, 618, and 659; 413, 431, 484, 523, 591, and 659; 382, 428, 484, 579, 621, and 671; 383, 428, 484, 523, 646, and 659; 372, 428, 484, 580, 591, and 660; 406, 429, 484, 527, 591, and 659; 383, 428, 517, 581, 595, and 659; 377, 437, 518, 582, 640, and 664; 369, 477, 487, 583, 651, and 659; 403, 464, 484, 534, 591, and 659; 383, 459, 484, 523, 606, and 659; 369, 454, 484, 584, 591, and 671; 372, 478, 519, 523, 591, and 680; 423, 429, 484, 523, 591, and 681; 383, 428, 484, 585, 591, and 659; 369, 434, 484, 557, 591, and 659; 382, 434, 484, 523, 649, and 659; 424, 479, 484, 523, 616, and 660; 376, 429, 484, 586, 591, and 666; 425, 428, 484, 523, 592, and 659; 369, 436, 484, 587, 652, and 659; 403, 428, 520, 588, 638, and 659; 417, 460, 484, 523, 591, and 659; 409, 460, 484, 523, 623, and 664; 404, 452, 484, 523, 591, and 659; 369, 428, 484, 523, 591, and 682; 383, 428, 521, 553, 653, and 659; 372, 480, 493, 523, 591, and 659; 369, 428, 484, 523, 654, and 659; 369, 477, 484, 523, 648, and 659; 369, 481, 484, 560, 591, and 659; 369, 452, 484, 523, 591, and 667; 409, 428, 484, 580, 606, and 659; 384, 452, 484, 589, 593, and 661; 377, 482, 484, 523, 591, and 659; 410, 483, 484, 523, 591, and 659; 384, 428, 489, 523, 591, and 659; 426, 429, 484, 523, 622, and 659; 376, 428, 484, 523, 637, and 676; 427, 428, 484, 523, 591, and 671; 373, 452, 506, 523, 591, and 659; 369, 428, 484, 590, 622, and 659; 369, 429, 521, 555, 591, and 661; 405, 428, 522, 523, 615, and 672; 376, 428, 510, 523, 591, and 659; 384, 428, 484, 523, 626, and 668; 410, 429, 484, 523, 591, and 659; 400, 452, 484, 523, 655, and 659; or 369, 434, 484, 523, 606, and 680.

In an embodiment, the antibody comprises the VH amino acid sequence of any one of SEQ ID NOs: 1-180.

In an embodiment, the antibody comprises the VL amino acid sequence of any one of SEQ ID NOs: 181-368.

In an embodiment, the VH and VL comprise the amino acid sequences, respectively, set forth in SEQ ID NOs: 1 and 181; 2 and 182; 3 and 183; 4 and 184; 5 and 185; 1 and 184; 6 and 184; 1 and 186; 7 and 187; 8 and 188; 9 and 189; 10 and 190; 4 and 191; 11 and 192; 12 and 193; 13 and 194; 14 and 195; 15 and 196; 16 and 184; 17 and 197; 18 and 198; 1 and 199; 19 and 200; 20 and 201; 21 and 202; 22 and 203; 23 and 204; 24 and 205; 25 and 184; 4 and 206; 26 and 207; 27 and 208; 28 and 209; 9 and 210; 29 and 211; 30 and 212; 31 and 213; 32 and 214; 33 and 215; 34 and 216; 17 and 217; 1 and 218; 35 and 184; 36 and 184; 35 and 219; 35 and 220; 37 and 184; 38 and 221; 39 and 222; 9 and 223; 9 and 224; 40 and 184; 41 and 225; 8 and 226; 42 and 227; 35 and 228; 43 and 229; 4 and 230; 9 and 231; 8 and 232; 1 and 233; 8 and 234; 44 and 184; 1 and 235; 45 and 236; 30 and 237; 46 and 184; 47 and 238; 48 and 239; 1 and 230; 49 and 190; 44 and 240; 50 and 184; 51 and 241; 52 and 242; 53 and 243; 54 and 184; 55 and 244; 56 and 245; 57 and 246; 58 and 247; 59 and 248; 60 and 249; 8 and 250; 61 and 184; 35 and 251; 62 and 252; 1 and 253; 63 and 254; 64 and 181; 65 and 255; 66 and 256; 67 and 257; 68 and 198; 35 and 258; 69 and 259; 70 and 260; 71 and 261; 72 and 262; 73 and 263; 74 and 264; 75 and 265; 76 and 266; 77 and 267; 4 and 205; 78 and 268; 1 and 269; 27 and 269; 79 and 269; 80 and 270; 81 and 269; 22 and 269; 82 and 269; 83 and 271; 84 and 272; 1 and 273; 8 and 274; 8 and 275; 22 and 276; 8 and 277; 85 and 278; 86 and 279; 87 and 269; 88 and 280; 89 and 269; 60 and 281; 90 and 269; 91 and 282; 22 and 283; 92 and 269; 93 and 284; 94 and 285; 95 and 286; 96 and 269; 73 and 287; 97 and 288; 68 and 289; 98 and 269; 99 and 290; 100 and 291; 4 and 292; 4 and 289; 101 and 284; 66 and 289; 89 and 293; 102 and 294; 103 and 269; 22 and 295; 104 and 296; 105 and 297; 106 and 270; 107 and 269; 67 and 269; 62 and 298; 66 and 269; 108 and 299; 109 and 300; 110 and 301; 111 and 302; 112 and 269; 113 and 303; 1 and 304; 72 and 305; 114 and 306; 115 and 307; 116 and 269; 117 and 308; 118 and 269; 110 and 309; 119 and 310; 120 and 311; 121 and 269; 122 and 312; 123 and 289; 9 and 313; 124 and 314; 120 and 289; 125 and 315; 110 and 316; 126 and 317; 127 and 318; 49 and 319; 128 and 320; 9 and 321; 22 and 322; 129 and 323; 130 and 269; 131 and 324; 132 and 325; 133 and 326; 134 and 327; 53 and 328; 135 and 272; 136 and 329; 4 and 301; 137 and 330; 138 and 269; 1 and 284; 22 and 331; 139 and 269; 140 and 332; 141 and 269; 142 and 333; 143 and 334; 144 and 335; 101 and 298; 1 and 336; 145 and 269; 146 and 337; 147 and 269; 17 and 338; 22 and 320; 4 and 339; 148 and 340; 149 and 341; 150 and 342; 151 and 343; 152 and 344; 94 and 289; 153 and 345; 154 and 346; 155 and 347; 22 and 348; 89 and 282; 156 and 349; 157 and 296; 158 and 350; 159 and 329; 24 and 351; 160 and 352; 161 and 269; 162 and 353; 163 and 269; 1 and 354; 164 and 355; 165 and 269; 1 and 356; 166 and 357; 167 and 358; 110 and 334; 87 and 359; 168 and 360; 169 and 269; 170 and 269; 171 and 269; 172 and 361; 8 and 362; 173 and 304; 174 and 269; 1 and 363; 175 and 364; 176 and 365; 177 and 269; 178 and 366; 179 and 269; 180 and 367; or 89 and 368.

In an embodiment, the antibody is a single-chain variable fragment (scFv).

In an embodiment, the antibody comprises a heavy chain constant region, or an Fc region thereof, optionally selected from the group consisting of a human $IgG_1$, $IgG_2$, $IgG_3$, $IgG_4$, $IgA_1$, and $IgA_2$.

In an embodiment, the heavy chain constant region is a human $IgG_1$.

In an embodiment, the heavy chain constant region is a human $IgG_4$.

In an embodiment, the amino acid sequence of the human $IgG_4$ heavy chain constant region comprises a P at position 228, numbered according to the EU numbering system.

In an embodiment, the heavy chain constant region is a variant of a wild-type heavy chain constant region, wherein the variant heavy chain constant region binds to an Fc gamma receptor (FcγR) with lower affinity than the wild-type heavy chain constant region binds to the FcγR.

In an embodiment, the amino acid sequence of the heavy chain constant region comprises: A at position 234; A at position 235; A, Q or G at position 297; or A or G at position 329, in each case numbered according to the EU numbering system.

In an embodiment, the amino acid sequence of the heavy chain constant region comprises: A at positions 234 and 235; A at positions 234, 235, and 329; or A at positions 234, 235, and G at position 329, in each case numbered according to the EU numbering system.

In an embodiment, the heavy chain constant region is a variant of a wild-type heavy chain constant region, and wherein the variant heavy chain constant region has an increased affinity for human neonatal Fc receptor (FcRn) at pH 6 relative to the affinity of the wild-type heavy chain constant region for human FcRn at pH 6.

In an embodiment, the amino acid sequence of the heavy chain constant region comprises: L and S at positions 428 and 434, respectively; K, F, and Y at positions 433, 434, and 436, respectively; or Y, T, and E at positions 252, 254, and 256, respectively, in each case numbered according to the EU numbering system.

In an embodiment, the antibody comprises a light chain constant region, optionally a human kappa or lambda constant region.

In one aspect, the present disclosure provides a polypeptide comprising a VH comprising the CDRH1, CDRH2, and CDRH3 amino acid sequences of any one of the VH amino acid sequences set forth in SEQ ID NOs: 1-180.

In an embodiment, the polypeptide comprises the CDRH1, CDRH2, and CDRH3 amino acid sequences, respectively, set forth in SEQ ID NOs: 369, 428, and 484; 370, 429, and 485; 371, 428, and 486; 372, 428, and 484; 373, 429, and 484; 374, 430, and 484; 375, 428, and 487; 376, 428, and 484; 377, 428, and 484; 378, 428, and 484; 379, 428, and 484; 372, 428, and 488; 376, 431, and 484; 380, 432, and 484; 372, 428, and 489; 381, 428, and 490; 382, 428, and 484; 381, 428, and 491; 377, 428, and 492; 376, 433, and 484; 383, 434, and 484; 383, 428, and 484; 384, 435, and 484; 369, 436, and 484; 372, 437, and 487; 385, 428, and 493; 386, 428, and 484; 372, 437, and 484; 387, 428, and 484; 385, 428, and 484; 372, 438, and 484;

388, 428, and 494; 369, 439, and 484; 389, 428, and 484; 381, 428, and 484; 376, 440, and 495; 390, 441, and 484; 370, 442, and 484; 391, 428, and 484; 392, 432, and 484; 377, 443, and 484; 393, 428, and 484; 383, 444, and 489; 394, 428, and 484; 383, 444, and 496; 376, 434, and 484; 395, 445, and 497; 396, 446, and 487; 392, 428, and 484; 393, 428, and 498; 376, 428, and 495; 369, 440, and 484; 397, 428, and 484; 389, 447, and 484; 398, 448, and 492; 373, 449, and 490; 399, 428, and 484; 400, 450, and 484; 401, 428, and 484; 390, 428, and 484; 400, 428, and 499; 384, 429, and 484; 402, 436, and 484; 381, 451, and 484; 403, 428, and 484; 369, 429, and 484; 404, 429, and 484; 372, 429, and 484; 388, 428, and 484; 405, 451, and 484; 406, 428, and 484; 400, 428, and 484; 404, 428, and 484; 384, 432, and 500; 376, 452, and 501; 407, 428, and 484; 375, 428, and 484; 408, 428, and 484; 369, 428, and 497; 403, 453, and 484; 402, 454, and 484; 383, 434, and 500; 376, 455, and 502; 383, 435, and 484; 376, 428, and 490; 369, 428, and 503; 409, 428, and 484; 383, 428, and 504; 369, 434, and 484; 369, 456, and 484; 370, 457, and 484; 404, 458, and 499; 410, 428, and 484; 383, 459, and 484; 407, 428, and 489; 374, 434, and 484; 411, 460, and 505; 383, 428, and 485; 386, 460, and 490; 412, 455, and 493; 383, 461, and 484; 376, 437, and 484; 383, 462, and 500; 400, 463, and 484; 376, 464, and 484; 400, 434, and 506; 369, 436, and 507; 377, 465, and 484; 413, 459, and 484; 369, 452, and 484; 414, 466, and 484; 373, 428, and 484; 415, 428, and 489; 369, 428, and 491; 403, 458, and 508; 392, 467, and 484; 369, 452, and 509; 388, 468, and 490; 377, 440, and 484; 370, 428, and 484; 384, 467, and 487; 392, 469, and 510; 378, 464, and 484; 416, 434, and 484; 370, 428, and 511; 376, 428, and 502; 417, 428, and 484; 376, 428, and 512; 381, 428, and 493; 383, 470, and 501; 404, 471, and 484; 418, 428, and 484; 383, 472, and 513; 419, 428, and 484; 372, 473, and 484; 383, 474, and 484; 420, 434, and 484; 370, 428, and 514; 369, 475, and 484; 421, 436, and 484; 378, 452, and 484; 376, 476, and 515; 376, 428, and 504; 422, 469, and 484; 369, 428, and 516; 405, 460, and 484; 413, 431, and 484; 406, 429, and 484; 383, 428, and 517; 377, 437, and 518; 369, 477, and 487; 403, 464, and 484; 369, 454, and 484; 372, 478, and 519; 423, 429, and 484; 382, 434, and 484; 424, 479, and 484; 376, 429, and 484; 425, 428, and 484; 403, 428, and 520; 417, 460, and 484; 409, 460, and 484; 404, 452, and 484; 383, 428, and 521; 372, 480, and 493; 369, 477, and 484; 369, 481, and 484; 384, 452, and 484; 377, 482, and 484; 410, 483, and 484; 384, 428, and 489; 426, 429, and 484; 427, 428, and 484; 373, 452, and 506; 369, 429, and 521; 405, 428, and 522; 376, 428, and 510; 384, 428, and 484; 410, 429, and 484; or 400, 452, and 484.

In an embodiment, the VH comprises the CDRH1, CDRH2, and CDRH3 amino acid sequences, respectively, set forth in SEQ ID NOs: 369, 428, and 484; 370, 429, and 485; 371, 428, and 486; 372, 428, and 484; 373, 429, and 484; 374, 430, and 484; 375, 428, and 487; 376, 428, and 484; 377, 428, and 484; 378, 428, and 484; 379, 428, and 484; 372, 428, and 488; 376, 431, and 484; 380, 432, and 484; 372, 428, and 489; 381, 428, and 490; 382, 428, and 484; 381, 428, and 491; 377, 428, and 492; 376, 433, and 484; 383, 434, and 484; 383, 428, and 484; 384, 435, and 484; 369, 436, and 484; 372, 437, and 487; 385, 428, and 493; 386, 428, and 484; 372, 437, and 484; 387, 428, and 484; 385, 428, and 484; 372, 438, and 484; 388, 428, and 494; 369, 439, and 484; 389, 428, and 484; 381, 428, and 484; 376, 440, and 495; 390, 441, and 484; 370, 442, and 484; 391, 428, and 484; 392, 432, and 484; 377, 443, and 484; 393, 428, and 484; 383, 444, and 489; 394, 428, and 484; 383, 444, and 496; 376, 434, and 484; 395, 445, and 497; 396, 446, and 487; 392, 428, and 484; 393, 428, and 498; 376, 428, and 495; 369, 440, and 484; 397, 428, and 484; 389, 447, and 484; 398, 448, and 492; 373, 449, and 490; 399, 428, and 484; 400, 450, and 484; 401, 428, and 484; 390, 428, and 484; 400, 428, and 499; 384, 429, and 484; 402, 436, and 484; 381, 451, and 484; 403, 428, and 484; 369, 429, and 484; 404, 429, and 484; 372, 429, and 484; 388, 428, and 484; 405, 451, and 484; 406, 428, and 484; 400, 428, and 484; 404, 428, and 484; 384, 432, and 500; 376, 452, and 501; 407, 428, and 484; 375, 428, and 484; 408, 428, and 484; 369, 428, and 497; 403, 453, and 484; 402, 454, and 484; 383, 434, and 500; 376, 455, and 502; 383, 435, and 484; 376, 428, and 490; 369, 428, and 503; 409, 428, and 484; 383, 428, and 504; 369, 434, and 484; 369, 456, and 484; 370, 457, and 484; 404, 458, and 499; 410, 428, and 484; 383, 459, and 484; 407, 428, and 489; 374, 434, and 484; 411, 460, and 505; 383, 428, and 485; 386, 460, and 490; 412, 455, and 493; 383, 461, and 484; 376, 437, and 484; 383, 462, and 500; 400, 463, and 484; 376, 464, and 484; 400, 434, and 506; 369, 436, and 507; 377, 465, and 484; 413, 459, and 484; 369, 452, and 484; 414, 466, and 484; 373, 428, and 484; 415, 428, and 489; 369, 428, and 491; 403, 458, and 508; 392, 467, and 484; 369, 452, and 509; 388, 468, and 490; 377, 440, and 484; 370, 428, and 484; 384, 467, and 487; 392, 469, and 510; 378, 464, and 484; 416, 434, and 484; 370, 428, and 511; 376, 428, and 502; 417, 428, and 484; 376, 428, and 512; 381, 428, and 493; 383, 470, and 501; 404, 471, and 484; 418, 428, and 484; 383, 472, and 513; 419, 428, and 484; 372, 473, and 484; 383, 474, and 484; 420, 434, and 484; 370, 428, and 514; 369, 475, and 484; 421, 436, and 484; 378, 452, and 484; 376, 476, and 515; 376, 428, and 504; 422, 469, and 484; 369, 428, and 516; 405, 460, and 484; 413, 431, and 484; 406, 429, and 484; 383, 428, and 517; 377, 437, and 518; 369, 477, and 487; 403, 464, and 484; 369, 454, and 484; 372, 478, and 519; 423, 429, and 484; 382, 434, and 484; 424, 479, and 484; 376, 429, and 484; 425, 428, and 484; 403, 428, and 520; 417, 460, and 484; 409, 460, and 484; 404, 452, and 484; 383, 428, and 521; 372, 480, and 493; 369, 477, and 484; 369, 481, and 484; 384, 452, and 484; 377, 482, and 484; 410, 483, and 484; 384, 428, and 489; 426, 429, and 484; 427, 428, and 484; 373, 452, and 506; 369, 429, and 521; 405, 428, and 522; 376, 428, and 510; 384, 428, and 484; 410, 429, and 484; or 400, 452, and 484.

In an embodiment, the VH comprises any one of the amino acid sequences set forth in SEQ ID NOs: 1-180.

In one aspect, the present disclosure provides a polypeptide comprising a VL comprising the CDRL1, CDRL2, and CDRL3 amino acid sequences of any one of the VL amino acid sequences set forth in SEQ ID NOs: 181-368.

In an embodiment, the polypeptide comprises the CDRL1, CDRL2, and CDRL3 amino acid sequences, respectively, set forth in SEQ ID NOs: 523, 591, and 656; 523, 592, and 657; 523, 593, and 658; 523, 591, and 659; 523, 594, and 659; 523, 595, and 660; 523, 596, and 659; 524, 591, and 659; 523, 591, and 661; 523, 591, and 662; 523, 597, and 658; 523, 598, and 662; 525, 599, and 659; 523, 600, and 663; 523, 591, and 664; 523, 601, and 659; 526, 597, and 665; 523, 602, and 659; 527, 591, and 661; 528, 591, and 662; 529, 603, and 662; 523, 604, and 666; 523, 605, and 667; 530, 606, and 659; 523, 607, and 659; 523, 608, and 659; 523, 609, and 662; 531, 591, and 663; 523, 608, and 661; 523, 610, and 659; 523, 611, and 668; 523, 611, and 658; 523, 596, and 662; 523, 612, and 667; 523, 613, and 668; 523, 591, and 669; 523, 591, and 663;

523, 614, and 659; 532, 615, and 662; 523, 616, and 670; 523, 591, and 668; 523, 617, and 671; 533, 595, and 659; 523, 618, and 659; 534, 619, and 662; 535, 620, and 659; 536, 621, and 659; 537, 603, and 671; 523, 622, and 659; 523, 617, and 659; 523, 623, and 659; 538, 607, and 672; 523, 616, and 671; 523, 624, and 659; 523, 620, and 659; 523, 625, and 660; 523, 602, and 671; 523, 611, and 663; 523, 626, and 670; 523, 606, and 673; 523, 627, and 671; 523, 628, and 671; 539, 591, and 662; 523, 591, and 670; 523, 611, and 659; 537, 613, and 671; 540, 598, and 659; 541, 591, and 659; 542, 629, and 659; 523, 591, and 671; 523, 630, and 667; 543, 631, and 659; 523, 632, and 664; 523, 597, and 661; 523, 633, and 659; 544, 607, and 659; 523, 630, and 659; 523, 591, and 665; 523, 610, and 674; 523, 634, and 671; 545, 591, and 661; 523, 635, and 667; 546, 591, and 659; 523, 636, and 664; 547, 591, and 663; 548, 619, and 659; 523, 637, and 659; 523, 638, and 659; 549, 591, and 659; 550, 591, and 675; 551, 591, and 659; 552, 591, and 659; 553, 591, and 676; 554, 591, and 659; 523, 591, and 676; 555, 606, and 659; 556, 591, and 659; 523, 637, and 677; 557, 591, and 659; 558, 591, and 659; 523, 591, and 677; 553, 639, and 659; 549, 591, and 667; 559, 617, and 666; 523, 591, and 672; 523, 606, and 659; 523, 592, and 670; 560, 591, and 667; 530, 591, and 659; 561, 603, and 666; 562, 591, and 659; 523, 616, and 660; 523, 602, and 677; 523, 616, and 659; 523, 630, and 660; 563, 591, and 659; 523, 640, and 659; 564, 591, and 659; 523, 641, and 677; 565, 591, and 662; 523, 642, and 664; 566, 643, and 659; 523, 644, and 667; 567, 606, and 659; 568, 591, and 659; 569, 645, and 659; 523, 603, and 659; 570, 628, and 678; 571, 630, and 663; 572, 591, and 664; 573, 591, and 670; 523, 646, and 659; 574, 591, and 670; 523, 647, and 667; 575, 591, and 659; 537, 591, and 659; 523, 635, and 670; 576, 591, and 659; 577, 606, and 659; 523, 648, and 679; 523, 592, and 659; 523, 595, and 659; 523, 600, and 659; 523, 649, and 664; 578, 641, and 659; 523, 591, and 667; 523, 606, and 660; 523, 650, and 656; 579, 621, and 671; 580, 591, and 660; 527, 591, and 659; 581, 595, and 659; 582, 640, and 664; 583, 651, and 659; 534, 591, and 659; 584, 591, and 671; 523, 591, and 680; 523, 591, and 681; 585, 591, and 659; 523, 649, and 659; 586, 591, and 666; 587, 652, and 659; 588, 638, and 659; 523, 623, and 664; 523, 591, and 682; 553, 653, and 659; 523, 654, and 659; 523, 648, and 659; 560, 591, and 659; 580, 606, and 659; 589, 593, and 661; 523, 637, and 676; 590, 622, and 659; 555, 591, and 661; 523, 615, and 672; 523, 626, and 668; 523, 655, and 659; or 523, 606, and 680.

In an embodiment, the VL comprises the CDRL1, CDRL2, and CDRL3 amino acid sequences, respectively, set forth in SEQ ID NOs: 523, 591, and 656; 523, 592, and 657; 523, 593, and 658; 523, 591, and 659; 523, 594, and 659; 523, 595, and 660; 523, 596, and 659; 524, 591, and 659; 523, 591, and 661; 523, 591, and 662; 523, 597, and 658; 523, 598, and 662; 525, 599, and 659; 523, 600, and 663; 523, 591, and 664; 523, 601, and 659; 526, 597, and 665; 523, 602, and 659; 527, 591, and 661; 528, 591, and 662; 529, 603, and 662; 523, 604, and 666; 523, 605, and 667; 530, 606, and 659; 523, 607, and 659; 523, 608, and 659; 523, 609, and 662; 531, 591, and 663; 523, 608, and 661; 523, 610, and 659; 523, 611, and 668; 523, 611, and 658; 523, 596, and 662; 523, 612, and 667; 523, 613, and 668; 523, 591, and 669; 523, 591, and 663; 523, 614, and 659; 532, 615, and 662; 523, 616, and 670; 523, 591, and 668; 523, 617, and 671; 533, 595, and 659; 523, 618, and 659; 534, 619, and 662; 535, 620, and 659; 536, 621, and 659; 537, 603, and 671; 523, 622, and 659; 523, 617, and 659; 523, 623, and 659; 538, 607, and 672; 523, 616, and 671; 523, 624, and 659; 523, 620, and 659; 523, 625, and 660; 523, 602, and 671; 523, 611, and 663; 523, 626, and 670; 523, 606, and 673; 523, 627, and 671; 523, 628, and 671; 539, 591, and 662; 523, 591, and 670; 523, 611, and 659; 537, 613, and 671; 540, 598, and 659; 541, 591, and 659; 542, 629, and 659; 523, 591, and 671; 523, 630, and 667; 543, 631, and 659; 523, 632, and 664; 523, 597, and 661; 523, 633, and 659; 544, 607, and 659; 523, 630, and 659; 523, 591, and 665; 523, 610, and 674; 523, 634, and 671; 545, 591, and 661; 523, 635, and 667; 546, 591, and 659; 523, 636, and 664; 547, 591, and 663; 548, 619, and 659; 523, 637, and 659; 523, 638, and 659; 549, 591, and 659; 550, 591, and 675; 551, 591, and 659; 552, 591, and 659; 553, 591, and 676; 554, 591, and 659; 523, 591, and 676; 555, 606, and 659; 556, 591, and 659; 523, 637, and 677; 557, 591, and 659; 558, 591, and 659; 523, 591, and 677; 553, 639, and 659; 549, 591, and 667; 559, 617, and 666; 523, 591, and 672; 523, 606, and 659; 523, 592, and 670; 560, 591, and 667; 530, 591, and 659; 561, 603, and 666; 562, 591, and 659; 523, 616, and 660; 523, 602, and 677; 523, 616, and 659; 523, 630, and 660; 563, 591, and 659; 523, 640, and 659; 564, 591, and 659; 523, 641, and 677; 565, 591, and 662; 523, 642, and 664; 566, 643, and 659; 523, 644, and 667; 567, 606, and 659; 568, 591, and 659; 569, 645, and 659; 523, 603, and 659; 570, 628, and 678; 571, 630, and 663; 572, 591, and 664; 573, 591, and 670; 523, 646, and 659; 574, 591, and 670; 523, 647, and 667; 575, 591, and 659; 537, 591, and 659; 523, 635, and 670; 576, 591, and 659; 577, 606, and 659; 523, 648, and 679; 523, 592, and 659; 523, 595, and 659; 523, 600, and 659; 523, 649, and 664; 578, 641, and 659; 523, 591, and 667; 523, 606, and 660; 523, 650, and 656; 579, 621, and 671; 580, 591, and 660; 527, 591, and 659; 581, 595, and 659; 582, 640, and 664; 583, 651, and 659; 534, 591, and 659; 584, 591, and 671; 523, 591, and 680; 523, 591, and 681; 585, 591, and 659; 523, 649, and 659; 586, 591, and 666; 587, 652, and 659; 588, 638, and 659; 523, 623, and 664; 523, 591, and 682; 553, 653, and 659; 523, 654, and 659; 523, 648, and 659; 560, 591, and 659; 580, 606, and 659; 589, 593, and 661; 523, 637, and 676; 590, 622, and 659; 555, 591, and 661; 523, 615, and 672; 523, 626, and 668; 523, 655, and 659; or 523, 606, and 680.

In an embodiment, the VL comprises any one of the amino acid sequences set forth in SEQ ID NOs: 181-368.

In an embodiment, an antibody or polypeptide disclosed herein is conjugated to a cytotoxic agent, cytostatic agent, toxin, radionuclide, or detectable label.

In one aspect, the present disclosure provides a polynucleotide encoding a VH and/or a VL of an antibody disclosed herein, or a polypeptide disclosed herein.

In one aspect, the present disclosure provides a vector comprising the polynucleotide disclosed herein.

In an embodiment, the vector is an adeno-associated virus (AAV) vector.

In one aspect, the present disclosure provides a recombinant host cell comprising:
(a) a polynucleotide disclosed herein;
(b) a vector disclosed herein;
(c) a first polynucleotide encoding a VH or heavy chain of an antibody disclosed herein, and a second polynucleotide encoding a VL or light chain of an antibody disclosed herein; or
(d) a first vector comprising a first polynucleotide encoding a VH or heavy chain of an antibody disclosed herein, and a second vector comprising a second polynucleotide encoding a VL or light chain of an antibody disclosed herein.

In one aspect, the present disclosure provides a pharmaceutical composition comprising an antibody or polypeptide disclosed herein, a polynucleotide disclosed herein, a vector disclosed herein, or a host cell disclosed herein, and a pharmaceutically acceptable carrier or excipient.

In one aspect, the present disclosure provides a method of producing an antibody or polypeptide, the method comprising culturing a host cell disclosed herein under suitable conditions such that the polynucleotide is expressed, and the antibody or polypeptide is produced.

In one aspect, the present disclosure provides a method of inhibiting an activity of PC in a subject, the method comprising administering to the subject an effective amount of an antibody or polypeptide disclosed herein, a polynucleotide disclosed herein, a vector disclosed herein, a host cell disclosed herein, or a pharmaceutical composition disclosed herein.

In one aspect, the present disclosure provides a method of treating an inflammatory disorder or degenerative disease in a subject, the method comprising administering to the subject an effective amount of an antibody or polypeptide disclosed herein, a polynucleotide disclosed herein, a vector disclosed herein, a host cell disclosed herein, or a pharmaceutical composition disclosed herein.

In one aspect, the present disclosure provides use of an antibody or polypeptide disclosed herein, a polynucleotide disclosed herein, a vector disclosed herein, a host cell disclosed herein, or a pharmaceutical composition disclosed herein, for the manufacture of a medicament for the treatment of an inflammatory disorder or degenerative disease in a subject in need thereof.

In one aspect, the present disclosure provides an antibody or polypeptide disclosed herein, a polynucleotide disclosed herein, a vector disclosed herein, a host cell disclosed herein, or a pharmaceutical composition disclosed herein, for use in medicine.

In one aspect, the present disclosure provides an antibody or polypeptide disclosed herein, a polynucleotide disclosed herein, a vector disclosed herein, a host cell disclosed herein, or a pharmaceutical composition disclosed herein, for use in the treatment of an inflammatory disorder or degenerative disease in a subject in need thereof.

In an embodiment, the inflammatory disorder or degenerative disease is selected from the group consisting of organ reperfusion injury such as myocardial infarction induced reperfusion injury, Kawasaki disease, non-alcoholic steatohepatitis (NASH), organ transplant rejection, atherosclerosis, Type 1 or Type 2 Diabetes, rheumatoid arthritis, osteoporosis, acute lung injury, asthma, chronic obstructive pulmonary disease (COPD), lung fibrosis, pain, Alzheimer's disease, amyotrophic lateral sclerosis (ALS), age-related macular degeneration (AMD), stroke, Huntington's disease, frontotemporal dementia (FTD), multiple sclerosis (MS), isolated demyelinating diseases of the central nervous system, osteoarthritis, Crohn's Disease, and ulcerative colitis.

DETAILED DESCRIPTION

The instant disclosure provides polypeptides (e.g., antibodies) that specifically bind to PC. Also provided are pharmaceutical compositions comprising these polypeptides, nucleic acids encoding these polypeptides, expression vectors and host cells for making these polypeptides, and methods of treating a subject using these polypeptides. The polypeptides provided herein are particularly advantageous because they bind PC with high affinity, display favorable stability, stress resistance, and immunogenicity profiles, and can be produced at high yields. The polypeptides provided herein are particularly useful for treating an inflammatory disorder or degenerative disease in a subject.

Definitions

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single-chain antibodies or single-chain Fvs (scFv), camelized antibodies, affibodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

"Multispecific antibodies" are antibodies (e.g., bispecific antibodies) that specifically bind to two or more different antigens or two or more different regions of the same antigen. Multispecific antibodies include bispecific antibodies that contain two different antigen-binding sites (exclusive of the Fc region). Multispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked single-chain antibodies or linked-single-chain Fvs (scFv), camelized antibodies, affybodies, linked Fab fragments, F(ab')$_2$ fragments, chemically-linked Fvs, and disulfide-linked Fvs (sdFv). Multispecific antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, multispecific antibodies described herein are IgG antibodies, or a class (e.g., human IgG$_1$, IgG$_2$, or IgG$_4$) or subclass thereof.

As used herein, the term "CDR" or "complementarity determining region" means the noncontiguous antigen combining sites found within the variable regions of heavy and light chain polypeptides. These particular regions have been described by, for example, Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., PC). CDRH1, CDRH2, and CDRH3 denote the heavy chain CDRs, and CDRL1, CDRL2, and CDRL3 denote the light chain CDRs.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable region are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In certain embodiments, the variable region comprises rodent or murine CDRs and primate (e.g., non-human primate) framework regions (FRs).

As used herein, the terms "VH" and "VL" refer to antibody heavy and light chain variable regions, respectively, as described in Kabat et al., (1991) Sequences of Proteins of Immunological Interest (NIH Publication No. 91-3242, Bethesda), which is herein incorporated by reference in its entirety.

As used herein, the term "constant region" is common in the art. The constant region is an antibody portion, e.g., a carboxyl terminal portion of a light and/or heavy chain, which is not directly involved in binding of an antibody to antigen but which can exhibit various effector functions, such as interaction with an Fc receptor (e.g., Fc gamma receptor).

As used herein, the term "heavy chain" when used in reference to an antibody can refer to any distinct type, e.g., alpha (α), delta (δ), epsilon (ε), gamma (γ), and mu (μ), based on the amino acid sequence of the constant region, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ), based on the amino acid sequence of the constant region. Light chain amino acid sequences are well known in the art. In specific embodiments, the light chain is a human light chain.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a $K_A$ that is at least 2 logs (e.g., factors of 10), 2.5 logs, 3 logs, 4 logs, or greater than the $K_A$ when the molecules bind non-specifically to another antigen.

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In certain embodiments, the subject is a human or non-human mammal. In certain embodiments, the subject is a human.

As used herein with respect to an antibody or polynucleotide, the term "isolated" refers to an antibody or polynucleotide that is separated from one or more contaminants (e.g., polypeptides, polynucleotides, lipids, or carbohydrates, etc.) which are present in a natural source of the antibody or polynucleotide. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides"

described herein are additionally contemplated as polynucleotides that may be, but need not be, isolated.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87:2264-2268, modified as in Karlin S & Altschul S F (1993) PNAS 90:5873-5877, each of which is herein incorporated by reference in its entirety. Such an algorithm is incorporated into the NBLAST and XBLAST programs of Altschul S F et al., (1990) J Mol Biol 215:403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25:3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

Anti-PC Antibodies

In one aspect, the instant disclosure provides polypeptides (e.g., antibodies) that specifically bind to PC. The amino acid sequences of exemplary antibodies are set forth in Table 1.

TABLE 1

Amino Acid Sequences of Exemplary Antibodies.

| Antibody | SEQ ID NO: | | | | | | | |
|---|---|---|---|---|---|---|---|---|
| | VH | VL | CDRH1 | CDRH2 | CDRH3 | CDRL1 | CDRL2 | CDRL3 |
| PcOxP_DB01_A06 | 1 | 181 | 369 | 428 | 484 | 523 | 591 | 656 |
| PcOxP_DB01_A12 | 2 | 182 | 370 | 429 | 485 | 523 | 592 | 657 |
| PcOxP_DB01_B01 | 3 | 183 | 371 | 428 | 486 | 523 | 593 | 658 |
| PcOxP_DB01_B04 | 4 | 184 | 372 | 428 | 484 | 523 | 591 | 659 |
| PcOxP_DB01_B05 | 5 | 185 | 373 | 429 | 484 | 523 | 594 | 659 |
| PcOxP_DB01_B07 | 1 | 184 | 369 | 428 | 484 | 523 | 591 | 659 |
| PcOxP_DB01_B08 | 6 | 184 | 374 | 430 | 484 | 523 | 591 | 659 |
| PcOxP_DB01_B09 | 1 | 186 | 369 | 428 | 484 | 523 | 595 | 660 |
| PcOxP_DB01_B11 | 7 | 187 | 375 | 428 | 487 | 523 | 596 | 659 |
| PcOxP_DB01_C01 | 8 | 188 | 376 | 428 | 484 | 524 | 591 | 659 |
| PcOxP_DB01_C03 | 9 | 189 | 377 | 428 | 484 | 523 | 591 | 661 |
| PcOxP_DB01_C04 | 10 | 190 | 378 | 428 | 484 | 523 | 591 | 662 |
| PcOxP_DB01_C05 | 4 | 191 | 372 | 428 | 484 | 523 | 597 | 658 |
| PcOxP_DB01_C06 | 11 | 192 | 379 | 428 | 484 | 523 | 598 | 662 |
| PcOxP_DB01_C08 | 12 | 193 | 372 | 428 | 488 | 525 | 599 | 659 |
| PcOxP_DB01_C12 | 13 | 194 | 376 | 431 | 484 | 523 | 600 | 663 |
| PcOxP_DB01_D02 | 14 | 195 | 380 | 432 | 484 | 523 | 591 | 664 |
| PcOxP_DB01_D05 | 15 | 196 | 372 | 428 | 489 | 523 | 601 | 659 |
| PcOxP_DB01_D08 | 16 | 184 | 381 | 428 | 490 | 523 | 591 | 659 |
| PcOxP_DB01_D09 | 17 | 197 | 382 | 428 | 484 | 526 | 597 | 665 |
| PcOxP_DB01_E04 | 18 | 198 | 381 | 428 | 491 | 523 | 602 | 659 |
| PcOxP_DB01_E05 | 1 | 199 | 369 | 428 | 484 | 527 | 591 | 661 |
| PcOxP_DB01_E06 | 19 | 200 | 377 | 428 | 492 | 528 | 591 | 662 |
| PcOxP_DB01_E11 | 20 | 201 | 376 | 433 | 484 | 529 | 603 | 662 |
| PcOxP_DB01_F04 | 21 | 202 | 383 | 434 | 484 | 523 | 604 | 666 |
| PcOxP_DB01_F10 | 22 | 203 | 383 | 428 | 484 | 523 | 605 | 667 |
| PcOxP_DB01_G01 | 23 | 204 | 384 | 435 | 484 | 530 | 606 | 659 |
| PcOxP_DB01_G09 | 24 | 205 | 369 | 436 | 484 | 523 | 607 | 659 |
| PcOxP_DB01_G11 | 25 | 184 | 372 | 437 | 487 | 523 | 591 | 659 |
| PcOxP_DB01_G12 | 4 | 206 | 372 | 428 | 484 | 523 | 608 | 659 |
| PcOxP_DB01_H04 | 26 | 207 | 385 | 428 | 493 | 523 | 609 | 662 |
| PcOxP_DB01_H08 | 27 | 208 | 386 | 428 | 484 | 531 | 591 | 663 |
| PcOxP_DB01_H10 | 28 | 209 | 372 | 437 | 484 | 523 | 608 | 661 |
| PcOxP_DB02_A06 | 9 | 210 | 377 | 428 | 484 | 523 | 610 | 659 |
| PcOxP_DB02_A09 | 29 | 211 | 387 | 428 | 484 | 523 | 611 | 668 |
| PcOxP_DB02_A10 | 30 | 212 | 385 | 428 | 484 | 523 | 611 | 658 |
| PcOxP_DB02_A11 | 31 | 213 | 372 | 438 | 484 | 523 | 596 | 662 |
| PcOxP_DB02_A12 | 32 | 214 | 388 | 428 | 494 | 523 | 612 | 667 |
| PcOxP_DB02_B02 | 33 | 215 | 369 | 439 | 484 | 523 | 613 | 668 |
| PcOxP_DB02_B06 | 34 | 216 | 389 | 428 | 484 | 523 | 591 | 669 |
| PcOxP_DB02_B10 | 17 | 217 | 382 | 428 | 484 | 523 | 591 | 663 |
| PcOxP_DB02_B12 | 1 | 218 | 369 | 428 | 484 | 523 | 614 | 659 |

TABLE 1-continued

Amino Acid Sequences of Exemplary Antibodies.

| Antibody | VH | VL | CDRH1 | CDRH2 | CDRH3 | CDRL1 | CDRL2 | CDRL3 |
|---|---|---|---|---|---|---|---|---|
| PcOxP_DB02_C01 | 35 | 184 | 381 | 428 | 484 | 523 | 591 | 659 |
| PcOxP_DB02_C02 | 36 | 184 | 376 | 440 | 495 | 523 | 591 | 659 |
| PcOxP_DB02_C06 | 35 | 219 | 381 | 428 | 484 | 532 | 615 | 662 |
| PcOxP_DB02_C09 | 35 | 220 | 381 | 428 | 484 | 523 | 616 | 670 |
| PcOxP_DB02_C11 | 37 | 184 | 390 | 441 | 484 | 523 | 591 | 659 |
| PcOxP_DB02_D01 | 38 | 221 | 370 | 442 | 484 | 523 | 591 | 668 |
| PcOxP_DB02_D09 | 39 | 222 | 391 | 428 | 484 | 523 | 617 | 671 |
| PcOxP_DB02_D10 | 9 | 223 | 377 | 428 | 484 | 533 | 595 | 659 |
| PcOxP_DB02_E01 | 9 | 224 | 377 | 428 | 484 | 523 | 618 | 659 |
| PcOxP_DB02_E06 | 40 | 184 | 392 | 432 | 484 | 523 | 591 | 659 |
| PcOxP_DB02_E10 | 41 | 225 | 377 | 443 | 484 | 534 | 619 | 662 |
| PcOxP_DB02_F02 | 8 | 226 | 376 | 428 | 484 | 535 | 620 | 659 |
| PcOxP_DB02_F07 | 42 | 227 | 393 | 428 | 484 | 536 | 621 | 659 |
| PcOxP_DB02_F12 | 35 | 228 | 381 | 428 | 484 | 537 | 603 | 671 |
| PcOxP_DB02_G06 | 43 | 229 | 383 | 444 | 489 | 523 | 622 | 659 |
| PcOxP_DB02_G07 | 4 | 230 | 372 | 428 | 484 | 523 | 617 | 659 |
| PcOxP_DB02_G09 | 9 | 231 | 377 | 428 | 484 | 523 | 623 | 659 |
| PcOxP_DB02_H03 | 8 | 232 | 376 | 428 | 484 | 538 | 607 | 672 |
| PcOxP_DB02_H10 | 1 | 233 | 369 | 428 | 484 | 523 | 616 | 671 |
| PcOxP_DB03_A03 | 8 | 234 | 376 | 428 | 484 | 523 | 624 | 659 |
| PcOxP_DB03_A08 | 44 | 184 | 394 | 428 | 484 | 523 | 591 | 659 |
| PcOxP_DB03_A09 | 1 | 235 | 369 | 428 | 484 | 523 | 620 | 659 |
| PcOxP_DB03_A11 | 45 | 236 | 383 | 444 | 496 | 523 | 625 | 660 |
| PcOxP_DB03_B02 | 30 | 237 | 385 | 428 | 484 | 523 | 602 | 671 |
| PcOxP_DB03_C03 | 46 | 184 | 376 | 434 | 484 | 523 | 591 | 659 |
| PcOxP_DB03_C06 | 47 | 238 | 395 | 445 | 497 | 523 | 611 | 663 |
| PcOxP_DB03_C11 | 48 | 239 | 396 | 446 | 487 | 523 | 626 | 670 |
| PcOxP_DB03_C12 | 1 | 230 | 369 | 428 | 484 | 523 | 617 | 659 |
| PcOxP_DB03_D01 | 49 | 190 | 392 | 428 | 484 | 523 | 591 | 662 |
| PcOxP_DB03_D07 | 44 | 240 | 394 | 428 | 484 | 523 | 606 | 673 |
| PcOxP_DB03_D08 | 50 | 184 | 393 | 428 | 498 | 523 | 591 | 659 |
| PcOxP_DB03_D11 | 51 | 241 | 376 | 428 | 495 | 523 | 627 | 671 |
| PcOxP_DB03_E01 | 52 | 242 | 369 | 440 | 484 | 523 | 628 | 671 |
| PcOxP_DB03_E02 | 53 | 243 | 397 | 428 | 484 | 539 | 591 | 662 |
| PcOxP_DB03_E07 | 54 | 184 | 389 | 447 | 484 | 523 | 591 | 659 |
| PcOxP_DB03_E08 | 55 | 244 | 398 | 448 | 492 | 523 | 591 | 670 |
| PcOxP_DB03_E09 | 56 | 245 | 373 | 449 | 490 | 523 | 611 | 659 |
| PcOxP_DB03_F01 | 57 | 246 | 399 | 428 | 484 | 537 | 613 | 671 |
| PcOxP_DB03_F10 | 58 | 247 | 400 | 450 | 484 | 540 | 598 | 659 |
| PcOxP_DB03_G02 | 59 | 248 | 401 | 428 | 484 | 541 | 591 | 659 |
| PcOxP_DB03_G03 | 60 | 249 | 390 | 428 | 484 | 542 | 629 | 659 |
| PcOxP_DB03_G06 | 8 | 250 | 376 | 428 | 484 | 523 | 591 | 671 |
| PcOxP_DB03_G07 | 61 | 184 | 400 | 428 | 499 | 523 | 591 | 659 |
| PcOxP_DB03_G10 | 35 | 251 | 381 | 428 | 484 | 523 | 630 | 667 |
| PcOxP_DB03_H03 | 62 | 252 | 384 | 429 | 484 | 543 | 631 | 659 |
| PcOxP_DB03_H07 | 1 | 253 | 369 | 428 | 484 | 523 | 632 | 664 |
| PcOxP_DB03_H08 | 63 | 254 | 402 | 436 | 484 | 523 | 597 | 661 |
| PcOxP_DB03_H09 | 64 | 181 | 381 | 451 | 484 | 523 | 591 | 656 |
| PcOxP_DB04_A07 | 65 | 255 | 403 | 428 | 484 | 523 | 633 | 659 |
| PcOxP_DB04_A09 | 66 | 256 | 369 | 429 | 484 | 544 | 607 | 659 |
| PcOxP_DB04_A10 | 67 | 257 | 404 | 429 | 484 | 523 | 630 | 659 |
| PcOxP_DB04_A12 | 68 | 198 | 372 | 429 | 484 | 523 | 602 | 659 |
| PcOxP_DB04_B06 | 35 | 258 | 381 | 428 | 484 | 523 | 591 | 665 |
| PcOxP_DB04_B08 | 69 | 259 | 388 | 428 | 484 | 523 | 610 | 674 |
| PcOxP_DB04_C03 | 70 | 260 | 405 | 451 | 484 | 523 | 634 | 671 |
| PcOxP_DB04_C08 | 71 | 261 | 406 | 428 | 484 | 545 | 591 | 661 |
| PcOxP_DB04_D08 | 72 | 262 | 400 | 428 | 484 | 523 | 635 | 667 |
| PcOxP_DB04_F06 | 73 | 263 | 404 | 428 | 484 | 546 | 591 | 659 |
| PcOxP_DB04_F11 | 74 | 264 | 384 | 432 | 500 | 523 | 636 | 664 |
| PcOxP_DB04_G06 | 75 | 265 | 376 | 452 | 501 | 547 | 591 | 663 |
| PcOxP_DB04_H03 | 76 | 266 | 407 | 428 | 484 | 548 | 619 | 659 |
| PcOxP_DB04_H07 | 77 | 267 | 375 | 428 | 484 | 523 | 637 | 659 |
| PcOxP_DB04_H08 | 4 | 205 | 372 | 428 | 484 | 523 | 607 | 659 |
| PcOxP_DB04_H10 | 78 | 268 | 408 | 428 | 484 | 523 | 638 | 659 |
| PcOxP_DB01_A03 | 1 | 269 | 369 | 428 | 484 | 523 | 591 | 659 |
| PcOxP_DB01_A04 | 27 | 269 | 386 | 428 | 484 | 523 | 591 | 659 |
| PcOxP_DB01_A05 | 79 | 269 | 369 | 428 | 497 | 523 | 591 | 659 |
| PcOxP_DB01_A08 | 80 | 270 | 403 | 453 | 484 | 549 | 591 | 659 |
| PcOxP_DB01_B02 | 81 | 269 | 402 | 454 | 484 | 523 | 591 | 659 |
| PcOxP_DB01_B03 | 22 | 269 | 383 | 428 | 484 | 523 | 591 | 659 |
| PcOxP_DB01_B06 | 82 | 269 | 383 | 434 | 500 | 523 | 591 | 659 |
| PcOxP_DB01_B10 | 83 | 271 | 376 | 455 | 502 | 550 | 591 | 675 |
| PcOxP_DB01_B12 | 84 | 272 | 383 | 435 | 484 | 523 | 591 | 664 |
| PcOxP_DB01_C07 | 1 | 273 | 369 | 428 | 484 | 523 | 602 | 659 |

TABLE 1-continued

Amino Acid Sequences of Exemplary Antibodies.

| | SEQ ID NO: | | | | | | | |
|---|---|---|---|---|---|---|---|---|
| Antibody | VH | VL | CDRH1 | CDRH2 | CDRH3 | CDRL1 | CDRL2 | CDRL3 |
| PcOxP_DB01_C09 | 8 | 274 | 376 | 428 | 484 | 551 | 591 | 659 |
| PcOxP_DB01_C10 | 8 | 275 | 376 | 428 | 484 | 552 | 591 | 659 |
| PcOxP_DB01_D01 | 22 | 276 | 383 | 428 | 484 | 553 | 591 | 676 |
| PcOxP_DB01_D04 | 8 | 277 | 376 | 428 | 484 | 554 | 591 | 659 |
| PcOxP_DB01_D06 | 85 | 278 | 376 | 428 | 490 | 523 | 591 | 676 |
| PcOxP_DB01_D07 | 86 | 279 | 369 | 428 | 503 | 555 | 606 | 659 |
| PcOxP_DB01_D10 | 87 | 269 | 409 | 428 | 484 | 523 | 591 | 659 |
| PcOxP_DB01_D11 | 88 | 280 | 383 | 428 | 504 | 556 | 591 | 659 |
| PcOxP_DB01_D12 | 89 | 269 | 369 | 434 | 484 | 523 | 591 | 659 |
| PcOxP_DB01_E01 | 60 | 281 | 390 | 428 | 484 | 523 | 637 | 677 |
| PcOxP_DB01_E02 | 90 | 269 | 369 | 456 | 484 | 523 | 591 | 659 |
| PcOxP_DB01_E03 | 91 | 282 | 370 | 457 | 484 | 557 | 591 | 659 |
| PcOxP_DB01_E07 | 22 | 283 | 383 | 428 | 484 | 558 | 591 | 659 |
| PcOxP_DB01_E08 | 92 | 269 | 404 | 458 | 499 | 523 | 591 | 659 |
| PcOxP_DB01_E09 | 93 | 284 | 410 | 428 | 484 | 523 | 591 | 677 |
| PcOxP_DB01_E10 | 94 | 285 | 383 | 459 | 484 | 553 | 639 | 659 |
| PcOxP_DB01_F01 | 95 | 286 | 407 | 428 | 489 | 549 | 591 | 667 |
| PcOxP_DB01_F03 | 96 | 269 | 374 | 434 | 484 | 523 | 591 | 659 |
| PcOxP_DB01_F06 | 73 | 287 | 404 | 428 | 484 | 559 | 617 | 666 |
| PcOxP_DB01_F07 | 97 | 288 | 411 | 460 | 505 | 523 | 591 | 672 |
| PcOxP_DB01_F08 | 68 | 289 | 372 | 429 | 484 | 523 | 606 | 659 |
| PcOxP_DB01_F11 | 98 | 269 | 383 | 428 | 485 | 523 | 591 | 659 |
| PcOxP_DB01_F12 | 99 | 290 | 386 | 460 | 490 | 523 | 601 | 659 |
| PcOxP_DB01_G02 | 100 | 291 | 412 | 455 | 493 | 523 | 592 | 670 |
| PcOxP_DB01_G03 | 4 | 292 | 372 | 428 | 484 | 560 | 591 | 667 |
| PcOxP_DB01_G04 | 4 | 289 | 372 | 428 | 484 | 523 | 606 | 659 |
| PcOxP_DB01_G05 | 101 | 284 | 383 | 461 | 484 | 523 | 591 | 677 |
| PcOxP_DB01_G06 | 66 | 289 | 369 | 429 | 484 | 523 | 606 | 659 |
| PcOxP_DB01_G07 | 89 | 293 | 369 | 434 | 484 | 530 | 591 | 659 |
| PcOxP_DB01_G10 | 102 | 294 | 376 | 437 | 484 | 561 | 603 | 666 |
| PcOxP_DB01_H01 | 103 | 269 | 383 | 462 | 500 | 523 | 591 | 659 |
| PcOxP_DB01_H02 | 22 | 295 | 383 | 428 | 484 | 562 | 591 | 659 |
| PcOxP_DB01_H03 | 104 | 296 | 400 | 463 | 484 | 523 | 616 | 660 |
| PcOxP_DB01_H06 | 105 | 297 | 376 | 464 | 484 | 523 | 602 | 677 |
| PcOxP_DB01_H07 | 106 | 270 | 400 | 434 | 506 | 549 | 591 | 659 |
| PcOxP_DB01_H09 | 107 | 269 | 369 | 436 | 507 | 523 | 591 | 659 |
| PcOxP_DB02_A04 | 67 | 269 | 404 | 429 | 484 | 523 | 591 | 659 |
| PcOxP_DB02_A05 | 62 | 298 | 384 | 429 | 484 | 523 | 616 | 659 |
| PcOxP_DB02_B04 | 66 | 269 | 369 | 429 | 484 | 523 | 591 | 659 |
| PcOxP_DB02_B07 | 108 | 299 | 377 | 465 | 484 | 523 | 630 | 660 |
| PcOxP_DB02_B09 | 109 | 300 | 413 | 459 | 484 | 563 | 591 | 659 |
| PcOxP_DB02_C03 | 110 | 301 | 369 | 452 | 484 | 523 | 591 | 663 |
| PcOxP_DB02_C04 | 111 | 302 | 414 | 466 | 484 | 523 | 640 | 659 |
| PcOxP_DB02_C05 | 112 | 269 | 373 | 428 | 484 | 523 | 591 | 659 |
| PcOxP_DB02_C08 | 113 | 303 | 415 | 428 | 489 | 564 | 591 | 659 |
| PcOxP_DB02_C10 | 1 | 304 | 369 | 428 | 484 | 523 | 591 | 671 |
| PcOxP_DB02_C12 | 72 | 305 | 400 | 428 | 484 | 523 | 641 | 677 |
| PcOxP_DB02_D02 | 114 | 306 | 369 | 428 | 491 | 565 | 591 | 662 |
| PcOxP_DB02_D03 | 115 | 307 | 403 | 458 | 508 | 523 | 642 | 664 |
| PcOxP_DB02_E02 | 116 | 269 | 392 | 467 | 484 | 523 | 591 | 659 |
| PcOxP_DB02_E03 | 117 | 308 | 369 | 452 | 509 | 566 | 643 | 659 |
| PcOxP_DB02_E08 | 118 | 269 | 388 | 468 | 490 | 523 | 591 | 659 |
| PcOxP_DB02_E09 | 110 | 309 | 369 | 452 | 484 | 523 | 644 | 667 |
| PcOxP_DB02_E11 | 119 | 310 | 377 | 440 | 484 | 567 | 606 | 659 |
| PcOxP_DB02_E12 | 120 | 311 | 370 | 428 | 484 | 523 | 591 | 656 |
| PcOxP_DB02_F04 | 121 | 269 | 384 | 467 | 487 | 523 | 591 | 659 |
| PcOxP_DB02_F06 | 122 | 312 | 392 | 469 | 510 | 568 | 591 | 659 |
| PcOxP_DB02_F09 | 123 | 289 | 378 | 464 | 484 | 523 | 606 | 659 |
| PcOxP_DB02_F10 | 9 | 313 | 377 | 428 | 484 | 569 | 645 | 659 |
| PcOxP_DB02_F11 | 124 | 314 | 416 | 434 | 484 | 523 | 603 | 659 |
| PcOxP_DB02_G02 | 120 | 289 | 370 | 428 | 484 | 523 | 606 | 659 |
| PcOxP_DB02_G03 | 125 | 315 | 370 | 428 | 511 | 570 | 628 | 678 |
| PcOxP_DB02_G04 | 110 | 316 | 369 | 452 | 484 | 571 | 630 | 663 |
| PcOxP_DB02_G05 | 126 | 317 | 376 | 428 | 502 | 572 | 591 | 664 |
| PcOxP_DB02_H02 | 127 | 318 | 417 | 428 | 484 | 523 | 591 | 665 |
| PcOxP_DB02_H04 | 49 | 319 | 392 | 428 | 484 | 573 | 591 | 670 |
| PcOxP_DB02_H05 | 128 | 320 | 376 | 428 | 512 | 523 | 646 | 659 |
| PcOxP_DB02_H06 | 9 | 321 | 377 | 428 | 484 | 574 | 591 | 670 |
| PcOxP_DB02_H07 | 22 | 322 | 383 | 428 | 484 | 523 | 647 | 667 |
| PcOxP_DB02_H08 | 129 | 323 | 381 | 428 | 493 | 575 | 591 | 659 |
| PcOxP_DB02_H09 | 130 | 269 | 383 | 470 | 501 | 523 | 591 | 659 |
| PcOxP_DB03_A04 | 131 | 324 | 404 | 471 | 484 | 537 | 591 | 659 |
| PcOxP_DB03_A05 | 132 | 325 | 418 | 428 | 484 | 523 | 635 | 670 |
| PcOxP_DB03_A06 | 133 | 326 | 383 | 472 | 513 | 576 | 591 | 659 |

TABLE 1-continued

Amino Acid Sequences of Exemplary Antibodies.

| Antibody | VH | VL | CDRH1 | CDRH2 | CDRH3 | CDRL1 | CDRL2 | CDRL3 |
|---|---|---|---|---|---|---|---|---|
| PcOxP_DB03_A07 | 134 | 327 | 419 | 428 | 484 | 577 | 606 | 659 |
| PcOxP_DB03_A10 | 53 | 328 | 397 | 428 | 484 | 523 | 648 | 679 |
| PcOxP_DB03_A12 | 135 | 272 | 372 | 473 | 484 | 523 | 591 | 664 |
| PcOxP_DB03_B01 | 136 | 329 | 383 | 474 | 484 | 523 | 592 | 659 |
| PcOxP_DB03_B03 | 4 | 301 | 372 | 428 | 484 | 523 | 591 | 663 |
| PcOxP_DB03_B06 | 137 | 330 | 420 | 434 | 484 | 523 | 595 | 659 |
| PcOxP_DB03_B07 | 138 | 269 | 370 | 428 | 514 | 523 | 591 | 659 |
| PcOxP_DB03_B08 | 1 | 284 | 369 | 428 | 484 | 523 | 591 | 677 |
| PcOxP_DB03_B09 | 22 | 331 | 383 | 428 | 484 | 523 | 600 | 659 |
| PcOxP_DB03_B10 | 139 | 269 | 369 | 475 | 484 | 523 | 591 | 659 |
| PcOxP_DB03_B11 | 140 | 332 | 421 | 436 | 484 | 523 | 649 | 664 |
| PcOxP_DB03_B12 | 141 | 269 | 378 | 452 | 484 | 523 | 591 | 659 |
| PcOxP_DB03_C01 | 142 | 333 | 376 | 476 | 515 | 578 | 641 | 659 |
| PcOxP_DB03_C04 | 143 | 334 | 376 | 428 | 504 | 523 | 591 | 667 |
| PcOxP_DB03_C08 | 144 | 335 | 422 | 469 | 484 | 523 | 606 | 660 |
| PcOxP_DB03_C10 | 101 | 298 | 383 | 461 | 484 | 523 | 616 | 659 |
| PcOxP_DB03_D02 | 1 | 336 | 369 | 428 | 484 | 523 | 650 | 656 |
| PcOxP_DB03_D03 | 145 | 269 | 369 | 428 | 516 | 523 | 591 | 659 |
| PcOxP_DB03_D10 | 146 | 337 | 405 | 460 | 484 | 523 | 618 | 659 |
| PcOxP_DB03_D12 | 147 | 269 | 413 | 431 | 484 | 523 | 591 | 659 |
| PcOxP_DB03_E03 | 17 | 338 | 382 | 428 | 484 | 579 | 621 | 671 |
| PcOxP_DB03_E04 | 22 | 320 | 383 | 428 | 484 | 523 | 646 | 659 |
| PcOxP_DB03_E11 | 4 | 339 | 372 | 428 | 484 | 580 | 591 | 660 |
| PcOxP_DB03_E12 | 148 | 340 | 406 | 429 | 484 | 527 | 591 | 659 |
| PcOxP_DB03_F02 | 149 | 341 | 383 | 428 | 517 | 581 | 595 | 659 |
| PcOxP_DB03_F03 | 150 | 342 | 377 | 437 | 518 | 582 | 640 | 664 |
| PcOxP_DB03_F05 | 151 | 343 | 369 | 477 | 487 | 583 | 651 | 659 |
| PcOxP_DB03_F07 | 152 | 344 | 403 | 464 | 484 | 534 | 591 | 659 |
| PcOxP_DB03_F09 | 94 | 289 | 383 | 459 | 484 | 523 | 606 | 659 |
| PcOxP_DB03_F11 | 153 | 345 | 369 | 454 | 484 | 584 | 591 | 671 |
| PcOxP_DB03_G01 | 154 | 346 | 372 | 478 | 519 | 523 | 591 | 680 |
| PcOxP_DB03_G09 | 155 | 347 | 423 | 429 | 484 | 523 | 591 | 681 |
| PcOxP_DB03_G11 | 22 | 348 | 383 | 428 | 484 | 585 | 591 | 659 |
| PcOxP_DB03_G12 | 89 | 282 | 369 | 434 | 484 | 557 | 591 | 659 |
| PcOxP_DB03_H02 | 156 | 349 | 382 | 434 | 484 | 523 | 649 | 659 |
| PcOxP_DB03_H10 | 157 | 296 | 424 | 479 | 484 | 523 | 616 | 660 |
| PcOxP_DB04_A04 | 158 | 350 | 376 | 429 | 484 | 586 | 591 | 666 |
| PcOxP_DB04_A05 | 159 | 329 | 425 | 428 | 484 | 523 | 592 | 659 |
| PcOxP_DB04_A11 | 24 | 351 | 369 | 436 | 484 | 587 | 652 | 659 |
| PcOxP_DB04_B01 | 160 | 352 | 403 | 428 | 520 | 588 | 638 | 659 |
| PcOxP_DB04_B07 | 161 | 269 | 417 | 460 | 484 | 523 | 591 | 659 |
| PcOxP_DB04_B10 | 162 | 353 | 409 | 460 | 484 | 523 | 623 | 664 |
| PcOxP_DB04_B11 | 163 | 269 | 404 | 452 | 484 | 523 | 591 | 659 |
| PcOxP_DB04_B12 | 1 | 354 | 369 | 428 | 484 | 523 | 591 | 682 |
| PcOxP_DB04_C09 | 164 | 355 | 383 | 428 | 521 | 553 | 653 | 659 |
| PcOxP_DB04_C10 | 165 | 269 | 372 | 480 | 493 | 523 | 591 | 659 |
| PcOxP_DB04_C11 | 1 | 356 | 369 | 428 | 484 | 523 | 654 | 659 |
| PcOxP_DB04_D01 | 166 | 357 | 369 | 477 | 484 | 523 | 648 | 659 |
| PcOxP_DB04_D05 | 167 | 358 | 369 | 481 | 484 | 560 | 591 | 659 |
| PcOxP_DB04_D07 | 110 | 334 | 369 | 452 | 484 | 523 | 591 | 667 |
| PcOxP_DB04_D09 | 87 | 359 | 409 | 428 | 484 | 580 | 606 | 659 |
| PcOxP_DB04_D10 | 168 | 360 | 384 | 452 | 484 | 589 | 593 | 661 |
| PcOxP_DB04_D12 | 169 | 269 | 377 | 482 | 484 | 523 | 591 | 659 |
| PcOxP_DB04_E05 | 170 | 269 | 410 | 483 | 484 | 523 | 591 | 659 |
| PcOxP_DB04_E06 | 171 | 269 | 384 | 428 | 489 | 523 | 591 | 659 |
| PcOxP_DB04_E08 | 172 | 361 | 426 | 429 | 484 | 523 | 622 | 659 |
| PcOxP_DB04_E12 | 8 | 362 | 376 | 428 | 484 | 523 | 637 | 676 |
| PcOxP_DB04_F01 | 173 | 304 | 427 | 428 | 484 | 523 | 591 | 671 |
| PcOxP_DB04_F03 | 174 | 269 | 373 | 452 | 506 | 523 | 591 | 659 |
| PcOxP_DB04_F05 | 1 | 363 | 369 | 428 | 484 | 590 | 622 | 659 |
| PcOxP_DB04_G01 | 175 | 364 | 369 | 429 | 521 | 555 | 591 | 661 |
| PcOxP_DB04_G03 | 176 | 365 | 405 | 428 | 522 | 523 | 615 | 672 |
| PcOxP_DB04_G05 | 177 | 269 | 376 | 428 | 510 | 523 | 591 | 659 |
| PcOxP_DB04_G08 | 178 | 366 | 384 | 428 | 484 | 523 | 626 | 668 |
| PcOxP_DB04_G09 | 179 | 269 | 410 | 429 | 484 | 523 | 591 | 659 |
| PcOxP_DB04_G11 | 180 | 367 | 400 | 452 | 484 | 523 | 655 | 659 |
| PcOxP_DB04_H01 | 89 | 368 | 369 | 434 | 484 | 523 | 606 | 680 |

In certain embodiments, the instant disclosure provides an antibody that specifically binds to PC, the antibody comprising a VH domain comprising one, two, or all three of the CDRs of a VH domain set forth in Table 1. In certain embodiments, the antibody comprises the CDRH1 of a VH domain set forth in Table 1. In certain embodiments, the antibody comprises the CDRH2 of a VH domain set forth in Table 1. In certain embodiments, the antibody comprises the CDRH3 of a VH domain set forth in Table 1.

In certain embodiments, the instant disclosure provides an antibody that specifically binds to PC, the antibody comprising a VL domain comprising one, two, or all three of the CDRs of a VL domain disclosed in Table 1. In certain embodiments, the antibody comprises the CDRL1 of a VL domain set forth in Table 1. In certain embodiments, the antibody comprises the CDRL2 of a VL domain set forth in Table 1. In certain embodiments, the antibody comprises the CDRL3 of a VL domain set forth in Table 1.

The individual CDRs of an antibody disclosed herein can be determined according to any CDR numbering scheme known in the art.

In certain embodiments, one or more of the CDRs of an antibody disclosed herein can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the instant disclosure provides antibodies that specifically bind to PC and comprise CDRs of an antibody disclosed in Table 1 herein as determined by the Kabat numbering scheme.

In certain embodiments, one or more of the CDRs of an antibody disclosed herein can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990) J Mol Biol 215 (1): 175-82; and U.S. Pat. No. 7,709,226, all of which are herein incorporated by reference in their entireties).

In certain embodiments, the instant disclosure provides antibodies that specifically bind to PC and comprise CDRs of an antibody disclosed in Table 1 herein, as determined by the Chothia numbering system.

In certain embodiments, one or more of the CDRs of an antibody disclosed herein can be determined according to MacCallum R M et al., (1996) J Mol Biol 262:732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides antibodies that specifically bind to PC and comprise CDRs of an antibody disclosed in Table 1 herein, as determined by the MacCallum numbering system.

In certain embodiments, the CDRs of an antibody disclosed herein can be determined according to the IMGT numbering system as described in: Lefranc M-P, (1999) The Immunologist 7:132-136; Lefranc M-P et al., (1999) Nucleic Acids Res 27:209-212, each of which is herein incorporated by reference in its entirety; and Lefranc M-P et al., (2009) Nucleic Acids Res 37: D1006-D1012.

In certain embodiments, the instant disclosure provides antibodies that specifically bind to PC and comprise CDRs of an antibody disclosed in Table 1 herein, as determined by the IMGT numbering system.

In certain embodiments, the CDRs of an antibody disclosed herein can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

In certain embodiments, the instant disclosure provides antibodies that specifically bind to PC and comprise CDRs of an antibody disclosed in Table 1 herein as determined by the AbM numbering scheme.

In certain embodiments, the CDRs of an antibody disclosed herein can be determined according to the AHo numbering system, as described in Honegger and Plückthun, A., J. Mol. Biol. 309:657-670 (2001), herein incorporated by reference in its entirety.

In certain embodiments, the instant disclosure provides antibodies that specifically bind to PC and comprise CDRs of an antibody disclosed in Table 1 herein, as determined by the AHo numbering system.

In certain embodiments, the individual CDRs of an antibody disclosed herein are each independently determined according to one of the Kabat, Chothia, MacCallum, IMGT, AHo, or AbM numbering schemes, or by structural analysis of the molecule, wherein the structural analysis identifies residues in the variable region(s) predicted to make contact with an epitope region of PC.

In certain embodiments, the instant disclosure provides an antibody or polypeptide that specifically binds PC, comprising a VH comprising the CDRH1, CDRH2, and CDRH3 amino acid sequences of any one of the VH amino acid sequences set forth in SEQ ID NOs: 1-180, and a VL comprising the CDRL1, CDRL2, and CDRL3 amino acid sequences of any one of the VL amino acid sequences set forth in SEQ ID NOs: 181-368, wherein each CDR is independently determined according to one of the Kabat, Chothia, MacCallum, IMGT, AHo, or AbM numbering schemes, or by structural analysis of the molecule, wherein the structural analysis identifies residues in the variable region(s) predicted to make contact with an epitope region of PC.

In certain embodiments, the instant disclosure provides an antibody or polypeptide that specifically binds to PC, wherein the antibody or polypeptide comprises the CDRH1, CDRH2, CDRH3, CDRL1, CDRL2, and CDRL3 amino acid sequences of the VH and VL amino acid sequences set forth in SEQ ID NOs: 1 and 181; 2 and 182; 3 and 183; 4 and 184; 5 and 185; 1 and 184; 6 and 184; 1 and 186; 7 and 187; 8 and 188; 9 and 189; 10 and 190; 4 and 191; 11 and 192; 12 and 193; 13 and 194; 14 and 195; 15 and 196; 16 and 184; 17 and 197; 18 and 198; 1 and 199; 19 and 200; 20 and 201; 21 and 202; 22 and 203; 23 and 204; 24 and 205; 25 and 184; 4 and 206; 26 and 207; 27 and 208; 28 and 209; 9 and 210; 29 and 211; 30 and 212; 31 and 213; 32 and 214; 33 and 215; 34 and 216; 17 and 217; 1 and 218; 35 and 184; 36 and 184; 35 and 219; 35 and 220; 37 and 184; 38 and 221; 39 and 222; 9 and 223; 9 and 224; 40 and 184; 41 and 225; 8 and 226; 42 and 227; 35 and 228; 43 and 229; 4 and 230; 9 and 231; 8 and 232; 1 and 233; 8 and 234; 44 and 184; 1 and 235; 45 and 236; 30 and 237; 46 and 184; 47 and 238; 48 and 239; 1 and 240; 49 and 190; 44 and 240; 50 and 184; 51 and 241; 52 and 242; 53 and 243; 54 and 184; 55 and 244; 56 and 245; 57 and 246; 58 and 247; 59 and 248; 60 and 249; 8 and 250; 61 and 184; 35 and 251; 62 and 252; 1 and 253; 63 and 254;

64 and 181; 65 and 255; 66 and 256; 67 and 257; 68 and 198; 35 and 258; 69 and 259; 70 and 260; 71 and 261; 72 and 262; 73 and 263; 74 and 264; 75 and 265; 76 and 266; 77 and 267; 4 and 205; 78 and 268; 1 and 269; 27 and 269; 79 and 269; 80 and 270; 81 and 269; 22 and 269; 82 and 269; 83 and 271; 84 and 272; 1 and 273; 8 and 274; 8 and 275; 22 and 276; 8 and 277; 85 and 278; 86 and 279; 87 and 269; 88 and 280; 89 and 269; 60 and 281; 90 and 269; 91 and 282; 22 and 283; 92 and 269; 93 and 284; 94 and 285; 95 and 286; 96 and 269; 73 and 287; 97 and 288; 68 and 289; 98 and 269; 99 and 290; 100 and 291; 4 and 292; 4 and 289; 101 and 284; 66 and 289; 89 and 293; 102 and 294; 103 and 269; 22 and 295; 104 and 296; 105 and 297; 106 and 270; 107 and 269; 67 and 269; 62 and 298; 66 and 269; 108 and 299; 109 and 300; 110 and 301; 111 and 302; 112 and 269; 113 and 303; 1 and 304; 72 and 305; 114 and 306; 115 and 307; 116 and 269; 117 and 308; 118 and 269; 110 and 309; 119 and 310; 120 and 311; 121 and 269; 122 and 312; 123 and 289; 9 and 313; 124 and 314; 120 and 289; 125 and 315; 110 and 316; 126 and 317; 127 and 318; 49 and 319; 128 and 320; 9 and 321; 22 and 322; 129 and 323; 130 and 269; 131 and 324; 132 and 325; 133 and 326; 134 and 327; 53 and 328; 135 and 272; 136 and 329; 4 and 301; 137 and 330; 138 and 269; 1 and 284; 22 and 331; 139 and 269; 140 and 332; 141 and 269; 142 and 333; 143 and 334; 144 and 335; 101 and 298; 1 and 336; 145 and 269; 146 and 337; 147 and 269; 17 and 338; 22 and 320; 4 and 339; 148 and 340; 149 and 341; 150 and 342; 151 and 343; 152 and 344; 94 and 289; 153 and 345; 154 and 346; 155 and 347; 22 and 348; 89 and 282; 156 and 349; 157 and 296; 158 and 350; 159 and 329; 24 and 351; 160 and 352; 161 and 269; 162 and 353; 163 and 269; 1 and 354; 164 and 355; 165 and 269; 1 and 356; 166 and 357; 167 and 358; 110 and 334; 87 and 359; 168 and 360; 169 and 269; 170 and 269; 171 and 269; 172 and 361; 8 and 362; 173 and 304; 174 and 269; 1 and 363; 175 and 364; 176 and 365; 177 and 269; 178 and 366; 179 and 269; 180 and 367; or 89 and 368, respectively.

In certain embodiments, the instant disclosure provides an antibody or polypeptide that specifically binds to PC, wherein the antibody or polypeptide comprises a VH comprising the CDRH1, CDRH2 and CDRH3 amino acid sequences set forth in SEQ ID NOs: 369, 428, and 484; 370, 429, and 485; 371, 428, and 486; 372, 428, and 484; 373, 429, and 484; 374, 430, and 484; 375, 428, and 487; 376, 428, and 484; 377, 428, and 484; 378, 428, and 484; 379, 428, and 484; 372, 428, and 488; 376, 431, and 484; 380, 432, and 484; 372, 428, and 489; 381, 428, and 490; 382, 428, and 484; 381, 428, and 491; 377, 428, and 492; 376, 433, and 484; 383, 434, and 484; 383, 428, and 484; 384, 435, and 484; 369, 436, and 484; 372, 437, and 487; 385, 428, and 493; 386, 428, and 484; 372, 437, and 484; 387, 428, and 484; 385, 428, and 484; 372, 438, and 484; 388, 428, and 494; 369, 439, and 484; 389, 428, and 484; 381, 428, and 484; 376, 440, and 495; 390, 441, and 484; 370, 442, and 484; 391, 428, and 484; 392, 432, and 484; 377, 443, and 484; 393, 428, and 484; 383, 444, and 489; 394, 428, and 484; 383, 444, and 496; 376, 434, and 484; 395, 445, and 497; 396, 446, and 487; 392, 428, and 484; 393, 428, and 498; 376, 428, and 495; 369, 440, and 484; 397, 428, and 484; 389, 447, and 484; 398, 448, and 492; 373, 449, and 490; 399, 428, and 484; 400, 450, and 484; 401, 428, and 484; 390, 428, and 484; 400, 428, and 499; 384, 429, and 484; 402, 436, and 484; 381, 451, and 484; 403, 428, and 484; 369, 429, and 484; 404, 429, and 484; 372, 429, and 484; 388, 428, and 484; 405, 451, and 484; 406, 428, and 484; 400, 428, and 484; 404, 428, and 484; 384, 432, and 500; 376, 452, and 501; 407, 428, and 484; 375, 428, and 484; 408, 428, and 484; 369, 428, and 497; 403, 453, and 484; 402, 454, and 484; 383, 434, and 500; 376, 455, and 502; 383, 435, and 484; 376, 428, and 490; 369, 428, and 503; 409, 428, and 484; 383, 428, and 504; 369, 434, and 484; 369, 456, and 484; 370, 457, and 484; 404, 458, and 499; 410, 428, and 484; 383, 459, and 484; 407, 428, and 489; 374, 434, and 484; 411, 460, and 505; 383, 428, and 485; 386, 460, and 490; 412, 455, and 493; 383, 461, and 484; 376, 437, and 484; 383, 462, and 500; 400, 463, and 484; 376, 464, and 484; 400, 434, and 506; 369, 436, and 507; 377, 465, and 484; 413, 459, and 484; 369, 452, and 484; 414, 466, and 484; 373, 428, and 484; 415, 428, and 489; 369, 428, and 491; 403, 458, and 508; 392, 467, and 484; 369, 452, and 509; 388, 468, and 490; 377, 440, and 484; 370, 428, and 484; 384, 467, and 487; 392, 469, and 510; 378, 464, and 484; 416, 434, and 484; 370, 428, and 511; 376, 428, and 502; 417, 428, and 484; 376, 428, and 512; 381, 428, and 493; 383, 470, and 501; 404, 471, and 484; 418, 428, and 484; 383, 472, and 513; 419, 428, and 484; 372, 473, and 484; 383, 474, and 484; 420, 434, and 484; 370, 428, and 514; 369, 475, and 484; 421, 436, and 484; 378, 452, and 484; 376, 476, and 515; 376, 428, and 504; 422, 469, and 484; 369, 428, and 516; 405, 460, and 484; 413, 431, and 484; 406, 429, and 484; 383, 428, and 517; 377, 437, and 518; 369, 477, and 487; 403, 464, and 484; 369, 454, and 484; 372, 478, and 519; 423, 429, and 484; 382, 434, and 484; 424, 479, and 484; 376, 429, and 484; 425, 428, and 484; 403, 428, and 520; 417, 460, and 484; 409, 460, and 484; 404, 452, and 484; 383, 428, and 521; 372, 480, and 493; 369, 477, and 484; 369, 481, and 484; 384, 452, and 484; 377, 482, and 484; 410, 483, and 484; 384, 428, and 489; 426, 429, and 484; 427, 428, and 484; 373, 452, and 506; 369, 429, and 521; 405, 428, and 522; 376, 428, and 510; 384, 428, and 484; 410, 429, and 484; or 400, 452, and 484, respectively.

In certain embodiments, the instant disclosure provides an antibody or polypeptide that specifically binds to PC, wherein the antibody or polypeptide comprises a VL comprising the CDRL1, CDRL2, and CDRL3 amino acid sequences set forth in SEQ ID NOs: 523, 591, and 656; 523, 592, and 657; 523, 593, and 658; 523, 591, and 659; 523, 594, and 659; 523, 595, and 660; 523, 596, and 659; 524, 591, and 659; 523, 591, and 661; 523, 591, and 662; 523, 597, and 658; 523, 598, and 662; 525, 599, and 659; 523, 600, and 663; 523, 591, and 664; 523, 601, and 659; 526, 597, and 665; 523, 602, and 659; 527, 591, and 661; 528, 591, and 662; 529, 603, and 662; 523, 604, and 666; 523, 605, and 667; 530, 606, and 659; 523, 607, and 659; 523, 608, and 659; 523, 609, and 662; 531, 591, and 663; 523, 608, and 661; 523, 610, and 659; 523, 611, and 668; 523, 611, and 658; 523, 596, and 662; 523, 612, and 667; 523, 613, and 668; 523, 591, and 669; 523, 591, and 663; 523, 614, and 659; 532, 615, and 662; 523, 616, and 670; 523, 591, and 668; 523, 617, and 671; 533, 595, and 659; 523, 618, and 659; 534, 619, and 662; 535, 620, and 659; 536, 621, and 659; 537, 603, and 671; 523, 622, and 659; 523, 617, and 659; 523, 623, and 659; 538, 607, and 672; 523, 616, and 671; 523, 624, and 659; 523, 620, and 659; 523, 625, and 660; 523, 602, and 671; 523, 611, and 663; 523, 626, and 670; 523, 606, and 673; 523, 627, and 671; 523, 628, and 671; 539, 591, and 662; 523, 591, and 670; 523, 611, and 659; 537, 613, and 671; 540, 598, and 659; 541, 591, and 659; 542, 629, and 659; 523, 591, and 671; 523, 630, and 667; 543, 631, and 659; 523, 632, and 664; 523, 597, and 661; 523, 633, and 659; 544, 607, and 659; 523, 630, and 659; 523, 591, and 665; 523, 610, and 674; 523, 634, and 671; 545, 591, and 661; 523, 635, and 667; 546, 591, and 659; 523, 636, and 664; 547, 591, and 663; 548, 619, and 659; 523, 637, and 659; 523, 638, and 659; 549, 591, and 659; 550, 591, and 675; 551, 591, and 659; 552, 591, and 659; 553, 591, and 676; 554, 591, and 659; 523, 591, and 676; 555, 606, and 659; 556, 591, and 659; 523, 637, and 677; 557, 591, and 659; 558, 591, and 659; 523, 591, and 677; 553, 639, and 659; 549, 591, and 667; 559, 617, and 666; 523, 591, and 672; 523, 606, and 659; 523, 592, and 670; 560, 591, and 667; 530, 591, and 659; 561, 603, and 666; 562, 591, and 659; 523, 616, and 660; 523, 602, and 677; 523, 616, and 659; 523, 630, and 660; 563, 591, and 659; 523, 640, and 659; 564, 591, and 659; 523, 641, and 677; 565, 591, and 662; 523, 642, and 664; 566, 643, and 659; 523, 644, and 667; 567, 606, and 659; 568, 591, and 659; 569, 645, and 659; 523, 603, and 659; 570, 628, and 678; 571, 630, and 663; 572, 591, and 664; 573, 591, and 670; 523, 646, and 659; 574, 591, and 670; 523, 647, and 667; 575, 591, and 659; 537, 591, and 659; 523, 635, and 670; 576, 591, and 659; 577, 606, and 659; 523, 648, and 679; 523, 592, and 659; 523, 595, and 659; 523, 600, and 659; 523, 649, and 664; 578, 641, and 659; 523, 591, and 667; 523, 606, and 660; 523, 650, and 656; 579, 621, and 671; 580, 591, and 660; 527, 591, and 659; 581, 595, and 659; 582, 640, and 664; 583, 651, and 659; 534, 591, and 659; 584, 591, and 671; 523, 591, and 680; 523, 591, and 681; 585, 591, and 659; 523, 649, and 659; 586, 591, and 666; 587, 652, and 659; 588, 638, and 659; 523, 623, and 664; 523, 591, and 682; 553, 653, and 659; 523, 654, and 659; 523, 648, and 659; 560, 591, and 659; 580, 606, and 659; 589, 593, and 661; 523, 637, and 676; 590, 622, and 659; 555, 591, and 661; 523, 615, and 672; 523, 626, and 668; 523, 655, and 659; or 523, 606, and 680; respectively.

In certain embodiments, the instant disclosure provides an antibody or polypeptide that specifically binds to PC, wherein the antibody or polypeptide comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 369, 428, 484, 523, 591, and 656; 370, 429, 485, 523, 592, and 657; 371, 428, 486, 523, 593, and 658; 372, 428, 484, 523, 591, and 659; 373, 429, 484, 523, 594, and 659; 369, 428, 484, 523, 591, and 659; 374, 430, 484, 523, 591, and 659; 369, 428, 484, 523, 595, and 660; 375, 428, 487, 523, 596, and 659; 376, 428, 484, 524, 591, and 659; 377, 428, 484, 523, 591, and 661; 378, 428, 484, 523, 591, and 662; 372, 428, 484, 523, 597, and 658; 379, 428, 484, 523, 598, and 662; 372, 428, 488, 525, 599, and 659; 376, 431, 484, 523, 600, and 663; 380, 432, 484, 523, 591, and 664; 372, 428, 489, 523, 601, and 659; 381, 428, 490, 523, 591, and 659; 382, 428, 484, 526, 597, and 665; 381, 428, 491, 523, 602, and 659; 369, 428, 484, 527, 591, and 661; 377, 428, 492, 528, 591, and 662; 376, 433, 484, 529, 603, and 662; 383, 434, 484, 523, 604, and 666; 383, 428, 484, 523, 605, and 667; 384, 435, 484, 530, 606, and 659; 369, 436, 484, 523, 607, and 659; 372, 437, 487, 523, 591, and 659; 372, 428, 484, 523, 608, and 659; 385, 428, 493, 523, 609, and 662; 386, 428, 484, 531, 591, and 663; 372, 437, 484, 523, 608, and 661; 377, 428, 484, 523, 610, and 659; 387, 428, 484, 523, 611, and 668; 385, 428, 484, 523, 611, and 658; 372, 438, 484, 523, 596, and 662; 388, 428, 494, 523, 612, and 667; 369, 439, 484, 523, 613, and 668; 389, 428, 484, 523, 591, and 669; 382, 428, 484, 523, 591, and 663; 369, 428, 484, 523, 614, and 659; 381, 428, 484, 523, 591, and 659; 376, 440, 495, 523, 591, and 659; 381, 428, 484, 532, 615, and 662; 381, 428, 484, 523, 616, and 670; 390, 441, 484, 523, 591, and 659; 370, 442, 484, 523, 591, and 668; 391, 428, 484, 523, 617, and 671; 377, 428, 484, 533, 595, and 659; 377, 428, 484, 523, 618, and 659; 392, 432, 484, 523, 591, and 659; 377, 443, 484, 534, 619, and 662; 376, 428, 484, 535, 620, and 659; 393, 428, 484, 536, 621, and 659; 381, 428, 484, 537, 603, and 671; 383, 444, 489, 523, 622, and 59; 372, 428, 484, 523, 617, and 659; 377, 428, 484, 523, 623, and 659; 376, 428, 484, 538, 607, and 672; 369, 428, 484, 523, 616, and 671; 376, 428, 484, 523, 624, and 659; 394, 428, 484, 523, 591, and 659; 369, 428, 484, 523, 620, and 659; 383, 444, 496, 523, 625, and 660; 385, 428, 484, 523, 602, and 671; 376, 434, 484, 523, 591, and 659; 395, 445, 497, 523, 611, and 663; 396, 446, 487, 523, 626, and 670; 369, 428, 484, 523, 617, and 659; 392, 428, 484, 523, 591, and 662; 394, 428, 484, 523, 606, and 673; 393, 428, 498, 523, 591, and 659; 376, 428, 495, 523, 627, and 671; 369, 440, 484, 523, 628, and 671; 397, 428, 484, 539, 591, and 662; 389, 447, 484, 523, 591, and 659; 398, 448, 492, 523, 591, and 670; 373, 449, 490, 523, 611, and 659; 399, 428, 484, 537, 613, and 671; 400, 450, 484, 540, 598, and 659; 401, 428, 484, 541, 591, and 659; 390, 428, 484, 542, 629, and 659; 376, 428, 484, 523, 591, and 671; 400, 428, 499, 523, 591, and 659; 381, 428, 484, 523, 630, and 667; 384, 429, 484, 543, 631, and 659; 369, 428, 484, 523, 632, and 664; 402, 436, 484, 523, 597, and 661; 381, 451, 484, 523, 591, and 656; 403, 428, 484, 523, 633, and 659; 369, 429, 484, 544, 607, and 659; 404, 429, 484, 523, 630, and 659; 372, 429, 484, 523, 602, and 659; 381, 428, 484, 523, 591, and 665; 388, 428, 484, 523, 610, and 674; 405, 451, 484, 523, 634, and 671; 406, 428, 484, 545, 591, and 661; 400, 428, 484, 523, 635, and 667; 404, 428, 484, 546, 591, and 659; 384, 432, 500, 523, 636, and 664; 376, 452, 501, 547, 591, and 663; 407, 428, 484, 548, 619, and 659; 375, 428, 484, 523, 637, and 659; 372, 428, 484, 523, 607, and 659; 408, 428, 484, 523, 638, and 659; 386, 428, 484, 523, 591, and 659; 369, 428, 497, 523, 591, and 659; 403, 453, 484, 549, 591, and 659; 402, 454, 484, 523, 591, and 659; 383, 428, 484, 523, 591, and 659; 383, 434, 500, 523, 591, and 659; 376, 455, 502, 550, 591, and 675; 383, 435, 484, 523, 591, and 664; 369, 428, 484, 523, 602, and 659; 376, 428, 484, 551, 591, and 659; 376, 428, 484, 552, 591, and 659; 383, 428, 484, 553, 591, and 676; 376, 428, 484, 554, 591, and 659; 376, 428, 490, 523, 591, and 676; 369, 428, 503, 555, 606, and 659; 409, 428, 484, 523, 591, and 659; 383, 428, 504, 556, 591, and 659; 369, 434, 484, 523, 591, and 659; 390, 428, 484, 523, 637, and 677; 369, 456, 484, 523, 591, and 659; 370, 457, 484, 557, 591, and 659; 383, 428, 484, 558, 591, and 659; 404, 458, 499, 523, 591, and 659; 410, 428, 484, 523, 591, and 677; 383, 459, 484, 553, 639, and 659; 407, 428, 489, 549, 591, and 667; 374, 434, 484, 523, 591, and 659; 404, 428, 484, 559, 617, and 666; 411, 460, 505, 523, 591, and 672; 372, 429, 484, 523, 606, and 659; 383, 428, 485, 523, 591, and 659; 386, 460, 490, 523, 601, and 659; 412, 455, 493, 523, 592, and 670; 372, 428, 484, 560, 591, and 667; 372, 428, 484, 523, 606, and 659; 383, 461, 484, 523, 591, and 677; 369, 429, 484, 523, 606, and 659; 369, 434, 484, 530, 591, and 659; 376, 437, 484, 561, 603, and 666; 383, 462, 500, 523, 591, and 659; 383, 428, 484, 562, 591, and 659; 400, 463, 484, 523, 616, and 660; 376, 464, 484, 523, 602, and 677; 400, 434, 506, 549, 591, and 659; 369, 436, 507, 523, 591, and 659; 404, 429, 484, 523, 591, and 659; 384, 429, 484, 523, 616, and 659; 369, 429, 484, 523, 591, and 659; 377, 465, 484, 523, 630, and 660; 413, 459, 484, 563, 591, and 659; 369, 452, 484, 523, 591, and 663; 414, 466, 484, 523, 640, and 659; 373, 428, 484, 523, 591, and 659; 415, 428, 489, 564, 591, and 659; 369, 428, 484, 523, 591, and 671; 400, 428, 484, 523, 641, and 677; 369, 428, 491, 565, 591, and 662; 403, 458, 508, 523, 642, and 664; 392, 467, 484, 523, 591, and 659; 369, 452, 509, 566, 643, and 659; 388, 468, 490, 523, 591, and 659; 369, 452, 484, 523, 644, and 667; 377, 440, 484, 567, 606, and 659; 370, 428, 484, 523, 591, and 656; 384, 467, 487, 523, 591, and 659; 392, 469, 510, 568, 591, and 659; 378, 464, 484, 523, 606, and 659; 377, 428, 484, 569, 645, and 659; 416, 434, 484, 523, 603, and 659; 370, 428, 484, 523, 606, and 659; 370, 428, 511, 570, 628, and 678; 369, 452, 484, 571, 630, and 663; 376, 428, 502, 572, 591, and 664; 417, 428, 484, 523, 591, and 665; 392, 428, 484, 573, 591, and 670; 376, 428, 512, 523, 646, and 659; 377, 428, 484, 574, 591, and 670; 383, 428, 484, 523, 647, and 667; 381, 428, 493, 575, 591, and 659; 383, 470, 501, 523, 591, and 659; 404, 471, 484, 537, 591, and 659; 418, 428, 484, 523, 635, and 670; 383, 472, 513, 576, 591, and 659; 419, 428, 484, 577, 606, and 659; 397, 428, 484, 523, 648, and 679; 372, 473, 484, 523, 591, and 664; 383, 474, 484, 523, 592, and 659; 372, 428, 484, 523, 591, and 663; 420, 434, 484, 523, 595, and 659; 370, 428, 514, 523, 591, and 659; 369, 428, 484, 523, 591, and 677; 383, 428, 484, 523, 600, and 659; 369, 475, 484, 523, 591, and 659; 421, 436, 484, 523, 649, and 664; 378, 452, 484, 523, 591, and 659; 376, 476, 515, 578, 641, and 659; 376, 428, 504, 523, 591, and 667; 422, 469, 484, 523, 606, and 660; 383, 461, 484, 523, 616, and 659; 369, 428, 484, 523, 650, and 656; 369, 428, 516, 523, 591, and 659; 405, 460, 484, 523, 618, and 659; 413, 431, 484, 523, 591, and 659; 382, 428, 484, 579, 621, and 671; 383, 428, 484, 523, 646, and 659; 372, 428, 484, 580, 591, and 660; 406, 429, 484, 527, 591, and 659; 383, 428, 517, 581, 595, and 659; 377, 437, 518, 582, 640, and 664; 369, 477, 487, 583, 651, and 659; 403, 464, 484, 534, 591, and 659; 383, 459, 484, 523, 606, and 659; 369, 454, 484, 584, 591, and 671; 372, 478, 519, 523, 591, and 680; 423, 429, 484, 523, 591, and 681; 383, 428, 484, 585, 591, and 659; 369, 434, 484, 557, 591, and 659; 382, 434, 484, 523, 649, and 659; 424, 479, 484, 523, 616, and 660; 376, 429, 484, 586, 591, and 666; 425, 428, 484, 523, 592, and 659; 369, 436, 484, 587, 652, and 659; 403, 428, 520, 588, 638, and 659; 417, 460, 484, 523, 591, and 659; 409, 460, 484, 523, 623, and 664; 404, 452, 484, 523, 591, and 659; 369, 428, 484, 523, 591, and 682; 383, 428, 521, 553, 653, and 659; 372, 480, 493, 523, 591, and 659; 369, 428, 484, 523, 654, and 659; 369, 477, 484, 523, 648, and 659; 369, 481, 484, 560, 591, and 659; 369, 452, 484, 523, 591, and 667; 409, 428, 484, 580, 606, and 659; 384, 452, 484, 589, 593, and 661; 377, 482, 484, 523, 591, and 659; 410, 483, 484, 523, 591, and 659; 384, 428, 489, 523, 591, and 659; 426, 429, 484, 523, 622, and 659; 376, 428, 484, 523, 637, and 676; 427, 428, 484, 523, 591, and 671; 373, 452, 506, 523, 591, and 659; 369, 428, 484, 590, 622, and 659; 369, 429, 521, 555, 591, and 661; 405, 428, 522, 523, 615, and 672; 376, 428, 510, 523, 591, and 659; 384, 428, 484, 523, 626, and 668; 410, 429, 484, 523, 591, and 659; 400, 452, 484, 523, 655, and 659; or 369, 434, 484, 523, 606, and 680, respectively.

In certain embodiments, the instant disclosure provides an antibody or polypeptide that specifically binds to PC, comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to any one of the amino acid sequences set forth in SEQ ID NOs: 1-180. In certain embodiments, the instant disclosure provides an antibody or polypeptide that specifically binds to PC, comprising a VH comprising any one of the amino acid sequences set forth in SEQ ID NOS: 1-180. In certain embodiments, the amino acid sequence of the VH consists of any one of the amino acid sequences set forth in SEQ ID NOs: 1-180.

In certain embodiments, the instant disclosure provides an antibody or polypeptide that specifically binds to PC, comprising a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to any one of the amino acid sequences set forth in SEQ ID NOs: 181-368. In certain embodiments, the instant disclosure provides an antibody or polypeptide that specifically binds to PC, comprising a VL comprising any one of the amino acid sequences set forth in SEQ ID NOs: 181-368. In certain embodiments, the amino acid sequence of the VL consists of any one of the amino acid sequences set forth in SEQ ID NOs: 181-368.

In certain embodiments, the instant disclosure provides an antibody or polypeptide that specifically binds to PC, comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to any one of the amino acid sequences set forth in SEQ ID NOs: 1-180, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to any one of the amino acid sequences set forth in SEQ ID NOs: 181-368. In certain embodiments, the instant disclosure provides an antibody or polypeptide that specifically binds to PC in, comprising a VH comprising any one of the amino acid sequences set forth in SEQ ID NOs: 1-180, and a VL comprising any one of the amino acid sequences set forth in SEQ ID NOs: 181-368. In certain embodiments, the amino acid sequence of the VH consists of any one of the amino acid sequences set forth in SEQ ID NOs: 1-180; and the amino acid sequence of the VL consists of any one of the amino acid sequences set forth in SEQ ID NOs: 181-368.

In certain embodiments, the instant disclosure provides an antibody or polypeptide that specifically binds to PC, comprising the VH and VL amino acid sequences set forth in SEQ ID NOs: 1 and 181; 2 and 182; 3 and 183; 4 and 184; 5 and 185; 1 and 184; 6 and 184; 1 and 186; 7 and 187; 8 and 188; 9 and 189; 10 and 190; 4 and 191; 11 and 192; 12 and 193; 13 and 194; 14 and 195; 15 and 196; 16 and 184; 17 and 197; 18 and 198; 1 and 199; 19 and 200; 20 and 201; 21 and 202; 22 and 203; 23 and 204; 24 and 205; 25 and 184; 4 and 206; 26 and 207; 27 and 208; 28 and 209; 9 and 210; 29 and 211; 30 and 212; 31 and 213; 32 and 214; 33 and 215; 34 and 216; 17 and 217; 1 and 218; 35 and 184; 36 and 184; 35 and 219; 35 and 220; 37 and 184; 38 and 221; 39 and 222; 9 and 223; 9 and 224; 40 and 184; 41 and 225; 8 and 226; 42 and 227; 35 and 228; 43 and 229; 4 and 230; 9 and 231; 8 and 232; 1 and 233; 8 and 234; 44 and 184; 1 and 235; 45 and 236; 30 and 237; 46 and 184; 47 and 238; 48 and 239; 1 and 230; 49 and 190; 44 and 240; 50 and 184; 51 and 241; 52 and 242; 53 and 243; 54 and 184; 55 and 244; 56 and 245; 57 and 246; 58 and 247; 59 and 248; 60 and 249; 8 and 250; 61 and 184; 35 and 251; 62 and 252; 1 and 253; 63 and 254; 64 and 181; 65 and 255; 66 and 256; 67 and 257; 68 and 198; 35 and 258; 69 and 259; 70 and 260; 71 and 261; 72 and 262; 73 and 263; 74 and 264; 75 and 265; 76 and 266; 77 and 267; 4 and 205; 78 and 268; 1 and 269; 27 and 269; 79 and 269; 80 and 270; 81 and 269; 22 and 269; 82 and 269; 83 and 271; 84 and 272; 1 and 273; 8 and 274; 8 and 275; 22 and 276; 8 and 277; 85 and 278; 86 and 279; 87 and 269; 88 and 280; 89 and 269; 60 and 281; 90 and 269; 91 and 282; 22 and 283; 92 and 269; 93 and 284; 94 and 285; 95 and 286; 96 and 269;

73 and 287; 97 and 288; 68 and 289; 98 and 269; 99 and 290; 100 and 291; 4 and 292; 4 and 289; 101 and 284; 66 and 289; 89 and 293; 102 and 294; 103 and 269; 22 and 295; 104 and 296; 105 and 297; 106 and 270; 107 and 269; 67 and 269; 62 and 298; 66 and 269; 108 and 299; 109 and 300; 110 and 301; 111 and 302; 112 and 269; 113 and 303; 1 and 304; 72 and 305; 114 and 306; 115 and 307; 116 and 269; 117 and 308; 118 and 269; 110 and 309; 119 and 310; 120 and 311; 121 and 269; 122 and 312; 123 and 289; 9 and 313; 124 and 314; 120 and 289; 125 and 315; 110 and 316; 126 and 317; 127 and 318; 49 and 319; 128 and 320; 9 and 321; 22 and 322; 129 and 323; 130 and 269; 131 and 324; 132 and 325; 133 and 326; 134 and 327; 53 and 328; 135 and 272; 136 and 329; 4 and 301; 137 and 330; 138 and 269; 1 and 284; 22 and 331; 139 and 269; 140 and 332; 141 and 269; 142 and 333; 143 and 334; 144 and 335; 101 and 298; 1 and 336; 145 and 269; 146 and 337; 147 and 269; 17 and 338; 22 and 320; 4 and 339; 148 and 340; 149 and 341; 150 and 342; 151 and 343; 152 and 344; 94 and 289; 153 and 345; 154 and 346; 155 and 347; 22 and 348; 89 and 282; 156 and 349; 157 and 296; 158 and 350; 159 and 329; 24 and 351; 160 and 352; 161 and 269; 162 and 353; 163 and 269; 1 and 354; 164 and 355; 165 and 269; 1 and 356; 166 and 357; 167 and 358; 110 and 334; 87 and 359; 168 and 360; 169 and 269; 170 and 269; 171 and 269; 172 and 361; 8 and 362; 173 and 304; 174 and 269; 1 and 363; 175 and 364; 176 and 365; 177 and 269; 178 and 366; 179 and 269; 180 and 367; or 89 and 368, respectively.

In certain embodiments, the amino acid sequences of VH and VL consist of the amino acid sequences set forth in SEQ ID NOs: 1 and 181; 2 and 182; 3 and 183; 4 and 184; 5 and 185; 1 and 184; 6 and 184; 1 and 186; 7 and 187; 8 and 188; 9 and 189; 10 and 190; 4 and 191; 11 and 192; 12 and 193; 13 and 194; 14 and 195; 15 and 196; 16 and 184; 17 and 197; 18 and 198; 1 and 199; 19 and 200; 20 and 201; 21 and 202; 22 and 203; 23 and 204; 24 and 205; 25 and 184; 4 and 206; 26 and 207; 27 and 208; 28 and 209; 9 and 210; 29 and 211; 30 and 212; 31 and 213; 32 and 214; 33 and 215; 34 and 216; 17 and 217; 1 and 218; 35 and 184; 36 and 184; 35 and 219; 35 and 220; 37 and 184; 38 and 221; 39 and 222; 9 and 223; 9 and 224; 40 and 184; 41 and 225; 8 and 226; 42 and 227; 35 and 228; 43 and 229; 4 and 230; 9 and 231; 8 and 232; 1 and 233; 8 and 234; 44 and 184; 1 and 235; 45 and 236; 30 and 237; 46 and 184; 47 and 238; 48 and 239; 1 and 230; 49 and 190; 44 and 240; 50 and 184; 51 and 241; 52 and 242; 53 and 243; 54 and 184; 55 and 244; 56 and 245; 57 and 246; 58 and 247; 59 and 248; 60 and 249; 8 and 250; 61 and 184; 35 and 251; 62 and 252; 1 and 253; 63 and 254; 64 and 181; 65 and 255; 66 and 256; 67 and 257; 68 and 198; 35 and 258; 69 and 259; 70 and 260; 71 and 261; 72 and 262; 73 and 263; 74 and 264; 75 and 265; 76 and 266; 77 and 267; 4 and 205; 78 and 268; 1 and 269; 27 and 269; 79 and 269; 80 and 270; 81 and 269; 22 and 269; 82 and 269; 83 and 271; 84 and 272; 1 and 273; 8 and 274; 8 and 275; 22 and 276; 8 and 277; 85 and 278; 86 and 279; 87 and 269; 88 and 280; 89 and 269; 60 and 281; 90 and 269; 91 and 282; 22 and 283; 92 and 269; 93 and 284; 94 and 285; 95 and 286; 96 and 269; 73 and 287; 97 and 288; 68 and 289; 98 and 269; 99 and 290; 100 and 291; 4 and 292; 4 and 289; 101 and 284; 66 and 289; 89 and 293; 102 and 294; 103 and 269; 22 and 295; 104 and 296; 105 and 297; 106 and 270; 107 and 269; 67 and 269; 62 and 298; 66 and 269; 108 and 299; 109 and 300; 110 and 301; 111 and 302; 112 and 269; 113 and 303; 1 and 304; 72 and 305; 114 and 306; 115 and 307; 116 and 269; 117 and 308; 118 and 269; 110 and 309; 119 and 310; 120 and 311; 121 and 269; 122 and 312; 123 and 289; 9 and 313; 124 and 314; 120 and 289; 125 and 315; 110 and 316; 126 and 317; 127 and 318; 49 and 319; 128 and 320; 9 and 321; 22 and 322; 129 and 323; 130 and 269; 131 and 324; 132 and 325; 133 and 326; 134 and 327; 53 and 328; 135 and 272; 136 and 329; 4 and 301; 137 and 330; 138 and 269; 1 and 284; 22 and 331; 139 and 269; 140 and 332; 141 and 269; 142 and 333; 143 and 334; 144 and 335; 101 and 298; 1 and 336; 145 and 269; 146 and 337; 147 and 269; 17 and 338; 22 and 320; 4 and 339; 148 and 340; 149 and 341; 150 and 342; 151 and 343; 152 and 344; 94 and 289; 153 and 345; 154 and 346; 155 and 347; 22 and 348; 89 and 282; 156 and 349; 157 and 296; 158 and 350; 159 and 329; 24 and 351; 160 and 352; 161 and 269; 162 and 353; 163 and 269; 1 and 354; 164 and 355; 165 and 269; 1 and 356; 166 and 357; 167 and 358; 110 and 334; 87 and 359; 168 and 360; 169 and 269; 170 and 269; 171 and 269; 172 and 361; 8 and 362; 173 and 304; 174 and 269; 1 and 363; 175 and 364; 176 and 365; 177 and 269; 178 and 366; 179 and 269; 180 and 367; or 89 and 368, respectively.

Any antibody format can be used in the antibodies disclosed herein. In certain embodiments, the antibody is a single chain antibody or single-chain Fv (scFv). In certain embodiments, the antibody is an scFv fused with an Fc region (scFv-Fc). In certain embodiments, the antibody is a Fab fragment. In certain embodiments, the antibody is a F(ab')$_2$ fragment.

In certain embodiments, the antibody or polypeptide disclosed herein is a multispecific antibody (e.g., a bispecific antibody) which specifically binds to PC and a second antigen.

In certain embodiments, the antibody or polypeptide disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac, and $^{186}$Re. In certain embodiments, the detectable label comprises a fluorescent moiety or a click chemistry handle.

Any immunoglobulin (Ig) constant region can be used in the polypeptides and antibodies disclosed herein. In certain embodiments, the Ig region is a human IgG, IgE, IgM, IgD, IgA, or IgY immunoglobulin molecule, any class (e.g., IgG$_1$, IgG$_2$, IgG$_3$, IgG$_4$, IgA$_1$, and IgA$_2$), or any subclass (e.g., IgG$_2$a and IgG$_2$b) of immunoglobulin molecule.

In certain embodiments, the instant disclosure provides a polypeptide (e.g., an antibody) that specifically binds to PC, the polypeptide comprising a heavy chain constant region, optionally selected from the group consisting of human IgG$_1$, IgG$_2$, IgG$_3$, IgG$_4$, IgA$_1$, and IgA$_2$.

In certain embodiments, the instant disclosure provides a polypeptide (e.g., an antibody) that specifically binds to PC, the polypeptide comprising a heavy chain constant region that is a variant of a wild-type heavy chain constant region, wherein the variant heavy chain constant region binds to an FcγR with lower affinity than the wild-type heavy chain constant region binds to the FcγR.

In certain embodiments, the instant disclosure provides an antibody that specifically binds to PC, the antibody comprising a heavy chain constant region comprising the amino acid sequence of SEQ ID NO: 683 or 684. In certain embodiments, the instant disclosure provides an antibody that specifically binds to PC, the antibody comprising a heavy chain constant region consisting of the amino acid sequence of SEQ ID NO: 683 or 684. In certain embodiments, the instant disclosure provides an antibody that specifically binds to PC, the antibody comprising an $IgG_1$ heavy chain constant region of any allotype or isoallotype. In certain embodiments, the instant disclosure provides an antibody that specifically binds to PC, the antibody comprising an $IgG_1$ heavy chain constant region of an allotype selected from the group consisting of G1m1 (a), G1m2 (x), G1m3 (f), and G1m17 (z). See, e.g., Jefferis and Lefranc (2009) mAbs 1 (4): 332-338.

In certain embodiments, one, two, or more mutations (e.g., amino acid substitutions) are introduced into an Fc region (e.g., a CH2 domain (residues 231-340 of human $IgG_1$) and/or a CH3 domain (residues 341-447 of human $IgG_1$), numbered according to the EU numbering system) and/or a hinge region (residues 216-230, numbered according to the EU numbering system) of an antibody described herein, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of an antibody described herein, such that the number of cysteine residues in the hinge region is altered (e.g., increased or decreased) as described in, e.g., U.S. Pat. No. 5,677,425, herein incorporated by reference in its entirety. The number of cysteine residues in the hinge region may be altered to, e.g., facilitate assembly of the light and heavy chains, or to alter (e.g., increase or decrease) the stability of the antibody.

In a specific embodiment, one, two, or more amino acid mutations (e.g., substitutions, insertions, or deletions) are introduced into an IgG constant region, or FcRn-binding fragment thereof (preferably an Fc or hinge-Fc fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375, and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant region, or FcRn-binding fragment thereof (preferably an Fc or hinge-Fc fragment) to decrease the half-life of the antibody in vivo. In other embodiments, one, two or more amino acid mutations (e.g., substitutions, insertions, or deletions) are introduced into an IgG constant region, or FcRn-binding fragment thereof (preferably an Fc or hinge-Fc fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281:23514-24, which is herein incorporated by reference in its entirety). In certain embodiments, an antibody comprises an IgG constant region comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into an Fc region (e.g., a CH2 domain (residues 231-340 of human $IgG_1$) and/or a CH3 domain (residues 341-447 of human $IgG_1$), numbered according to the EU numbering system) and/or a hinge region (residues 216-230, numbered according to the EU numbering system) of an antibody described herein, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109:6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild-type heavy chain constant region, wherein the variant heavy chain constant region binds to FcγRIIB with higher affinity than the wild-type heavy chain constant region binds to FcγRIIB. In certain embodiments, the variant heavy chain constant region is a variant human heavy chain constant region, e.g., a variant human $IgG_1$, a variant human $IgG_2$, or a variant human $IgG_4$ heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant region Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant region and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276:6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A330L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant region of an $IgG_1$ with an N297Q or N297A amino acid substitution, numbered according to the EU numbering system. In certain embodiments, an antibody described herein comprises the constant region of an $IgG_1$ with a mutation selected from the group consisting of D265A, P329A, and a combination thereof, numbered according to the EU numbering system. In another embodiment, an antibody described herein comprises the constant region of an $IgG_1$ with a mutation selected from the group consisting of L234A, L235A, and a combination thereof, numbered according to the EU numbering system. In another embodiment, an antibody described herein comprises the constant region of an $IgG_1$ with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG, heavy chain, numbered according to the EU numbering system, are not L, L, and D, respectively. This approach is described in detail in International Publication No. WO 14/108483, which is herein incorporated by reference in its entirety. In certain embodiments, the amino acids corresponding to positions L234, L235, and D265 in a human $IgG_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogic et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant region of an $IgG_1$, wherein the modification increases the ability of the antibody to mediate antibody dependent cellular cytotoxicity (ADCC). In certain embodiments, 0.1, 1, or 10 μg/mL of the antibody is capable of inducing cell death of at least 20%, 25%, 30%, 35%, 40%, 45%, 50%, 55%, or 60% of PC-expressing cells within 1, 2, or 3 hours, as assessed by methods described herein and/or known to a person of skill in the art. In certain embodiments, the modified constant region of an $IgG_1$ comprises S239D and I332E substitutions, numbered according to the EU numbering system. In certain embodiments, the modified constant region of an $IgG_1$ comprises S239D, A330L, and I332E substitutions, numbered according to the EU numbering system. In certain embodiments, the modified constant region of an $IgG_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an $IgG_4$ antibody and the serine at amino acid residue 228 of the heavy chain, numbered according to the EU numbering system, is substituted for proline. In certain embodiments, the instant disclosure provides an antibody that specifically binds to PC, the antibody comprising a heavy chain constant region comprising the amino acid sequence of SEQ ID NO: 684.

In certain embodiments, any of the constant region mutations or modifications described herein can be introduced into one or both heavy chain constant regions of an antibody described herein having two heavy chain constant regions.

Pharmaceutical Compositions

Provided herein are compositions comprising an anti-PC antibody disclosed herein having the desired degree of purity in a physiologically acceptable carrier, excipient, or stabilizer (see, e.g., Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates, including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™ PLURONIC™ or polyethylene glycol (PEG).

In a specific embodiment, pharmaceutical compositions comprise an anti-PC antibody disclosed herein, and optionally one or more additional prophylactic or therapeutic agents, in a pharmaceutically acceptable carrier. In a specific embodiment, pharmaceutical compositions comprise an anti-PC antibody disclosed herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in decreasing or inhibiting PC activity and treating a condition, such as an inflammatory disorder. In certain embodiments, the present disclosure relates to a pharmaceutical composition of the present disclosure comprising an anti-PC antibody of the present disclosure for use as a medicament. In another embodiment, the present disclosure relates to a pharmaceutical composition of the present disclosure for use in a method for the treatment of an inflammatory disorder.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering, or chelating agents and other pharmaceutically acceptable substances. Examples of aqueous vehicles include Sodium Chloride Injection, Ringer's Injection, Isotonic Dextrose Injection, Sterile Water Injection, Dextrose and Lactated Ringer's Injection. Nonaqueous parenteral vehicles include fixed oils of vegetable origin, cottonseed oil, corn oil, sesame oil, and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose, and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol, and propylene glycol for water miscible vehicles; and sodium hydroxide, hydrochloric acid, citric acid, or lactic acid for pH adjustment.

A pharmaceutical composition can be formulated for any route of administration to a subject. Specific examples of routes of administration include intranasal, oral, pulmonary, transdermal, intradermal, and parenteral. Parenteral administration, characterized by either subcutaneous, intramuscular, or intravenous injection, is also contemplated herein. Injectables can be prepared in conventional forms, either as liquid solutions or suspensions, solid forms suitable for solution or suspension in liquid prior to injection, or as emulsions. The injectables, solutions, and emulsions also contain one or more excipients. Suitable excipients are, for example, water, saline, dextrose, glycerol, or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol, and mixtures thereof.

Topical mixtures comprising an antibody are prepared as described for the local and systemic administration. The resulting mixture can be a solution, suspension, emulsion, or the like and can be formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

An anti-PC antibody disclosed herein can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in certain embodiments, have diameters of less than 50 microns, in certain embodiments less than 10 microns.

An anti-PC antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions, and other mixtures. It may also be reconstituted and formulated as solids or gels. The lyophilized powder is prepared by dissolving antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose, or other suitable agent. The solvent may also contain a buffer, such as citrate, sodium or potassium phosphate or other such buffer known to those of skill in the art at, in certain embodiments, about neutral pH. Subsequent sterile filtration of the solution followed by lyophilization under standard conditions known to those of skill in the art provides the desired formulation. In certain embodiments, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-PC antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874, all of which are herein incorporated by reference in their entireties.

The compositions to be used for in vivo administration can be sterile. This is readily accomplished by filtration through, e.g., sterile filtration membranes.

Methods of Use and Uses

In another aspect, the instant disclosure provides a method of treating a subject using the anti-PC antibodies disclosed herein. Any disease or disorder in a subject that would benefit from decrease of oxidized phospholipid function can be treated using the anti-PC antibodies disclosed herein.

In certain embodiments, the anti-PC antibodies disclosed herein are particularly useful for inhibiting an activity of PC in a subject. In certain embodiments, the anti-PC antibodies disclosed herein are particularly useful for inhibiting the inflammatory activity of PC in a subject. In certain embodiments, the anti-PC antibodies disclosed herein are particularly useful for treating an inflammatory disorder or degenerative disease. In certain embodiments, the anti-PC antibodies disclosed herein can be used as an anti-inflammatory agent and/or as an anti-atherosclerotic agent. In certain embodiments, the anti-PC antibodies disclosed herein can be used to treat pain. In certain embodiments, the anti-PC antibodies disclosed herein can be used to treat osteoporosis. In certain embodiments, the anti-PC antibodies disclosed herein can be used to treat fibrotic disease, including, without limitation, lung fibrosis. In certain embodiments, the anti-PC antibodies disclosed herein can be used to treat NETosis-driven diseases, including, without limitation, anti-neutrophil cytoplasmic antibody (ANCA) vasculitis and Type I diabetes. In certain embodiments, the anti-PC antibodies disclosed herein can be used to treat chronic obstructive pulmonary disease (COPD). In certain embodiments, the anti-PC antibodies disclosed herein can be used to treat acute respiratory diseases, acute fulminating pneumonias, or other similar disorders. In certain embodiments, the anti-PC antibodies disclosed herein can be used to treat severe asthma. In certain embodiments, the anti-PC antibodies disclosed herein can be used to treat patients with acute hepatitis, or with non-alcoholic steatohepatitis (NASH) and metabolic syndrome. In certain embodiments, the anti-PC antibodies disclosed herein can be used as an anti-atherosclerotic agent to treat cardiovascular disease and calcific aortic stenosis (CAS). In certain embodiments, the anti-PC antibodies disclosed herein can be used to treat patients with acute coronary syndromes or with "crescendo angina." In certain embodiments, the anti-PC antibodies disclosed herein can be used as a proactive measure in treating high risk patients, e.g., patients who have a propensity for stroke or developing atherosclerosis. In certain embodiments, the anti-PC antibodies disclosed herein can be used treat high risk patients with coronary artery disease (CAD). Thus, the anti-PC antibodies disclosed herein can be used to treat inflammatory diseases and disorders, cardiovascular diseases, and diseases associated with oxidized phospholipids, including, without limitation, atherosclerosis, acute coronary syndrome, acute myocardial infarction, myocardial infarction (heart attack), stable and unstable angina pectoris, aneurysms, coronary artery disease (CAD), ischemic heart disease, ischemic myocardium, cardiac and sudden cardiac death, cardiomyopathy, congestive heart failure, heart failure, stenosis, peripheral arterial disease (PAD), intermittent claudication, critical limb ischemia, and stroke. See, U.S. Pat. No. 11,008,381, which is incorporated herein by reference in its entirety.

In certain embodiments, the anti-PC antibodies disclosed herein can be used to treat cardiovascular disease, atherosclerosis, rheumatoid arthritis, osteoarthritis, lung tissue injury (e.g., caused by smoking), brain lesions, apoptosis, senescence, Crohn's disease, ulcerative colitis, fatty liver disease (e.g., NASH), and non-alcoholic fatty liver disease (NAFLD). Thus, the anti-PC antibodies disclosed herein can be used to treat inflammatory diseases and disorders, cardiovascular diseases, liver diseases and disorder (e.g., NASH, NAFLD) and diseases associated with oxidative stress and damage. In certain embodiments, the anti-PC antibodies disclosed herein can be used to treat non-alcoholic fatty liver disease. In certain embodiments, the anti-PC antibodies disclosed herein can be used to treat non-alcoholic steatohepatitis (NASH). In certain embodiments, the anti-PC antibodies disclosed herein can be used to inhibit the progression of NAFLD to NASH. In certain embodiments, the anti-PC antibodies disclosed herein can be used to treat or inhibit atherogenesis. See, U.S. Pat. No. 11,168,148, which is incorporated herein by reference in its entirety.

In certain embodiments, the anti-PC antibodies disclosed herein can be used to treat reperfusion injury. In certain embodiments, reperfusion injury comprises organ reperfusion injury. In certain embodiments, reperfusion injury comprises ischemic-reperfusion injury. In certain embodiments, organ reperfusion injury is induced by an ischemic event (e.g., myocardial infarction induced reperfusion injury). In certain embodiments, the anti-PC antibodies disclosed herein can be used to treat a subject that is at risk of suffering or has suffered an ischemic event, including, without limitation, an ischemic event associated with a condition selected from the group consisting of cerebral ischemia; intestinal ischemia; spinal cord ischemia; cardiovascular ischemia; myocardial ischemia associated with myocardial infarction; myocardial ischemia associated with congestive heart failure (CHF), ischemia associated with age-related macular degeneration (AME); liver ischemia; kidney/renal ischemia; dermal ischemia; vasoconstriction-induced tissue ischemia; penile ischemia as a consequence of priapism and erectile dysfunction; ischemia associated with thromboembolytic disease; ischemia associated with microvascular disease; ischemia associated with thrombosis; and ischemia associated with diabetic ulcers, gangrenous conditions, post-trauma syndrome, cardiac arrest resuscitation, hypothermia, peripheral nerve damage and neuropathies. In certain embodiments, the anti-PC antibodies disclosed herein can be used to treat a subject that is at risk of suffering or has suffered an ischemic event that is the result of an induced injury, including, without limitation, from surgery, transplantation, accidental trauma, and mechanical support devices. In certain embodiments, the anti-PC antibodies disclosed herein can be used to treat a subject that is at risk of suffering or has suffered an ischemic event that is the result of heart surgery, kidney surgery, brain surgery, liver surgery, and bypass surgery. In certain embodiments, the anti-PC antibodies disclosed herein can be used to treat acute ischemic stroke. In certain embodiments, the anti-PC antibodies disclosed herein can be used to treat reperfusion-driven indications including transplantation of organs such as the liver, heart, and kidney. In certain embodiments, the anti-PC antibodies disclosed herein can be used to treat a disease associated with thrombosis, including, without limitation sickle cell disease, deep vein thrombosis, pulmonary embolism, cardiac embolism, hypercoagulable state, thrombophilia, Factor V Leiden, Antithrombin III deficiency, Protein C deficiency, Protein S deficiency, Prothrombin gene mutation (G20210A), hyperhomocysteinemia, antiphospholipid antibody syndrome (APS), anticardiolipin antibody (ACLA) thrombosis syndrome, and lupus anticoagulant (LA) syndrome. In certain embodiments, the anti-PC antibodies disclosed herein can be used to treat or inhibit atherogenesis. See, U.S. patent application Ser. No. 16/759,331, which is incorporated herein by reference in its entirety.

In certain embodiments, the anti-PC antibodies disclosed herein can be used to treat a toll-like receptor 2 (TLR2)-mediated disease or disorder, including, without limitation, Kawasaki disease including IVIG-refractory Kawasaki Disease, type 2 diabetes, rheumatoid arthritis, dermatologic disease, multiple sclerosis, systemic lupus erythematosus, ulcerative colitis, Graves' Disease, Sjögren's syndrome, autoimmune thyroid diseases, or vasculitis. See, U.S. patent application Ser. No. 16/965,271, which is incorporated herein by reference in its entirety.

In certain embodiments, the anti-PC antibodies disclosed herein can be used to treat bacterial infection. In certain embodiments, the anti-PC antibodies disclosed herein can be used to treat neuroinflammatory diseases, including, without limitation, amyotrophic lateral sclerosis (ALS), Parkinson's disease (PD), and Alzheimer's disease (AD). In certain embodiments, the anti-PC antibodies disclosed herein can be used to treat Huntington's disease, frontotemporal dementia (FTD), multiple sclerosis (MS), clinically isolated syndrome (CIS), and other demyelinating diseases of the central nervous system. In certain embodiments, the anti-PC antibodies disclosed herein can be used to treat ocular disease, including, without limitation, age-related macular degeneration (AMD) and geographic atrophy (GA).

In certain embodiments, these methods further comprise administering an additional therapeutic agent to the subject. In certain embodiments, the additional therapeutic agent is a HMG-COA reductase inhibitor (statin), immunosuppressive agent, ezetimide, perixosome, nicotinic acid, squalene inhibitor, proliferative activated receptor (PPAR) agonist, cholesteryl ester transfer protein (CETP) inhibitor, ApoA-1 Milano, corticosteroid, non-steroidal anti-inflammatory drug, steroidal anti-inflammatory drug, analgesic, growth factor, anti-atherosclerosis drug, anti-proliferative agent, HSP, Beta-2-glycoprotein-I, and any derivative and analog thereof.

HMGCoA reductase inhibitors (statins) are well-known drugs that effectively reduce low-density lipoprotein (LDL)-cholesterol levels by inhibiting the enzyme that regulates the rate of cholesterol production and increasing the clearance of LDL-cholesterol (LDL-C) present in the blood by the liver. Non-limiting examples of commonly prescribed statins include Atorvastatin, Fluvastatin, Lovastatin, Pravastatin, and Simvastatin.

Non-limiting examples of immunosuppressive agents include biologics such as infliximab, abatacept, adalimumab, anakinra, certolizumab, etanercept, golimumab, ixekizumab, natalizumab, rituximab, secukinumab, tocilizumab, ustekinumab, canakinumab, and vedolizumab, calcineurin inhibitors such as cyclosporine and tacrolimus, mTOR inhibitors such as sirolimus and everolimus, inosine monophosphate dehydrogenase (IMDH) inhibitors such as azathioprine, leflunomide, and mycophenolate, methotrexate, monoclonal antibodies such as daclizumab and basiliximab, muromonab-CD3, and Janus kinase inhibitors such as tofacitinib.

Ezetimibe is the first of a new class of cholesterol absorption inhibitors that potently and selectively inhibits dietary and biliary cholesterol absorption at the brush border of the intestinal epithelium, without affecting the absorption of triglyceride or fat-soluble vitamins. Ezetimibe thus reduces overall cholesterol delivery to the liver, secondarily inducing increased expression of LDL receptors, resulting in an increased removal of LDL-C from the plasma.

The peroxisome is a single-membrane organelle present in nearly all eukaryotic cells. One of the most important metabolic processes of the peroxisome is the β-oxidation of long and very long chain fatty acids. The peroxisome is also involved in bile acid synthesis, cholesterol synthesis, plasmalogen synthesis, amino acid metabolism, and purine metabolism.

Nicotinic acid is a known agent that lowers total cholesterol, LDL-cholesterol, and triglyceride levels, while raising high-density lipoprotein (HDL)-cholesterol levels. There are three types of nicotinic acid drugs: immediate release, timed release, and extended release. Nicotinic acid or niacin, the water-soluble B vitamin, improves all lipoproteins when given in doses well above the vitamin requirement.

Squalene, an isoprenoid compound structurally similar to beta-carotene, is an intermediate metabolite in the synthesis of cholesterol. In humans, about 60 percent of dietary squalene is absorbed. It is transported in serum generally in association with very low-density lipoproteins and is distributed ubiquitously in human tissues, with the greatest concentration in the skin, where it is one of the major components of skin surface lipids. Squalene inhibitors (e.g., monooxygenase and synthase) serve as cholesterol biosynthesis inhibitors.

Proliferative Activated Receptor (PPAR) agonists, e.g., fibrates, are fatty acid-activated members of the nuclear receptor superfamily that play important roles in lipid and glucose metabolism, and have been implicated in obesity-related metabolic diseases such as hyperlipidemia, insulin resistance, and coronary artery disease. Fibrates are generally effective in lowering elevated plasma triglycerides and cholesterol and act as PPAR agonists. The most pronounced effect of fibrates includes a decrease in plasma triglyceride-rich lipoproteins (TRLs). Levels of LDL-C generally decrease in individuals with elevated baseline plasma concentrations, and HDL cholesterol (HDL-C) levels are usually increased when baseline plasma concentrations are low. Non-limiting examples of commonly prescribed fibrates include bezafibrate, gemfibrozil, and fenofibrate.

Cholesteryl Ester Transfer Protein (CETP) inhibitors play a major role in atherogenesis, by reducing cholesteryl ester accumulation within macrophages and the arterial wall, and thus reducing foam cell formation and affecting the cholesterol absorption. The most promising presently known CETP inhibitor is avisimibe.

ApoA-1 Milano is typically used as a recombinant complex with phospholipid (ETC-216) and produces significant regression of coronary atherosclerosis.

Non-limiting examples of non-steroidal anti-inflammatory drugs include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of analgesics (pain relievers) include aspirin and other salicylates (such as choline or magnesium salicylate), ibuprofen, ketoprofen, naproxen sodium, and acetaminophen.

Growth factors are hormones which have numerous functions, including regulation of adhesion molecule production, altering cellular proliferation, increasing vascularization, enhancing collagen synthesis, regulating bone metabolism, and altering migration of cells into given area. Non-limiting examples of growth factors include insulin-like growth factor-1 (IGF-1), transforming growth factor-β (TGF-β), a bone morphogenic protein (BMP), and the like.

Non-limiting examples of anti-proliferative agents include an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier, miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of chemotherapeutic agents include, for example, a nitrogen mustard, an epipodophyllotoxin, an antibiotic, a platinum coordination complex, bleomycin, doxorubicin, paclitaxel, ctoposide, 4-OH cyclophosphamide, and cisplatinum.

The HSP family consists of approximately 25 proteins discerned by their molecular weights with highly conserved structures. Almost all humans have cellular and humoral immune reactions against microbial heat-shock protein 60 (HSP60). Because a high degree of antigenic homology exists between microbial (bacterial and parasitic) and human HSP60, the 'cost' of immunity to microbes might be the danger of cross-reactivity with human HSP60 expressed by the endothelial cells of stressed arteries. Genuine autoimmunity against altered autologous HSP60 might trigger this process also (Wick et al., TRENDS in Immunology. 2001;

22 (12): 665-669). HSP has been implicated as a target autoantigen in several experimental autoimmune diseases (arthritis, type I diabetes). Anti-HSP65 as well as anti-HSP60 antibodies have been demonstrably associated with atheromatous lesions in humans. Studies conducted in rabbits and mice show that the generation of an HSP65-induced immune response by immunization with the recombinant protein or with an HSP65-rich preparation of *Mycobacterium tuberculosis* enhances atherogenesis. As autoimmune processes pointing to HSP65 as a possible antigenic candidate, creating a state of unresponsiveness by induction of mucosal "tolerization" has been employed in order to block these responses, our group reported that early atherosclerosis was attenuated in HSP65-fed mice, compared with either BSA or PBS fed mice (Harats et al., J Am Coll Cardiol. 2002; 40:1333-1338), this was further supported by Maron who demonstrated that nasal vaccination with HSP reduces the inflammatory process associated with atherosclerosis (Maron ct al., Circulation. 2002; 106:1708-1715).

Beta-2-glycoprotein I (beta2GPI) is a phospholipid binding protein shown to serve as a target for prothrombotic anti-phospholipid antibodies. It has recently been demonstrated to drive an immune mediated reaction and enhance murine atherosclerosis. β-Antibodies to beta-2-GPI have the ability to activate monocytes and endothelial cells and can induce an immune response to beta2GPI in atherosclerosis-prone mice accelerated atherosclerosis. When beta2GPI-reactive lymph node and spleen cells were transferred to LDL-receptor-deficient mice they promoted fatty streak formation, proving a direct proatherogenic role for beta2GPI-specific lymphocytes. Inducing immunological tolerance to beta2GPI by prior oral feeding with the antigen resulted in a significant reduction in the extent of atherosclerotic lesions. Thus, beta2GPI is a candidate player in the atherosclerotic plaque, and can possibly be employed as an immunomodulator of plaque progression. Oral feeding with of beta2GPI inhibited lymph node cell reactivity to beta2GPI in mice immunized against the human protein. IL-4 and IL-10 production was upregulated in lymph node cells of beta2GPI-tolerant mice immunized against beta2GPI, upon priming with the respective protein. Thus, oral administration of beta2GPI is an effective means of suppressing atherogenesis in mice (George et al., Cardiovasc Res. 2004; 62 (3): 603-9).

In certain embodiments, the anti-PC antibodies or pharmaceutical compositions disclosed herein synergize with the additional therapeutic agent.

In certain embodiments, the present disclosure relates to an antibody and/or pharmaceutical composition of the present disclosure for use in a method of the present disclosure, wherein the method further comprises administering an additional therapeutic agent to the subject. In certain embodiments, the present disclosure relates to (a) an antibody and/or pharmaceutical composition of the present disclosure, and (b) an additional therapeutic agent for use as a medicament. In certain embodiments, the present disclosure relates to (a) an antibody and/or pharmaceutical composition of the present disclosure, and (b) an additional therapeutic agent for use in a method for the treatment of an inflammatory disorder. In a further embodiment, the present disclosure relates to a pharmaceutical composition, kit or kit-of-parts comprising (a) an antibody and/or pharmaceutical composition of the present disclosure, and (b) an additional therapeutic agent. In certain embodiments, the additional therapeutic agent is an HMG-COA reductase inhibitor (statin), immunosuppressive agent, ezetimibe, peroxisome, nicotinic acid, squalene inhibitor, proliferative activated receptor (PPAR) agonist, cholesteryl ester transfer protein (CETP) inhibitor, ApoA-1 Milano, non-steroidal anti-inflammatory drug, steroidal anti-inflammatory drug, analgesic, growth factor, anti-atherosclerosis drug, anti-proliferative agent, HSP, or Beta-2-glycoprotein-I.

The anti-PC antibody and the additional therapeutic agent (e.g., HMG-COA reductase inhibitor (statin), immunosuppressive agent, ezetimibe, peroxisome, nicotinic acid, squalene inhibitor, proliferative activated receptor (PPAR) agonist, cholesteryl ester transfer protein (CETP) inhibitor, ApoA-1 Milano, non-steroidal anti-inflammatory drug, steroidal anti-inflammatory drug, analgesic, growth factor, anti-atherosclerosis drug, anti-proliferative agent, HSP, or Beta-2-glycoprotein-I) can be administered separately, sequentially, or concurrently as separate dosage forms.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-PC antibody described herein can also be used to assay OxPL levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-PC antibody described herein can be labeled and used in combination with an anti-PC antibody to detect OxPL levels. Therefore, in certain embodiments, the present disclosure relates to the use of an anti-PC antibody of the present disclosure for in vitro detection of OxPL in a biological sample. In a further embodiment, the present disclosure relates to the use of an anti-PC antibody of the disclosure, for assaying and/or detecting OxPL levels in a biological sample in vitro or ex vivo, optionally wherein the anti-PC antibody is conjugated to a radionuclide or detectable label, and/or carries a label described herein, and/or wherein an immunohistological method is used.

Assaying for the level of OxPL is intended to include qualitatively or quantitatively measuring or estimating the level of OxPL in a first biological sample either directly (e.g., by determining or estimating absolute OxPL level) or relatively (e.g., by comparing to the disease associated OxPL level in a second biological sample). OxPL level in the first biological sample can be measured or estimated and compared to a standard OxPL level, the standard being taken, for example, from a second biological sample obtained from an individual not having the disorder or being determined by averaging levels from a population of individuals not having the disorder. As will be appreciated in the art, once the "standard" OxPL level is known, it can be used repeatedly as a standard for comparison. Therefore, in a further embodiment, the present disclosure relates to an in vitro method for assaying and/or detecting OxPL levels, for example human OxPL levels, in a biological sample, comprising qualitatively or quantitatively measuring or estimating the level of OxPL, for example of human OxPL, in a biological sample, by an immunohistological method.

As used herein, the term "biological sample" refers to any biological sample obtained from a subject, cell line, tissue, or other source of cells potentially containing oxidized phospholipids. Methods for obtaining tissue biopsies and body fluids from animals (e.g., humans or cynomolgus monkeys) are well known in the art. Biological samples include peripheral blood mononuclear cells (PBMCs).

An anti-PC antibody described herein can be used for prognostic, diagnostic, monitoring, and screening applications, including in vitro and in vivo applications well known and standard to the skilled artisan and based on the present description. Prognostic, diagnostic, monitoring, and screening assays and kits for in vitro assessment and evaluation of immune system status and/or immune response may be utilized to predict, diagnose, and monitor to evaluate patient samples, including those known to have or suspected of having an immune system dysfunction or with regard to an anticipated or desired immune system response or antigen response. The assessment and evaluation of immune system status and/or immune response is also useful in determining the suitability of a patient for a clinical trial of a drug or for the administration of a particular therapeutic agent or antibody, including combinations thereof, versus a different agent or antibody. In vivo applications include directed cell therapy and immune system modulation and radio imaging of immune responses. Therefore, in certain embodiments, the present disclosure relates to an anti-PC antibody and/or pharmaceutical composition of the present disclosure for use as a diagnostic. In certain embodiments, the present disclosure relates to an anti-PC antibody and/or pharmaceutical composition of the present disclosure for use in a method for the prediction, diagnosis, and/or monitoring of a subject having or suspected to have an immune system dysfunction and/or with regard to an anticipated or desired immune system response or antigen response. In another embodiment, the present disclosure relates to the use of an anti-PC antibody of the disclosure, for predicting, diagnosing, and/or monitoring of a subject having or suspected to have an immune system dysfunction and/or with regard to an antici-pated or desired immune system response or antigen response, by assaying and/or detecting human OxPL levels in a biological sample of the subject in vitro or in vivo.

In certain embodiments, an anti-PC antibody can be used in immunohistochemistry of biopsy samples. In certain embodiments, the method is an in vitro method. In another embodiment, an anti-PC antibody can be used to detect levels of OxPL, or levels of cells which contain OxPL, the levels of which can then be linked to certain disease symptoms. Anti-PC antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-PC antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-PC antibody may carry or may be conjugated to a radioactive label or radionuclide, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac, and $^{186}$Re. When radioactive labels are used, currently available counting procedures known in the art may be utilized to identify and quantitate the specific binding of an anti-PC antibody to PC. In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with an anti-PC antibody under conditions that allow for the formation of a complex between the anti-PC antibody and PC. Any complexes formed between the anti-PC antibody and PC, are detected and compared in the sample and the control. In light of the specific binding of the anti-PC antibodies described herein for PC, the anti-PC antibodies can be used to specifically detect PC. The anti-PC antibodies described herein can also be used to purify PC via immunoaffinity purification. Also included herein is an assay system which may be prepared in the form of a test kit, kit, or kit-of-parts for the quantitative analysis of the extent of the presence of, for instance, PC/PC ligand complexes. The system, test kit, kit, or kit-of-parts may comprise a labeled component, e.g., a labeled antibody, and one or more additional immunochemical reagents.

Polynucleotides, Vectors, and Methods of Producing Antibodies

In another aspect, provided herein are polynucleotides comprising a nucleotide sequence encoding an antibody, or a portion thereof, described herein or a fragment thereof (e.g., a VL and/or VH; and a light chain and/or heavy chain) that specifically binds to a PC antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecules having less than about 15%, 10%, 5%, 2%, 1%, 0.5%, or 0.1% (in particular less than about 10%) of other material, e.g., cellular material, culture medium, other nucleic acid molecules, chemical precursors, and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to PC and comprises an amino acid sequence as described herein, as well as antibodies which compete with such antibodies for binding to PC (e.g., in a dose-dependent manner), or which binds to the same epitope as that of such antibodies.

In certain aspects, provided herein are polynucleotides comprising a nucleotide sequence encoding the light chain or heavy chain of antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1). In certain embodiments, a polynucleotide encodes a VH, VL, heavy chain, and/or light chain of a described herein. In another embodiment, a polynucleotide encodes the first VH and the first VL of a described herein. In another embodiment, a polynucleotide encodes the second VH and the second VL of a described herein. In another embodiment, a polynucleotide encodes the first heavy chain and the first light chain of a described herein. In another embodiment, a polynucleotide encodes the second heavy chain and the second light chain of a described herein. In another embodiment, a polynucleotide encodes the VH and/or the VL, or the heavy chain and/or the light chain, of an antibody described herein.

Also provided herein are polynucleotides encoding an anti-PC antibody that are optimized, e.g., by codon/RNA optimization, replacement with heterologous signal sequences, and elimination of mRNA instability elements. Methods to generate optimized nucleic acids encoding an anti-PC antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-PC antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-PC antibody encoded by polynucleotides that have not been optimized.

In certain embodiments, an optimized polynucleotide sequence encoding an anti-PC antibody described herein or a fragment thereof (e.g., VL domain and/or VH domain) can hybridize to an antisense (e.g., complementary) polynucleotide of an unoptimized polynucleotide sequence encoding an anti-PC antibody described herein or a fragment thereof (e.g., VL domain and/or VH domain). In specific embodiments, an optimized nucleotide sequence encoding an anti-PC antibody described herein or a fragment hybridizes under high stringency conditions to antisense polynucleotide of an unoptimized polynucleotide sequence encoding an anti-PC antibody described herein or a fragment thereof. In a specific embodiment, an optimized nucleotide sequence encoding an anti-PC antibody described herein or a fragment thereof hybridizes under high stringency, intermediate, or lower stringency hybridization conditions, to an antisense polynucleotide of an unoptimized nucleotide sequence encoding an anti-PC antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17:242-6, herein incorporated by reference in its entirety), which, briefly, involves the synthesis of overlapping oligonucleotides containing portions of the sequence encoding the antibody, annealing, and ligating of those oligonucleotides, and then amplification of the ligated oligonucleotides by PCR.

Alternatively, a polynucleotide encoding an antigen-binding region of a described here or an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning.

If a clone containing a nucleic acid encoding a particular antigen-binding region or antibody is not available, but the sequence of the antigen-binding region or antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence, or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-PC antibodies described herein can be readily isolated and sequenced using conventional procedures (e.g., by using oligonucleotide probes that are capable of binding specifically to genes encoding the heavy and light chains of the anti-PC antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-PC antibodies in the recombinant host cells.

To generate whole antibodies or antigen-binding regions, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant regions, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant regions in place of the murine sequences, or by covalently joining to the immunoglobulin coding sequence all or part of the coding sequence for a non-immunoglobulin polypeptide.

Also provided are polynucleotides that hybridize under high stringency, intermediate, or lower stringency hybridization conditions, to polynucleotides that encode an antibody described herein. In specific embodiments, polynucleotides described herein hybridize under high stringency, intermediate, or lower stringency hybridization conditions, to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions is known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to PC, and related polynucleotides and expression vectors. Provided herein are vectors (e.g., expression vectors) comprising polynucleotides comprising nucleotide sequences encoding anti-PC antibodies or a fragment for recombinant expression in host cells, preferably in mammalian cells (e.g., CHO cells). Also provided herein are host cells comprising such vectors for recombinantly expressing anti-PC antibodies described herein (e.g., human or humanized antibody). In a particular aspect, provided herein are methods for producing an antibody described herein, comprising expressing the antibody from a host cell.

Recombinant expression of an antibody described herein (e.g., a full-length antigen-binding region or antibody or heavy and/or light chain of an antibody described herein) that specifically binds to PC generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing an antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding containing an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of the entire heavy, the entire light chain, or both the entire heavy and light chains.

In certain embodiments, a vector comprises a polynucleotide encoding a VH, VL, heavy chain, and/or light chain of an antibody described herein. In another embodiment, a vector comprises a polynucleotide encoding the VH and the VL of an antibody described herein. In another embodiment, a vector comprises a polynucleotide encoding the heavy chain and the light chain of an antibody described herein.

An expression vector can be transferred to a cell (e.g., host cell) by conventional techniques and the resulting cells can then be cultured by conventional techniques to produce containing an antibody described herein or a fragment thereof. Thus, provided herein are host cells containing a polynucleotide encoding containing an antibody described herein or fragments thereof, or a heavy or light chain thereof, or fragment thereof, or a single-chain antibody described herein, operably linked to a promoter for expression of such sequences in the host cell.

In another embodiment, a host cell comprises a polynucleotide encoding the VH and VL of an antibody described herein. In another embodiment, a host cell comprises a vector comprising a polynucleotide encoding the VH and VL of an antibody described herein. In another embodiment, a host cell comprises a first polynucleotide encoding the VH of an antibody described herein, and a second polynucleotide encoding the VL of an antibody described herein. In another embodiment, a host cell comprises a first vector comprising a first polynucleotide encoding the VH of an antibody described herein, and a second vector comprising a second polynucleotide encoding the VL of an antibody described herein.

In specific embodiments, a heavy chain/heavy chain variable region expressed by a first cell is associated with a light chain/light chain variable region of a second cell to form an anti-PC antibody described herein. In certain embodiments, provided herein is a population of host cells comprising such first host cell and such second host cell.

In certain embodiments, provided herein is a population of vectors comprising a first vector comprising a polynucleotide encoding a light chain/light chain variable region of an anti-PC antibody described herein, and a second vector comprising a polynucleotide encoding a heavy chain/heavy chain variable region of an anti-PC antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA or cosmid DNA expression vectors containing antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7030, HsS78Bst, HeLa, and NIH 3T3, HEK-293T, HepG2, SP210, R1.1, B-W, L-M, BSC1, BSC40, YB/20, and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In certain embodiments, cells for expressing antibodies described herein are human cells, e.g., human cell lines. In a specific embodiment, a mammalian expression vector is pOptiVEC™ or pcDNA3.3. In certain embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus, are an effective expression system for antibodies (Foccking M K & Hofstetter H (1986) Gene 45:101-5; and Cockett M I et al., (1990) Biotechnology 8 (7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to PC is regulated by a constitutive promoter, inducible promoter, or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ructher U & Mueller-Hill B (1983) EMBO J 2:1791-1794), in which the coding sequence can be ligated individually into the vector in frame with the lac Z coding region so that a fusion protein is produced; pIN vectors (Inouye S & Inouye M (1985) Nuc Acids Res 13:3101-3109; Van Hecke G & Schuster S M (1989) J Biol Chem 24:5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (see, e.g., Logan J & Shenk T (1984) PNAS 81 (12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153:516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells. In certain embodiments, anti-PC antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-PC antibody described herein can be engineered. In specific embodiments, a cell provided herein stably expresses a light chain/light chain variable region and a heavy chain/heavy chain variable region which associate to form an antigen-binding region or an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-PC described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11 (1): 223-32), hypoxanthine-guanine phosphoribosyltransferase (Szybalska E H & Szybalski W (1962) PNAS 48 (12): 2026-2034) and adenine phosphoribosyltransferase (Lowy I et al., (1980) Cell 22 (3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77 (6): 3567-70; O'Hare K et al., (1981) PNAS 78:1527-31); gpt, which confers resistance to mycophenolic acid (Mulligan R C & Berg P (1981) PNAS 78 (4): 2072-6); neo, which confers resistance to the aminoglycoside G-418 (Wu G Y & Wu C H (1991) Biotherapy 3:87-95; Tolstoshev P (1993) Ann Rev Pharmacol Toxicol 32:573-596; Mulligan R C (1993) Science 260:926-932; and Morgan R A & Anderson W F (1993) Ann Rev Biochem 62:191-217; Nabel G J & Felgner P L (1993) Trends Biotechnol 11 (5): 211-5); and hygro, which confers resistance to hygromycin (Santerre R F et al., (1984) Gene 30 (1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al., (eds.), Current Protocols in Human Genetics, John Wiley & Sons, NY (1994); Colbère-Garapin F et al., (1981) J Mol Biol 150:1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the protein will also increase (Crouse G F et al., (1983) Mol Cell Biol 3:257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322:562-565; and Köhler G (1980) PNAS 77:2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10, or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. In certain embodiments, an isolated antibody is one that is substantially free of other antibodies with different antigenic specificities than the isolated antibody. For example, in certain embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Anti-PC antibodies or fragments thereof can be produced by any method known in the art for the synthesis of proteins or antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is prepared, expressed, created, or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an anti-PC antibody comprising culturing a cell or host cell described herein. In certain embodiments, the method is performed in vitro. In a certain aspect, provided herein is a method of making an anti-PC antibody comprising expressing (e.g., recombinantly expressing) the antibody using a cell or host cell described herein (e.g., a cell or a host cell comprising polynucleotides encoding an antibody described herein). In certain embodiments, the cell is an isolated cell. In certain embodiments, the exogenous polynucleotides have been introduced into the cell. In certain embodiments, the method further comprises the step of purifying the antibody obtained from the cell or host cell.

In certain embodiments, an antibody is produced by expressing in a cell a polynucleotide encoding the VH and VL of an antibody described herein under suitable conditions so that the polynucleotides are expressed and the antibody is produced. In another embodiment, an antibody is produced by expressing in a cell a polynucleotide encoding the heavy chain and light chain of an antibody described herein under suitable conditions so that the polynucleotides are expressed and the antibody is produced. In certain embodiments, an antibody is produced by expressing in a cell a first polynucleotide encoding the VH of an antibody described herein, and a second polynucleotide encoding the VL of an antibody described herein, under suitable conditions so that the polynucleotides are expressed and the antibody is produced. In certain embodiments, an antibody is produced by expressing in a cell a first polynucleotide encoding the heavy chain of an antibody described herein, and a second polynucleotide encoding the light chain of an antibody described herein, under suitable conditions so that the polynucleotides are expressed and the antibody is produced.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art, including the use of hybridoma, recombinant, and phage display technologies, or a combination thereof. For example, monoclonal antibodies can be produced using hybridoma techniques, including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to PC as determined, e.g., by ELISA or other antigen-binding or competitive binding assay known in the art, or in the examples provided herein. In certain embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256:495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding regions, each monovalent binding region capable of binding to an epitope on the antigen. Each monovalent binding region can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster, or macaque monkey, is immunized to elicit lymphocytes that produce or are capable of producing antibodies that will specifically bind to the protein (e.g., PC) used for immunization. Alternatively, lymphocytes may be immunized in vitro. Lymphocytes then are fused with myeloma cells using a suitable fusing agent, such as polyethylene glycol, to form a hybridoma cell (Goding J W (ed.), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., PC) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133:3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against PC. The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (ed.), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize PC, and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli, and the E. coli is infected with helper phage. Phage used in these methods are typically filamentous phage, including fd and M13, and the VH and VL domains are usually recombinantly fused to either the phage gene III or gene VIII. Phage expressing an antigen-binding region that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182:41-50; Ames R S et al., (1995) J Immunol Methods 184:177-186; Kettleborough C A et al., (1994) Eur J Immunol 24:952-958; Persic L et al., (1997) Gene 187:9-18; Burton D R & Barbas C F (1994) Advan Immunol 57:191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108, all of which are herein incorporated by reference in their entireties.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12 (6): 864-9; Sawai H et al., (1995) Am J Reprod Immunol 34:26-34; and Better M et al., (1988) *Science* 240:1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. Human kappa and lambda constant region sequences are known to those of skill in the art. Examples of human kappa and lambda constant region sequences are set forth in SEQ ID NOS: 688-693. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229:1202-7; Oi V T & Morrison S L (1986) BioTechniques 4:214-221; Gillies S D et al., (1989) J Immunol Methods 125:191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In certain embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA, and IgE, and any isotype, including IgG$_1$, IgG$_2$, IgG$_3$, and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28 (4/5): 489-498; Studnicka G M et al., (1994) Prot Engineering 7 (6): 805-814; and Roguska M A et al., (1994) PNAS 91:969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169:1119-25; Caldas C et al., (2000) Protein Eng. 13 (5): 353-60; Morea V et al., (2000) Methods 20 (3): 267-79; Baca M et al., (1997) J Biol Chem 272 (16): 10678-84; Roguska M A et al., (1996) Protein Eng 9 (10): 895 904; Couto J R et al., (1995) Cancer Res. 55 (23 Supp): 5973s-5977s; Couto J R et al., (1995) Cancer Res 55 (8): 1717-22; Sandhu J S (1994) Gene 150 (2): 409-10; and Pedersen J T et al., (1994) J Mol Biol 235 (3): 959-73, all of which are herein incorporated by reference in their entireties. See also, U.S. Application Publication No. US 2005/0042664 A1 (Feb. 24, 2005) and International Publication No. WO 2008/020079, which are herein incorporated by reference in their entireties.

Methods for making multispecific antibodies (e.g., bispecific antibodies) have been described, see, for example, U.S. Pat. Nos. 7,951,917; 7,183,076; 8,227,577; 5,837,242; 5,989,830; 5,869,620; 6,132,992; and 8,586,713, all of which are herein incorporated by reference in their entireties.

Bispecific, bivalent antibodies, and methods of making them, are described, for instance in U.S. Pat. Nos. 5,731,168, 5,807,706, 5,821,333, and U.S. Appl. Publ. Nos. 2003/

020734 and 2002/0155537; each of which is herein incorporated by reference in its entirety. Bispecific tetravalent antibodies, and methods of making them are described, for instance, in Int. Appl. Publ. Nos. WO 02/096948 and WO 00/44788, the disclosures of both of which are herein incorporated by reference in its entirety. See generally, Int. Appl. Publ. Nos. WO 93/17715, WO 92/08802, WO 91/00360, and WO 92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

A bispecific antibody as described herein can be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110 (13): 5145-5150. The DuoBody technology can be used to combine one half of a first monospecific antibody, or first antigen-binding region, containing two heavy and two light chains with one half of a second monospecific antibody, or second antigen-binding region, containing two heavy and two light chains. The resultant heterodimer contains one heavy chain and one light chain from the first antibody, or first antigen-binding region, paired with one heavy chain and one light chain from the second antibody, or second antigen-binding region. When both of the monospecific antibodies, or antigen-binding regions, recognize different epitopes on different antigens, the resultant heterodimer is a bispecific antibody.

The DuoBody technology requires that each of the monospecific antibodies, or antigen-binding regions includes a heavy chain constant region with a single point mutation in the CH3 domain. The point mutations allow for a stronger interaction between the CH3 domains in the resultant bispecific antibody than between the CH3 domains in either of the monospecific antibodies, or antigen-binding regions. The single point mutation in each monospecific antibody, or antigen-binding region, is at residue 366, 368, 370, 399, 405, 407, or 409, numbered according to the EU numbering system, in the CH3 domain of the heavy chain constant region, as described, e.g., in International Publication No. WO 2011/131746. Moreover, the single point mutation is located at a different residue in one monospecific antibody, or antigen-binding region, as compared to the other monospecific antibody, or antigen-binding region. For example, one monospecific antibody, or antigen-binding region, can comprise the mutation F405L (i.e., a mutation from phenylalanine to leucine at residue 405), while the other monospecific antibody, or antigen-binding region, can comprise the mutation K409R (i.e., a mutation from lysine to arginine at residue 409), numbered according to the EU numbering system. The heavy chain constant regions of the monospecific antibodies, or antigen-binding regions, can be an $IgG_1$, $IgG_2$, $IgG_3$, or $IgG_4$ isotype (e.g., a human $IgG_1$ isotype), and a bispecific antibody produced by the DuoBody technology can retain Fc-mediated effector functions.

Another method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the disclosure have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., $IgG_1$ or $IgG_3$) or different subclasses (e.g., $IgG_1$ and $IgG_3$, or $IgG_3$ and $IgG_4$).

Bispecific antibodies can, in some instances contain, $IgG_4$ and $IgG_1$, $IgG_4$ and $IgG_2$, $IgG_4$ and $IgG_3$, or $IgG_1$ and $IgG_3$ chain heterodimers. Such heterodimeric heavy chain antibodies can routinely be engineered by, for example, modifying selected amino acids forming the interface of the CH3 domains in human $IgG_4$ and the $IgG_1$ or $IgG_3$, so as to favor heterodimeric heavy chain formation.

In certain embodiments, an antibody described herein, which binds to the same epitope of PC as an anti-PC antibody described herein, is a human antibody. In certain embodiments, an antibody described herein, which competitively blocks (e.g., in a dose-dependent manner) any one of the antibodies described herein, from binding to PC, is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., PC). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, all of which are herein incorporated by reference in their entireties. Examples of mice capable of producing human antibodies include the Xeno-Mouse™ (Abgenix, Inc.; U.S. Pat. Nos. 6,075,181 and 6,150,184), the HuAb-Mouse™ (Medarex, Inc./Gen Pharm; U.S. Pat. Nos. 5,545,806 and 5,569,825), the TransChromo Mouse™ (Kirin) and the KM Mouse™ (Medarex/Kirin), all of which are herein incorporated by reference in their entireties.

Human antibodies that specifically bind to PC can be made by a variety of methods known in the art, including the phage display methods described above using antibody libraries derived from human immunoglobulin sequences. See also, U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., PC). Such methods are known and are described in the art, see, e.g., Shinmoto H et al., (2004) Cytotechnology 46:19-23; Naganawa Y et al., (2005) Human Antibodies 14:27-31, each of which is herein incorporated by reference in its entirety.

Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In certain embodiments, a kit comprises an antibody described herein, preferably purified antibody, in one or more containers. In a specific embodiment, kits described herein contain a substantially isolated PC antigen as a control. In another specific embodiment, the kits described herein further comprise a control antibody which does not react with PC antigen. In another specific embodiment, kits described herein contain one or more elements for detecting the binding of an antibody to an PC antigen (e.g., the antibody can be conjugated to a detectable substrate such as a fluorescent compound, an enzymatic substrate, a radioactive compound, or a luminescent compound, or a second antibody which recognizes the first antibody can be conjugated to a detectable substrate). In specific embodiments, a kit provided herein can include a recombinantly produced or chemically synthesized PC antigen. The PC antigen provided in the kit can also be attached to a solid support. In a more specific embodiment, the detecting means of the above-described kit includes a solid support to which an PC antigen is attached. Such a kit can also include a non-attached reporter-labeled anti-human antibody or anti-mouse/rat antibody. In this embodiment, binding of the antibody to the PC antigen can be detected by binding of the said reporter-labeled antibody. In certain embodiments, the present disclosure relates to the use of a kit of the present disclosure for in vitro assaying and/or detecting PC antigen in a biological sample.

EXAMPLES

The following examples are offered by way of illustration and not by way of limitation.

Example 1: Screening Summary

A multi-factor optimization platform was used for antibody optimization. The platform was designed to optimize for affinity, removal of liabilities, thermostability, species cross-reactivity, and selective activation.

E06 variable heavy (VH) and variable kappa (VK) CDR sequences were grafted onto 4 fully human VH germlines (VH1-46, VH3-15, VH3-23, VH5-51) and 4 fully human VK germlines (VK1-39, VK2-28, VK3-15, VK4-1) respectively. Of the sixteen combinations made, two were selected for platform library construction: E06_VK 1-39/VH 3-23 and E06_VK 4-1/VH 3-23. The individual VH and VK sequences are set forth in Table 2.

TABLE 2

Grafted VH and VK Sequences.

| | Sequence (CDR sequences underlined) | SEQ ID NO: |
|---|---|---|
| E06_VH3-23 | EVQLLESGGGLVQPGGSLRLSCAASGFTFSDFYMEWVRQAP GKGLEWVAASRNKANDYTTEYADSVKGRFTISRDNSKNTL YLQMNSLRAEDTAVYYCARDYYGSSYWYFDVWGQGTLVT VSS | 8 |
| E06_VK1-39 | DIQMTQSPSSLSASVGDRVTITCTASESLYSSKHKVHYLAW YQQKPGKAPKLLIYGASNRYIGVPSRFSGSGSGTDFTLTISSL QPEDFATYYCAQFYSYPLTFGQGTKVEIK | 685 |
| E06_VK4-1 | DIVMTQSPDSLAVSLGERATINCTASESLYSSKHKVHYLAW YQQKPGQPPKLLIYGASNRYIGVPDRFSGSGSGTDFTLTISSL QAEDVAVYYCAQFYSYPLTFGGGTKVEIK | 269 |

Phage display libraries of scFv reformatted framework grafts were designed based on structural and sequence analyses to retain CDR residues identified to exhibit key target binding interactions. The remaining CDR residues were used for guided 3-way sequence space exploration to maximize tolerability of human residues while limiting the potential impact on target binding. First, CDRH1, CDRH2, CDRL1, CDRL2, and CDRL3 were modified from parental CDR towards human germline CDRs with up to 4 changes per CDR. Second, CDRH1, CDRH2, CDRL1, CDRL2, and CDRL3 were modified from germline towards parental CDR residues with up to 4 changes. Third, all CDRs were subjected to single amino acid NNK walks omitting residue changes that would generate biochemical liabilities. E06 VK 1-39/VH 3-23 and VK 4-1/VH 3-23 scFv libraries were combined, resulting in a total size of $4 \times 10^9$ transformants (referred to as the "platform library").

Phosphocholine (PC) conjugated peptides were used for phage panning and scFv primary screening by ELISA. A summary of PC conjugated peptides used is set forth in Table 3.

TABLE 3

Phosphocholine (PC) Conjugated Peptides Used for Screening.

| Peptide # | Conjugation | Tag | Full Sequence |
|---|---|---|---|
| 1 | PC | Biotin | Biotin-AGGGGSGGGGSGGGGSAAA-[Tyr(PC)]-acid (SEQ ID NO: 686) |
| 2 | PC | — | AGGGGSGGGGSGGGGSAAA-[Tyr(PC)]-acid (SEQ ID NO: 686) |
| 4 | — | Biotin | Biotin-AGGGGSGGGGSGGGGSAAA-Tyr-acid (SEQ ID NO: 686) |
| 5 | PC | Biotin | Biotin-AEAAAKEAAAKEAAAKEAAAKAAA-[Tyr(PC)]-acid (SEQ ID NO: 687) |
| 6 | PC | — | AEAAAKEAAAKEAAAKEAAAKAAA-[Tyr(PC)]-acid (SEQ ID NO: 687) |
| 8 | — | Biotin | Biotin-AEAAAKEAAAKEAAAKEAAAKAAA-Tyr-acid (SEQ ID NO: 687) |

PC = p-diazophenyl phosphoryl choline

Phage-peptide complexes were captured on the biotin tag of the peptides with streptavidin coated beads. After washing, bound phage were eluted using triethylamine and titered to determine enrichment. After each round of panning, eluted phage were used to infected *E. coli* ER2738 for propagation of phage particles to be used in subsequent rounds of selections.

Single colonies from the Round 4 panning arms (380 colonies from each; 1140 colonies in total) were cultured and scFvs were Sanger sequenced. 736 unique sequences were re-arrayed onto 96-well plates and proceeded to primary screening by scFv ELISA on Peptides 1, 4, 5, and 8.

A total of 368 unique binders to Peptide 5 and/or Peptide 1 from the primary screen were re-arrayed and proceeded to secondary screening by ELISA (n=2) on Peptides 1, 4, 5, and 8, as well as BSA. A total of 257 unique scFvs were identified with good reproducibility between primary and secondary screening data, and between replicates. These 257 sequences bound specifically to at least one of Peptide 1 and Peptide 5, with no binding to Peptide 4, Peptide 8, or BSA (thresholds for positive OD450 were determined using average OD450 for negative controls (a PD-1 specific scFv)+ 3×SD: See Example 2 for method).

Example 2: scFv ELISA Summary

Periplasmic extract (PPE) containing scFv was generated by osmotic shock. Starter cultures (2×YT with 2% glucose, tetracycline (15 µg/mL) and carbenicillin (100 µg/mL), 700 µl/well in deep well plate) were inoculated with 5-10 µl of glycerol stock and grown over night at 30° C. and 700 rpm. The following day, expression cultures (2×YT with 0.1% glucose and carbenicillin (100 µg/mL), 1 ml/well in deep well plates) were inoculated with 30 µl starter culture and allowed to grow to OD600 0.5 at 37° C. and 700 rpm. Cultures were induced with 1 mM IPTG and grown for 6 hours at 25° C. and 700 rpm.

After 6 hours, plates were centrifuged to pellet bacteria and stored overnight at −20° C. The next day, pellets were thawed and resuspended in 80 µl Periplasmic Extraction Buffer with protease inhibitors and put on a shaker for 10 minutes at 4° C. and 500 rpm. After 10 minutes, 240 µl water and protease inhibitor were added to each well and incubated for 1 hour at 4° C. shaking at 500 rpm. Plates were then centrifuged at 4300×g for 10 min at 4° C. Supernatants were passed through a filter plate and stored at −80° C.

For ELISA analysis of scFv binding, 96-well polystyrene plates were coated with Peptide 1, 4, 5, 8 or 100 µL BSA (10 µg/mL) in PBS at 4° C. overnight. Plates were washed three times with PBS-Tween and blocked with 100 µL 1% BSA-TBS for 1 hour at room temperature. 96-well streptavidin coated plates were coated with 100 µL biotinylated PC-peptides (1 µg/mL) in PBS for 1 hour at room temperature.

All plates were washed three times with PBS-Tween before 40 µL aliquots of PPE were added to assay plates along with 50 µL 10% BSA, and plates were incubated for 1 hour at room temperature. After washing, 100 µL HRP conjugated anti-V5 in 5% BSA was added, and plates were incubated at room temperature for 30 mins. Plates were washed and 100 µL TMB substrate was added. Color was left to develop at room temperature before the reaction was stopped with 100 µL 1N HCl. The amount of scFv bound to each well was quantitated from absorbance measurement at 450 nm (OD450). Binding data for the 257 unique scFvs identified in Example 1 are summarized in Table 4.

TABLE 4 scFv ELISA Data.

| Binder | SEQ ID NO: VH | VL | OD450 Peptide 1 | Peptide 4 | Peptide 5 | Peptide 8 | BSA |
|---|---|---|---|---|---|---|---|
| PcOxP_DB01_A06 | 1 | 181 | 0.74 | 0.06 | 1.18 | 0.06 | 0.10 |
| PcOxP_DB01_A12 | 2 | 182 | 0.29 | 0.06 | 1.04 | 0.05 | 0.09 |
| PcOxP_DB01_B01 | 3 | 183 | 0.87 | 0.07 | 0.90 | 0.05 | 0.10 |
| PcOxP_DB01_B04 | 4 | 184 | 0.57 | 0.06 | 1.02 | 0.05 | 0.08 |
| PcOxP_DB01_B05 | 5 | 185 | 0.23 | 0.05 | 0.74 | 0.05 | 0.10 |
| PcOxP_DB01_B07 | 1 | 184 | 1.07 | 0.06 | 1.36 | 0.05 | 0.11 |
| PcOxP_DB01_B08 | 6 | 184 | 0.41 | 0.06 | 0.89 | 0.05 | 0.10 |
| PcOxP_DB01_B09 | 1 | 186 | 1.00 | 0.05 | 1.42 | 0.05 | 0.10 |
| PcOxP_DB01_B11 | 7 | 187 | 1.11 | 0.05 | 1.32 | 0.04 | 0.09 |
| PcOxP_DB01_C01 | 8 | 188 | 0.71 | 0.06 | 1.13 | 0.05 | 0.11 |
| PcOxP_DB01_C03 | 9 | 189 | 0.98 | 0.06 | 1.37 | 0.05 | 0.10 |
| PcOxP_DB01_C04 | 10 | 190 | 1.38 | 0.05 | 1.42 | 0.05 | 0.08 |
| PcOxP_DB01_C05 | 4 | 191 | 0.79 | 0.06 | 1.11 | 0.06 | 0.11 |
| PcOxP_DB01_C06 | 11 | 192 | 1.18 | 0.05 | 1.31 | 0.05 | 0.08 |
| PcOxP_DB01_C08 | 12 | 193 | 0.38 | 0.06 | 0.79 | 0.05 | 0.10 |
| PcOxP_DB01_C12 | 13 | 194 | 0.88 | 0.05 | 1.18 | 0.05 | 0.08 |
| PcOxP_DB01_D02 | 14 | 195 | 0.56 | 0.06 | 1.27 | 0.05 | 0.09 |
| PcOxP_DB01_D05 | 15 | 196 | 0.87 | 0.06 | 1.56 | 0.05 | 0.10 |
| PcOxP_DB01_D08 | 16 | 184 | 0.58 | 0.05 | 1.08 | 0.05 | 0.08 |
| PcOxP_DB01_D09 | 17 | 197 | 0.27 | 0.05 | 0.66 | 0.05 | 0.07 |
| PcOxP_DB01_E04 | 18 | 198 | 0.55 | 0.05 | 1.12 | 0.04 | 0.07 |
| PcOxP_DB01_E05 | 1 | 199 | 0.95 | 0.06 | 1.39 | 0.06 | 0.11 |
| PcOxP_DB01_E06 | 19 | 200 | 0.68 | 0.05 | 1.05 | 0.05 | 0.09 |
| PcOxP_DB01_E11 | 20 | 201 | 0.62 | 0.05 | 0.73 | 0.06 | 0.09 |
| PcOxP_DB01_F04 | 21 | 202 | 0.36 | 0.05 | 0.57 | 0.05 | 0.09 |
| PcOxP_DB01_F10 | 22 | 203 | 0.68 | 0.05 | 0.98 | 0.05 | 0.09 |
| PcOxP_DB01_G01 | 23 | 204 | 0.58 | 0.06 | 1.33 | 0.05 | 0.09 |
| PcOxP_DB01_G09 | 24 | 205 | 0.92 | 0.06 | 1.40 | 0.05 | 0.11 |
| PcOxP_DB01_G11 | 25 | 184 | 0.99 | 0.06 | 1.32 | 0.06 | 0.09 |
| PcOxP_DB01_G12 | 4 | 206 | 0.75 | 0.07 | 1.33 | 0.06 | 0.09 |
| PcOxP_DB01_H04 | 26 | 207 | 2.01 | 0.07 | 1.92 | 0.07 | 0.11 |
| PcOxP_DB01_H08 | 27 | 208 | 0.56 | 0.06 | 0.85 | 0.06 | 0.09 |
| PcOxP_DB01_H10 | 28 | 209 | 0.60 | 0.06 | 1.39 | 0.06 | 0.08 |
| PcOxP_DB02_A06 | 9 | 210 | 1.12 | 0.05 | 1.07 | 0.05 | 0.10 |
| PcOxP_DB02_A09 | 29 | 211 | 0.98 | 0.05 | 1.30 | 0.04 | 0.11 |
| PcOxP_DB02_A10 | 30 | 212 | 0.42 | 0.05 | 0.90 | 0.04 | 0.11 |
| PcOxP_DB02_A11 | 31 | 213 | 0.64 | 0.04 | 0.89 | 0.04 | 0.09 |
| PcOxP_DB02_A12 | 32 | 214 | 0.20 | 0.05 | 0.27 | 0.06 | 0.06 |
| PcOxP_DB02_B02 | 33 | 215 | 0.49 | 0.05 | 0.98 | 0.05 | 0.11 |
| PcOxP_DB02_B06 | 34 | 216 | 0.35 | 0.07 | 0.79 | 0.04 | 0.11 |
| PcOxP_DB02_B10 | 17 | 217 | 0.67 | 0.04 | 1.03 | 0.04 | 0.08 |
| PcOxP_DB02_B12 | 1 | 218 | 2.33 | 0.05 | 1.34 | 0.05 | 0.10 |
| PcOxP_DB02_C01 | 35 | 184 | 1.03 | 0.06 | 1.47 | 0.05 | 0.10 |
| PcOxP_DB02_C02 | 36 | 184 | 0.35 | 0.05 | 0.62 | 0.05 | 0.10 |
| PcOxP_DB02_C06 | 35 | 219 | 0.54 | 0.05 | 1.03 | 0.05 | 0.11 |
| PcOxP_DB02_C09 | 35 | 220 | 0.69 | 0.05 | 1.01 | 0.04 | 0.10 |
| PcOxP_DB02_C11 | 37 | 184 | 0.12 | 0.05 | 0.24 | 0.04 | 0.10 |
| PcOxP_DB02_D01 | 38 | 221 | 0.31 | 0.05 | 0.35 | 0.05 | 0.09 |
| PcOxP_DB02_D09 | 39 | 222 | 0.16 | 0.05 | 0.44 | 0.04 | 0.11 |
| PcOxP_DB02_D10 | 9 | 223 | 0.69 | 0.05 | 1.01 | 0.04 | 0.10 |
| PcOxP_DB02_E01 | 9 | 224 | 0.43 | 0.05 | 0.63 | 0.10 | 0.11 |
| PcOxP_DB02_E06 | 40 | 184 | 0.06 | 0.04 | 0.08 | 0.04 | 0.10 |
| PcOxP_DB02_E10 | 41 | 225 | 0.52 | 0.04 | 0.79 | 0.04 | 0.09 |
| PcOxP_DB02_F02 | 8 | 226 | 0.37 | 0.05 | 0.60 | 0.05 | 0.11 |
| PcOxP_DB02_F07 | 42 | 227 | 0.43 | 0.05 | 0.91 | 0.05 | 0.10 |
| PcOxP_DB02_F12 | 35 | 228 | 0.50 | 0.04 | 0.81 | 0.04 | 0.07 |
| PcOxP_DB02_G06 | 43 | 229 | 0.43 | 0.06 | 0.87 | 0.05 | 0.08 |
| PcOxP_DB02_G07 | 4 | 230 | 0.52 | 0.05 | 0.99 | 0.09 | 0.10 |
| PcOxP_DB02_G09 | 9 | 231 | 0.35 | 0.05 | 0.71 | 0.04 | 0.10 |
| PcOxP_DB02_H03 | 8 | 232 | 0.27 | 0.05 | 0.82 | 0.05 | 0.08 |
| PcOxP_DB02_H10 | 1 | 233 | 1.43 | 0.05 | 1.39 | 0.05 | 0.08 |
| PcOxP_DB03_A03 | 8 | 234 | 0.54 | 0.06 | 0.81 | 0.06 | 0.09 |
| PcOxP_DB03_A08 | 44 | 184 | 0.67 | 0.06 | 0.71 | 0.05 | 0.11 |
| PcOxP_DB03_A09 | 1 | 235 | 1.02 | 0.05 | 1.09 | 0.05 | 0.09 |
| PcOxP_DB03_A11 | 45 | 236 | 1.12 | 0.05 | 1.08 | 0.05 | 0.08 |
| PcOxP_DB03_B02 | 30 | 237 | 2.02 | 0.05 | 1.64 | 0.05 | 0.07 |
| PcOxP_DB03_C03 | 46 | 184 | 1.36 | 0.05 | 1.66 | 0.05 | 0.09 |
| PcOxP_DB03_C06 | 47 | 238 | 0.64 | 0.05 | 0.61 | 0.05 | 0.07 |
| PcOxP_DB03_C11 | 48 | 239 | 1.14 | 0.05 | 0.75 | 0.04 | 0.07 |
| PcOxP_DB03_C12 | 1 | 230 | 2.74 | 0.05 | 1.77 | 0.05 | 0.09 |
| PcOxP_DB03_D01 | 49 | 190 | 2.51 | 0.05 | 1.60 | 0.05 | 0.08 |
| PcOxP_DB03_D07 | 44 | 240 | 0.75 | 0.06 | 0.95 | 0.05 | 0.12 |
| PcOxP_DB03_D08 | 50 | 184 | 0.54 | 0.05 | 0.57 | 0.05 | 0.10 |
| PcOxP_DB03_D11 | 51 | 241 | 0.50 | 0.06 | 0.66 | 0.05 | 0.08 |
| PcOxP_DB03_E01 | 52 | 242 | 2.50 | 0.06 | 2.11 | 0.06 | 0.09 |
| PcOxP_DB03_E02 | 53 | 243 | 2.00 | 0.06 | 1.49 | 0.05 | 0.11 |
| PcOxP_DB03_E07 | 54 | 184 | 0.78 | 0.05 | 0.86 | 0.05 | 0.08 |
| PcOxP_DB03_E08 | 55 | 244 | 0.87 | 0.05 | 0.92 | 0.05 | 0.09 |
| PcOxP_DB03_E09 | 56 | 245 | 0.39 | 0.05 | 0.72 | 0.05 | 0.08 |
| PcOxP_DB03_F01 | 57 | 246 | 0.58 | 0.05 | 0.80 | 0.05 | 0.09 |
| PcOxP_DB03_F10 | 58 | 247 | 0.65 | 0.05 | 0.85 | 0.07 | 0.09 |
| PcOxP_DB03_G02 | 59 | 248 | 1.33 | 0.04 | 1.59 | 0.05 | 0.07 |
| PcOxP_DB03_G03 | 60 | 249 | 1.57 | 0.05 | 1.80 | 0.08 | 0.08 |
| PcOxP_DB03_G06 | 8 | 250 | 2.48 | 0.06 | 2.01 | 0.06 | 0.10 |
| PcOxP_DB03_G07 | 61 | 184 | 2.18 | 0.06 | 1.67 | 0.06 | 0.10 |
| PcOxP_DB03_G10 | 35 | 251 | 1.80 | 0.05 | 1.21 | 0.05 | 0.11 |
| PcOxP_DB03_H03 | 62 | 252 | 0.27 | 0.07 | 1.32 | 0.07 | 0.12 |
| PcOxP_DB03_H07 | 1 | 253 | 1.91 | 0.05 | 1.64 | 0.05 | 0.08 |
| PcOxP_DB03_H08 | 63 | 254 | 0.91 | 0.06 | 1.18 | 0.06 | 0.12 |
| PcOxP_DB03_H09 | 64 | 181 | 0.93 | 0.06 | 1.25 | 0.06 | 0.11 |
| PcOxP_DB04_A07 | 65 | 255 | 1.54 | 0.05 | 2.11 | 0.05 | 0.09 |
| PcOxP_DB04_A09 | 66 | 256 | 1.16 | 0.06 | 1.96 | 0.06 | 0.12 |
| PcOxP_DB04_A10 | 67 | 257 | 0.74 | 0.05 | 1.61 | 0.06 | 0.11 |
| PcOxP_DB04_A12 | 68 | 198 | 0.71 | 0.07 | 1.38 | 0.06 | 0.12 |
| PcOxP_DB04_B06 | 35 | 258 | 0.66 | 0.06 | 1.06 | 0.06 | 0.10 |
| PcOxP_DB04_B08 | 69 | 259 | 1.33 | 0.06 | 1.56 | 0.05 | 0.11 |
| PcOxP_DB04_C03 | 70 | 260 | 1.34 | 0.06 | 1.87 | 0.06 | 0.10 |
| PcOxP_DB04_C08 | 71 | 261 | 0.69 | 0.05 | 1.07 | 0.06 | 0.08 |
| PcOxP_DB04_D08 | 72 | 262 | 1.60 | 0.07 | 1.96 | 0.07 | 0.12 |
| PcOxP_DB04_F06 | 73 | 263 | 0.75 | 0.06 | 1.30 | 0.06 | 0.10 |
| PcOxP_DB04_F11 | 74 | 264 | 0.58 | 0.07 | 1.27 | 0.06 | 0.10 |
| PcOxP_DB04_G06 | 75 | 265 | 1.03 | 0.06 | 1.12 | 0.07 | 0.11 |
| PcOxP_DB04_H03 | 76 | 266 | 0.80 | 0.07 | 1.05 | 0.08 | 0.10 |
| PcOxP_DB04_H07 | 77 | 267 | 0.58 | 0.06 | 1.02 | 0.05 | 0.09 |
| PcOxP_DB04_H08 | 4 | 205 | 0.85 | 0.07 | 1.42 | 0.06 | 0.09 |
| PcOxP_DB04_H10 | 78 | 268 | 0.54 | 0.08 | 1.01 | 0.07 | 0.10 |
| PcOxP_DB01_A03 | 1 | 269 | 0.86 | 0.05 | 1.38 | 0.04 | 0.07 |
| PcOxP_DB01_A04 | 27 | 269 | 0.31 | 0.04 | 0.75 | 0.04 | 0.07 |
| PcOxP_DB01_A05 | 79 | 269 | 0.83 | 0.04 | 1.28 | 0.04 | 0.06 |
| PcOxP_DB01_A08 | 80 | 270 | 0.16 | 0.05 | 1.12 | 0.05 | 0.09 |
| PcOxP_DB01_B02 | 81 | 269 | 0.68 | 0.06 | 1.41 | 0.05 | 0.09 |
| PcOxP_DB01_B03 | 22 | 269 | 0.82 | 0.05 | 1.25 | 0.05 | 0.08 |
| PcOxP_DB01_B06 | 82 | 269 | 0.79 | 0.05 | 1.45 | 0.05 | 0.08 |
| PcOxP_DB01_B10 | 83 | 271 | 0.52 | 0.05 | 1.11 | 0.05 | 0.08 |
| PcOxP_DB01_B12 | 84 | 272 | 0.56 | 0.06 | 1.19 | 0.05 | 0.09 |
| PcOxP_DB01_C07 | 1 | 273 | 0.53 | 0.04 | 1.10 | 0.04 | 0.05 |
| PcOxP_DB01_C09 | 8 | 274 | 0.27 | 0.05 | 0.94 | 0.05 | 0.07 |
| PcOxP_DB01_C10 | 8 | 275 | 0.13 | 0.04 | 0.53 | 0.04 | 0.07 |
| PcOxP_DB01_D01 | 22 | 276 | 0.85 | 0.05 | 1.12 | 0.04 | 0.06 |
| PcOxP_DB01_D04 | 8 | 277 | 0.45 | 0.08 | 0.87 | 0.06 | 0.07 |
| PcOxP_DB01_D06 | 85 | 278 | 0.41 | 0.04 | 0.69 | 0.04 | 0.06 |
| PcOxP_DB01_D07 | 86 | 279 | 0.14 | 0.04 | 0.60 | 0.04 | 0.05 |
| PcOxP_DB01_D10 | 87 | 269 | 0.15 | 0.05 | 0.44 | 0.04 | 0.06 |
| PcOxP_DB01_D11 | 88 | 280 | 1.37 | 0.06 | 2.09 | 0.05 | 0.08 |
| PcOxP_DB01_D12 | 89 | 269 | 0.85 | 0.05 | 1.48 | 0.05 | 0.06 |
| PcOxP_DB01_E01 | 60 | 281 | 0.75 | 0.05 | 1.48 | 0.04 | 0.05 |
| PcOxP_DB01_E02 | 90 | 269 | 0.46 | 0.05 | 1.02 | 0.05 | 0.07 |
| PcOxP_DB01_E03 | 91 | 282 | 0.86 | 0.05 | 1.54 | 0.05 | 0.08 |
| PcOxP_DB01_E07 | 22 | 283 | 0.87 | 0.05 | 1.51 | 0.05 | 0.07 |
| PcOxP_DB01_E08 | 92 | 269 | 0.47 | 0.05 | 0.82 | 0.04 | 0.06 |
| PcOxP_DB01_E09 | 93 | 284 | 0.77 | 0.04 | 1.26 | 0.04 | 0.06 |
| PcOxP_DB01_E10 | 94 | 285 | 0.60 | 0.07 | 1.11 | 0.07 | 0.11 |
| PcOxP_DB01_F01 | 95 | 286 | 0.60 | 0.05 | 1.78 | 0.05 | 0.08 |
| PcOxP_DB01_F03 | 96 | 269 | 0.80 | 0.07 | 1.41 | 0.08 | 0.08 |
| PcOxP_DB01_F06 | 73 | 287 | 0.12 | 0.05 | 0.53 | 0.04 | 0.07 |
| PcOxP_DB01_F07 | 97 | 288 | 0.31 | 0.04 | 0.81 | 0.04 | 0.06 |
| PcOxP_DB01_F08 | 68 | 289 | 0.52 | 0.04 | 1.22 | 0.04 | 0.06 |
| PcOxP_DB01_F11 | 98 | 269 | 1.55 | 0.07 | 1.92 | 0.05 | 0.07 |
| PcOxP_DB01_F12 | 99 | 290 | 0.76 | 0.05 | 1.43 | 0.05 | 0.06 |
| PcOxP_DB01_G02 | 100 | 291 | 0.82 | 0.05 | 1.20 | 0.04 | 0.06 |
| PcOxP_DB01_G03 | 4 | 292 | 0.43 | 0.05 | 0.94 | 0.05 | 0.07 |
| PcOxP_DB01_G04 | 4 | 289 | 0.56 | 0.05 | 1.01 | 0.07 | 0.07 |
| PcOxP_DB01_G05 | 101 | 284 | 0.69 | 0.05 | 1.24 | 0.05 | 0.08 |
| PcOxP_DB01_G06 | 66 | 289 | 0.73 | 0.05 | 1.32 | 0.04 | 0.06 |

TABLE 4-continued scFv ELISA Data.

| Binder | SEQ ID NO: VH | VL | Peptide 1 | Peptide 4 | Peptide 5 | Peptide 8 | BSA |
|---|---|---|---|---|---|---|---|
| PcOxP_DB01_G07 | 89 | 293 | 0.46 | 0.05 | 1.20 | 0.04 | 0.07 |
| PcOxP_DB01_G10 | 102 | 294 | 0.71 | 0.05 | 1.52 | 0.05 | 0.10 |
| PcOxP_DB01_H01 | 103 | 269 | 0.82 | 0.07 | 1.23 | 0.06 | 0.09 |
| PcOxP_DB01_H02 | 22 | 295 | 0.74 | 0.07 | 1.10 | 0.06 | 0.10 |
| PcOxP_DB01_H03 | 104 | 296 | 0.46 | 0.07 | 1.29 | 0.06 | 0.10 |
| PcOxP_DB01_H06 | 105 | 297 | 0.96 | 0.05 | 1.79 | 0.07 | 0.11 |
| PcOxP_DB01_H07 | 106 | 270 | 0.10 | 0.05 | 0.92 | 0.05 | 0.07 |
| PcOxP_DB01_H09 | 107 | 269 | 0.06 | 0.09 | 0.09 | 0.04 | 0.09 |
| PcOxP_DB02_A04 | 67 | 269 | 0.33 | 0.04 | 0.82 | 0.04 | 0.09 |
| PcOxP_DB02_A05 | 62 | 298 | 0.99 | 0.05 | 1.24 | 0.04 | 0.07 |
| PcOxP_DB02_B04 | 66 | 269 | 0.75 | 0.05 | 1.32 | 0.04 | 0.08 |
| PcOxP_DB02_B07 | 108 | 299 | 0.40 | 0.04 | 0.77 | 0.04 | 0.06 |
| PcOxP_DB02_B09 | 109 | 300 | 0.27 | 0.04 | 0.83 | 0.04 | 0.07 |
| PcOxP_DB02_C03 | 110 | 301 | 0.54 | 0.05 | 0.61 | 0.05 | 0.10 |
| PcOxP_DB02_C04 | 111 | 302 | 0.37 | 0.05 | 0.75 | 0.05 | 0.08 |
| PcOxP_DB02_C05 | 112 | 269 | 0.64 | 0.04 | 0.92 | 0.04 | 0.06 |
| PcOxP_DB02_C08 | 113 | 303 | 0.22 | 0.06 | 0.39 | 0.04 | 0.06 |
| PcOxP_DB02_C10 | 1 | 304 | 0.44 | 0.05 | 0.92 | 0.04 | 0.06 |
| PcOxP_DB02_C12 | 72 | 305 | 0.97 | 0.04 | 1.58 | 0.04 | 0.07 |
| PcOxP_DB02_D02 | 114 | 306 | 0.16 | 0.04 | 0.27 | 0.04 | 0.05 |
| PcOxP_DB02_D03 | 115 | 307 | 0.42 | 0.04 | 0.71 | 0.04 | 0.08 |
| PcOxP_DB02_E02 | 116 | 269 | 0.09 | 0.04 | 0.34 | 0.05 | 0.06 |
| PcOxP_DB02_E03 | 117 | 308 | 0.39 | 0.04 | 0.75 | 0.05 | 0.08 |
| PcOxP_DB02_E08 | 118 | 269 | 0.24 | 0.04 | 0.49 | 0.04 | 0.07 |
| PcOxP_DB02_E09 | 110 | 309 | 0.56 | 0.04 | 0.74 | 0.04 | 0.07 |
| PcOxP_DB02_E11 | 119 | 310 | 0.23 | 0.04 | 0.76 | 0.04 | 0.06 |
| PcOxP_DB02_E12 | 120 | 311 | 0.26 | 0.05 | 0.58 | 0.06 | 0.06 |
| PcOxP_DB02_F04 | 121 | 269 | 0.47 | 0.04 | 0.74 | 0.05 | 0.09 |
| PcOxP_DB02_F06 | 122 | 312 | 0.16 | 0.04 | 0.45 | 0.04 | 0.06 |
| PcOxP_DB02_F09 | 123 | 289 | 0.39 | 0.04 | 0.93 | 0.04 | 0.08 |
| PcOxP_DB02_F10 | 9 | 313 | 0.51 | 0.05 | 1.20 | 0.04 | 0.09 |
| PcOxP_DB02_F11 | 124 | 314 | 0.23 | 0.04 | 0.66 | 0.04 | 0.08 |
| PcOxP_DB02_G02 | 120 | 289 | 1.01 | 0.04 | 1.13 | 0.04 | 0.06 |
| PcOxP_DB02_G03 | 125 | 315 | 0.06 | 0.05 | 0.10 | 0.05 | 0.06 |
| PcOxP_DB02_G04 | 110 | 316 | 0.32 | 0.05 | 0.70 | 0.05 | 0.11 |
| PcOxP_DB02_G05 | 126 | 317 | 1.49 | 0.05 | 1.80 | 0.07 | 0.11 |
| PcOxP_DB02_H02 | 127 | 318 | 0.07 | 0.04 | 0.19 | 0.06 | 0.06 |
| PcOxP_DB02_H04 | 49 | 319 | 0.22 | 0.05 | 0.20 | 0.04 | 0.06 |
| PcOxP_DB02_H05 | 128 | 320 | 0.20 | 0.04 | 0.44 | 0.04 | 0.09 |
| PcOxP_DB02_H06 | 9 | 321 | 0.92 | 0.05 | 1.04 | 0.05 | 0.07 |
| PcOxP_DB02_H07 | 22 | 322 | 0.56 | 0.04 | 0.88 | 0.05 | 0.07 |
| PcOxP_DB02_H08 | 129 | 323 | 0.40 | 0.04 | 1.34 | 0.06 | 0.07 |
| PcOxP_DB02_H09 | 130 | 269 | 0.25 | 0.04 | 0.58 | 0.04 | 0.07 |
| PcOxP_DB03_A04 | 131 | 324 | 0.19 | 0.04 | 0.47 | 0.04 | 0.06 |
| PcOxP_DB03_A05 | 132 | 325 | 0.93 | 0.04 | 0.78 | 0.04 | 0.06 |
| PcOxP_DB03_A06 | 133 | 326 | 0.99 | 0.05 | 1.07 | 0.05 | 0.08 |
| PcOxP_DB03_A07 | 134 | 327 | 0.94 | 0.04 | 1.01 | 0.04 | 0.06 |
| PcOxP_DB03_A10 | 53 | 328 | 0.60 | 0.04 | 0.54 | 0.04 | 0.06 |
| PcOxP_DB03_A12 | 135 | 272 | 2.28 | 0.06 | 1.67 | 0.05 | 0.07 |
| PcOxP_DB03_B01 | 136 | 329 | 0.21 | 0.04 | 0.64 | 0.04 | 0.06 |
| PcOxP_DB03_B03 | 4 | 301 | 1.12 | 0.04 | 1.10 | 0.04 | 0.07 |
| PcOxP_DB03_B06 | 137 | 330 | 0.68 | 0.04 | 1.01 | 0.05 | 0.06 |
| PcOxP_DB03_B07 | 138 | 269 | 0.66 | 0.06 | 0.81 | 0.05 | 0.12 |
| PcOxP_DB03_B08 | 1 | 284 | 2.63 | 0.05 | 1.95 | 0.04 | 0.07 |
| PcOxP_DB03_B09 | 22 | 331 | 1.09 | 0.05 | 0.89 | 0.05 | 0.08 |
| PcOxP_DB03_B10 | 139 | 269 | 0.41 | 0.04 | 0.71 | 0.04 | 0.07 |
| PcOxP_DB03_B11 | 140 | 332 | 0.50 | 0.05 | 0.72 | 0.05 | 0.07 |
| PcOxP_DB03_B12 | 141 | 269 | 1.21 | 0.05 | 0.85 | 0.05 | 0.06 |
| PcOxP_DB03_C01 | 142 | 333 | 0.84 | 0.05 | 1.47 | 0.05 | 0.08 |
| PcOxP_DB03_C04 | 143 | 334 | 2.11 | 0.04 | 1.72 | 0.05 | 0.07 |
| PcOxP_DB03_C08 | 144 | 335 | 0.98 | 0.05 | 0.90 | 0.05 | 0.06 |
| PcOxP_DB03_C10 | 101 | 298 | 1.10 | 0.05 | 1.10 | 0.04 | 0.07 |
| PcOxP_DB03_D02 | 1 | 336 | 0.67 | 0.05 | 1.37 | 0.04 | 0.09 |
| PcOxP_DB03_D03 | 145 | 269 | 0.73 | 0.04 | 1.11 | 0.04 | 0.10 |
| PcOxP_DB03_D10 | 146 | 337 | 1.19 | 0.05 | 1.41 | 0.06 | 0.06 |
| PcOxP_DB03_D12 | 147 | 269 | 0.20 | 0.04 | 0.30 | 0.04 | 0.06 |
| PcOxP_DB03_E03 | 17 | 338 | 0.27 | 0.04 | 0.79 | 0.04 | 0.05 |
| PcOxP_DB03_E04 | 22 | 320 | 0.96 | 0.06 | 1.20 | 0.04 | 0.08 |
| PcOxP_DB03_E11 | 4 | 339 | 1.40 | 0.05 | 1.58 | 0.05 | 0.07 |
| PcOxP_DB03_E12 | 148 | 340 | 0.57 | 0.06 | 0.88 | 0.06 | 0.06 |
| PcOxP_DB03_F02 | 149 | 341 | 1.56 | 0.05 | 1.68 | 0.05 | 0.07 |
| PcOxP_DB03_F03 | 150 | 342 | 1.13 | 0.05 | 1.93 | 0.05 | 0.08 |
| PcOxP_DB03_F05 | 151 | 343 | 0.73 | 0.05 | 1.04 | 0.04 | 0.06 |
| PcOxP_DB03_F07 | 152 | 344 | 0.53 | 0.05 | 1.19 | 0.05 | 0.08 |
| PcOxP_DB03_F09 | 94 | 289 | 0.72 | 0.05 | 1.12 | 0.05 | 0.08 |
| PcOxP_DB03_F11 | 153 | 345 | 1.47 | 0.06 | 1.43 | 0.06 | 0.12 |
| PcOxP_DB03_G01 | 154 | 346 | 0.66 | 0.05 | 1.19 | 0.05 | 0.09 |
| PcOxP_DB03_G09 | 155 | 347 | 0.74 | 0.05 | 1.07 | 0.05 | 0.07 |
| PcOxP_DB03_G11 | 22 | 348 | 0.26 | 0.05 | 0.72 | 0.05 | 0.10 |
| PcOxP_DB03_G12 | 89 | 282 | 1.57 | 0.06 | 1.91 | 0.05 | 0.08 |
| PcOxP_DB03_H02 | 156 | 349 | 1.07 | 0.05 | 1.69 | 0.04 | 0.05 |
| PcOxP_DB03_H10 | 157 | 296 | 0.24 | 0.04 | 0.39 | 0.07 | 0.05 |
| PcOxP_DB04_A04 | 158 | 350 | 1.09 | 0.08 | 1.90 | 0.08 | 0.11 |
| PcOxP_DB04_A05 | 159 | 329 | 0.72 | 0.04 | 1.29 | 0.04 | 0.06 |
| PcOxP_DB04_A11 | 24 | 351 | 0.64 | 0.07 | 1.60 | 0.08 | 0.10 |
| PcOxP_DB04_B01 | 160 | 352 | 0.45 | 0.05 | 0.78 | 0.05 | 0.06 |
| PcOxP_DB04_B07 | 161 | 269 | 0.93 | 0.06 | 1.33 | 0.05 | 0.09 |
| PcOxP_DB04_B10 | 162 | 353 | 1.05 | 0.05 | 1.56 | 0.04 | 0.06 |
| PcOxP_DB04_B11 | 163 | 269 | 0.26 | 0.05 | 0.31 | 0.05 | 0.08 |
| PcOxP_DB04_B12 | 1 | 354 | 0.13 | 0.04 | 0.34 | 0.04 | 0.09 |
| PcOxP_DB04_C09 | 164 | 355 | 0.55 | 0.07 | 1.21 | 0.06 | 0.11 |
| PcOxP_DB04_C10 | 165 | 269 | 0.54 | 0.06 | 1.03 | 0.05 | 0.08 |
| PcOxP_DB04_C11 | 1 | 356 | 0.81 | 0.05 | 1.34 | 0.04 | 0.07 |
| PcOxP_DB04_D01 | 166 | 357 | 1.23 | 0.06 | 1.66 | 0.06 | 0.07 |
| PcOxP_DB04_D05 | 167 | 358 | 0.87 | 0.05 | 1.27 | 0.06 | 0.08 |
| PcOxP_DB04_D07 | 110 | 334 | 1.02 | 0.05 | 1.05 | 0.05 | 0.08 |
| PcOxP_DB04_D09 | 87 | 359 | 0.41 | 0.05 | 0.83 | 0.08 | 0.06 |
| PcOxP_DB04_D10 | 168 | 360 | 1.14 | 0.05 | 1.35 | 0.05 | 0.07 |
| PcOxP_DB04_D12 | 169 | 269 | 0.64 | 0.06 | 1.03 | 0.05 | 0.08 |
| PcOxP_DB04_E05 | 170 | 269 | 0.67 | 0.06 | 1.03 | 0.05 | 0.09 |
| PcOxP_DB04_E06 | 171 | 269 | 1.04 | 0.04 | 1.59 | 0.05 | 0.07 |
| PcOxP_DB04_E08 | 172 | 361 | 1.39 | 0.06 | 2.01 | 0.05 | 0.09 |
| PcOxP_DB04_E12 | 8 | 362 | 1.03 | 0.05 | 1.39 | 0.05 | 0.07 |
| PcOxP_DB04_F01 | 173 | 304 | 0.56 | 0.07 | 0.85 | 0.07 | 0.09 |
| PcOxP_DB04_F03 | 174 | 269 | 0.58 | 0.06 | 0.87 | 0.05 | 0.10 |
| PcOxP_DB04_F05 | 1 | 363 | 0.76 | 0.06 | 0.97 | 0.05 | 0.07 |
| PcOxP_DB04_G01 | 175 | 364 | 0.63 | 0.07 | 1.39 | 0.09 | 0.09 |
| PcOxP_DB04_G03 | 176 | 365 | 0.19 | 0.04 | 0.40 | 0.05 | 0.07 |
| PcOxP_DB04_G05 | 177 | 269 | 1.20 | 0.05 | 1.67 | 0.05 | 0.07 |
| PcOxP_DB04_G08 | 178 | 366 | 1.39 | 0.05 | 1.67 | 0.05 | 0.07 |
| PcOxP_DB04_G09 | 179 | 269 | 0.48 | 0.05 | 1.08 | 0.06 | 0.08 |
| PcOxP_DB04_G11 | 180 | 367 | 0.68 | 0.05 | 0.79 | 0.05 | 0.07 |
| PcOxP_DB04_H01 | 89 | 368 | 1.22 | 0.06 | 1.80 | 0.07 | 0.07 |

Example 3: IgG ELISA Summary 48 scFv were selected and reformatted along with the parental E06 antibody into human IgG1 using standard techniques. For ELISA analysis of antibody binding, 384-well polystyrene microtitre plates were coated with 20 μL of antigen (PC-BSA at 5 μg/mL) in PBS for 2 hours at room temperature. Plates were washed three times with DEL-FIA® wash buffer, then blocked with 20 μL/well 1% BSA-TBS for 1 hour at room temperature. After washing, 15 μL of the titrated antibody in 1% BSA-TBS was added to wells and incubated for 1 hour at room temperature. After further washing, 15 μL/well of DELFIA® Eu-N1 Anti-Human IgG secondary antibody in TBS was added to wells and incubated for 1 hour at room temperature. Plates were washed again, and the amount of antibody binding to each well was quantitated from TRF measurement following 5 min incubation at room temperature with DELFIA® enhancement buffer. Binding data of the parental E06 IgG1 antibody and various IgG1 binders are summarized in Table 5. No binding to BSA was detected for any of the antibodies shown in Table 5.

Physical properties (melting temperature, aggregation temperature, and polydispersity index) of the antibodies were determined using an Uncle instrument (Unchained Labs). Physical properties of the parental E06 IgG1 antibody and various IgG1 binders are summarized in Table 5.

TABLE 5

IgG ELISA Data.

| Antibody | EC50 (nM) PC BSA | Physical Properties | | |
|---|---|---|---|---|
| | | Melting Temp. Tm (° C.) | Aggregation Temp. Tagg (° C.) | Poly-dispersity Index (PDI) |
| E06 parental IgG1 | 0.390 | 69.5 | 66.3 | 0.07 |
| PcOxP_DB01_G05 | 0.263 | 71.5 | 71.65 | 0.246 |
| PcOxP_DB01_G09 | 0.308 | 72.5 | 73.44 | 0.058 |
| PcOxP_DB01_H01 | 0.275 | 71.58 | 74.57 | 0.093 |
| PcOxP_DB03_B11 | 0.299 | 71.24 | 74.52 | 0.104 |
| PcOxP_DB03_C10 | 0.285 | 72 | 73.29 | 0.167 |
| PcOxP_DB03_H08 | 0.445 | 68.7 | 69.56 | 0.182 |
| PcOxP_DB04_A11 | 0.413 | 71.5 | 72.03 | 0.097 |
| PcOxP_DB04_E05 | 0.282 | 70.53 | 72.22 | 0.126 |
| PcOxP_DB01_A06 | 0.43 | 71.21 | 72.53 | 0.197 |
| PcOxP_DB01_B09 | 0.317 | 71.5 | 74.55 | 0.036 |
| PcOxP_DB01_C04 | 0.310 | 33.5 | 72.81 | 0.11 |
| PcOxP_DB01_D01 | 0.274 | 70.5 | 70.73 | 0.029 |
| PcOxP_DB01_D11 | 0.242 | 69.14 | 69.67 | 0.124 |
| PcOxP_DB01_E05 | 0.417 | 71.5 | 73.26 | 0.106 |
| PcOxP_DB01_E10 | 0.316 | 72.2 | 74.66 | 0.172 |
| PcOxP_DB01_F01 | 0.672 | 73 | 72.68 | 0.347 |
| PcOxP_DB01_G10 | 0.407 | 71.5 | 72.96 | 0.027 |
| PcOxP_DB01_H02 | 0.43 | 72.12 | 74.88 | 0.304 |
| PcOxP_DB01_H04 | 0.456 | 72 | 72.97 | 0.436 |
| PcOxP_DB02_A06 | 0.643 | 70 | 70.54 | 0.235 |
| PcOxP_DB02_C01 | 0.64 | 71.5 | 72.51 | 0.207 |
| PcOxP_DB02_H07 | 0.423 | 71.74 | 74.2 | 0.192 |
| PcOxP_DB03_A09 | 0.664 | 70.5 | 72.92 | 0.095 |
| PcOxP_DB03_B09 | 0.426 | 71 | 73.2 | 0.047 |
| PcOxP_DB03_C03 | 0.339 | 70.22 | 73.18 | 0.231 |
| PcOxP_DB03_C12 | 0.436 | 70 | 73.79 | 0.098 |
| PcOxP_DB03_D08 | 0.401 | 70.23 | 71.27 | 0.149 |
| PcOxP_DB03_E01 | 0.857 | 72.01 | 73.07 | 0.166 |
| PcOxP_DB03_G07 | 0.636 | 73.06 | 74.2 | 0.223 |
| PcOxP_DB03_G12 | 0.557 | 72.74 | 73.67 | 0.06 |
| PcOxP_DB04_A09 | 0.269 | 72.5 | 72.15 | 0.023 |
| PcOxP_DB04_E08 | 0.251 | 72.73 | 76.24 | 0.167 |
| PcOxP_DB01_F06 | 0.216 | 72.18 | 71.28 | 0.219 |
| PcOxP_DB02_F10 | 0.659 | 72 | 73.59 | 0.12 |
| PcOxP_DB02_G04 | 0.231 | 70 | 67.12 | 0.143 |
| PcOxP_DB04_G01 | 0.257 | 72.5 | 74.34 | 0.288 |
| PcOxP_DB01_B06 | 0.219 | 72.6 | 74.28 | 0.437 |
| PcOxP_DB01_F04 | 0.344 | 71 | 70.95 | 0.184 |
| PcOxP_DB01_F11 | 0.244 | 71.18 | 76.16 | 0.074 |
| PcOxP_DB01_H08 | 0.244 | 70.51 | 70.08 | 0.092 |
| PcOxP_DB02_A05 | 0.264 | 71.5 | 73.63 | 0.25 |
| PcOxP_DB02_B04 | 0.278 | 71.58 | 76.93 | 0.078 |
| PcOxP_DB03_F09 | 0.28 | 72.62 | 73.62 | 0.129 |
| PcOxP_DB03_G03 | 0.216 | 58.52 | 73.65 | 0.22 |
| PcOxP_DB03_G11 | 0.244 | 73.06 | 74.11 | 0.217 |
| PcOxP_DB03_H03 | 0.229 | 70.5 | 70.1 | 0.156 |
| PcOxP_DB04_A04 | 0.294 | 74 | 76.96 | 0.134 |
| PcOxP_DB02_C09 | 0.394 | 72 | 68.48 | 0.265 |

Example 4: Further IgG Characterization

Select human IgG1 antibodies (see Example 3) were further analyzed for antibody yield, stress testing, and immunogenicity characteristics. Yield was determined by transfection of HEK293 cells and subsequent expression in 25 mL cultures. For several of the antibodies, yield was determined in a scaled-up 40 L transient transfection culture. Antibody products were purified using protein A, and the resulting amount of antibody was measured via absorbance at 280 nm (OD280). The yield values for the parental E06 IgG1 antibody and select IgG1 binders are shown in Table 6.

TABLE 6

Yield Data.

| Antibody | Yield - 25 mL culture (mg) | Yield - 40 L culture (mg/L) |
|---|---|---|
| E06 parental IgG1 | — | 15 |
| PcOxP_DB01_H08 | 3.3 | 649 |
| PcOxP_DB03_C03 | 3.4 | 392 |
| PcOxP_DB01_F11 | 8.5 | |
| PcOxP_DB01_B09 | 5.2 | |
| PcOxP_DB01_G09 | 4.8 | |
| PcOxP_DB03_C12 | 3.1 | |
| PcOxP_DB01_E05 | 5.1 | |

The parental E06 IgG1 antibody and the human IgG1 PcOxP_DB01_H08 antibody were analyzed in forced degradation studies to compare the relative stability and resistance to stress between the antibodies. Samples of each antibody were subjected to temperature stress, oxidation stress, and low and high pH stress, and the samples were analyzed and compared to non-stressed samples. Various analytical techniques were used to analyze the samples. In addition to concentration measurement and visual inspection, chemical stability was assessed via protein level RPC-MS at the intact and reduced antibody level, peptide mapping analysis under reducing conditions, iCIEF analysis, and CGE-SDS in non-reducing and reducing conditions, and physical stability was assessed using SE-HPLC.

For temperature stress, samples of each antibody were stored at 40° C. for 2 weeks, 3 weeks, or 4 weeks. For low pH stress, the pH in samples of each antibody was adjusted to 3.2 using 0.12M HCl, and the samples were incubated at 25° C. for 2 hours prior to buffer exchange back to formulation buffer. For high pH stress (forced deamidation), the pH in samples of each antibody was adjusted to 9.0 using 0.5 M Tris pH 11, and the samples were incubated for 3 days at 37° C. prior to buffer exchange back to formulation buffer. For oxidative stress, 3% $H_2O_2$ solution was added to samples of each antibody to reach a final concentration of 0.03%, and the samples were incubated for 1 day at 25° C. prior to buffer exchange back to formulation buffer. The stress testing and stability assay results are summarized qualitatively in Table 7 ("+": moderately stable; "++": highly stable).

TABLE 7

Stress Testing and Stability Comparison.

| Antibody | Storage at 40° C. | Low pH stress | Forced deamidation | Oxidative stress |
|---|---|---|---|---|
| E06 parental IgG1 | + | ++ | + | ++ |
| PcOxP_DB01_H08 | ++ | ++ | ++ | ++ |

In vivo immunogenicity for the parental E06 IgG1 antibody and the human IgG1 PcOxP_DB01_H08 and PcOxP_DB03_C03 antibodies was predicted using the in vitro Epibase® immunogenicity assay (Lonza Biologics), the in silico Epibase® platform (Lonza Biologics) and the in silico ISPRI™ platform (EpiVax, Inc.). The immunogenicity profiles are summarized in Table 8. Overall, the immunogenicity assays show that PcOxP_DB01_H08 and PcOxP_DB03_C03 each have a low immunogenicity risk and a favorable profile when compared with several established antibody drugs.

TABLE 8

Immunogenicity Assay Data.

| Antibody | In vitro Epibase® (% responders)* | In silico Epibase® score | In silico ISPRI™ score** |
|---|---|---|---|
| E06 parental IgG1 | 17 | 2203 | +7.44 |
| PcOxP_DB01_H08 | 16 | 906 | −50.09 |
| PcOxP_DB03_C03 | 22 | 1048 | |

*32 donor samples, KLH positive control shows 100% effect
**a score of 0 indicates predicted immunogenic responses in approximately 5% of patients

SEQUENCE LISTING

| SEQ ID NO | SEQUENCE |
|---|---|
| 1 | EVQLLESGGGLVQPGGSLRLSCAASGFTFSDYYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 2 | EVQLLESGGGLVQPGGSLRLSCAASGFGFSDFYMEWVRQAPGKGLEWVAASRNKWNDYTTEY ADSVKGRFTISRDNSKNTLYLQMNSLRAEDTAVYYCARDYYGSSYWYYDVWGQGTLVTVSS |
| 3 | EVQLLESGGGLVQPGGSLRLSCAASGFTFSDQYIEWVRQAPGKGLEWVAASRNKANDYTTEY ADSVKGRFTISRDNSKNTLYLQMNSLRAEDTAVYYCARDYLGSSYWYFDVWGQGTLVTVSS |
| 4 | EVQLLESGGGLVQPGGSLRLSCAASGFTFSDGYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 5 | EVQLLESGGGLVQPGGSLRLSCAASGFTASDFYMEWVRQAPGKGLEWVAASRNKWNDYTTEY ADSVKGRFTISRDNSKNTLYLQMNSLRAEDTAVYYCARDYYGSSYWYFDVWGQGTLVTVSS |
| 6 | EVQLLESGGGLVQPGGSLRLSCAASGFTFSDSYMEWVRQAPGKGLEWVAASRNKANDYTTSY ADSVKGRFTISRDNSKNTLYLQMNSLRAEDTAVYYCARDYYGSSYWYFDVWGQGTLVTVSS |
| 7 | EVQLLESGGGLVQPGGSLRLSCAASGFTFEDFYMEWVRQAPGKGLEWVAASRNKANDYTTEY ADSVKGRFTISRDNSKNTLYLQMNSLRAEDTAVYYCARDYFGSSYWYFDVWGQGTLVTVSS |
| 8 | EVQLLESGGGLVQPGGSLRLSCAASGFTFSDFYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 9 | EVQLLESGGGLVQPGGSLRLSCAASGFTFSDQYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 10 | EVQLLESGGGLVQPGGSLRLSCAASGFQFSDFYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 11 | EVQLLESGGGLVQPGGSLRLSCAASGFEESDNYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 12 | EVQLLESGGGLVQPGGSLRLSCAASGFTFSDGYMEWVRQAPGKGLEWVAASRNKANDYTTEY ADSVKGRFTISRDNSKNTLYLQMNSLRAEDTAVYYCARDYYASSYWYFDVWGQGTLVTVSS |
| 13 | EVQLLESGGGLVQPGGSLRLSCAASGFTFSDFYMEWVRQAPGKGLEWVAASRNKANDYTTEL ADSVKGRFTISRDNSKNTLYLQMNSLRAEDTAVYYCARDYYGSSYWYFDVWGQGTLVTVSS |
| 14 | EVQLLESGGGLVQPGGSLRLSCAASGFEFSDFYMEWVRQAPGKGLEWVAASRGKGNSYTTEY ADSVKGRFTISRDNSKNTLYLQMNSLRAEDTAVYYCARDYYGSSYWYFDVWGQGTLVTVSS |
| 15 | EVQLLESGGGLVQPGGSLRLSCAASGFTFSDGYMEWVRQAPGKGLEWVAASRNKANDYTTEY ADSVKGRFTISRDNSKNTLYLQMNSLRAEDTAVYYCARDYYGSPYWYFDVWGQGTLVTVSS |
| 16 | EVQLLESGGGLVQPGGSLRLSCAASGFTFSDAYMEWVRQAPGKGLEWVAASRNKANDYTTEY ADSVKGRFTISRDNSKNTLYLQMNSLRAEDTAVYYCARDYYGSSYWYFDSWGQGTLVTVSS |
| 17 | EVQLLESGGGLVQPGGSLRLSCAASGFTFSDFYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 18 | EVQLLESGGGLVQPGGSLRLSCAASGFTFSDAYMEWVRQAPGKGLEWVAASRNKANDYTTEY ADSVKGRFTISRDNSKNTLYLQMNSLRAEDTAVYYCARDYYGSSYWYFDTWGQGTLVTVSS |

-continued

| SEQ ID NO | SEQUENCE |
|---|---|
| 19 | EVQLLESGGGLVQPGGSLRLSCAASGFTFSDQYMEWVRQAPGKGLEWVAASRNKANDYTTEY<br>ADSVKGRFTISRDNSKNTLYLQMNSLRAEDTAVYYCARDYYGSSYWYFDLWGQGTLVTVSS |
| 20 | EVQLLESGGGLVQPGGSLRLSCAASGFTFSDFYMEWVRQAPGKGLEWVAASRNKANDYVTEY<br>ADSVKGRFTISRDNSKNTLYLQMNSLRAEDTAVYYCARDYYGSSYWYFDVWGQGTLVTVSS |
| 21 | EVQLLESGGGLVQPGGSLRLSCAASGFTFSSYYMEWVRQAPGKGLEWVAASRNKYNDYTTEY<br>ADSVKGRFTISRDNSKNTLYLQMNSLRAEDTAVYYCARDYYGSSYWYFDVWGQGTLVTVSS |
| 22 | EVQLLESGGGLVQPGGSLRLSCAASGFTFSSYYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 23 | EVQLLESGGGLVQPGGSLRLSCAASGFTGSDFYMEWVRQAPGKGLEWVAASRNKGNSYTTEY<br>ADSVKGRFTISRDNSKNTLYLQMNSLRAEDTAVYYCARDYYGSSYWYFDVWGQGTLVTVSS |
| 24 | EVQLLESGGGLVQPGGSLRLSCAASGFTFSDYYMEWVRQAPGKGLEWVAASRNKANTYTTEY<br>ADSVKGRFTISRDNSKNTLYLQMNSLRAEDTAVYYCARDYYGSSYWYFDVWGQGTLVTVSS |
| 25 | EVQLLESGGGLVQPGGSLRLSCAASGFTFSDGYMEWVRQAPGKGLEWVAASRNKNNDYTTEY<br>ADSVKGRFTISRDNSKNTLYLQMNSLRAEDTAVYYCARDYFGSSYWYFDVWGQGTLVTVSS |
| 26 | EVQLLESGGGLVQPGGSLRLSCAASGFAFSDFYMEWVRQAPGKGLEWVAASRNKANDYTTEY<br>ADSVKGRFTISRDNSKNTLYLQMNSLRAEDTAVYYCARDYYGSHYWYFDVWGQGTLVTVSS |
| 27 | EVQLLESGGGLVQPGGSLRLSCAASGFTHSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 28 | EVQLLESGGGLVQPGGSLRLSCAASGFTFSDGYMEWVRQAPGKGLEWVAASRNKNNDYTTEY<br>ADSVKGRFTISRDNSKNTLYLQMNSLRAEDTAVYYCARDYYGSSYWYFDVWGQGTLVTVSS |
| 29 | EVQLLESGGGLVQPGGSLRLSCAASGFTFSDTYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 30 | EVQLLESGGGLVQPGGSLRLSCAASGFAFSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 31 | EVQLLESGGGLVQPGGSLRLSCAASGFTFSDGYMEWVRQAPGKGLEWVAASRNIANDYTTEY<br>ADSVKGRFTISRDNSKNTLYLQMNSLRAEDTAVYYCARDYYGSSYWYFDVWGQGTLVTVSS |
| 32 | EVQLLESGGGLVQPGGSLRLSCAASGFTFSDDYMEWVRQAPGKGLEWVAASRNKANDYTTEY<br>ADSVKGRFTISRDNSKNTLYLQMNSLRAEDTAVYYCARDYQGSSYWYFDVWGQGTLVTVSS |
| 33 | EVQLLESGGGLVQPGGSLRLSCAASGFTFSDYYMEWVRQAPGKGLEWVAASRNSGNDYTTEY<br>ADSVKGRFTISRDNSKNTLYLQMNSLRAEDTAVYYCARDYYGSSYWYFDVWGQGTLVTVSS |
| 34 | EVQLLESGGGLVQPGGSLRLSCAASGFTFSDNYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 35 | EVQLLESGGGLVQPGGSLRLSCAASGFTFSDAYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 36 | EVQLLESGGGLVQPGGSLRLSCAASGFTFSDFYMEWVRQAPGKGLEWVAASRNKANDYTVEY<br>ADSVKGRFTISRDNSKNTLYLQMNSLRAEDTAVYYCARDYYGHSYWYFDVWGQGTLVTVSS |
| 37 | EVQLLESGGGLVQPGGSLRLSCAASGFTSSDFYMEWVRQAPGKGLEWVAASRNKANDYYTEY<br>ADSVKGRFTISRDNSKNTLYLQMNSLRAEDTAVYYCARDYYGSSYWYFDVWGQGTLVTVSS |
| 38 | EVQLLESGGGLVQPGGSLRLSCAASGFGFSDFYMEWVRQAPGKGLEWVAASRHKANDYTTEY<br>ADSVKGRFTISRDNSKNTLYLQMNSLRAEDTAVYYCARDYYGSSYWYFDVWGQGTLVTVSS |
| 39 | EVQLLESGGGLVQPGGSLRLSCAASGFTFSTFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 40 | EVQLLESGGGLVQPGGSLRLSCAASGFTFSDEYMEWVRQAPGKGLEWVAASRGKGNSYTTEY<br>ADSVKGRFTISRDNSKNTLYLQMNSLRAEDTAVYYCARDYYGSSYWYFDVWGQGTLVTVSS |
| 41 | EVQLLESGGGLVQPGGSLRLSCAASGFTFSDQYMEWVRQAPGKGLEWVAASRNKANDYQTEY<br>ADSVKGRFTISRDNSKNTLYLQMNSLRAEDTAVYYCARDYYGSSYWYFDVWGQGTLVTVSS |
| 42 | EVQLLESGGGLVQPGGSLRLSCAASGFWFSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 43 | EVQLLESGGGLVQPGGSLRLSCAASGFTFSSYYMEWVRQAPGKGLEWVAASRNQANDYTTEY<br>ADSVKGRFTISRDNSKNTLYLQMNSLRAEDTAVYYCARDYYGSPYWYFDVWGQGTLVTVSS |

-continued

SEQUENCE LISTING

| SEQ ID NO | SEQUENCE |
|---|---|
| 44 | EVQLLESGGGLVQPGGSLRLSCAASGFTFSDVYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 45 | EVQLLESGGGLVQPGGSLRLSCAASGFTFSSYYMEWVRQAPGKGLEWVAASRNQANDYTTEYADSVKGRFTISRDNSKNTLYLQMNSLRAEDTAVYYCARDYYGSSYWYLDVWGQGTLVTVSS |
| 46 | EVQLLESGGGLVQPGGSLRLSCAASGFTFSDFYMEWVRQAPGKGLEWVAASRNKYNDYTTEYADSVKGRFTISRDNSKNTLYLQMNSLRAEDTAVYYCARDYYGSSYWYFDVWGQGTLVTVSS |
| 47 | EVQLLESGGGLVQPGGSLRLSCAASGATFSDFYMEWVRQAPGKGLEWVAASRNGANDYTTEYADSVKGRFTISRDNSKNTLYLQMNSLRAEDTAVYYCARDYYGNSYWYFDVWGQGTLVTVSS |
| 48 | EVQLLESGGGLVQPGGSLRLSCAASGFDFSDFYMEWVRQAPGKGLEWVAASRNKANDYTTDYADSVKGRETISRDNSKNTLYLQMNSLRAEDTAVYYCARDYFGSSYWYFDVWGQGTLVTVSS |
| 49 | EVQLLESGGGLVQPGGSLRLSCAASGFTFSDEYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 50 | EVQLLESGGGLVQPGGSLRLSCAASGFWFSDFYMEWVRQAPGKGLEWVAASRNKANDYTTEYADSVKGRFTISRDNSKNTLYLQMNSLRAEDTAVYYCARDYYGSAYWYFDVWGQGTLVTVSS |
| 51 | EVQLLESGGGLVQPGGSLRLSCAASGFTFSDFYMEWVRQAPGKGLEWVAASRNKANDYTTEYADSVKGRFTISRDNSKNTLYLQMNSLRAEDTAVYYCARDYYGHSYWYFDVWGQGTLVTVSS |
| 52 | EVQLLESGGGLVQPGGSLRLSCAASGFTFSDYYMEWVRQAPGKGLEWVAASRNKANDYTVEYADSVKGRFTISRDNSKNTLYLQMNSLRAEDTAVYYCARDYYGSSYWYFDVWGQGTLVTVSS |
| 53 | EVQLLESGGGLVQPGGSLRLSCAASGWTFSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 54 | EVQLLESGGGLVQPGGSLRLSCAASGFTFSDNYMEWVRQAPGKGLEWVAASRNKANDYTNEYADSVKGRFTISRDNSKNTLYLQMNSLRAEDTAVYYCARDYYGSSYWYFDVWGQGTLVTVSS |
| 55 | EVQLLESGGGLVQPGGSLRLSCAASGFTFSSFYMEWVRQAPGKGLEWVAASRNAANDYTTEYADSVKGRFTISRDNSKNTLYLQMNSLRAEDTAVYYCARDYYGSSYWYFDLWGQGTLVTVSS |
| 56 | EVQLLESGGGLVQPGGSLRLSCAASGFTASDFYMEWVRQAPGKGLEWVAASRNKANDQTTEYADSVKGRFTISRDNSKNTLYLQMNSLRAEDTAVYYCARDYYGSSYWYFDSWGQGTLVTVSS |
| 57 | EVQLLESGGGLVQPGGSLRLSCAASGFTFNDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 58 | EVQLLESGGGLVQPGGSLRLSCAASGFTFSDHYMEWVRQAPGKGLEWVAASRNSGNSYTTEYADSVKGRFTISRDNSKNTLYLQMNSLRAEDTAVYYCARDYYGSSYWYFDVWGQGTLVTVSS |
| 59 | EVQLLESGGGLVQPGGSLRLSCAASGFTFSDGYIEWVRQAPGKGLEWVAASRNKANDYTTEYADSVKGRFTISRDNSKNTLYLQMNSLRAEDTAVYYCARDYYGSSYWYFDVWGQGTLVTVSS |
| 60 | EVQLLESGGGLVQPGGSLRLSCAASGFTSSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 61 | EVQLLESGGGLVQPGGSLRLSCAASGFTFSDHYMEWVRQAPGKGLEWVAASRNKANDYTTEYADSVKGRFTISRDNSKNTLYLQMNSLRAEDTAVYYCARDYYGQSYWYFDVWGQGTLVTVSS |
| 62 | EVQLLESGGGLVQPGGSLRLSCAASGFTGSDFYMEWVRQAPGKGLEWVAASRNKWNDYTTEYADSVKGRFTISRDNSKNTLYLQMNSLRAEDTAVYYCARDYYGSSYWYFDVWGQGTLVTVSS |
| 63 | EVQLLESGGGLVQPGGSLRLSCAASGGTFSDFYMEWVRQAPGKGLEWVAASRNKANTYTTEYADSVKGRFTISRDNSKNTLYLQMNSLRAEDTAVYYCARDYYGSSYWYFDVWGQGTLVTVSS |
| 64 | EVQLLESGGGLVQPGGSLRLSCAASGFTFSDAYMEWVRQAPGKGLEWVAASRNKANSYTTEYADSVKGRFTISRDNSKNTLYLQMNSLRAEDTAVYYCARDYYGSSYWYFDVWGQGTLVTVSS |
| 65 | EVQLLESGGGLVQPGGSLRLSCAASGFTQSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 66 | EVQLLESGGGLVQPGGSLRLSCAASGFTFSDYYMEWVRQAPGKGLEWVAASRNKWNDYTTEYADSVKGRFTISRDNSKNTLYLQMNSLRAEDTAVYYCARDYYGSSYWYFDVWGQGTLVTVSS |
| 67 | EVQLLESGGGLVQPGGSLRLSCAASGDTFSDFYMEWVRQAPGKGLEWVAASRNKWNDYTTEYADSVKGRFTISRDNSKNTLYLQMNSLRAEDTAVYYCARDYYGSSYWYFDVWGQGTLVTVSS |

SEQUENCE LISTING

| SEQ ID NO | SEQUENCE |
|---|---|
| 68 | EVQLLESGGGLVQPGGSLRLSCAASGFTFSDGYMEWVRQAPGKGLEWVAASRNKWNDYTTEYADSVKGRFTISRDNSKNTLYLQMNSLRAEDTAVYYCARDYYGSSYWYFDVWGQGTLVTVSS |
| 69 | EVQLLESGGGLVQPGGSLRLSCAASGFTFSDDYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 70 | EVQLLESGGGLVQPGGSLRLSCAASGFTTSDFYMEWVRQAPGKGLEWVAASRNKANSYTTEYADSVKGRFTISRDNSKNTLYLQMNSLRAEDTAVYYCARDYYGSSYWYFDVWGQGTLVTVSS |
| 71 | EVQLLESGGGLVQPGGSLRLSCAASGFTFSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 72 | EVQLLESGGGLVQPGGSLRLSCAASGFTFSDHYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 73 | EVQLLESGGGLVQPGGSLRLSCAASGDTFSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 74 | EVQLLESGGGLVQPGGSLRLSCAASGFTGSDFYMEWVRQAPGKGLEWVAASRGKGNSYTTEYADSVKGRFTISRDNSKNTLYLQMNSLRAEDTAVYYCARDYYGSSTWYFDVWGQGTLVTVSS |
| 75 | EVQLLESGGGLVQPGGSLRLSCAASGFTFSDFYMEWVRQAPGKGLEWVAASRWKANDYTTEYADSVKGRFTISRDNSKNTLYLQMNSLRAEDTAVYYCARDYYESSYWYFDVWGQGTLVTVSS |
| 76 | EVQLLESGGGLVQPGGSLRLSCAASGEPFSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 77 | EVQLLESGGGLVQPGGSLRLSCAASGFTFEDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 78 | EVQLLESGGGLVQPGGSLRLSCAASGATFSDFYVEWVRQAPGKGLEWVAASRNKANDYTTEYADSVKGRFTISRDNSKNTLYLQMNSLRAEDTAVYYCARDYYGSSYWYFDVWGQGTLVTVSS |
| 79 | EVQLLESGGGLVQPGGSLRLSCAASGFTFSDYYMEWVRQAPGKGLEWVAASRNKANDYTTEYADSVKGRFTISRDNSKNTLYLQMNSLRAEDTAVYYCARDYYGNSYWYFDVWGQGTLVTVSS |
| 80 | EVQLLESGGGLVQPGGSLRLSCAASGFTQSDFYMEWVRQAPGKGLEWVAAIRNKANSYTTEYADSVKGRFTISRDNSKNTLYLQMNSLRAEDTAVYYCARDYYGSSYWYFDVWGQGTLVTVSS |
| 81 | EVQLLESGGGLVQPGGSLRLSCAASGGTFSDFYMEWVRQAPGKGLEWVAASRNKANSYTTAYADSVKGRFTISRDNSKNTLYLQMNSLRAEDTAVYYCARDYYGSSYWYFDVWGQGTLVTVSS |
| 82 | EVQLLESGGGLVQPGGSLRLSCAASGFTFSSYYMEWVRQAPGKGLEWVAASRNKYNDYTTEYADSVKGRFTISRDNSKNTLYLQMNSLRAEDTAVYYCARDYYGSSTWYFDVWGQGTLVTVSS |
| 83 | EVQLLESGGGLVQPGGSLRLSCAASGFTFSDFYMEWVRQAPGKGLEWVAASRNKANDYTTTYADSVKGRFTISRDNSKNTLYLQMNSLRAEDTAVYYCARDYYGSSHWYFDVWGQGTLVTVSS |
| 84 | EVQLLESGGGLVQPGGSLRLSCAASGFTFSSYYMEWVRQAPGKGLEWVAASRNKGNSYTTEYADSVKGRFTISRDNSKNTLYLQMNSLRAEDTAVYYCARDYYGSSYWYFDVWGQGTLVTVSS |
| 85 | EVQLLESGGGLVQPGGSLRLSCAASGFTFSDFYMEWVRQAPGKGLEWVAASRNKANDYTTEYADSVKGRFTISRDNSKNTLYLQMNSLRAEDTAVYYCARDYYGSSYWYFDSWGQGTLVTVSS |
| 86 | EVQLLESGGGLVQPGGSLRLSCAASGFTFSDYYMEWVRQAPGKGLEWVAASRNKANDYTTEYADSVKGRFTISRDNSKNTLYLQMNSLRAEDTAVYYCARDYYGDSYWYFDVWGQGTLVTVSS |
| 87 | EVQLLESGGGLVQPGGSLRLSCAASGFTDSDFYMEWVRQAPGKGLEWVAASRNKANDYTTEYADSVKGRFTISRDNSKNTLYLQMNSLRAEDTAVYYCARDYYGSSYWYFDVWGQGTLVTVSS |
| 88 | EVQLLESGGGLVQPGGSLRLSCAASGFTFSSYYMEWVRQAPGKGLEWVAASRNKANDYTTEYADSVKGRFTISRDNSKNTLYLQMNSLRAEDTAVYYCARDYYGSSYWYNDVWGQGTLVTVSS |
| 89 | EVQLLESGGGLVQPGGSLRLSCAASGFTFSDYYMEWVRQAPGKGLEWVAASRNKYNDYTTEYADSVKGRFTISRDNSKNTLYLQMNSLRAEDTAVYYCARDYYGSSYWYFDVWGQGTLVTVSS |
| 90 | EVQLLESGGGLVQPGGSLRLSCAASGFTFSDYYMEWVRQAPGKGLEWVAASRNKGNDYTTEYADSVKGRFTISRDNSKNTLYLQMNSLRAEDTAVYYCARDYYGSSYWYFDVWGQGTLVTVSS |
| 91 | EVQLLESGGGLVQPGGSLRLSCAASGFGFSDFYMEWVRQAPGKGLEWVGASRNKHNDYTTEYADSVKGRFTISRDNSKNTLYLQMNSLRAEDTAVYYCARDYYGSSYWYFDVWGQGTLVTVSS |
| 92 | EVQLLESGGGLVQPGGSLRLSCAASGDTFSDFYMEWVRQAPGKGLEWVAASRNKANAYTTEYADSVKGRFTISRDNSKNTLYLQMNSLRAEDTAVYYCARDYYGQSYWYFDVWGQGTLVTVSS |

SEQUENCE LISTING

| SEQ ID NO | SEQUENCE |
|---|---|
| 93 | EVQLLESGGGLVQPGGSLRLSCAASGNTFSDFYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 94 | EVQLLESGGGLVQPGGSLRLSCAASGFTFSSYYMEWVRQAPGKGLEWVAASRNKENDYTTEY ADSVKGRFTISRDNSKNTLYLQMNSLRAEDTAVYYCARDYYGSSYWYFDVWGQGTLVTVSS |
| 95 | EVQLLESGGGLVQPGGSLRLSCAASGFPFSDFYMEWVRQAPGKGLEWVAASRNKANDYTTEY ADSVKGRFTISRDNSKNTLYLQMNSLRAEDTAVYYCARDYYGSPYWYFDVWGQGTLVTVSS |
| 96 | EVQLLESGGGLVQPGGSLRLSCAASGFTFSDSYMEWVRQAPGKGLEWVAASRNKYNDYTTEY ADSVKGRFTISRDNSKNTLYLQMNSLRAEDTAVYYCARDYYGSSYWYFDVWGQGTLVTVSS |
| 97 | EVQLLESGGGLVQPGGSLRLSCAASGDTFSDFYLEWVRQAPGKGLEWVAASRNKANGYTTEY ADSVKGRFTISRDNSKNTLYLQMNSLRAEDTAVYYCARDYYHSSYWYFDVWGQGTLVTVSS |
| 98 | EVQLLESGGGLVQPGGSLRLSCAASGFTFSSYYMEWVRQAPGKGLEWVAASRNKANDYTTEY ADSVKGRFTISRDNSKNTLYLQMNSLRAEDTAVYYCARDYYGSSYWYYDVWGQGTLVTVSS |
| 99 | EVQLLESGGGLVQPGGSLRLSCAASGFTHSDFYMEWVRQAPGKGLEWVAASRNKANGYTTEY ADSVKGRFTISRDNSKNTLYLQMNSLRAEDTAVYYCARDYYGSSYWYFDSWGQGTLVTVSS |
| 100 | EVQLLESGGGLVQPGGSLRLSCAASGFLFSDFYMEWVRQAPGKGLEWVAASRNKANDYTTTY ADSVKGRFTISRDNSKNTLYLQMNSLRAEDTAVYYCARDYYGSHYWYFDVWGQGTLVTVSS |
| 101 | EVQLLESGGGLVQPGGSLRLSCAASGFTFSSYYMEWVRQAPGKGLEWVAASRNKANEYTTEY ADSVKGRFTISRDNSKNTLYLQMNSLRAEDTAVYYCARDYYGSSYWYFDVWGQGTLVTVSS |
| 102 | EVQLLESGGGLVQPGGSLRLSCAASGFTFSDFYMEWVRQAPGKGLEWVAASRNKNNDYTTEY ADSVKGRFTISRDNSKNTLYLQMNSLRAEDTAVYYCARDYYGSSYWYFDVWGQGTLVTVSS |
| 103 | EVQLLESGGGLVQPGGSLRLSCAASGFTFSSYYMEWVRQAPGKGLEWVAASRNKANLYTTEY ADSVKGRFTISRDNSKNTLYLQMNSLRAEDTAVYYCARDYYGSSTWYFDVWGQGTLVTVSS |
| 104 | EVQLLESGGGLVQPGGSLRLSCAASGFTFSDHYMEWVRQAPGKGLEWVAASRGKGNSYTTAY ADSVKGRFTISRDNSKNTLYLQMNSLRAEDTAVYYCARDYYGSSYWYFDVWGQGTLVTVSS |
| 105 | EVQLLESGGGLVQPGGSLRLSCAASGFTFSDFYMEWVRQAPGKGLEWVAASRNKGNSYTTAY ADSVKGRFTISRDNSKNTLYLQMNSLRAEDTAVYYCARDYYGSSYWYFDVWGQGTLVTVSS |
| 106 | EVQLLESGGGLVQPGGSLRLSCAASGFTFSDHYMEWVRQAPGKGLEWVAASRNKYNDYTTEY ADSVKGRFTISRDNSKNTLYLQMNSLRAEDTAVYYCARDIYGSSYWYFDVWGQGTLVTVSS |
| 107 | EVQLLESGGGLVQPGGSLRLSCAASGFTFSDYYMEWVRQAPGKGLEWVAASRNKANTYTTEY ADSVKGRFTISRDNSKNTLYLQMNSLRAEDTAVYYCARDYYGSSYWYDDVWGQGTLVTVSS |
| 108 | EVQLLESGGGLVQPGGSLRLSCAASGFTFSDQYMEWVRQAPGKGLEWVAASRNNANDYTTEY ADSVKGRFTISRDNSKNTLYLQMNSLRAEDTAVYYCARDYYGSSYWYFDVWGQGTLVTVSS |
| 109 | EVQLLESGGGLVQPGGSLRLSCAASGFTNSDFYMEWVRQAPGKGLEWVAASRNKENDYTTEY ADSVKGRFTISRDNSKNTLYLQMNSLRAEDTAVYYCARDYYGSSYWYFDVWGQGTLVTVSS |
| 110 | EVQLLESGGGLVQPGGSLRLSCAASGFTFSDYYMEWVRQAPGKGLEWVAASRWKANDYTTEY ADSVKGRFTISRDNSKNTLYLQMNSLRAEDTAVYYCARDYYGSSYWYFDVWGQGTLVTVSS |
| 111 | EVQLLESGGGLVQPGGSLRLSCAASGQTFSDFYMEWVRQAPGKGLEWVAASRNKANGYTTEY TDSVKGRFTISRDNSKNTLYLQMNSLRAEDTAVYYCARDYYGSSYWYFDVWGQGTLVTVSS |
| 112 | EVQLLESGGGLVQPGGSLRLSCAASGFTASDFYMEWVRQAPGKGLEWVAASRNKANDYTTEY ADSVKGRFTISRDNSKNTLYLQMNSLRAEDTAVYYCARDYYGSSYWYFDVWGQGTLVTVSS |
| 113 | EVQLLESGGGLVQPGGSLRLSCAASGFTFSDPYMEWVRQAPGKGLEWVAASRNKANDYTTEY ADSVKGRFTISRDNSKNTLYLQMNSLRAEDTAVYYCARDYYGSPYWYFDVWGQGTLVTVSS |
| 114 | EVQLLESGGGLVQPGGSLRLSCAASGFTFSDYYMEWVRQAPGKGLEWVAASRNKANDYTTEY ADSVKGRFTISRDNSKNTLYLQMNSLRAEDTAVYYCARDYYGSSYWYFDTWGQGTLVTVSS |
| 115 | EVQLLESGGGLVQPGGSLRLSCAASGFTQSDFYMEWVRQAPGKGLEWVAASRNKANAYTTEY ADSVKGRFTISRDNSKNTLYLQMNSLRAEDTAVYYCARDYYGYSYWYFDVWGQGTLVTVSS |
| 116 | EVQLLESGGGLVQPGGSLRLSCAASGFTFSDEYMEWVRQAPGKGLEWVAASRNSGNSYTTAY ADSVKGRFTISRDNSKNTLYLQMNSLRAEDTAVYYCARDYYGSSYWYFDVWGQGTLVTVSS |

SEQUENCE LISTING

| SEQ ID NO | SEQUENCE |
|---|---|
| 117 | EVQLLESGGGLVQPGGSLRLSCAASGFTFSDYYMEWVRQAPGKGLEWVAASRWKANDYTTEY<br>ADSVKGRFTISRDNSKNTLYLQMNSLRAEDTAVYYCARDYYGSSQWYFDVWGQGTLVTVSS |
| 118 | EVQLLESGGGLVQPGGSLRLSCAASGFTFSDDYMEWVRQAPGKGLEWVAATRNKANDYTTEY<br>ADSVKGRFTISRDNSKNTLYLQMNSLRAEDTAVYYCARDYYGSSYWYFDSWGQGTLVTVSS |
| 119 | EVQLLESGGGLVQPGGSLRLSCAASGFTFSDQYMEWVRQAPGKGLEWVAASRNKANDYTVEY<br>ADSVKGRFTISRDNSKNTLYLQMNSLRAEDTAVYYCARDYYGSSYWYFDVWGQGTLVTVSS |
| 120 | EVQLLESGGGLVQPGGSLRLSCAASGFGFSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 121 | EVQLLESGGGLVQPGGSLRLSCAASGFTGSDFYMEWVRQAPGKGLEWVAASRNSGNSYTTAY<br>ADSVKGRFTISRDNSKNTLYLQMNSLRAEDTAVYYCARDYFGSSYWYFDVWGQGTLVTVSS |
| 122 | EVQLLESGGGLVQPGGSLRLSCAASGFTFSDEYMEWVRQAPGKGLEWVAASRNKANDFTTEY<br>ADSVKGRFTISRDNSKNTLYLQMNSLRAEDTAVYYCARDFYGSSYWYFDVWGQGTLVTVSS |
| 123 | EVQLLESGGGLVQPGGSLRLSCAASGFQFSDFYMEWVRQAPGKGLEWVAASRNKGNSYTTAY<br>ADSVKGRFTISRDNSKNTLYLQMNSLRAEDTAVYYCARDYYGSSYWYFDVWGQGTLVTVSS |
| 124 | EVQLLESGGGLVQPGGSLRLSCAASGTTFSDFYMEWVRQAPGKGLEWVAASRNKYNDYTTEY<br>ADSVKGRFTISRDNSKNTLYLQMNSLRAEDTAVYYCARDYYGSSYWYFDVWGQGTLVTVSS |
| 125 | EVQLLESGGGLVQPGGSLRLSCAASGFGFSDFYMEWVRQAPGKGLEWVAASRNKANDYTTEY<br>ADSVKGRFTISRDNSKNTLYLQMNSLRAEDTAVYYCARDYYGSSYWYHDVWGQGTLVTVSS |
| 126 | EVQLLESGGGLVQPGGSLRLSCAASGFTFSDFYMEWVRQAPGKGLEWVAASRNKANDYTTEY<br>ADSVKGRFTISRDNSKNTLYLQMNSLRAEDTAVYYCARDYYGSSHWYFDVWGQGTLVTVSS |
| 127 | EVQLLESGGGLVQPGGSLRLSCAASGPTFSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 128 | EVQLLESGGGLVQPGGSLRLSCAASGFTFSDFYMEWVRQAPGKGLEWVAASRNKANDYTTEY<br>ADSVKGRFTISRDNSKNTLYLQMNSLRAEDTAVYYCARDYYGSSYWYFDPWGQGTLVTVSS |
| 129 | EVQLLESGGGLVQPGGSLRLSCAASGFTFSDAYMEWVRQAPGKGLEWVAASRNKANDYTTEY<br>ADSVKGRFTISRDNSKNTLYLQMNSLRAEDTAVYYCARDYYGSHYWYFDVWGQGTLVTVSS |
| 130 | EVQLLESGGGLVQPGGSLRLSCAASGFTFSSYYMEWVRQAPGKGLEWVAASRNKANDYTYEY<br>ADSVKGRFTISRDNSKNTLYLQMNSLRAEDTAVYYCARDYYESSYWYFDVWGQGTLVTVSS |
| 131 | EVQLLESGGGLVQPGGSLRLSCAASGDTFSDFYMEWVRQAPGKGLEWVAASRNKANDYSTEY<br>ADSVKGRFTISRDNSKNTLYLQMNSLRAEDTAVYYCARDYYGSSYWYFDVWGQGTLVTVSS |
| 132 | EVQLLESGGGLVQPGGSLRLSCAASGFTFSEFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 133 | EVQLLESGGGLVQPGGSLRLSCAASGFTFSSYYMEWVRQAPGKGLEWVAASRSKANDYTTEY<br>ADSVKGRFTISRDNSKNTLYLQMNSLRAEDTAVYYCARDYYGSQYWYFDVWGQGTLVTVSS |
| 134 | EVQLLESGGGLVQPGGSLRLSCAASGFHFSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 135 | EVQLLESGGGLVQPGGSLRLSCAASGFTFSDGYMEWVRQAPGKGLEWVAASRNKANDYTTAY<br>ADSVKGRFTISRDNSKNTLYLQMNSLRAEDTAVYYCARDYYGSSYWYFDVWGQGTLVTVSS |
| 136 | EVQLLESGGGLVQPGGSLRLSCAASGFTFSSYYMEWVRQAPGKGLEWVAASRNTANDYTTEY<br>ADSVKGRFTISRDNSKNTLYLQMNSLRAEDTAVYYCARDYYGSSYWYFDVWGQGTLVTVSS |
| 137 | EVQLLESGGGLVQPGGSLRLSCAASGITFSDFYMEWVRQAPGKGLEWVAASRNKYNDYTTEY<br>ADSVKGRFTISRDNSKNTLYLQMNSLRAEDTAVYYCARDYYGSSYWYFDVWGQGTLVTVSS |
| 138 | EVQLLESGGGLVQPGGSLRLSCAASGFGFSDFYMEWVRQAPGKGLEWVAASRNKANDYTTEY<br>ADSVKGRFTISRDNSKNTLYLQMNSLRAEDTAVYYCARDYYSSSYWYFDVWGQGTLVTVSS |
| 139 | EVQLLESGGGLVQPGGSLRLSCAASGFTFSDYYMEWVRQAPGKGLEWVAASRNKANDYNTEY<br>ADSVKGRFTISRDNSKNTLYLQMNSLRAEDTAVYYCARDYYGSSYWYFDVWGQGTLVTVSS |
| 140 | EVQLLESGGGLVQPGGSLRLSCAASGFTFSDFYVEWVRQAPGKGLEWVAASRNKANTYTTEY<br>ADSVKGRFTISRDNSKNTLYLQMNSLRAEDTAVYYCARDYYGSSYWYFDVWGQGTLVTVSS |
| 141 | EVQLLESGGGLVQPGGSLRLSCAASGFQFSDFYMEWVRQAPGKGLEWVAASRWKANDYTTEY<br>ADSVKGRFTISRDNSKNTLYLQMNSLRAEDTAVYYCARDYYGSSYWYFDVWGQGTLVTVSS |

SEQUENCE LISTING

| SEQ ID NO | SEQUENCE |
|---|---|
| 142 | EVQLLESGGGLVQPGGSLRLSCAASGFTFSDFYMEWVRQAPGKGLEWVAASRNKANDYTTEV<br>ADSVKGRFTISRDNSKNTLYLQMNSLRAEDTAVYYCARDYYGSSNWYFDVWGQGTLVTVSS |
| 143 | EVQLLESGGGLVQPGGSLRLSCAASGFTFSDFYMEWVRQAPGKGLEWVAASRNKANDYTTEY<br>ADSVKGRFTISRDNSKNTLYLQMNSLRAEDTAVYYCARDYYGSSYWYNDVWGQGTLVTVSS |
| 144 | EVQLLESGGGLVQPGGSLRLSCAASGSTFSDFYMEWVRQAPGKGLEWVAASRNKANDETTEY<br>ADSVKGRFTISRDNSKNTLYLQMNSLRAEDTAVYYCARDYYGSSYWYFDVWGQGTLVTVSS |
| 145 | EVQLLESGGGLVQPGGSLRLSCAASGFTFSDYYMEWVRQAPGKGLEWVAASRNKANDYTTEY<br>ADSVKGRFTISRDNSKNTLYLQMNSLRAEDTAVYYCARDYYESSYWYFDVWGQGTLVTVSS |
| 146 | EVQLLESGGGLVQPGGSLRLSCAASGFTTSDFYMEWVRQAPGKGLEWVAASRNKANGYTTEY<br>ADSVKGRFTISRDNSKNTLYLQMNSLRAEDTAVYYCARDYYGSSYWYFDVWGQGTLVTVSS |
| 147 | EVQLLESGGGLVQPGGSLRLSCAASGFTNSDFYMEWVRQAPGKGLEWVAASRNKANDYTTEL<br>ADSVKGRFTISRDNSKNTLYLQMNSLRAEDTAVYYCARDYYGSSYWYFDVWGQGTLVTVSS |
| 148 | EVQLLESGGGLVQPGGSLRLSCAASGETFSDFYMEWVRQAPGKGLEWVAASRNKWNDYTTEY<br>ADSVKGRFTISRDNSKNTLYLQMNSLRAEDTAVYYCARDYYGSSYWYFDVWGQGTLVTVSS |
| 149 | EVQLLESGGGLVQPGGSLRLSCAASGFTFSSYYMEWVRQAPGKGLEWVAASRNKANDYTTEY<br>ADSVKGRFTISRDNSKNTLYLQMNSLRAEDTAVYYCARDYYDSSYWYFDVWGQGTLVTVSS |
| 150 | EVQLLESGGGLVQPGGSLRLSCAASGFTFSDQYMEWVRQAPGKGLEWVAASRNKNNDYTTEY<br>ADSVKGRFTISRDNSKNTLYLQMNSLRAEDTAVYYCARDYYGASYWYFDVWGQGTLVTVSS |
| 151 | EVQLLESGGGLVQPGGSLRLSCAASGFTFSDYYMEWVRQAPGKGLEWVAASRNKGNDYTTAY<br>ADSVKGRFTISRDNSKNTLYLQMNSLRAEDTAVYYCARDYFGSSYWYFDVWGQGTLVTVSS |
| 152 | EVQLLESGGGLVQPGGSLRLSCAASGFTQSDFYMEWVRQAPGKGLEWVAASRNKGNSYTTAY<br>ADSVKGRFTISRDNSKNTLYLQMNSLRAEDTAVYYCARDYYGSSYWYFDVWGQGTLVTVSS |
| 153 | EVQLLESGGGLVQPGGSLRLSCAASGFTFSDYYMEWVRQAPGKGLEWVAASRNKANSYTTAY<br>ADSVKGRFTISRDNSKNTLYLQMNSLRAEDTAVYYCARDYYGSSYWYFDVWGQGTLVTVSS |
| 154 | EVQLLESGGGLVQPGGSLRLSCAASGFTFSDGYMEWVRQAPGKGLEWVAASRNKANFYTTEY<br>ADSVKGRFTISRDNSKNTLYLQMNSLRAEDTAVYYCARDHYGSSYWYFDVWGQGTLVTVSS |
| 155 | EVQLLESGGGLVQPGGSLRLSCAASGFSFSDFYMEWVRQAPGKGLEWVAASRNKWNDYTTEY<br>ADSVKGRFTISRDNSKNTLYLQMNSLRAEDTAVYYCARDYYGSSYWYFDVWGQGTLVTVSS |
| 156 | EVQLLESGGGLVQPGGSLRLSCAASGFTFSDFYMEWVRQAPGKGLEWVAASRNKYNDYTTEY<br>ADSVKGRFTISRDNSKNTLYLQMNSLRAEDTAVYYCARDYYGSSYWYFDVWGQGTLVTVSS |
| 157 | EVQLLESGGGLVQPGGSLRLSCAASGFTFDDFYMEWVRQAPGKGLEWVAASRNEANDYTTEY<br>ADSVKGRFTISRDNSKNTLYLQMNSLRAEDTAVYYCARDYYGSSYWYFDVWGQGTLVTVSS |
| 158 | EVQLLESGGGLVQPGGSLRLSCAASGFTFSDFYMEWVRQAPGKGLEWVAASRNKWNDYTTEY<br>ADSVKGRFTISRDNSKNTLYLQMNSLRAEDTAVYYCARDYYGSSYWYFDVWGQGTLVTVSS |
| 159 | EVQLLESGGGLVQPGGSLRLSCAASGFTFSDFYIEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 160 | EVQLLESGGGLVQPGGSLRLSCAASGFTQSDFYMEWVRQAPGKGLEWVAASRNKANDYTTEY<br>ADSVKGRFTISRDNSKNTLYLQMNSLRAEDTAVYYCARDYYGESYWYFDVWGQGTLVTVSS |
| 161 | EVQLLESGGGLVQPGGSLRLSCAASGPTFSDFYMEWVRQAPGKGLEWVAASRNKANGYTTEY<br>ADSVKGRFTISRDNSKNTLYLQMNSLRAEDTAVYYCARDYYGSSYWYFDVWGQGTLVTVSS |
| 162 | EVQLLESGGGLVQPGGSLRLSCAASGFTDSDFYMEWVRQAPGKGLEWVAASRNKANGYTTEY<br>ADSVKGRFTISRDNSKNTLYLQMNSLRAEDTAVYYCARDYYGSSYWYFDVWGQGTLVTVSS |
| 163 | EVQLLESGGGLVQPGGSLRLSCAASGDTFSDFYMEWVRQAPGKGLEWVAASRWKANDYTTEY<br>ADSVKGRFTISRDNSKNTLYLQMNSLRAEDTAVYYCARDYYGSSYWYFDVWGQGTLVTVSS |
| 164 | EVQLLESGGGLVQPGGSLRLSCAASGFTFSSYYMEWVRQAPGKGLEWVAASRNKANDYTTEY<br>ADSVKGRFTISRDNSKNTLYLQMNSLRAEDTAVYYCARDYYLSSYWYFDVWGQGTLVTVSS |
| 165 | EVQLLESGGGLVQPGGSLRLSCAASGFTFSDGYMEWVRQAPGKGLEWVAAIRNKANDYTTEY<br>ADSVKGRFTISRDNSKNTLYLQMNSLRAEDTAVYYCARDYYGSHYWYFDVWGQGTLVTVSS |

| SEQ ID NO | SEQUENCE |
|---|---|
| 166 | EVQLLESGGGLVQPGGSLRLSCAASGFTFSDYYMEWVRQAPGKGLEWVAASRNKGNDYTTAY<br>ADSVKGRFTISRDNSKNTLYLQMNSLRAEDTAVYYCARDYYGSSYWYFDVWGQGTLVTVSS |
| 167 | EVQLLESGGGLVQPGGSLRLSCAASGFTFSDYYMEWVRQAPGKGLEWVAASRNVANDYTTEY<br>ADSVKGRFTISRDNSKNTLYLQMNSLRAEDTAVYYCARDYYGSSYWYFDVWGQGTLVTVSS |
| 168 | EVQLLESGGGLVQPGGSLRLSCAASGFTGSDFYMEWVRQAPGKGLEWVAASRWKANDYTTEY<br>ADSVKGRFTISRDNSKNTLYLQMNSLRAEDTAVYYCARDYYGSSYWYFDVWGQGTLVTVSS |
| 169 | EVQLLESGGGLVQPGGSLRLSCAASGFTFSDQYMEWVRQAPGKGLEWVAASRNKANDWTTEY<br>ADSVKGRFTISRDNSKNTLYLQMNSLRAEDTAVYYCARDYYGSSYWYFDVWGQGTLVTVSS |
| 170 | EVQLLESGGGLVQPGGSLRLSCAASGNTFSDFYMEWVRQAPGKGLEWVAASRNKANYYTTEY<br>ADSVKGRFTISRDNSKNTLYLQMNSLRAEDTAVYYCARDYYGSSYWYFDVWGQGTLVTVSS |
| 171 | EVQLLESGGGLVQPGGSLRLSCAASGFTGSDFYMEWVRQAPGKGLEWVAASRNKANDYTTEY<br>ADSVKGRFTISRDNSKNTLYLQMNSLRAEDTAVYYCARDYYGSPYWYFDVWGQGTLVTVSS |
| 172 | EVQLLESGGGLVQPGGSLRLSCAASGFTSSDFYLEWVRQAPGKGLEWVAASRNKWNDYTTEY<br>ADSVKGRFTISRDNSKNTLYLQMNSLRAEDTAVYYCARDYYGSSYWYFDVWGQGTLVTVSS |
| 173 | EVQLLESGGGLVQPGGSLRLSCAASGFTFSPFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 174 | EVQLLESGGGLVQPGGSLRLSCAASGFTASDFYMEWVRQAPGKGLEWVAASRWKANDYTTEY<br>ADSVKGRFTISRDNSKNTLYLQMNSLRAEDTAVYYCARDIYGSSYWYFDVWGQGTLVTVSS |
| 175 | EVQLLESGGGLVQPGGSLRLSCAASGFTFSDYYMEWVRQAPGKGLEWVAASRNKWNDYTTEY<br>ADSVKGRFTISRDNSKNTLYLQMNSLRAEDTAVYYCARDYYLSSYWYFDVWGQGTLVTVSS |
| 176 | EVQLLESGGGLVQPGGSLRLSCAASGFTTSDFYMEWVRQAPGKGLEWVAASRNKANDYTTEY<br>ADSVKGRFTISRDNSKNTLYLQMNSLRAEDTAVYYCARDYYGSSYWYFDYWGQGTLVTVSS |
| 177 | EVQLLESGGGLVQPGGSLRLSCAASGFTFSDFYMEWVRQAPGKGLEWVAASRNKANDYTTEY<br>ADSVKGRFTISRDNSKNTLYLQMNSLRAEDTAVYYCARDFYGSSYWYFDVWGQGTLVTVSS |
| 178 | EVQLLESGGGLVQPGGSLRLSCAASGFTGSDFYMEWVRQAPGKGLEWVAASRNKANDYTTEY<br>ADSVKGRFTISRDNSKNTLYLQMNSLRAEDTAVYYCARDYYGSSYWYFDVWGQGTLVTVSS |
| 179 | EVQLLESGGGLVQPGGSLRLSCAASGNTFSDFYMEWVRQAPGKGLEWVAASRNKWNDYTTEY<br>ADSVKGRFTISRDNSKNTLYLQMNSLRAEDTAVYYCARDYYGSSYWYFDVWGQGTLVTVSS |
| 180 | EVQLLESGGGLVQPGGSLRLSCAASGFTFSDHYMEWVRQAPGKGLEWVAASRWKANDYTTEY<br>ADSVKGRFTISRDNSKNTLYLQMNSLRAEDTAVYYCARDYYGSSYWYFDVWGQGTLVTVSS |
| 181 | DIQMTQSPSSLSASVGDRVTITCTASESLYSSKHKVHYLAWYQQKPGKAPKLLIYGASNRYI<br>GVPSRFSGSGSGTDFTLTISSLQPEDFATYYCAEFYSYPLTFGGGTKVEIK |
| 182 | DIQMTQSPSSLSASVGDRVTITCTASESLYSSKHKVHYLAWYQQKPGKAPKLLIYGASNREI<br>GVPSRFSGSGSGTDFTLTISSLQPEDFATYYCQQFYSYPLTFGGGTKVEIK |
| 183 | DIQMTQSPSSLSASVGDRVTITCTASESLYSSKHKVHYLAWYQQKPGKAPKLLIYGASHRYI<br>GVPSRFSGSGSGTDFTLTISSLQPEDFATYYCAQFYAYPLTFGGGTKVEIK |
| 184 | DIQMTQSPSSLSASVGDRVTITCTASESLYSSKHKVHYLAWYQQKPGKAPKLLIYGASNRYI<br>GVPSRESGSGSGTDFTLTISSLQPEDFATYYCAQFYSYPLTFGGGTKVEIK |
| 185 | DIQMTQSPSSLSASVGDRVTITCTASESLYSSKHKVHYLAWYQQKPGKAPKLLIYGASSLQI<br>GVPSRFSGSGSGTDFTLTISSLQPEDFATYYCAQFYSYPLTFGGGTKVEIK |
| 186 | DIQMTQSPSSLSASVGDRVTITCTASESLYSSKHKVHYLAWYQQKPGKAPKLLIYGASNRYT<br>GVPSRFSGSGSGTDFTLTISSLQPEDFATYYCAQFYHYPLTFGGGTKVEIK |
| 187 | DIQMTQSPSSLSASVGDRVTITCTASESLYSSKHKVHYLAWYQQKPGKAPKLLIYGASNRYH<br>GVPSRFSGSGSGTDFTLTISSLQPEDFATYYCAQFYSYPLTFGGGTKVEIK |
| 188 | DIQMTQSPSSLSASVGDRVTITCVASESLYSSKHKVHYLAWYQQKPGKAPKLLIYGASNRYI<br>GVPSRFSGSGSGTDFTLTISSLQPEDFATYYCAQFYSYPLTFGGGTKVEIK |
| 189 | DIQMTQSPSSLSASVGDRVTITCTASESLYSSKHKVHYLAWYQQKPGKAPKLLIYGASNRYI<br>GVPSRFSGSGSGTDFTLTISSLQPEDFATYYCAQFYQYPLTFGGGTKVEIK |
| 190 | DIQMTQSPSSLSASVGDRVTITCTASESLYSSKHKVHYLAWYQQKPGKAPKLLIYGASNRYI<br>GVPSRFSGSGSGTDFTLTISSLQPEDFATYYCAQFYYYPLTFGGGTKVEIK |

-continued

SEQUENCE LISTING

| SEQ ID NO | SEQUENCE |
|---|---|
| 191 | DIQMTQSPSSLSASVGDRVTITCTASESLYSSKHKVHYLAWYQQKPGKAPKLLIYGSSNRYI GVPSRFSGSGSGTDFTLTISSLQPEDFATYYCAQFYAYPLTFGGGTKVEIK |
| 192 | DIQMTQSPSSLSASVGDRVTITCTASESLYSSKHKVHYLAWYQQKPGKAPKLLIYGASNRFI GVPSRESGSGSGTDFTLTISSLQPEDFATYYCAQFYYYPLTFGGGTKVEIK |
| 193 | DIQMTQSPSSLSASVGDRVTITCRASESISSSKNKVHYLAWYQQKPGKAPKLLIYGASNRYY GVPSRFSGSGSGTDFTLTISSLQPEDFATYYCAQFYSYPLTFGGGTKVEIK |
| 194 | DIQMTQSPSSLSASVGDRVTITCTASESLYSSKHKVHYLAWYQQKPGKAPKLLIYGAANRYI GVPSRESGSGSGTDFTLTISSLQPEDFATYYCAQFYVYPLTFGGGTKVEIK |
| 195 | DIQMTQSPSSLSASVGDRVTITCTASESLYSSKHKVHYLAWYQQKPGKAPKLLIYGASNRYI GVPSRFSGSGSGTDFTLTISSLQPEDFATYYCGQFYSYPLTFGGGTKVEIK |
| 196 | DIQMTQSPSSLSASVGDRVTITCTASESLYSSKHKVHYLAWYQQKPGKAPKLLIYGASNRYV GVPSRFSGSGSGTDFTLTISSLQPEDFATYYCAQFYSYPLTFGGGTKVEIK |
| 197 | DIQMTQSPSSLSASVGDRVTITCTASESLYSAKHKVHYLAWYQQKPGKAPKLLIYGSSNRYI GVPSRFSGSGSGTDFTLTISSLQPEDFATYYCAQFYDYPLTFGGGTKVEIK |
| 198 | DIQMTQSPSSLSASVGDRVTITCTASESLYSSKHKVHYLAWYQQKPGKAPKLLIYGASNRYD GVPSRFSGSGSGTDFTLTISSLQPEDFATYYCAQFYSYPLTFGGGTKVEIK |
| 199 | DIQMTQSPSSLSASVGDRVTITCTASESLYSSKHKVNYLAWYQQKPGKAPKLLIYGASNRYI GVPSRFSGSGSGTDFTLTISSLQPEDFATYYCAQFYQYPLTFGGGTKVEIK |
| 200 | DIQMTQSPSSLSASVGDRVTITCTASESLYSSKHKVHYVAWYQQKPGKAPKLLIYGASNRYI GVPSRFSGSGSGTDFTLTISSLQPEDFATYYCAQFYYYPLTFGGGTKVEIK |
| 201 | DIQMTQSPSSLSASVGDRVTITCTASFSLYSSKHKVHYLAWYQQKPGKAPKLLIYGASNRYP GVPSRFSGSGSGTDFTLTISSLQPEDFATYYCAQFYYYPLTFGGGTKVEIK |
| 202 | DIQMTQSPSSLSASVGDRVTITCTASESLYSSKHKVHYLAWYQQKPGKAPKLLIYGAVNRYI GVPSRFSGSGSGTDFTLTISSLQPEDFATYYCAQFYRYPLTFGGGTKVEIK |
| 203 | DIQMTQSPSSLSASVGDRVTITCTASESLYSSKHKVHYLAWYQQKPGKAPKLLIYGASNGYI GVPSRFSGSGSGTDFTLTISSLQPEDFATYYCAQFYTYPLTFGGGTKVEIK |
| 204 | DIQMTQSPSSLSASVGDRVTITCTASESLYGSKHKVHYLAWYQQKPGKAPKLLIYGASNRYS GVPSRESGSGSGTDFTLTISSLQPEDFATYYCAQFYSYPLTFGGGTKVEIK |
| 205 | DIQMTQSPSSLSASVGDRVTITCTASESLYSSKHKVHYLAWYQQKPGKAPKLLIYGASNLYS GVPSRFSGSGSGTDFTLTISSLQPEDFATYYCAQFYSYPLTFGGGTKVEIK |
| 206 | DIQMTQSPSSLSASVGDRVTITCTASESLYSSKHKVHYLAWYQQKPGKAPKLLIYGASNRYF GVPSRFSGSGSGTDFTLTISSLQPEDFATYYCAQFYSYPLTFGGGTKVEIK |
| 207 | DIQMTQSPSSLSASVGDRVTITCTASESLYSSKHKVHYLAWYQQKPGKAPKLLIYGASNLQS GVPSRFSGSGSGTDFTLTISSLQPEDFATYYCAQFYYYPLTFGGGTKVEIK |
| 208 | DIQMTQSPSSLSASVGDRVTITCRASESISSSKHKHYLAWYQQKPGKAPKLLIYGASNRYIG VPSRFSGSGSGTDFTLTISSLQPEDFATYYCAQFYVYPLTFGGGTKVEIK |
| 209 | DIQMTQSPSSLSASVGDRVTITCTASESLYSSKHKVHYLAWYQQKPGKAPKLLIYGASNRYF GVPSRFSGSGSGTDFTLTISSLQPEDFATYYCAQFYQYPLTFGGGTKVEIK |
| 210 | DIQMTQSPSSLSASVGDRVTITCTASESLYSSKHKVHYLAWYQQKPGKAPKLLIYGLSNRYI GVPSRFSGSGSGTDFTLTISSLQPEDFATYYCAQFYSYPLTFGGGTKVEIK |
| 211 | DIQMTQSPSSLSASVGDRVTITCTASESLYSSKHKVHYLAWYQQKPGKAPKLLIYGASNRQS GVPSRFSGSGSGTDFTLTISSLQPEDFATYYCAQFYWPLTFGGGTKVEIK |
| 212 | DIQMTQSPSSLSASVGDRVTITCTASESLYSSKHKVHYLAWYQQKPGKAPKLLIYGASNRQS GVPSRFSGSGSGTDFTLTISSLQPEDFATYYCAQFYAYPLTFGGGTKVEIK |
| 213 | DIQMTQSPSSLSASVGDRVTITCTASESLYSSKHKVHYLAWYQQKPGKAPKLLIYGASNRYH GVPSRESGSGSGTDFTLTISSLQPEDFATYYCAQFYYYPLTFGGGTKVEIK |
| 214 | DIQMTQSPSSLSASVGDRVTITCTASESLYSSKHKVHYLAWYQQKPGKAPKLLIYGAFNRYT GVPSRFSGSGSGTDFTLTISSLQPEDFATYYCAQFYTYPLTFGGGTKVEIK |

SEQUENCE LISTING

| SEQ ID NO | SEQUENCE |
|---|---|
| 215 | DIQMTQSPSSLSASVGDRVTITCTASESLYSSKHKVHYLAWYQQKPGKAPKLLIYGASNRLIGVPSRFSGSGSGTDFTLTISSLQPEDFATYYCAQFYWYPLTFGGGTKVEIK |
| 216 | DIQMTQSPSSLSASVGDRVTITCTASESLYSSKHKVHYLAWYQQKPGKAPKLLIYGASNRYIGVPSRFSGSGSGTDFTLTISSLQPEDFATYYCTQFYSYPLTFGGGTKVEIK |
| 217 | DIQMTQSPSSLSASVGDRVTITCTASESLYSSKHKVHYLAWYQQKPGKAPKLLIYGASNRYIGVPSRFSGSGSGTDFTLTISSLQPEDFATYYCAQFYVYPLTFGGGTKVEIK |
| 218 | DIQMTQSPSSLSASVGDRVTITCTASESLYSSKHKVHYLAWYQQKPGKAPKLLIYGQSNRYIGVPSRFSGSGSGTDFTLTISSLQPEDFATYYCAQFYSYPLTFGGGTKVEIK |
| 219 | DIQMTQSPSSLSASVGDRVTITCTASEWLYSSKHKVHYLAWYQQKPGKAPKLLIYGASNRNIGVPSRFSGSGSGTDFTLTISSLQPEDFATYYCAQFYYYPLTFGGGTKVEIK |
| 220 | DIQMTQSPSSLSASVGDRVTITCTASESLYSSKHKVHYLAWYQQKPGKAPKLLIYGAGNRYIGVPSRFSGSGSGTDFTLTISSLQPEDFATYYCAQFYFYPLTFGGGTKVEIK |
| 221 | DIQMTQSPSSLSASVGDRVTITCTASESLYSSKHKVHYLAWYQQKPGKAPKLLIYGASNRYIGVPSRFSGSGSGTDFTLTISSLQPEDFATYYCAQFYWYPLTFGGGTKVEIK |
| 222 | DIQMTQSPSSLSASVGDRVTITCTASESLYSSKHKVHYLAWYQQKPGKAPKLLIYGASNRYGGVPSRFSGSGSGTDFTLTISSLQPEDFATYYCAQFYEYPLTFGGGTKVEIK |
| 223 | DIQMTQSPSSLSASVGDRVTITCTATESLYSSKHKVHYLAWYQQKPGKAPKLLIYGASNRYTGVPSRFSGSGSGTDFTLTISSLQPEDFATYYCAQFYSYPLTFGGGTKVEIK |
| 224 | DIQMTQSPSSLSASVGDRVTITCTASESLYSSKHKVHYLAWYQQKPGKAPKLLIYGASGRYIGVPSRFSGSGSGTDFTLTISSLQPEDFATYYCAQFYSYPLTFGGGTKVEIK |
| 225 | DIQMTQSPSSLSASVGDRVTITCTASESLYSGKHKVHYLAWYQQKPGKAPKLLIYGASNLQIGVPSRESGSGSGTDFTLTISSLQPEDFATYYCAQFYYYPLTFGGGTKVEIK |
| 226 | DIQMTQSPSSLSASVGDRVTITCFASESLYSSKHKVHYLAWYQQKPGKAPKLLIYGASNRGIGVPSRFSGSGSGTDFTLTISSLQPEDFATYYCAQFYSYPLTFGGGTKVEIK |
| 227 | DIQMTQSPSSLSASVGDRVTITCTASQSLYSSKNKVHYLAWYQQKPGKAPKLLIYGESNRYIGVPSRFSGSGSGTDFTLTISSLQPEDFATYYCAQFYSYPLTFGGGTKVEIK |
| 228 | DIQMTQSPSSLSASVGDRVTITCEASESLYSSKHKVHYLAWYQQKPGKAPKLLIYGASNRYPGVPSRFSGSGSGTDFTLTISSLQPEDFATYYCAQFYEYPLTFGGGTKVEIK |
| 229 | DIQMTQSPSSLSASVGDRVTITCTASESLYSSKHKVHYLAWYQQKPGKAPKLLIYGVSNRYIGVPSRFSGSGSGTDFTLTISSLQPEDFATYYCAQFYSYPLTFGGGTKVEIK |
| 230 | DIQMTQSPSSLSASVGDRVTITCTASESLYSSKHKVHYLAWYQQKPGKAPKLLIYGASNRYGGVPSRFSGSGSGTDFTLTISSLQPEDFATYYCAQFYSYPLTFGGGTKVEIK |
| 231 | DIQMTQSPSSLSASVGDRVTITCTASESLYSSKHKVHYLAWYQQKPGKAPKLLIYGASNRPIGVPSRFSGSGSGTDFTLTISSLQPEDFATYYCAQFYSYPLTFGGGTKVEIK |
| 232 | DIQMTQSPSSLSASVGDRVTITCTASESISSSKHKVHYLAWYQQKPGKAPKLLIYGASNLYSGVPSRFSGSGSGTDFTLTISSLQPEDFATYYCAHFYSYPLTFGGGTKVEIK |
| 233 | DIQMTQSPSSLSASVGDRVTITCTASESLYSSKHKVHYLAWYQQKPGKAPKLLIYGAGNRYIGVPSRFSGSGSGTDFTLTISSLQPEDFATYYCAQFYEYPLTFGGGTKVEIK |
| 234 | DIQMTQSPSSLSASVGDRVTITCTASESLYSSKHKVHYLAWYQQKPGKAPKLLIYGASFRYIGVPSRESGSGSGTDFTLTISSLQPEDFATYYCAQFYSYPLTFGGGTKVEIK |
| 235 | DIQMTQSPSSLSASVGDRVTITCTASESLYSSKHKVHYLAWYQQKPGKAPKLLIYGASNRGIGVPSRFSGSGSGTDFTLTISSLQPEDFATYYCAQFYSYPLTFGGGTKVEIK |
| 236 | DIQMTQSPSSLSASVGDRVTITCTASESLYSSKHKVHYLAWYQQKPGKAPKLLIYGADNRYIGVPSRESGSGSGTDFTLTISSLQPEDFATYYCAQFYHYPLTFGGGTKVEIK |
| 237 | DIQMTQSPSSLSASVGDRVTITCTASESLYSSKHKVHYLAWYQQKPGKAPKLLIYGASNRYDGVPSRFSGSGSGTDFTLTISSLQPEDFATYYCAQFYEYPLTFGGGTKVEIK |
| 238 | DIQMTQSPSSLSASVGDRVTITCTASESLYSSKHKVHYLAWYQQKPGKAPKLLIYGASNRQSGVPSRFSGSGSGTDFTLTISSLQPEDFATYYCAQFYVYPLTFGGGTKVEIK |
| 239 | DIQMTQSPSSLSASVGDRVTITCTASESLYSSKHKVHYLAWYQQKPGKAPKLLIYGASNRYQGVPSRFSGSGSGTDFTLTISSLQPEDFATYYCAQFYFYPLTFGGGTKVEIK |

SEQUENCE LISTING

| SEQ ID NO | SEQUENCE |
|---|---|
| 240 | DIQMTQSPSSLSASVGDRVTITCTASESLYSSKHKVHYLAWYQQKPGKAPKLLIYGASNRYSGVPSRFSGSGSGTDFTLTISSLQPEDFATYYCAQFYKYPLTFGGGTKVEIK |
| 241 | DIQMTQSPSSLSASVGDRVTITCTASESLYSSKHKVHYLAWYQQKPGKAPKLLIYGASSRYIGVPSRFSGSGSGTDFTLTISSLQPEDFATYYCAQFYEYPLTFGGGTKVEIK |
| 242 | DIQMTQSPSSLSASVGDRVTITCTASESLYSSKHKVHYLAWYQQKPGKAPKLLIYGTSNRYIGVPSRFSGSGSGTDFTLTISSLQPEDFATYYCAQFYEYPLTFGGGTKVEIK |
| 243 | DIQMTQSPSSLSASVGDRVTITCTASESLYSQKHKVHYLAWYQQKPGKAPKLLIYGASNRYIGVPSRFSGSGSGTDFTLTISSLQPEDFATYYCAQFYYYPLTFGGGTKVEIK |
| 244 | DIQMTQSPSSLSASVGDRVTITCTASESLYSSKHKVHYLAWYQQKPGKAPKLLIYGASNRYIGVPSRESGSGSGTDFTLTISSLQPEDFATYYCAQFYFYPLTFGGGTKVEIK |
| 245 | DIQMTQSPSSLSASVGDRVTITCTASESLYSSKHKVHYLAWYQQKPGKAPKLLIYGASNRQSGVPSRFSGSGSGTDFTLTISSLQPEDFATYYCAQFYSYPLTFGGGTKVEIK |
| 246 | DIQMTQSPSSLSASVGDRVTITCEASESLYSSKHKVHYLAWYQQKPGKAPKLLIYGASNRLIGVPSRFSGSGSGTDFTLTISSLQPEDFATYYCAQFYEYPLTFGGGTKVEIK |
| 247 | DIQMTQSPSSLSASVGDRVTITCTASESLYSSKHSVHYLAWYQQKPGKAPKLLIYGASNRFIGVPSRFSGSGSGTDFTLTISSLQPEDFATYYCAQFYSYPLTFGGGTKVEIK |
| 248 | DIQMTQSPSSLSASVGDRVTITCTASEELYSSKHKVHYLAWYQQKPGKAPKLLIYGASNRYIGVPSRFSGSGSGTDFTLTISSLQPEDFATYYCAQFYSYPLTFGGGTKVEIK |
| 249 | DIQMTQSPSSLSASVGDRVTITCTASQSISSSKHKVHYLAWYQQKPGKAPKLLIYGASNHYIGVPSRFSGSGSGTDFTLTISSLQPEDFATYYCAQFYSYPLTFGGGTKVEIK |
| 250 | DIQMTQSPSSLSASVGDRVTITCTASESLYSSKHKVHYLAWYQQKPGKAPKLLIYGASNRYIGVPSRFSGSGSGTDFTLTISSLQPEDFATYYCAQFYEYPLTFGGGTKVEIK |
| 251 | DIQMTQSPSSLSASVGDRVTITCTASESLYSSKHKVHYLAWYQQKPGKAPKLLIYGASNRQIGVPSRFSGSGSGTDFTLTISSLQPEDFATYYCAQFYTYPLTFGGGTKVEIK |
| 252 | DIQMTQSPSSLSASVGDRVTITCTASESLSSSKHKHYLAWYQQKPGKAPKLLIYGASSRYSGVPSRFSGSGSGTDFTLTISSLQPEDFATYYCAQFYSYPLTFGGGTKVEIK |
| 253 | DIQMTQSPSSLSASVGDRVTITCTASESLYSSKHKVHYLAWYQQKPGKAPKLLIYGASNRDIGVPSRFSGSGSGTDFTLTISSLQPEDFATYYCGQFYSYPLTFGGGTKVEIK |
| 254 | DIQMTQSPSSLSASVGDRVTITCTASESLYSSKHKVHYLAWYQQKPGKAPKLLIYGSSNRYIGVPSRFSGSGSGTDFTLTISSLQPEDFATYYCAQFYQYPLTFGGGTKVEIK |
| 255 | DIQMTQSPSSLSASVGDRVTITCTASESLYSSKHKVHYLAWYQQKPGKAPKLLIYGISNRYIGVPSRFSGSGSGTDFTLTISSLQPEDFATYYCAQFYSYPLTFGGGTKVEIK |
| 256 | DIQMTQSPSSLSASVGDRVTITCTAEESLYSSKHKVHYLAWYQQKPGKAPKLLIYGASNLYSGVPSRFSGSGSGTDFTLTISSLQPEDFATYYCAQFYSYPLTFGGGTKVEIK |
| 257 | DIQMTQSPSSLSASVGDRVTITCTASESLYSSKHKVHYLAWYQQKPGKAPKLLIYGASNRQIGVPSRFSGSGSGTDFTLTISSLQPEDFATYYCAQFYSYPLTFGGGTKVEIK |
| 258 | DIQMTQSPSSLSASVGDRVTITCTASESLYSSKHKVHYLAWYQQKPGKAPKLLIYGASNRYIGVPSRESGSGSGTDFTLTISSLQPEDFATYYCAQFYDYPLTFGGGTKVEIK |
| 259 | DIQMTQSPSSLSASVGDRVTITCTASESLYSSKHKVHYLAWYQQKPGKAPKLLIYGLSNRYIGVPSRFSGSGSGTDFTLTISSLQPEDFATYYCAQFFSYPLTFGGGTKVEIK |
| 260 | DIQMTQSPSSLSASVGDRVTITCTASESLYSSKHKVHYLAWYQQKPGKAPKLLIYGASSLYSGVPSRFSGSGSGTDFTLTISSLQPEDFATYYCAQFYEYPLTFGGGTKVEIK |
| 261 | DIQMTQSPSSLSASVGDRVTITCTASESLYSSKHGVHYLAWYQQKPGKAPKLLIYGASNRYIGVPSRFSGSGSGTDFTLTISSLQPEDFATYYCAQFYQYPLTFGGGTKVEIK |
| 262 | DIQMTQSPSSLSASVGDRVTITCTASESLYSSKHKVHYLAWYQQKPGKAPKLLIYGASNRAIGVPSRFSGSGSGTDFTLTISSLQPEDFATYYCAQFYTYPLTFGGGTKVEIK |
| 263 | DIQMTQSPSSLSASVGDRVTITCTASESLSSSKHKVHYLAWYQQKPGKAPKLLIYGASNRYIGVPSRFSGSGSGTDFTLTISSLQPEDFATYYCAQFYSYPLTFGGGTKVEIK |

-continued

| SEQ ID NO | SEQUENCE |
|---|---|
| 264 | DIQMTQSPSSLSASVGDRVTITCTASESLYSSKHKVHYLAWYQQKPGKAPKLLIYGASNRYAGVPSRFSGSGSGTDFTLTISSLQPEDFATYYCGQFYSYPLTFGGGTKVEIK |
| 265 | DIQMTQSPSSLSASVGDRVTITCTASQSLYSSKHKVHYLAWYQQKPGKAPKLLIYGASNRYIGVPSRFSGSGSGTDFTLTISSLQPEDFATYYCAQFYVYPLTFGGGTKVEIK |
| 266 | DIQMTQSPSSLSASVGDRVTITCRASESLYSSLHKYLAWYQQKPGKAPKLLIYGASNLQIGVPSRFSGSGSGTDFTLTISSLQPEDFATYYCAQFYSYPLTFGGGTKVEIK |
| 267 | DIQMTQSPSSLSASVGDRVTITCTASESLYSSKHKVHYLAWYQQKPGKAPKLLIYGASNRVIGVPSRFSGSGSGTDFTLTISSLQPEDFATYYCAQFYSYPLTFGGGTKVEIK |
| 268 | DIQMTQSPSSLSASVGDRVTITCTASESLYSSKHKVHYLAWYQQKPGKAPKLLIYGPSNRYIGVPSRFSGSGSGTDFTLTISSLQPEDFATYYCAQFYSYPLTFGGGTKVEIK |
| 269 | DIVMTQSPDSLAVSLGERATINCTASESLYSSKHKVHYLAWYQQKPGQPPKLLIYGASNRYIGVPDRFSGSGSGTDFTLTISSLQAEDVAVYYCAQFYSYPLTFGGGTKVEIK |
| 270 | DIVMTQSPDSLAVSLGERATINCTASESVYSSKNKKHYLAWYQQKPGQPPKLLIYGASNRYIGVPDRFSGSGSGTDFTLTISSLQAEDVAVYYCAQFYSYPLTFGGGTKVEIK |
| 271 | DIVMTQSPDSLAVSLGERATINCTASESLYSSKGKVHYLAWYQQKPGQPPKLLIYGASNRYIGVPDRFSGSGSGTDFTLTISSLQAEDVAVYYCVQFYSYPLTFGGGTKVEIK |
| 272 | DIVMTQSPDSLAVSLGERATINCTASESLYSSKHKVHYLAWYQQKPGQPPKLLIYGASNRYIGVPDRFSGSGSGTDFTLTISSLQAEDVAVYYCGQFYSYPLTFGGGTKVEIK |
| 273 | DIVMTQSPDSLAVSLGERATINCTASESLYSSKHKVHYLAWYQQKPGQPPKLLIYGASNRYDGVPDRFSGSGSGTDFTLTISSLQAEDVAVYYCAQFYSYPLTFGGGTKVEIK |
| 274 | DIVMTQSPDSLAVSLGERATINCTASQSVYSSKNKVHYLAWYQQKPGQPPKLLIYGASNRYIGVPDRFSGSGSGTDFTLTISSLQAEDVAVYYCAQFYSYPLTFGGGTKVEIK |
| 275 | DIVMTQSPDSLAVSLGERATINCTSSQSLLSSSHNKNYLAWYQQKPGQPPKLLIYGASNRYIGVPDRFSGSGSGTDFTLTISSLQAEDVAVYYCAQFYSYPLTFGGGTKVEIK |
| 276 | DIVMTQSPDSLAVSLGERATINCTASESLYSPKHKVHYLAWYQQKPGQPPKLLIYGASNRYIGVPDRFSGSGSGTDFTLTISSLQAEDVAVYYCAQFYIYPLTFGGGTKVEIK |
| 277 | DIVMTQSPDSLAVSLGERATINCTASESLWSSKHKVHYLAWYQQKPGQPPKLLIYGASNRYIGVPDRFSGSGSGTDFTLTISSLQAEDVAVYYCAQFYSYPLTFGGGTKVEIK |
| 278 | DIVMTQSPDSLAVSLGERATINCTASESLYSSKHKVHYLAWYQQKPGQPPKLLIYGASNRYIGVPDRFSGSGSGTDFTLTISSLQAEDVAVYYCAQFYIYPLTFGGGTKVEIK |
| 279 | DIVMTQSPDSLAVSLGERATINCKASQSVLSSKNNVNYLAWYQQKPGQPPKLLIYGASNRYSGVPDRFSGSGSGTDFTLTISSLQAEDVAVYYCAQFYSYPLTFGGGTKVEIK |
| 280 | DIVMTQSPDSLAVSLGERATINCTASESLYSSKWKVHYLAWYQQKPGQPPKLLIYGASNRYIGVPDRFSGSGSGTDFTLTISSLQAEDVAVYYCAQFYSYPLTFGGGTKVEIK |
| 281 | DIVMTQSPDSLAVSLGERATINCTASESLYSSKHKVHYLAWYQQKPGQPPKLLIYGASNRVIGVPDRFSGSGSGTDFTLTISSLQAEDVAVYYCANFYSYPLTFGGGTKVEIK |
| 282 | DIVMTQSPDSLAVSLGERATINCKSSESVYSSKHKKHYLAWYQQKPGQPPKLLIYGASNRYIGVPDRFSGSGSGTDFTLTISSLQAEDVAVYYCAQFYSYPLTFGGGTKVEIK |
| 283 | DIVMTQSPDSLAVSLGERATINCTASESLYSSKHKVDYLAWYQQKPGQPPKLLIYGASNRYIGVPDRFSGSGSGTDFTLTISSLQAEDVAVYYCAQFYSYPLTFGGGTKVEIK |
| 284 | DIVMTQSPDSLAVSLGERATINCTASESLYSSKHKVHYLAWYQQKPGQPPKLLIYGASNRYIGVPDRFSGSGSGTDFTLTISSLQAEDVAVYYCANFYSYPLTFGGGTKVEIK |
| 285 | DIVMTQSPDSLAVSLGERATINCTASESLYSPKHKVHYLAWYQQKPGQPPKLLIYGAFNRYIGVPDRFSGSGSGTDFTLTISSLQAEDVAVYYCAQFYSYPLTFGGGTKVEIK |
| 286 | DIVMTQSPDSLAVSLGERATINCTASESVYSSKNKKHYLAWYQQKPGQPPKLLIYGASNRYIGVPDRFSGSGSGTDFTLTISSLQAEDVAVYYCAQFYTYPLTFGGGTKVEIK |
| 287 | DIVMTQSPDSLAVSLGERATINCKSSQSLYYSSNKKNYLAWYQQKPGQPPKLLIYGASNRYGGVPDRFSGSGSGTDFTLTISSLQAEDVAVYYCAQFYRYPLTFGGGTKVEIK |
| 288 | DIVMTQSPDSLAVSLGERATINCTASESLYSSKHKVHYLAWYQQKPGQPPKLLIYGASNRYIGVPDRFSGSGSGTDFTLTISSLQAEDVAVYYCAHFYSYPLTFGGGTKVEIK |

| SEQ ID NO | SEQUENCE |
|---|---|
| 289 | DIVMTQSPDSLAVSLGERATINCTASESLYSSKHKVHYLAWYQQKPGQPPKLLIYGASNRYS GVPDRFSGSGSGTDFTLTISSLQAEDVAVYYCAQFYSYPLTFGGGTKVEIK |
| 290 | DIVMTQSPDSLAVSLGERATINCTASESLYSSKHKVHYLAWYQQKPGQPPKLLIYGASNRYV GVPDRFSGSGSGTDFTLTISSLQAEDVAVYYCAQFYSYPLTFGGGTKVEIK |
| 291 | DIVMTQSPDSLAVSLGERATINCTASESLYSSKHKVHYLAWYQQKPGQPPKLLIYGASNREI GVPDRFSGSGSGTDFTLTISSLQAEDVAVYYCAQFYFYPLTFGGGTKVEIK |
| 292 | DIVMTQSPDSLAVSLGERATINCTASTSLYSSKHKVHYLAWYQQKPGQPPKLLIYGASNRYI GVPDRFSGSGSGTDFTLTISSLQAEDVAVYYCAQFYTYPLTFGGGTKVEIK |
| 293 | DIVMTQSPDSLAVSLGERATINCTASESLYGSKHKVHYLAWYQQKPGQPPKLLIYGASNRYI GVPDRFSGSGSGTDFTLTISSLQAEDVAVYYCAQFYSYPLTFGGGTKVEIK |
| 294 | DIVMTQSPDSLAVSLGERATINCKASQSLYSSKHKKHYLAWYQQKPGQPPKLLIYGASNRYP GVPDRFSGSGSGTDFTLTISSLQAEDVAVYYCAQFYRYPLTFGGGTKVEIK |
| 295 | DIVMTQSPDSLAVSLGERATINCTASSSLYSSKHKVHYLAWYQQKPGQPPKLLIYGASNRYI GVPDRFSGSGSGTDFTLTISSLQAEDVAVYYCAQFYSYPLTFGGGTKVEIK |
| 296 | DIVMTQSPDSLAVSLGERATINCTASESLYSSKHKVHYLAWYQQKPGQPPKLLIYGAGNRYI GVPDRFSGSGSGTDFTLTISSLQAEDVAVYYCAQFYHYPLTFGGGTKVEIK |
| 297 | DIVMTQSPDSLAVSLGERATINCTASESLYSSKHKVHYLAWYQQKPGQPPKLLIYGASNRYD GVPDRFSGSGSGTDFTLTISSLQAEDVAVYYCANFYSYPLTFGGGTKVEIK |
| 298 | DIVMTQSPDSLAVSLGERATINCTASESLYSSKHKVHYLAWYQQKPGQPPKLLIYGAGNRYI GVPDRFSGSGSGTDFTLTISSLQAEDVAVYYCAQFYSYPLTFGGGTKVEIK |
| 299 | DIVMTQSPDSLAVSLGERATINCTASESLYSSKHKVHYLAWYQQKPGQPPKLLIYGASNRQI GVPDRFSGSGSGTDFTLTISSLQAEDVAVYYCAQFYHYPLTFGGGTKVEIK |
| 300 | DIVMTQSPDSLAVSLGERATINCTASESLYSVKHKVHYLAWYQQKPGQPPKLLIYGASNRYI GVPDRFSGSGSGTDFTLTISSLQAEDVAVYYCAQFYSYPLTFGGGTKVEIK |
| 301 | DIVMTQSPDSLAVSLGERATINCTASESLYSSKHKVHYLAWYQQKPGQPPKLLIYGASNRYI GVPDRFSGSGSGTDFTLTISSLQAEDVAVYYCAQFYVYPLTFGGGTKVEIK |
| 302 | DIVMTQSPDSLAVSLGERATINCTASESLYSSKHKVHYLAWYQQKPGQPPKLLIYGANNRYI GVPDRFSGSGSGTDFTLTISSLQAEDVAVYYCAQFYSYPLTFGGGTKVEIK |
| 303 | DIVMTQSPDSLAVSLGERATINCGASESLYSSKSKVHYLAWYQQKPGQPPKLLIYGASNRYI GVPDRFSGSGSGTDFTLTISSLQAEDVAVYYCAQFYSYPLTFGGGTKVEIK |
| 304 | DIVMTQSPDSLAVSLGERATINCTASESLYSSKHKVHYLAWYQQKPGQPPKLLIYGASNRYI GVPDRFSGSGSGTDFTLTISSLQAEDVAVYYCAQFYEYPLTFGGGTKVEIK |
| 305 | DIVMTQSPDSLAVSLGERATINCTASESLYSSKHKVHYLAWYQQKPGQPPKLLIYGAHNRYI GVPDRFSGSGSGTDFTLTISSLQAEDVAVYYCANFYSYPLTFGGGTKVEIK |
| 306 | DIVMTQSPDSLAVSLGERATINCTSSESVYSSSHKVHYLAWYQQKPGQPPKLLIYGASNRYI GVPDRFSGSGSGTDFTLTISSLQAEDVAVYYCAQFYYYPLTFGGGTKVEIK |
| 307 | DIVMTQSPDSLAVSLGERATINCTASESLYSSKHKVHYLAWYQQKPGQPPKLLIYGNSNRYI GVPDRFSGSGSGTDFTLTISSLQAEDVAVYYCGQFYSYPLTFGGGTKVEIK |
| 308 | DIVMTQSPDSLAVSLGERATINCTASESLYSSKHKKNYLAWYQQKPGQPPKLLIYGASWRYI GVPDRFSGSGSGTDFTLTISSLQAEDVAVYYCAQFYSYPLTFGGGTKVEIK |
| 309 | DIVMTQSPDSLAVSLGERATINCTASESLYSSKHKVHYLAWYQQKPGQPPKLLIYGASTRYS GVPDRFSGSGSGTDFTLTISSLQAEDVAVYYCAQFYTYPLTFGGGTKVEIK |
| 310 | DIVMTQSPDSLAVSLGERATINCKSSESLLYSKNNKNYLAWYQQKPGQPPKLLIYGASNRYS GVPDRFSGSGSGTDFTLTISSLQAEDVAVYYCAQFYSYPLTFGGGTKVEIK |
| 311 | DIVMTQSPDSLAVSLGERATINCTASESLYSSKHKVHYLAWYQQKPGQPPKLLIYGASNRYI GVPDRFSGSGSGTDFTLTISSLQAEDVAVYYCAEFYSYPLTFGGGTKVEIK |
| 312 | DIVMTQSPDSLAVSLGERATINCTASESIYSSKHKVHYLAWYQQKPGQPPKLLIYGASNRYI GVPDRFSGSGSGTDFTLTISSLQAEDVAVYYCAQFYSYPLTFGGGTKVEIK |

SEQUENCE LISTING

| SEQ ID NO | SEQUENCE |
|---|---|
| 313 | DIVMTQSPDSLAVSLGERATINCTSSQSVLSSKHNKNYLAWYQQKPGQPPKLLIYGASNRYW<br>GVPDRFSGSGSGTDFTLTISSLQAEDVAVYYCAQFYSYPLTFGGGTKVEIK |
| 314 | DIVMTQSPDSLAVSLGERATINCTASESLYSSKHKVHYLAWYQQKPGQPPKLLIYGASNRYP<br>GVPDRFSGSGSGTDFTLTISSLQAEDVAVYYCAQFYSYPLTFGGGTKVEIK |
| 315 | DIVMTQSPDSLAVSLGERATINCTASEDLYSSKHKVHYLAWYQQKPGQPPKLLIYGTSNRYI<br>GVPDRFSGSGSGTDFTLTISSLQAEDVAVYYCAQYYSYPLTFGGGTKVEIK |
| 316 | DIVMTQSPDSLAVSLGERATINCKASQSVLYSKNKKHYLAWYQQKPGQPPKLLIYGASNRQI<br>GVPDRFSGSGSGTDFTLTISSLQAEDVAVYYCAQFYVYPLTFGGGTKVEIK |
| 317 | DIVMTQSPDSLAVSLGERATINCTASESLYSSKHKLHYLAWYQQKPGQPPKLLIYGASNRYI<br>GVPDRFSGSGSGTDFTLTISSLQAEDVAVYYCGQFYSYPLTFGGGTKVEIK |
| 318 | DIVMTQSPDSLAVSLGERATINCTASESLYSSKHKVHYLAWYQQKPGQPPKLLIYGASNRYI<br>GVPDRFSGSGSGTDFTLTISSLQAEDVAVYYCAQFYDYPLTFGGGTKVEIK |
| 319 | DIVMTQSPDSLAVSLGERATINCTASESLYSSKHKVVYLAWYQQKPGQPPKLLIYGASNRYI<br>GVPDRFSGSGSGTDFTLTISSLQAEDVAVYYCAQFYFYPLTFGGGTKVEIK |
| 320 | DIVMTQSPDSLAVSLGERATINCTASESLYSSKHKVHYLAWYQQKPGQPPKLLIYGASNRYL<br>GVPDRFSGSGSGTDFTLTISSLQAEDVAVYYCAQFYSYPLTFGGGTKVEIK |
| 321 | DIVMTQSPDSLAVSLGERATINCTSSESLYSSKNKVNYLAWYQQKPGQPPKLLIYGASNRYI<br>GVPDRFSGSGSGTDFTLTISSLQAEDVAVYYCAQFYFYPLTFGGGTKVEIK |
| 322 | DIVMTQSPDSLAVSLGERATINCTASESLYSSKHKVHYLAWYQQKPGQPPKLLIYGASNRYN<br>GVPDRFSGSGSGTDFTLTISSLQAEDVAVYYCAQFYTYPLTFGGGTKVEIK |
| 323 | DIVMTQSPDSLAVSLGERATINCTSSQSLYSSKHNKHYLAWYQQKPGQPPKLLIYGASNRYI<br>GVPDRFSGSGSGTDFTLTISSLQAEDVAVYYCAQFYSYPLTFGGGTKVEIK |
| 324 | DIVMTQSPDSLAVSLGERATINCEASESLYSSKHKVHYLAWYQQKPGQPPKLLIYGASNRYI<br>GVPDRFSGSGSGTDFTLTISSLQAEDVAVYYCAQFYSYPLTFGGGTKVEIK |
| 325 | DIVMTQSPDSLAVSLGERATINCTASESLYSSKHKVHYLAWYQQKPGQPPKLLIYGASNRAI<br>GVPDRFSGSGSGTDFTLTISSLQAEDVAVYYCAQFYFYPLTFGGGTKVEIK |
| 326 | DIVMTQSPDSLAVSLGERATINCTASESLYSNKHKVHYLAWYQQKPGQPPKLLIYGASNRYI<br>GVPDRFSGSGSGTDFTLTISSLQAEDVAVYYCAQFYSYPLTFGGGTKVEIK |
| 327 | DIVMTQSPDSLAVSLGERATINCTASENLYSSKHKVHYLAWYQQKPGQPPKLLIYGASNRYS<br>GVPDRFSGSGSGTDFTLTISSLQAEDVAVYYCAQFYSYPLTFGGGTKVEIK |
| 328 | DIVMTQSPDSLAVSLGERATINCTASESLYSSKHKVHYLAWYQQKPGQPPKLLIYGASQRYI<br>GVPDRFSGSGSGTDFTLTISSLQAEDVAVYYCAQFYLYPLTFGGGTKVEIK |
| 329 | DIVMTQSPDSLAVSLGERATINCTASESLYSSKHKVHYLAWYQQKPGQPPKLLIYGASNREI<br>GVPDRFSGSGSGTDFTLTISSLQAEDVAVYYCAQFYSYPLTFGGGTKVEIK |
| 330 | DIVMTQSPDSLAVSLGERATINCTASESLYSSKHKVHYLAWYQQKPGQPPKLLIYGASNRYT<br>GVPDRFSGSGSGTDFTLTISSLQAEDVAVYYCAQFYSYPLTFGGGTKVEIK |
| 331 | DIVMTQSPDSLAVSLGERATINCTASESLYSSKHKVHYLAWYQQKPGQPPKLLIYGAANRYI<br>GVPDRFSGSGSGTDFTLTISSLQAEDVAVYYCAQFYSYPLTFGGGTKVEIK |
| 332 | DIVMTQSPDSLAVSLGERATINCTASESLYSSKHKVHYLAWYQQKPGQPPKLLIYGAQNRYI<br>GVPDRFSGSGSGTDFTLTISSLQAEDVAVYYCGQFYSYPLTFGGGTKVEIK |
| 333 | DIVMTQSPDSLAVSLGERATINCTASESLYSSKIKVHYLAWYQQKPGQPPKLLIYGAHNRYI<br>GVPDRFSGSGSGTDFTLTISSLQAEDVAVYYCAQFYSYPLTFGGGTKVEIK |
| 334 | DIVMTQSPDSLAVSLGERATINCTASESLYSSKHKVHYLAWYQQKPGQPPKLLIYGASNRYI<br>GVPDRFSGSGSGTDFTLTISSLQAEDVAVYYCAQFYTYPLTFGGGTKVEIK |
| 335 | DIVMTQSPDSLAVSLGERATINCTASESLYSSKHKVHYLAWYQQKPGQPPKLLIYGASNRYS<br>GVPDRFSGSGSGTDFTLTISSLQAEDVAVYYCAQFYHYPLTFGGGTKVEIK |
| 336 | DIVMTQSPDSLAVSLGERATINCTASESLYSSKHKVHYLAWYQQKPGQPPKLLIYGATNRYI<br>GVPDRFSGSGSGTDFTLTISSLQAEDVAVYYCAEFYSYPLTFGGGTKVEIK |
| 337 | DIVMTQSPDSLAVSLGERATINCTASESLYSSKHKVHYLAWYQQKPGQPPKLLIYGASGRYI<br>GVPDRFSGSGSGTDFTLTISSLQAEDVAVYYCAQFYSYPLTFGGGTKVEIK |

-continued

| SEQ ID NO | SEQUENCE |
|---|---|
| 338 | DIVMTQSPDSLAVSLGERATINCKSSQSLLYSKNNVNYLAWYQQKPGQPPKLLIYGESNRYI GVPDRFSGSGSGTDFTLTISSLQAEDVAVYYCAQFYEYPLTFGGGTKVEIK |
| 339 | DIVMTQSPDSLAVSLGERATINCKSSESLYSSKNKVHYLAWYQQKPGQPPKLLIYGASNRYI GVPDRFSGSGSGTDFTLTISSLQAEDVAVYYCAQFYHPLTFGGGTKVEIK |
| 340 | DIVMTQSPDSLAVSLGERATINCTASESLYSSKHKVNYLAWYQQKPGQPPKLLIYGASNRYI GVPDRFSGSGSGTDFTLTISSLQAEDVAVYYCAQFYSYPLTFGGGTKVEIK |
| 341 | DIVMTQSPDSLAVSLGERATINCTSSESLLSSKHKVHYLAWYQQKPGQPPKLLIYGASNRYT GVPDRFSGSGSGTDFTLTISSLQAEDVAVYYCAQFYSYPLTFGGGTKVEIK |
| 342 | DIVMTQSPDSLAVSLGERATINCTASQSVYSSKHKKHYLAWYQQKPGQPPKLLIYGANNRYI GVPDRFSGSGSGTDFTLTISSLQAEDVAVYYCGQFYSYPLTFGGGTKVEIK |
| 343 | DIVMTQSPDSLAVSLGERATINCTASQSVYSSKHNKHYLAWYQQKPGQPPKLLIYGASNPYI GVPDRFSGSGSGTDFTLTISSLQAEDVAVYYCAQFYSYPLTFGGGTKVEIK |
| 344 | DIVMTQSPDSLAVSLGERATINCTASESLYSGKHKVHYLAWYQQKPGQPPKLLIYGASNRYI GVPDRFSGSGSGTDFTLTISSLQAEDVAVYYCAQFYSYPLTFGGGTKVEIK |
| 345 | DIVMTQSPDSLAVSLGERATINCTSSQSLLYSSNKKHYLAWYQQKPGQPPKLLIYGASNRYI GVPDRFSGSGSGTDFTLTISSLQAEDVAVYYCAQFYEYPLTFGGGTKVEIK |
| 346 | DIVMTQSPDSLAVSLGERATINCTASESLYSSKHKVHYLAWYQQKPGQPPKLLIYGASNRYI GVPDRFSGSGSGTDFTLTISSLQAEDVAVYYCAQFYNYPLTFGGGTKVEIK |
| 347 | DIVMTQSPDSLAVSLGERATINCTASESLYSSKHKVHYLAWYQQKPGQPPKLLIYGASNRYI GVPDRFSGSGSGTDFTLTISSLQAEDVAVYYCASFYSYPLTFGGGTKVEIK |
| 348 | DIVMTQSPDSLAVSLGERATINCKSSQSVLSSKHKKNYLAWYQQKPGQPPKLLIYGASNRYI GVPDRFSGSGSGTDFTLTISSLQAEDVAVYYCAQFYSYPLTFGGGTKVEIK |
| 349 | DIVMTQSPDSLAVSLGERATINCTASESLYSSKHKVHYLAWYQQKPGQPPKLLIYGAQNRYI GVPDRFSGSGSGTDFTLTISSLQAEDVAVYYCAQFYSYPLTFGGGTKVEIK |
| 350 | DIVMTQSPDSLAVSLGERATINCTASQSVYSSKNKKHYLAWYQQKPGQPPKLLIYGASNRYI GVPDRFSGSGSGTDFTLTISSLQAEDVAVYYCAQFYRYPLTFGGGTKVEIK |
| 351 | DIVMTQSPDSLAVSLGERATINCTASESVLSSKHKKNYLAWYQQKPGQPPKLLIYGASTRYI GVPDRFSGSGSGTDFTLTISSLQAEDVAVYYCAQFYSYPLTFGGGTKVEIK |
| 352 | DIVMTQSPDSLAVSLGERATINCTASVSLYSSKHKVHYLAWYQQKPGQPPKLLIYGPSNRYI GVPDRFSGSGSGTDFTLTISSLQAEDVAVYYCAQFYSYPLTFGGGTKVEIK |
| 353 | DIVMTQSPDSLAVSLGERATINCTASESLYSSKHKVHYLAWYQQKPGQPPKLLIYGASNRPI GVPDRFSGSGSGTDFTLTISSLQAEDVAVYYCGQFYSYPLTFGGGTKVEIK |
| 354 | DIVMTQSPDSLAVSLGERATINCTASESLYSSKHKVHYLAWYQQKPGQPPKLLIYGASNRYI GVPDRFSGSGSGTDFTLTISSLQAEDVAVYYCAAFYSYPLTFGGGTKVEIK |
| 355 | DIVMTQSPDSLAVSLGERATINCTASESLYSPKHKVHYLAWYQQKPGQPPKLLIYGAENRYI GVPDRFSGSGSGTDFTLTISSLQAEDVAVYYCAQFYSYPLTFGGGTKVEIK |
| 356 | DIVMTQSPDSLAVSLGERATINCTASESLYSSKHKVHYLAWYQQKPGQPPKLLIYGASHRQI GVPDRFSGSGSGTDFTLTISSLQAEDVAVYYCAQFYSYPLTFGGGTKVEIK |
| 357 | DIVMTQSPDSLAVSLGERATINCTASESLYSSKHKVHYLAWYQQKPGQPPKLLIYGASQRYI GVPDRFSGSGSGTDFTLTISSLQAEDVAVYYCAQFYSYPLTFGGGTKVEIK |
| 358 | DIVMTQSPDSLAVSLGERATINCTASTSLYSSKHKVHYLAWYQQKPGQPPKLLIYGASNRYI GVPDRFSGSGSGTDFTLTISSLQAEDVAVYYCAQFYSYPLTFGGGTKVEIK |
| 359 | DIVMTQSPDSLAVSLGERATINCKSSESLYSSKNKVHYLAWYQQKPGQPPKLLIYGASNRYS GVPDRFSGSGSGTDFTLTISSLQAEDVAVYYCAQFYSYPLTFGGGTKVEIK |
| 360 | DIVMTQSPDSLAVSLGERATINCTASESLYSTKHKVHYLAWYQQKPGQPPKLLIYGASHRYI GVPDRFSGSGSGTDFTLTISSLQAEDVAVYYCAQFYQYPLTFGGGTKVEIK |
| 361 | DIVMTQSPDSLAVSLGERATINCTASESLYSSKHKVHYLAWYQQKPGQPPKLLIYGVSNRYI GVPDRFSGSGSGTDFTLTISSLQAEDVAVYYCAQFYSYPLTFGGGTKVEIK |

SEQUENCE LISTING

| SEQ ID NO | SEQUENCE |
|---|---|
| 362 | DIVMTQSPDSLAVSLGERATINCTASESLYSSKHKVHYLAWYQQKPGQPPKLLIYGASNRVIGVPDRFSGSGSGTDFTLTISSLQAEDVAVYYCAQFYIYPLTFGGGTKVEIK |
| 363 | DIVMTQSPDSLAVSLGERATINCTASESLYSSNHKVHYLAWYQQKPGQPPKLLIYGVSNRYIGVPDRFSGSGSGTDFTLTISSLQAEDVAVYYCAQFYSYPLTFGGGTKVEIK |
| 364 | DIVMTQSPDSLAVSLGERATINCKASQSVLSSKNNVNYLAWYQQKPGQPPKLLIYGASNRYIGVPDRFSGSGSGTDFTLTISSLQAEDVAVYYCAQFYQYPLTFGGGTKVEIK |
| 365 | DIVMTQSPDSLAVSLGERATINCTASESLYSSKHKVHYLAWYQQKPGQPPKLLIYGASNRNIGVPDRFSGSGSGTDFTLTISSLQAEDVAVYYCAHFYSYPLTFGGGTKVEIK |
| 366 | DIVMTQSPDSLAVSLGERATINCTASESLYSSKHKVHYLAWYQQKPGQPPKLLIYGASNRYQGVPDRFSGSGSGTDFTLTISSLQAEDVAVYYCAQFYWYPLTFGGGTKVEIK |
| 367 | DIVMTQSPDSLAVSLGERATINCTASESLYSSKHKVHYLAWYQQKPGQPPKLLIYGASNTYIGVPDRFSGSGSGTDFTLTISSLQAEDVAVYYCAQFYSYPLTFGGGTKVEIK |
| 368 | DIVMTQSPDSLAVSLGERATINCTASESLYSSKHKVHYLAWYQQKPGQPPKLLIYGASNRYSGVPDRFSGSGSGTDFTLTISSLQAEDVAVYYCAQFYNYPLTFGGGTKVEIK |
| 369 | FTFSDYYME |
| 370 | FGFSDFYME |
| 371 | FTFSDQYIE |
| 372 | FTFSDGYME |
| 373 | FTASDFYME |
| 374 | FTFSDSYME |
| 375 | FTFEDFYME |
| 376 | FTFSDFYME |
| 377 | FTFSDQYME |
| 378 | FQFSDFYME |
| 379 | FEFSDNYME |
| 380 | FEFSDFYME |
| 381 | FTFSDAYME |
| 382 | FTFSDFYME |
| 383 | FTFSSYYME |
| 384 | FTGSDFYME |
| 385 | FAFSDFYME |
| 386 | FTHSDFYME |
| 387 | FTFSDTYME |
| 388 | FTFSDDYME |
| 389 | FTFSDNYME |
| 390 | FTSSDFYME |
| 391 | FTFSTFYME |
| 392 | FTFSDEYME |
| 393 | FWFSDFYME |
| 394 | FTFSDVYME |
| 395 | ATFSDFYME |

| SEQ ID NO | SEQUENCE |
|---|---|
| 396 | FDFSDFYME |
| 397 | WTFSDFYME |
| 398 | FTFSSFYME |
| 399 | FTFNDFYME |
| 400 | FTFSDHYME |
| 401 | FTFSDGYIE |
| 402 | GTFSDFYME |
| 403 | FTQSDFYME |
| 404 | DTFSDFYME |
| 405 | FTTSDFYME |
| 406 | ETFSDFYME |
| 407 | FPFSDFYME |
| 408 | ATFSDFYVE |
| 409 | FTDSDFYME |
| 410 | NTFSDFYME |
| 411 | DTFSDFYLE |
| 412 | FLFSDFYME |
| 413 | FTNSDFYME |
| 414 | QTFSDFYME |
| 415 | FTFSDPYME |
| 416 | TTFSDFYME |
| 417 | PTFSDFYME |
| 418 | FTFSEFYME |
| 419 | FHFSDFYME |
| 420 | ITFSDFYME |
| 421 | FTFSDFYVE |
| 422 | STFSDFYME |
| 423 | FSFSDFYME |
| 424 | FTFDDFYME |
| 425 | FTFSDFYIE |
| 426 | FTSSDFYLE |
| 427 | FTFSPFYME |
| 428 | AASRNKANDYTTEYA |
| 429 | AASRNKWNDYTTEYA |
| 430 | AASRNKANDYTTSYA |
| 431 | AASRNKANDYTTELA |
| 432 | AASRGKGNSYTTEYA |

| SEQ ID NO | SEQUENCE |
|---|---|
| 433 | AASRNKANDYVTEYA |
| 434 | AASRNKYNDYTTEYA |
| 435 | AASRNKGNSYTTEYA |
| 436 | AASRNKANTYTTEYA |
| 437 | AASRNKNNDYTTEYA |
| 438 | AASRNIANDYTTEYA |
| 439 | AASRNSGNDYTTEYA |
| 440 | AASRNKANDYTVEYA |
| 441 | AASRNKANDYYTEYA |
| 442 | AASRHKANDYTTEYA |
| 443 | AASRNKANDYQTEYA |
| 444 | AASRNQANDYTTEYA |
| 445 | AASRNGANDYTTEYA |
| 446 | AASRNKANDYTTDYA |
| 447 | AASRNKANDYTNEYA |
| 448 | AASRNAANDYTTEYA |
| 449 | AASRNKANDQTTEYA |
| 450 | AASRNSGNSYTTEYA |
| 451 | AASRNKANSYTTEYA |
| 452 | AASRWKANDYTTEYA |
| 453 | AAIRNKANSYTTEYA |
| 454 | AASRNKANSYTTAYA |
| 455 | AASRNKANDYTTTYA |
| 456 | AASRNKGNDYTTEYA |
| 457 | GASRNKHNDYTTEYA |
| 458 | AASRNKANAYTTEYA |
| 459 | AASRNKFNDYTTEYA |
| 460 | AASRNKANGYTTEYA |
| 461 | AASRNKANEYTTEYA |
| 462 | AASRNKANLYTTEYA |
| 463 | AASRGKGNSYTTAYA |
| 464 | AASRNKGNSYTTAYA |
| 465 | AASRNNANDYTTEYA |
| 466 | AASRNKANGYTTEYT |
| 467 | AASRNSGNSYTTAYA |
| 468 | AATRNKANDYTTEYA |
| 469 | AASRNKANDFTTEYA |

-continued

| SEQ ID NO | SEQUENCE |
|---|---|
| 470 | AASRNKANDYTYEYA |
| 471 | AASRNKANDYSTEYA |
| 472 | AASRSKANDYTTEYA |
| 473 | AASRNKANDYTTAYA |
| 474 | AASRNTANDYTTEYA |
| 475 | AASRNKANDYNTEYA |
| 476 | AASRNKANDYTTEVA |
| 477 | AASRNKGNDYTTAYA |
| 478 | AASRNKANFYTTEYA |
| 479 | AASRNEANDYTTEYA |
| 480 | AAIRNKANDYTTEYA |
| 481 | AASRNVANDYTTEYA |
| 482 | AASRNKANDWTTEYA |
| 483 | AASRNKANYYTTEYA |
| 484 | CARDYYGSSYWYFDVW |
| 485 | CARDYYGSSYWYYDVW |
| 486 | CARDYLGSSYWYFDVW |
| 487 | CARDYFGSSYWYFDVW |
| 488 | CARDYYASSYWYFDVW |
| 489 | CARDYYGSPYWYFDVW |
| 490 | CARDYYGSSYWYFDSW |
| 491 | CARDYYGSSYWYFDTW |
| 492 | CARDYYGSSYWYFDLW |
| 493 | CARDYYGSHYWYFDVW |
| 494 | CARDYQGSSYWYFDVW |
| 495 | CARDYYGHSYWYFDVW |
| 496 | CARDYYGSSYWYLDVW |
| 497 | CARDYYGNSYWYFDVW |
| 498 | CARDYYGSAYWYFDVW |
| 499 | CARDYYGQSYWYFDVW |
| 500 | CARDYYGSSTWYFDVW |
| 501 | CARDYYESSYWYFDVW |
| 502 | CARDYYGSSHWYFDVW |
| 503 | CARDYYGDSYWYFDVW |
| 504 | CARDYYGSSYWYNDVW |
| 505 | CARDYYHSSYWYFDVW |
| 506 | CARDIYGSSYWYFDVW |

-continued

| SEQ ID NO | SEQUENCE |
|---|---|
| 507 | CARDYYGSSYWYDDVW |
| 508 | CARDYYGYSYWYFDVW |
| 509 | CARDYYGSSQWYFDVW |
| 510 | CARDFYGSSYWYFDVW |
| 511 | CARDYYGSSYWYHDVW |
| 512 | CARDYYGSSYWYFDPW |
| 513 | CARDYYGSQYWYFDVW |
| 514 | CARDYYSSSYWYFDVW |
| 515 | CARDYYGSSNWYFDVW |
| 516 | CARDYYFSSYWYFDVW |
| 517 | CARDYYDSSYWYFDVW |
| 518 | CARDYYGASYWYFDVW |
| 519 | CARDHYGSSYWYFDVW |
| 520 | CARDYYGESYWYFDVW |
| 521 | CARDYYLSSYWYFDVW |
| 522 | CARDYYGSSYWYFDYW |
| 523 | TASESLYSSKHKVHYLA |
| 524 | VASESLYSSKHKVHYLA |
| 525 | RASESISSSKNKVHYLA |
| 526 | TASESLYSAKHKVHYLA |
| 527 | TASESLYSSKHKVNYLA |
| 528 | TASESLYSSKHKVHYVA |
| 529 | TASFSLYSSKHKVHYLA |
| 530 | TASESLYGSKHKVHYLA |
| 531 | RASESISSSKHKHYLA |
| 532 | TASEWLYSSKHKVHYLA |
| 533 | TATESLYSSKHKVHYLA |
| 534 | TASESLYSGKHKVHYLA |
| 535 | FASESLYSSKHKVHYLA |
| 536 | TASQSLYSSKNKVHYLA |
| 537 | EASESLYSSKHKVHYLA |
| 538 | TASESISSSKHKVHYLA |
| 539 | TASESLYSQKHKVHYLA |
| 540 | TASESLYSSKHSVHYLA |
| 541 | TASEELYSSKHKVHYLA |
| 542 | TASQSISSSKHKVHYLA |
| 543 | TASESLSSSKHKHYLA |

-continued

| SEQ ID NO | SEQUENCE |
|---|---|
| 544 | TAEESLYSSKHKVHYLA |
| 545 | TASESLYSSKHGVHYLA |
| 546 | TASESLSSSKHKVHYLA |
| 547 | TASQSLYSSKHKVHYLA |
| 548 | RASESLYSSLHKYLA |
| 549 | TASESVYSSKNKKHYLA |
| 550 | TASESLYSSKGKVHYLA |
| 551 | TASQSVYSSKNKVHYLA |
| 552 | TSSQSLLSSSHNKNYLA |
| 553 | TASESLYSPKHKVHYLA |
| 554 | TASESLWSSKHKVHYLA |
| 555 | KASQSVLSSKNNVNYLA |
| 556 | TASESLYSSKWKVHYLA |
| 557 | KSSESVYSSKHKKHYLA |
| 558 | TASESLYSSKHKVDYLA |
| 559 | KSSQSLYYSSNKKNYLA |
| 560 | TASTSLYSSKHKVHYLA |
| 561 | KASQSLYSSKHKKHYLA |
| 562 | TASSSLYSSKHKVHYLA |
| 563 | TASESLYSVKHKVHYLA |
| 564 | GASESLYSSKSKVHYLA |
| 565 | TSSESVYSSSHKVHYLA |
| 566 | TASESLYSSKHKKNYLA |
| 567 | KSSESLLYSKNNKNYLA |
| 568 | TASESIYSSKHKVHYLA |
| 569 | TSSQSVLSSKHNKNYLA |
| 570 | TASEDLYSSKHKVHYLA |
| 571 | KASQSVLYSKNKKHYLA |
| 572 | TASESLYSSKHKLHYLA |
| 573 | TASESLYSSKHKVVYLA |
| 574 | TSSESLYSSKNKVNYLA |
| 575 | TSSQSLYSSKHNKHYLA |
| 576 | TASESLYSNKHKVHYLA |
| 577 | TASENLYSSKHKVHYLA |
| 578 | TASESLYSSKIKVHYLA |
| 579 | KSSQSLLYSKNNVNYLA |
| 580 | KSSESLYSSKNKVHYLA |

-continued

| SEQUENCE LISTING | |
|---|---|
| SEQ ID NO | SEQUENCE |
| 581 | TSSESLLSSKHKVHYLA |
| 582 | TASQSVYSSKHKKHYLA |
| 583 | TASQSVYSSKHNKHYLA |
| 584 | TSSQSLLYSSNKKHYLA |
| 585 | KSSQSVLSSKHKKNYLA |
| 586 | TASQSVYSSKNKKHYLA |
| 587 | TASESVLSSKHKKNYLA |
| 588 | TASVSLYSSKHKVHYLA |
| 589 | TASESLYSTKHKVHYLA |
| 590 | TASESLYSSNHKVHYLA |
| 591 | GASNRYI |
| 592 | GASNREI |
| 593 | GASHRYI |
| 594 | GASSLQI |
| 595 | GASNRYT |
| 596 | GASNRYH |
| 597 | GSSNRYI |
| 598 | GASNRFI |
| 599 | GASNRYY |
| 600 | GAANRYI |
| 601 | GASNRYV |
| 602 | GASNRYD |
| 603 | GASNRYP |
| 604 | GAVNRYI |
| 605 | GASNGYI |
| 606 | GASNRYS |
| 607 | GASNLYS |
| 608 | GASNRYF |
| 609 | GASNLQS |
| 610 | GLSNRYI |
| 611 | GASNRQS |
| 612 | GAFNRYT |
| 613 | GASNRLI |
| 614 | GQSNRYI |
| 615 | GASNRNI |
| 616 | GAGNRYI |
| 617 | GASNRYG |

-continued

| SEQ ID NO | SEQUENCE |
|---|---|
| 618 | GASGRYI |
| 619 | GASNLQI |
| 620 | GASNRGI |
| 621 | GESNRYI |
| 622 | GVSNRYI |
| 623 | GASNRPI |
| 624 | GASFRYI |
| 625 | GADNRYI |
| 626 | GASNRYQ |
| 627 | GASSRYI |
| 628 | GTSNRYI |
| 629 | GASNHYI |
| 630 | GASNRQI |
| 631 | GASSRYS |
| 632 | GASNRDI |
| 633 | GISNRYI |
| 634 | GASSLYS |
| 635 | GASNRAI |
| 636 | GASNRYA |
| 637 | GASNRVI |
| 638 | GPSNRYI |
| 639 | GAFNRYI |
| 640 | GANNRYI |
| 641 | GAHNRYI |
| 642 | GNSNRYI |
| 643 | GASWRYI |
| 644 | GASTRYS |
| 645 | GASNRYW |
| 646 | GASNRYL |
| 647 | GASNRYN |
| 648 | GASQRYI |
| 649 | GAQNRYI |
| 650 | GATNRYI |
| 651 | GASNPYI |
| 652 | GASTRYI |
| 653 | GAENRYI |
| 654 | GASHRQI |

-continued

| SEQ ID NO | SEQUENCE |
|---|---|
| 655 | GASNTYI |
| 656 | CAEFYSYPLTF |
| 657 | CQQFYSYPLTF |
| 658 | CAQFYAYPLTE |
| 659 | CAQFYSYPLTE |
| 660 | CAQFYHYPLTF |
| 661 | CAQFYQYPLTF |
| 662 | CAQFYYYPLTF |
| 663 | CAQFYVYPLTF |
| 664 | CGQFYSYPLTF |
| 665 | CAQFYDYPLTF |
| 666 | CAQFYRYPLTF |
| 667 | CAQFYTYPLTF |
| 668 | CAQFYWYPLTF |
| 669 | CTQFYSYPLTF |
| 670 | CAQFYFYPLTF |
| 671 | CAQFYEYPLTF |
| 672 | CAHFYSYPLTF |
| 673 | CAQFYKYPLTF |
| 674 | CAQFFSYPLTF |
| 675 | CVQFYSYPLTF |
| 676 | CAQFYIYPLTF |
| 677 | CANFYSYPLTF |
| 678 | CAQYYSYPLTF |
| 679 | CAQFYLYPLTF |
| 680 | CAQFYNYPLTF |
| 681 | CASFYSYPLTF |
| 682 | CAAFYSYPLTF |
| 683 | ASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKSRWQQGNVFSCSV MHEALHNHYTQKSLSLSPG |
| 684 | ASTKGPSVFPLAPCSRSTSESTAALGCLVKDYFPEPVTVSWNSGALTSGVHTFPAVLQSSGL YSLSSVVTVPSSSLGTKTYTCNVDHKPSNTKVDKRVESKYGPPCPPCPAPEFLGGPSVFLFP PKPKDTLMISRTPEVTCVVVDVSQEDPEVQFNWYVDGVEVHNAKTKPREEQENSTYRVVSVL TVLHQDWLNGKEYKCKVSNKGLPSSIEKTISKAKGQPREPQVYTLPPSQEEMTKNQVSLTCL VKGFYPSDIAVEWESNGQPENNYKTTPPVLDSDGSFFLYSRLTVDKSRWQEGNVFSCSVMHE ALHNHYTQKSLSLSLG |
| 685 | DIQMTQSPSSLSASVGDRVTITCTASESLYSSKHKVHYLAWYQQKPGKAPKLLIYGASNRYI GVPSRFSGSGSGTDFTLTISSLQPEDFATYYCAQFYSYPLTFGQGTKVEIK |

SEQUENCE LISTING

| SEQ ID NO | SEQUENCE |
|---|---|
| 686 | AGGGGSGGGGSGGGGSAAA<br>(Note: peptide can be conjugated with biotin at the N terminus residue, PC linked Tyr at the C terminus residue) |
| 687 | AEAAAKEAAAKEAAAKEAAAKAAA<br>(Note: peptide can be conjugated with biotin at the N terminus residue, PC linked Tyr at the C terminus residue |
| 688 | RTVAAPSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC |
| 689 | GQPKANPTVTLFPPSSEELQANKATLVCLISDFYPGAVTVAWKADGSPVKAGVETTKPSKQS<br>NNKYAASSYLSLTPEQWKSHRSYSCQVTHEGSTVEKTVAPTECS |
| 690 | GQPKAAPSVTLFPPSSEELQANKATLVCLISDFYPGAVTVAWKADSSPVKAGVETTTPSKQS<br>NNKYAASSYLSLTPEQWKSHRSYSCQVTHEGSTVEKTVAPTECS |
| 691 | GQPKAAPSVTLFPPSSEELQANKATLVCLISDFYPGAVTVAWKADSSPVKAGVETTTPSKQS<br>NNKYAASSYLSLTPEQWKSHKSYSCQVTHEGSTVEKTVAPTECS |
| 692 | GQPKAAPSVTLFPPSSEELQANKATLVCLISDFYPGAVKVAWKADGSPVNTGVETTTPSKQS<br>NNKYAASSYLSLTPEQWKSHRSYSCQVTHEGSTVEKTVAPAECS |
| 693 | GQPKAAPSVTLFPPSSEELQANKATLVCLVSDFNPGAVTVAWKADGSPVKVGVETTKPSKQS<br>NNKYAASSYLSLTPEQWKSHRSYSCRVTHEGSTVEKTVAPAECS |

The invention is not to be limited in scope by the specific embodiments described herein. Indeed, various modifications of the invention in addition to those described will become apparent to those skilled in the art from the foregoing description. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An antibody that specifically binds phosphocholine (PC), the antibody comprising: a VH comprising the CDRH1, CDRH2, and CDRH3 amino acid sequences of the VH amino acid sequence set forth in SEQ ID NO: 27; and a VL comprising the CDRL1, CDRL2, and CDRL3 amino acid sequences of the VL amino acid sequence set forth in SEQ ID NO: 208.

2. The antibody of claim 1, wherein the antibody comprises the CDRH1, CDRH2, and CDRH3 amino acid sequences, respectively, set forth in SEQ ID NOs: 386, 428, and 484.

3. The antibody of claim 1, wherein the antibody comprises the CDRL1, CDRL2, and CDRL3 amino acid sequences, respectively, set forth in SEQ ID NOs: 531, 591, and 663.

4. The antibody of claim 1, wherein the antibody comprises the CDRH1, CDRH2, CDRH3, CDRL1, CDRL2, and CDRL3 amino acid sequences, respectively, set forth in SEQ ID NOs: 386, 428, 484, 531, 591, and 663.

5. The antibody of claim 1, wherein the antibody comprises the VH amino acid sequence of SEQ ID NO: 27.

6. The antibody of claim 1, wherein the antibody comprises the VL amino acid sequence of SEQ ID NO: 208.

7. The antibody of claim 1, wherein the VH and VL comprise the amino acid sequences, respectively, set forth in SEQ ID NOs: 27 and 208.

8. The antibody of claim 2, wherein the antibody is a single-chain variable fragment (scFv).

9. The antibody of claim 1, wherein the antibody comprises a heavy chain constant region, or an Fc region thereof.

10. The antibody of claim 9, wherein the heavy chain constant region is selected from the group consisting of a human $IgG_1$, $IgG_2$, $IgG_3$, $IgG_4$, $IgA_1$, and $IgA_2$.

11. The antibody of claim 9, wherein the heavy chain constant region is a human $IgG_1$.

12. The antibody of claim 9, wherein the heavy chain constant region is a human $IgG_4$.

13. The antibody of claim 12, wherein the human $IgG_4$ heavy chain constant region comprises a P at position 228, numbered according to the EU numbering system.

14. The antibody of claim 11, wherein the heavy chain constant region comprises: A at position 234; A at position 235; A, Q or G at position 297; or A or G at position 329, in each case numbered according to the EU numbering system.

15. The antibody of claim 11, wherein the heavy chain constant region comprises: A at positions 234 and 235; A at positions 234, 235, and 329; or A at positions 234, 235, and G at position 329, in each case numbered according to the EU numbering system.

16. The antibody of claim 11, wherein the heavy chain constant region comprises: L and S at positions 428 and 434, respectively; K, F, and Y at positions 433, 434, and 436, respectively; or Y, T, and E at positions 252, 254, and 256, respectively, in each case numbered according to the EU numbering system.

17. The antibody of claim 1, wherein the antibody comprises a light chain constant region.

18. The antibody of claim 17, wherein the light chain constant region is a human kappa or lambda constant region.

19. The antibody of claim 1, further comprising a cytotoxic agent, cytostatic agent, toxin, radionuclide, or detectable label.

20. A composition comprising the antibody of claim 1 and a pharmaceutically acceptable carrier or excipient.

* * * * *

SEQUENCE LISTING

```
Sequence total quantity: 693
SEQ ID NO: 1              moltype = AA   length = 123
FEATURE                   Location/Qualifiers
source                    1..123
                          mol_type = protein
                          organism = synthetic construct
SEQUENCE: 1
EVQLLESGGG LVQPGGSLRL SCAASGFTFS DYYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 2              moltype = AA   length = 123
FEATURE                   Location/Qualifiers
source                    1..123
                          mol_type = protein
                          organism = synthetic construct
SEQUENCE: 2
EVQLLESGGG LVQPGGSLRL SCAASGFGFS DFYMEWVRQA PGKGLEWVAA SRNKWNDYTT    60
EYADSVKGRF TISRDNSKNT LYLQMNSLRA EDTAVYYCAR DYYGSSYWYY DVWGQGTLVT   120
VSS                                                                 123

SEQ ID NO: 3              moltype = AA   length = 123
FEATURE                   Location/Qualifiers
source                    1..123
                          mol_type = protein
                          organism = synthetic construct
SEQUENCE: 3
EVQLLESGGG LVQPGGSLRL SCAASGFTFS DQYIEWVRQA PGKGLEWVAA SRNKANDYTT    60
EYADSVKGRF TISRDNSKNT LYLQMNSLRA EDTAVYYCAR DYLGSSYWYF DVWGQGTLVT   120
VSS                                                                 123

SEQ ID NO: 4              moltype = AA   length = 123
```

```
FEATURE                 Location/Qualifiers
source                  1..123
                        mol_type = protein
                        organism = synthetic construct
SEQUENCE: 4
EVQLLESGGG LVQPGGSLRL SCAASGFTFS DGYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 5            moltype = AA  length = 123
FEATURE                 Location/Qualifiers
source                  1..123
                        mol_type = protein
                        organism = synthetic construct
SEQUENCE: 5
EVQLLESGGG LVQPGGSLRL SCAASGFTAS DFYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                 123

SEQ ID NO: 6            moltype = AA  length = 123
FEATURE                 Location/Qualifiers
source                  1..123
                        mol_type = protein
                        organism = synthetic construct
SEQUENCE: 6
EVQLLESGGG LVQPGGSLRL SCAASGFTFS DSYMEWVRQA PGKGLEWVAA SRNKANDYTT    60
SYADSVKGRF TISRDNSKNT LYLQMNSLRA EDTAVYYCAR DYYGSSYWYF DVWGQGTLVT   120
VSS                                                                 123

SEQ ID NO: 7            moltype = AA  length = 123
FEATURE                 Location/Qualifiers
source                  1..123
                        mol_type = protein
                        organism = synthetic construct
SEQUENCE: 7
EVQLLESGGG LVQPGGSLRL SCAASGFTFE DFYMEWVRQA PGKGLEWVAA SRNKANDYTT    60
EYADSVKGRF TISRDNSKNT LYLQMNSLRA EDTAVYYCAR DYFGSSYWYF DVWGQGTLVT   120
VSS                                                                 123

SEQ ID NO: 8            moltype = AA  length = 123
FEATURE                 Location/Qualifiers
source                  1..123
                        mol_type = protein
                        organism = synthetic construct
SEQUENCE: 8
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 9            moltype = AA  length = 123
FEATURE                 Location/Qualifiers
source                  1..123
                        mol_type = protein
                        organism = synthetic construct
SEQUENCE: 9
EVQLLESGGG LVQPGGSLRL SCAASGFTFS DQYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 10           moltype = AA  length = 123
FEATURE                 Location/Qualifiers
source                  1..123
                        mol_type = protein
                        organism = synthetic construct
SEQUENCE: 10
EVQLLESGGG LVQPGGSLRL SCAASGFQFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 11           moltype = AA  length = 123
FEATURE                 Location/Qualifiers
source                  1..123
                        mol_type = protein
                        organism = synthetic construct
SEQUENCE: 11
EVQLLESGGG LVQPGGSLRL SCAASGFEFS DNYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123
```

```
SEQ ID NO: 12           moltype = AA   length = 123
FEATURE                 Location/Qualifiers
source                  1..123
                        mol_type = protein
                        organism = synthetic construct
SEQUENCE: 12
EVQLLESGGG LVQPGGSLRL SCAASGFTFS DGYMEWVRQA PGKGLEWVAA SRNKANDYTT     60
EYADSVKGRF TISRDNSKNT LYLQMNSLRA EDTAVYYCAR DYYASSYWYF DVWGQGTLVT    120
VSS                                                                  123

SEQ ID NO: 13           moltype = AA   length = 123
FEATURE                 Location/Qualifiers
source                  1..123
                        mol_type = protein
                        organism = synthetic construct
SEQUENCE: 13
EVQLLESGGG LVQPGGSLRL SCAASGFTFS DFYMEWVRQA PGKGLEWVAA SRNKANDYTT     60
ELADSVKGRF TISRDNSKNT LYLQMNSLRA EDTAVYYCAR DYYGSSYWYF DVWGQGTLVT    120
VSS                                                                  123

SEQ ID NO: 14           moltype = AA   length = 123
FEATURE                 Location/Qualifiers
source                  1..123
                        mol_type = protein
                        organism = synthetic construct
SEQUENCE: 14
EVQLLESGGG LVQPGGSLRL SCAASGFEFS DFYMEWVRQA PGKGLEWVAA SRGKGNSYTT     60
EYADSVKGRF TISRDNSKNT LYLQMNSLRA EDTAVYYCAR DYYGSSYWYF DVWGQGTLVT    120
VSS                                                                  123

SEQ ID NO: 15           moltype = AA   length = 123
FEATURE                 Location/Qualifiers
source                  1..123
                        mol_type = protein
                        organism = synthetic construct
SEQUENCE: 15
EVQLLESGGG LVQPGGSLRL SCAASGFTFS DGYMEWVRQA PGKGLEWVAA SRNKANDYTT     60
EYADSVKGRF TISRDNSKNT LYLQMNSLRA EDTAVYYCAR DYYGSPYWYF DVWGQGTLVT    120
VSS                                                                  123

SEQ ID NO: 16           moltype = AA   length = 123
FEATURE                 Location/Qualifiers
source                  1..123
                        mol_type = protein
                        organism = synthetic construct
SEQUENCE: 16
EVQLLESGGG LVQPGGSLRL SCAASGFTFS DAYMEWVRQA PGKGLEWVAA SRNKANDYTT     60
EYADSVKGRF TISRDNSKNT LYLQMNSLRA EDTAVYYCAR DYYGSSYWYF DSWGQGTLVT    120
VSS                                                                  123

SEQ ID NO: 17           moltype = AA   length = 123
FEATURE                 Location/Qualifiers
source                  1..123
                        mol_type = protein
                        organism = synthetic construct
SEQUENCE: 17
EVQLLESGGG LVQPGGSLRL SCAASGFTES DFYMEWVRQA PGKGLEWVAA SRNKANDYTT     60
EYADSVKGRF TISRDNSKNT LYLQMNSLRA EDTAVYYCAR DYYGSSYWYF DVWGQGTLVT    120
VSS                                                                  123

SEQ ID NO: 18           moltype = AA   length = 123
FEATURE                 Location/Qualifiers
source                  1..123
                        mol_type = protein
                        organism = synthetic construct
SEQUENCE: 18
EVQLLESGGG LVQPGGSLRL SCAASGFTFS DAYMEWVRQA PGKGLEWVAA SRNKANDYTT     60
EYADSVKGRF TISRDNSKNT LYLQMNSLRA EDTAVYYCAR DYYGSSYWYF DTWGQGTLVT    120
VSS                                                                  123

SEQ ID NO: 19           moltype = AA   length = 123
FEATURE                 Location/Qualifiers
source                  1..123
                        mol_type = protein
                        organism = synthetic construct
SEQUENCE: 19
EVQLLESGGG LVQPGGSLRL SCAASGFTFS DQYMEWVRQA PGKGLEWVAA SRNKANDYTT     60
EYADSVKGRF TISRDNSKNT LYLQMNSLRA EDTAVYYCAR DYYGSSYWYF DLWGQGTLVT    120
VSS                                                                  123
```

```
SEQ ID NO: 20              moltype = AA   length = 123
FEATURE                    Location/Qualifiers
source                     1..123
                           mol_type = protein
                           organism = synthetic construct
SEQUENCE: 20
EVQLLESGGG LVQPGGSLRL SCAASGFTFS DFYMEWVRQA PGKGLEWVAA SRNKANDYVT    60
EYADSVKGRF TISRDNSKNT LYLQMNSLRA EDTAVYYCAR DYYGSSYWYF DVWGQGTLVT   120
VSS                                                                 123

SEQ ID NO: 21              moltype = AA   length = 123
FEATURE                    Location/Qualifiers
source                     1..123
                           mol_type = protein
                           organism = synthetic construct
SEQUENCE: 21
EVQLLESGGG LVQPGGSLRL SCAASGFTFS SYYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                 123

SEQ ID NO: 22              moltype = AA   length = 123
FEATURE                    Location/Qualifiers
source                     1..123
                           mol_type = protein
                           organism = synthetic construct
SEQUENCE: 22
EVQLLESGGG LVQPGGSLRL SCAASGFTFS SYYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 23              moltype = AA   length = 123
FEATURE                    Location/Qualifiers
source                     1..123
                           mol_type = protein
                           organism = synthetic construct
SEQUENCE: 23
EVQLLESGGG LVQPGGSLRL SCAASGFTGS DFYMEWVRQA PGKGLEWVAA SRNKGNSYTT    60
EYADSVKGRF TISRDNSKNT LYLQMNSLRA EDTAVYYCAR DYYGSSYWYF DVWGQGTLVT   120
VSS                                                                 123

SEQ ID NO: 24              moltype = AA   length = 123
FEATURE                    Location/Qualifiers
source                     1..123
                           mol_type = protein
                           organism = synthetic construct
SEQUENCE: 24
EVQLLESGGG LVQPGGSLRL SCAASGFTFS DYYMEWVRQA PGKGLEWVAA SRNKANTYTT    60
EYADSVKGRF TISRDNSKNT LYLQMNSLRA EDTAVYYCAR DYYGSSYWYF DVWGQGTLVT   120
VSS                                                                 123

SEQ ID NO: 25              moltype = AA   length = 123
FEATURE                    Location/Qualifiers
source                     1..123
                           mol_type = protein
                           organism = synthetic construct
SEQUENCE: 25
EVQLLESGGG LVQPGGSLRL SCAASGFTFS DGYMEWVRQA PGKGLEWVAA SRNKNNDYTT    60
EYADSVKGRF TISRDNSKNT LYLQMNSLRA EDTAVYYCAR DYFGSSYWYF DVWGQGTLVT   120
VSS                                                                 123

SEQ ID NO: 26              moltype = AA   length = 123
FEATURE                    Location/Qualifiers
source                     1..123
                           mol_type = protein
                           organism = synthetic construct
SEQUENCE: 26
EVQLLESGGG LVQPGGSLRL SCAASGFAFS DFYMEWVRQA PGKGLEWVAA SRNKANDYTT    60
EYADSVKGRF TISRDNSKNT LYLQMNSLRA EDTAVYYCAR DYYGSHYWYF DVWGQGTLVT   120
VSS                                                                 123

SEQ ID NO: 27              moltype = AA   length = 123
FEATURE                    Location/Qualifiers
source                     1..123
                           mol_type = protein
                           organism = synthetic construct
SEQUENCE: 27
EVQLLESGGG LVQPGGSLRL SCAASGFTHS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
```

-continued

```
VSS                                                                        123

SEQ ID NO: 28           moltype = AA  length = 123
FEATURE                 Location/Qualifiers
source                  1..123
                        mol_type = protein
                        organism = synthetic construct
SEQUENCE: 28
EVQLLESGGG LVQPGGSLRL SCAASGFTFS DGYMEWVRQA PGKGLEWVAA SRNKNNDYTT            60
EYADSVKGRF TISRDNSKNT LYLQMNSLRA EDTAVYYCAR DYYGSSYWYF DVWGQGTLVT           120
VSS                                                                        123

SEQ ID NO: 29           moltype = AA  length = 123
FEATURE                 Location/Qualifiers
source                  1..123
                        mol_type = protein
                        organism = synthetic construct
SEQUENCE: 29
EVQLLESGGG LVQPGGSLRL SCAASGFTFS DTYMEWVRQA PGKGLEWVAA SRNKANDYTT            60
EYADSVKGRF TISRDNSKNT LYLQMNSLRA EDTAVYYCAR DYYGSSYWYF DVWGQGTLVT           120
VSS                                                                        123

SEQ ID NO: 30           moltype = AA  length = 123
FEATURE                 Location/Qualifiers
source                  1..123
                        mol_type = protein
                        organism = synthetic construct
SEQUENCE: 30
EVQLLESGGG LVQPGGSLRL SCAASGFAFS DFYMEWVRQA PGKGLEWVAA SRNKANDYTT            60
EYADSVKGRF TISRDNSKNT LYLQMNSLRA EDTAVYYCAR DYYGSSYWYF DVWGQGTLVT           120
VSS                                                                        123

SEQ ID NO: 31           moltype = AA  length = 123
FEATURE                 Location/Qualifiers
source                  1..123
                        mol_type = protein
                        organism = synthetic construct
SEQUENCE: 31
EVQLLESGGG LVQPGGSLRL SCAASGFTFS DGYMEWVRQA PGKGLEWVAA SRNIANDYTT            60
EYADSVKGRF TISRDNSKNT LYLQMNSLRA EDTAVYYCAR DYYGSSYWYF DVWGQGTLVT           120
VSS                                                                        123

SEQ ID NO: 32           moltype = AA  length = 123
FEATURE                 Location/Qualifiers
source                  1..123
                        mol_type = protein
                        organism = synthetic construct
SEQUENCE: 32
EVQLLESGGG LVQPGGSLRL SCAASGFTFS DDYMEWVRQA PGKGLEWVAA SRNKANDYTT            60
EYADSVKGRF TISRDNSKNT LYLQMNSLRA EDTAVYYCAR DYQGSSYWYF DVWGQGTLVT           120
VSS                                                                        123

SEQ ID NO: 33           moltype = AA  length = 123
FEATURE                 Location/Qualifiers
source                  1..123
                        mol_type = protein
                        organism = synthetic construct
SEQUENCE: 33
EVQLLESGGG LVQPGGSLRL SCAASGFTFS DYYMEWVRQA PGKGLEWVAA SRNSGNDYTT            60
EYADSVKGRF TISRDNSKNT LYLQMNSLRA EDTAVYYCAR DYYGSSYWYF DVWGQGTLVT           120
VSS                                                                        123

SEQ ID NO: 34           moltype = AA  length = 123
FEATURE                 Location/Qualifiers
source                  1..123
                        mol_type = protein
                        organism = synthetic construct
SEQUENCE: 34
EVQLLESGGG LVQPGGSLRL SCAASGFTFS DNYMEWVRQA PGKGLEWVAA SRNKANDYTT            60
EYADSVKGRF TISRDNSKNT LYLQMNSLRA EDTAVYYCAR DYYGSSYWYF DVWGQGTLVT           120
VSS                                                                        123

SEQ ID NO: 35           moltype = AA  length = 123
FEATURE                 Location/Qualifiers
source                  1..123
                        mol_type = protein
                        organism = synthetic construct
SEQUENCE: 35
EVQLLESGGG LVQPGGSLRL SCAASGFTFS DAYMEWVRQA PGKGLEWVAA SRNKANDYTT            60
```

EYADSVKGRF TISRDNSKNT LYLQMNSLRA EDTAVYYCAR DYYGSSYWYF DVWGQGTLVT   120
VSS                                                                123

SEQ ID NO: 36          moltype = AA  length = 123
FEATURE                Location/Qualifiers
source                 1..123
                       mol_type = protein
                       organism = synthetic construct
SEQUENCE: 36
EVQLLESGGG LVQPGGSLRL SCAASGFTFS DFYMEWVRQA PGKGLEWVAA SRNKANDYTV   60
EYADSVKGRF TISRDNSKNT LYLQMNSLRA EDTAVYYCAR DYYGHSYWYF DVWGQGTLVT   120
VSS                                                                123

SEQ ID NO: 37          moltype = AA  length = 123
FEATURE                Location/Qualifiers
source                 1..123
                       mol_type = protein
                       organism = synthetic construct
SEQUENCE: 37
EVQLLESGGG LVQPGGSLRL SCAASGFTSS DFYMEWVRQA PGKGLEWVAA SRNKANDYYT   60
EYADSVKGRF TISRDNSKNT LYLQMNSLRA EDTAVYYCAR DYYGSSYWYF DVWGQGTLVT   120
VSS                                                                123

SEQ ID NO: 38          moltype = AA  length = 123
FEATURE                Location/Qualifiers
source                 1..123
                       mol_type = protein
                       organism = synthetic construct
SEQUENCE: 38
EVQLLESGGG LVQPGGSLRL SCAASGFGFS DFYMEWVRQA PGKGLEWVAA SRHKANDYTT   60
EYADSVKGRF TISRDNSKNT LYLQMNSLRA EDTAVYYCAR DYYGSSYWYF DVWGQGTLVT   120
VSS                                                                123

SEQ ID NO: 39          moltype = AA  length = 123
FEATURE                Location/Qualifiers
source                 1..123
                       mol_type = protein
                       organism = synthetic construct
SEQUENCE: 39
EVQLLESGGG LVQPGGSLRL SCAASGFTFS TFYMEWVRQA PGKGLEWVAA SRNKANDYTT   60
EYADSVKGRF TISRDNSKNT LYLQMNSLRA EDTAVYYCAR DYYGSSYWYF DVWGQGTLVT   120
VSS                                                                123

SEQ ID NO: 40          moltype = AA  length = 123
FEATURE                Location/Qualifiers
source                 1..123
                       mol_type = protein
                       organism = synthetic construct
SEQUENCE: 40
EVQLLESGGG LVQPGGSLRL SCAASGFTFS DEYMEWVRQA PGKGLEWVAA SRGKGNSYTT   60
EYADSVKGRF TISRDNSKNT LYLQMNSLRA EDTAVYYCAR DYYGSSYWYF DVWGQGTLVT   120
VSS                                                                123

SEQ ID NO: 41          moltype = AA  length = 123
FEATURE                Location/Qualifiers
source                 1..123
                       mol_type = protein
                       organism = synthetic construct
SEQUENCE: 41
EVQLLESGGG LVQPGGSLRL SCAASGFTFS DQYMEWVRQA PGKGLEWVAA SRNKANDYQT   60
EYADSVKGRF TISRDNSKNT LYLQMNSLRA EDTAVYYCAR DYYGSSYWYF DVWGQGTLVT   120
VSS                                                                123

SEQ ID NO: 42          moltype = AA  length = 123
FEATURE                Location/Qualifiers
source                 1..123
                       mol_type = protein
                       organism = synthetic construct
SEQUENCE: 42
EVQLLESGGG LVQPGGSLRL SCAASGFWFS DFYMEWVRQA PGKGLEWVAA SRNKANDYTT   60
EYADSVKGRF TISRDNSKNT LYLQMNSLRA EDTAVYYCAR DYYGSSYWYF DVWGQGTLVT   120
VSS                                                                123

SEQ ID NO: 43          moltype = AA  length = 123
FEATURE                Location/Qualifiers
source                 1..123
                       mol_type = protein
                       organism = synthetic construct
SEQUENCE: 43

```
EVQLLESGGG LVQPGGSLRL SCAASGFTFS SYYMEWVRQA PGKGLEWVAA SRNQANDYTT    60
EYADSVKGRF TISRDNSKNT LYLQMNSLRA EDTAVYYCAR DYYGSPYWYF DVWGQGTLVT   120
VSS                                                                123

SEQ ID NO: 44           moltype = AA   length = 123
FEATURE                 Location/Qualifiers
source                  1..123
                        mol_type = protein
                        organism = synthetic construct
SEQUENCE: 44
EVQLLESGGG LVQPGGSLRL SCAASGFTFS DVYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 45           moltype = AA   length = 123
FEATURE                 Location/Qualifiers
source                  1..123
                        mol_type = protein
                        organism = synthetic construct
SEQUENCE: 45
EVQLLESGGG LVQPGGSLRL SCAASGFTFS SYYMEWVRQA PGKGLEWVAA SRNQANDYTT    60
EYADSVKGRF TISRDNSKNT LYLQMNSLRA EDTAVYYCAR DYYGSSYWYL DVWGQGTLVT   120
VSS                                                                123

SEQ ID NO: 46           moltype = AA   length = 123
FEATURE                 Location/Qualifiers
source                  1..123
                        mol_type = protein
                        organism = synthetic construct
SEQUENCE: 46
EVQLLESGGG LVQPGGSLRL SCAASGFTFS DFYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                123

SEQ ID NO: 47           moltype = AA   length = 123
FEATURE                 Location/Qualifiers
source                  1..123
                        mol_type = protein
                        organism = synthetic construct
SEQUENCE: 47
EVQLLESGGG LVQPGGSLRL SCAASGATFS DFYMEWVRQA PGKGLEWVAA SRNGANDYTT    60
EYADSVKGRF TISRDNSKNT LYLQMNSLRA EDTAVYYCAR DYYGNSYWYF DVWGQGTLVT   120
VSS                                                                123

SEQ ID NO: 48           moltype = AA   length = 123
FEATURE                 Location/Qualifiers
source                  1..123
                        mol_type = protein
                        organism = synthetic construct
SEQUENCE: 48
EVQLLESGGG LVQPGGSLRL SCAASGFDFS DFYMEWVRQA PGKGLEWVAA SRNKANDYTT    60
DYADSVKGRF TISRDNSKNT LYLQMNSLRA EDTAVYYCAR DYFGSSYWYF DVWGQGTLVT   120
VSS                                                                123

SEQ ID NO: 49           moltype = AA   length = 123
FEATURE                 Location/Qualifiers
source                  1..123
                        mol_type = protein
                        organism = synthetic construct
SEQUENCE: 49
EVQLLESGGG LVQPGGSLRL SCAASGFTFS DEYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 50           moltype = AA   length = 123
FEATURE                 Location/Qualifiers
source                  1..123
                        mol_type = protein
                        organism = synthetic construct
SEQUENCE: 50
EVQLLESGGG LVQPGGSLRL SCAASGFWFS DFYMEWVRQA PGKGLEWVAA SRNKANDYTT    60
EYADSVKGRF TISRDNSKNT LYLQMNSLRA EDTAVYYCAR DYYGSAYWYF DVWGQGTLVT   120
VSS                                                                123

SEQ ID NO: 51           moltype = AA   length = 123
FEATURE                 Location/Qualifiers
source                  1..123
                        mol_type = protein
                        organism = synthetic construct
```

```
SEQUENCE: 51
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DYYGHSYWYF DVWGQGTLVT   120
VSS                                                                 123

SEQ ID NO: 52           moltype = AA  length = 123
FEATURE                 Location/Qualifiers
source                  1..123
                        mol_type = protein
                        organism = synthetic construct
SEQUENCE: 52
EVQLLESGGG LVQPGGSLRL SCAASGFTFS DYYMEWVRQA PGKGLEWVAA SRNKANDYTV    60
EYADSVKGRF TISRDNSKNT LYLQMNSLRA EDTAVYYCAR DYYGSSYWYF DVWGQGTLVT   120
VSS                                                                 123

SEQ ID NO: 53           moltype = AA  length = 123
FEATURE                 Location/Qualifiers
source                  1..123
                        mol_type = protein
                        organism = synthetic construct
SEQUENCE: 53
EVQLLESGGG LVQPGGSLRL SCAASGWTFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 54           moltype = AA  length = 123
FEATURE                 Location/Qualifiers
source                  1..123
                        mol_type = protein
                        organism = synthetic construct
SEQUENCE: 54
EVQLLESGGG LVQPGGSLRL SCAASGFTFS DNYMEWVRQA PGKGLEWVAA SRNKANDYTN    60
EYADSVKGRF TISRDNSKNT LYLQMNSLRA EDTAVYYCAR DYYGSSYWYF DVWGQGTLVT   120
VSS                                                                 123

SEQ ID NO: 55           moltype = AA  length = 123
FEATURE                 Location/Qualifiers
source                  1..123
                        mol_type = protein
                        organism = synthetic construct
SEQUENCE: 55
EVQLLESGGG LVQPGGSLRL SCAASGFTFS SFYMEWVRQA PGKGLEWVAA SRNAANDYTT    60
EYADSVKGRF TISRDNSKNT LYLQMNSLRA EDTAVYYCAR DYYGSSYWYF DLWGQGTLVT   120
VSS                                                                 123

SEQ ID NO: 56           moltype = AA  length = 123
FEATURE                 Location/Qualifiers
source                  1..123
                        mol_type = protein
                        organism = synthetic construct
SEQUENCE: 56
EVQLLESGGG LVQPGGSLRL SCAASGFTAS DFYMEWVRQA PGKGLEWVAA SRNKANDQTT    60
EYADSVKGRF TISRDNSKNT LYLQMNSLRA EDTAVYYCAR DYYGSSYWYF DSWGQGTLVT   120
VSS                                                                 123

SEQ ID NO: 57           moltype = AA  length = 123
FEATURE                 Location/Qualifiers
source                  1..123
                        mol_type = protein
                        organism = synthetic construct
SEQUENCE: 57
EVQLLESGGG LVQPGGSLRL SCAASGFTFN DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 58           moltype = AA  length = 123
FEATURE                 Location/Qualifiers
source                  1..123
                        mol_type = protein
                        organism = synthetic construct
SEQUENCE: 58
EVQLLESGGG LVQPGGSLRL SCAASGFTFS DHYMEWVRQA PGKGLEWVAA SRNSGNSYTT    60
EYADSVKGRF TISRDNSKNT LYLQMNSLRA EDTAVYYCAR DYYGSSYWYF DVWGQGTLVT   120
VSS                                                                 123

SEQ ID NO: 59           moltype = AA  length = 123
FEATURE                 Location/Qualifiers
source                  1..123
                        mol_type = protein
```

```
                        organism = synthetic construct
SEQUENCE: 59
EVQLLESGGG LVQPGGSLRL SCAASGFTFS DGYIEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 60           moltype = AA  length = 123
FEATURE                 Location/Qualifiers
source                  1..123
                        mol_type = protein
                        organism = synthetic construct
SEQUENCE: 60
EVQLLESGGG LVQPGGSLRL SCAASGFTSS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 61           moltype = AA  length = 123
FEATURE                 Location/Qualifiers
source                  1..123
                        mol_type = protein
                        organism = synthetic construct
SEQUENCE: 61
EVQLLESGGG LVQPGGSLRL SCAASGFTFS DHYMEWVRQA PGKGLEWVAA SRNKANDYTT    60
EYADSVKGRF TISRDNSKNT LYLQMNSLRA EDTAVYYCAR DYYGQSYWYF DVWGQGTLVT   120
VSS                                                                123

SEQ ID NO: 62           moltype = AA  length = 123
FEATURE                 Location/Qualifiers
source                  1..123
                        mol_type = protein
                        organism = synthetic construct
SEQUENCE: 62
EVQLLESGGG LVQPGGSLRL SCAASGFTGS DFYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                123

SEQ ID NO: 63           moltype = AA  length = 123
FEATURE                 Location/Qualifiers
source                  1..123
                        mol_type = protein
                        organism = synthetic construct
SEQUENCE: 63
EVQLLESGGG LVQPGGSLRL SCAASGGTFS DFYMEWVRQA PGKGLEWVAA SRNKANTYTT    60
EYADSVKGRF TISRDNSKNT LYLQMNSLRA EDTAVYYCAR DYYGSSYWYF DVWGQGTLVT   120
VSS                                                                123

SEQ ID NO: 64           moltype = AA  length = 123
FEATURE                 Location/Qualifiers
source                  1..123
                        mol_type = protein
                        organism = synthetic construct
SEQUENCE: 64
EVQLLESGGG LVQPGGSLRL SCAASGFTFS DAYMEWVRQA PGKGLEWVAA SRNKANSYTT    60
EYADSVKGRF TISRDNSKNT LYLQMNSLRA EDTAVYYCAR DYYGSSYWYF DVWGQGTLVT   120
VSS                                                                123

SEQ ID NO: 65           moltype = AA  length = 123
FEATURE                 Location/Qualifiers
source                  1..123
                        mol_type = protein
                        organism = synthetic construct
SEQUENCE: 65
EVQLLESGGG LVQPGGSLRL SCAASGFTQS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 66           moltype = AA  length = 123
FEATURE                 Location/Qualifiers
source                  1..123
                        mol_type = protein
                        organism = synthetic construct
SEQUENCE: 66
EVQLLESGGG LVQPGGSLRL SCAASGFTFS DYYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                123

SEQ ID NO: 67           moltype = AA  length = 123
FEATURE                 Location/Qualifiers
source                  1..123
```

```
                        mol_type = protein
                        organism = synthetic construct
SEQUENCE: 67
EVQLLESGGG LVQPGGSLRL SCAASGDTFS DFYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                123

SEQ ID NO: 68           moltype = AA  length = 123
FEATURE                 Location/Qualifiers
source                  1..123
                        mol_type = protein
                        organism = synthetic construct
SEQUENCE: 68
EVQLLESGGG LVQPGGSLRL SCAASGFTFS DGYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                123

SEQ ID NO: 69           moltype = AA  length = 123
FEATURE                 Location/Qualifiers
source                  1..123
                        mol_type = protein
                        organism = synthetic construct
SEQUENCE: 69
EVQLLESGGG LVQPGGSLRL SCAASGFTFS DDYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 70           moltype = AA  length = 123
FEATURE                 Location/Qualifiers
source                  1..123
                        mol_type = protein
                        organism = synthetic construct
SEQUENCE: 70
EVQLLESGGG LVQPGGSLRL SCAASGFTTS DFYMEWVRQA PGKGLEWVAA SRNKANSYTT    60
EYADSVKGRF TISRDNSKNT LYLQMNSLRA EDTAVYYCAR DYYGSSYWYF DVWGQGTLVT   120
VSS                                                                123

SEQ ID NO: 71           moltype = AA  length = 123
FEATURE                 Location/Qualifiers
source                  1..123
                        mol_type = protein
                        organism = synthetic construct
SEQUENCE: 71
EVQLLESGGG LVQPGGSLRL SCAASGETFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 72           moltype = AA  length = 123
FEATURE                 Location/Qualifiers
source                  1..123
                        mol_type = protein
                        organism = synthetic construct
SEQUENCE: 72
EVQLLESGGG LVQPGGSLRL SCAASGFTFS DHYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 73           moltype = AA  length = 123
FEATURE                 Location/Qualifiers
source                  1..123
                        mol_type = protein
                        organism = synthetic construct
SEQUENCE: 73
EVQLLESGGG LVQPGGSLRL SCAASGDTFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 74           moltype = AA  length = 123
FEATURE                 Location/Qualifiers
source                  1..123
                        mol_type = protein
                        organism = synthetic construct
SEQUENCE: 74
EVQLLESGGG LVQPGGSLRL SCAASGFTGS DFYMEWVRQA PGKGLEWVAA SRGKGNSYTT    60
EYADSVKGRF TISRDNSKNT LYLQMNSLRA EDTAVYYCAR DYYGSSTWYF DVWGQGTLVT   120
VSS                                                                123

SEQ ID NO: 75           moltype = AA  length = 123
FEATURE                 Location/Qualifiers
```

```
source                   1..123
                         mol_type = protein
                         organism = synthetic construct
SEQUENCE: 75
EVQLLESGGG LVQPGGSLRL SCAASGFTFS DFYMEWVRQA PGKGLEWVAA SRWKANDYTT      60
EYADSVKGRF TISRDNSKNT LYLQMNSLRA EDTAVYYCAR DYYESSYWYF DVWGQGTLVT     120
VSS                                                                   123

SEQ ID NO: 76            moltype = AA  length = 123
FEATURE                  Location/Qualifiers
source                   1..123
                         mol_type = protein
                         organism = synthetic construct
SEQUENCE: 76
EVQLLESGGG LVQPGGSLRL SCAASGFPFS DFYMEWVRQA PGKGLEWVAA SRNKANDYTT      60
EYADSVKGRF TISRDNSKNT LYLQMNSLRA EDTAVYYCAR DYYGSSYWYF DVWGQGTLVT     120
VSS                                                                   123

SEQ ID NO: 77            moltype = AA  length = 123
FEATURE                  Location/Qualifiers
source                   1..123
                         mol_type = protein
                         organism = synthetic construct
SEQUENCE: 77
EVQLLESGGG LVQPGGSLRL SCAASGFTFE DFYMEWVRQA PGKGLEWVAA SRNKANDYTT      60
EYADSVKGRF TISRDNSKNT LYLQMNSLRA EDTAVYYCAR DYYGSSYWYF DVWGQGTLVT     120
VSS                                                                   123

SEQ ID NO: 78            moltype = AA  length = 123
FEATURE                  Location/Qualifiers
source                   1..123
                         mol_type = protein
                         organism = synthetic construct
SEQUENCE: 78
EVQLLESGGG LVQPGGSLRL SCAASGATFS DFYVEWVRQA PGKGLEWVAA SRNKANDYTT      60
EYADSVKGRF TISRDNSKNT LYLQMNSLRA EDTAVYYCAR DYYGSSYWYF DVWGQGTLVT     120
VSS                                                                   123

SEQ ID NO: 79            moltype = AA  length = 123
FEATURE                  Location/Qualifiers
source                   1..123
                         mol_type = protein
                         organism = synthetic construct
SEQUENCE: 79
EVQLLESGGG LVQPGGSLRL SCAASGFTFS DYYMEWVRQA PGKGLEWVAA SRNKANDYTT      60
EYADSVKGRF TISRDNSKNT LYLQMNSLRA EDTAVYYCAR DYYGNSYWYF DVWGQGTLVT     120
VSS                                                                   123

SEQ ID NO: 80            moltype = AA  length = 123
FEATURE                  Location/Qualifiers
source                   1..123
                         mol_type = protein
                         organism = synthetic construct
SEQUENCE: 80
EVQLLESGGG LVQPGGSLRL SCAASGFTQS DFMEWVRQA PGKGLEWVAA IRNKANSYTT       60
EYADSVKGRF TISRDNSKNT LYLQMNSLRA EDTAVYYCAR DYYGSSYWYF DVWGQGTLVT     120
VSS                                                                   123

SEQ ID NO: 81            moltype = AA  length = 123
FEATURE                  Location/Qualifiers
source                   1..123
                         mol_type = protein
                         organism = synthetic construct
SEQUENCE: 81
EVQLLESGGG LVQPGGSLRL SCAASGGTFS DFYMEWVRQA PGKGLEWVAA SRNKANSYTT      60
AYADSVKGRF TISRDNSKNT LYLQMNSLRA EDTAVYYCAR DYYGSSYWYF DVWGQGTLVT     120
VSS                                                                   123

SEQ ID NO: 82            moltype = AA  length = 123
FEATURE                  Location/Qualifiers
source                   1..123
                         mol_type = protein
                         organism = synthetic construct
SEQUENCE: 82
EVQLLESGGG LVQPGGSLRL SCAASGFTFS SYYMEWVRQA PGKGLEWVAA SRNKYNDYTT      60
EYADSVKGRF TISRDNSKNT LYLQMNSLRA EDTAVYYCAR DYYGSSTWYF DVWGQGTLVT     120
VSS                                                                   123

SEQ ID NO: 83            moltype = AA  length = 123
```

```
FEATURE                 Location/Qualifiers
source                  1..123
                        mol_type = protein
                        organism = synthetic construct
SEQUENCE: 83
EVQLLESGGG LVQPGGSLRL SCAASGFTFS DFYMEWVRQA PGKGLEWVAA SRNKANDYTT    60
TYADSVKGRF TISRDNSKNT LYLQMNSLRA EDTAVYYCAR DYYGSSHWYF DVWGQGTLVT   120
VSS                                                                 123

SEQ ID NO: 84           moltype = AA   length = 123
FEATURE                 Location/Qualifiers
source                  1..123
                        mol_type = protein
                        organism = synthetic construct
SEQUENCE: 84
EVQLLESGGG LVQPGGSLRL SCAASGFTFS SYYMEWVRQA PGKGLEWVAA SRNKGNSYTT    60
EYADSVKGRF TISRDNSKNT LYLQMNSLRA EDTAVYYCAR DYYGSSYWYF DVWGQGTLVT   120
VSS                                                                 123

SEQ ID NO: 85           moltype = AA   length = 123
FEATURE                 Location/Qualifiers
source                  1..123
                        mol_type = protein
                        organism = synthetic construct
SEQUENCE: 85
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DYYGSSYWYF DSWGQGTLVT   120
VSS                                                                 123

SEQ ID NO: 86           moltype = AA   length = 123
FEATURE                 Location/Qualifiers
source                  1..123
                        mol_type = protein
                        organism = synthetic construct
SEQUENCE: 86
EVQLLESGGG LVQPGGSLRL SCAASGFTFS DYYMEWVRQA PGKGLEWVAA SRNKANDYTT    60
EYADSVKGRF TISRDNSKNT LYLQMNSLRA EDTAVYYCAR DYYGDSYWYF DVWGQGTLVT   120
VSS                                                                 123

SEQ ID NO: 87           moltype = AA   length = 123
FEATURE                 Location/Qualifiers
source                  1..123
                        mol_type = protein
                        organism = synthetic construct
SEQUENCE: 87
EVQLLESGGG LVQPGGSLRL SCAASGFTDS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 88           moltype = AA   length = 123
FEATURE                 Location/Qualifiers
source                  1..123
                        mol_type = protein
                        organism = synthetic construct
SEQUENCE: 88
EVQLLESGGG LVQPGGSLRL SCAASGFTFS SYYMEWVRQA PGKGLEWVAA SRNKANDYTT    60
EYADSVKGRF TISRDNSKNT LYLQMNSLRA EDTAVYYCAR DYYGSSYWYN DVWGQGTLVT   120
VSS                                                                 123

SEQ ID NO: 89           moltype = AA   length = 123
FEATURE                 Location/Qualifiers
source                  1..123
                        mol_type = protein
                        organism = synthetic construct
SEQUENCE: 89
EVQLLESGGG LVQPGGSLRL SCAASGFTFS DYYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                 123

SEQ ID NO: 90           moltype = AA   length = 123
FEATURE                 Location/Qualifiers
source                  1..123
                        mol_type = protein
                        organism = synthetic construct
SEQUENCE: 90
EVQLLESGGG LVQPGGSLRL SCAASGFTFS DYYMEWVRQA PGKGLEWVAA SRNKGNDYTT    60
EYADSVKGRF TISRDNSKNT LYLQMNSLRA EDTAVYYCAR DYYGSSYWYF DVWGQGTLVT   120
VSS                                                                 123
```

```
SEQ ID NO: 91            moltype = AA  length = 123
FEATURE                  Location/Qualifiers
source                   1..123
                         mol_type = protein
                         organism = synthetic construct
SEQUENCE: 91
EVQLLESGGG LVQPGGSLRL SCAASGFGFS DFYMEWVRQA PGKGLEWVGA SRNKHNDYTT    60
EYADSVKGRF TISRDNSKNT LYLQMNSLRA EDTAVYYCAR DYYGSSYWYF DVWGQGTLVT   120
VSS                                                                 123

SEQ ID NO: 92            moltype = AA  length = 123
FEATURE                  Location/Qualifiers
source                   1..123
                         mol_type = protein
                         organism = synthetic construct
SEQUENCE: 92
EVQLLESGGG LVQPGGSLRL SCAASGDTFS DFYMEWVRQA PGKGLEWVAA SRNKANAYTT    60
EYADSVKGRF TISRDNSKNT LYLQMNSLRA EDTAVYYCAR DYYGQSYWYF DVWGQGTLVT   120
VSS                                                                 123

SEQ ID NO: 93            moltype = AA  length = 123
FEATURE                  Location/Qualifiers
source                   1..123
                         mol_type = protein
                         organism = synthetic construct
SEQUENCE: 93
EVQLLESGGG LVQPGGSLRL SCAASGNTFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 94            moltype = AA  length = 123
FEATURE                  Location/Qualifiers
source                   1..123
                         mol_type = protein
                         organism = synthetic construct
SEQUENCE: 94
EVQLLESGGG LVQPGGSLRL SCAASGFTFS SYYMEWVRQA PGKGLEWVAA SRNKFNDYTT    60
EYADSVKGRF TISRDNSKNT LYLQMNSLRA EDTAVYYCAR DYYGSSYWYF DVWGQGTLVT   120
VSS                                                                 123

SEQ ID NO: 95            moltype = AA  length = 123
FEATURE                  Location/Qualifiers
source                   1..123
                         mol_type = protein
                         organism = synthetic construct
SEQUENCE: 95
EVQLLESGGG LVQPGGSLRL SCAASGFPFS DFYMEWVRQA PGKGLEWVAA SRNKANDYTT    60
EYADSVKGRF TISRDNSKNT LYLQMNSLRA EDTAVYYCAR DYYGSPYWYF DVWGQGTLVT   120
VSS                                                                 123

SEQ ID NO: 96            moltype = AA  length = 123
FEATURE                  Location/Qualifiers
source                   1..123
                         mol_type = protein
                         organism = synthetic construct
SEQUENCE: 96
EVQLLESGGG LVQPGGSLRL SCAASGFTFS DSYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                 123

SEQ ID NO: 97            moltype = AA  length = 123
FEATURE                  Location/Qualifiers
source                   1..123
                         mol_type = protein
                         organism = synthetic construct
SEQUENCE: 97
EVQLLESGGG LVQPGGSLRL SCAASGDTFS DFYLEWVRQA PGKGLEWVAA SRNKANGYTT    60
EYADSVKGRF TISRDNSKNT LYLQMNSLRA EDTAVYYCAR DYYHSSYWYF DVWGQGTLVT   120
VSS                                                                 123

SEQ ID NO: 98            moltype = AA  length = 123
FEATURE                  Location/Qualifiers
source                   1..123
                         mol_type = protein
                         organism = synthetic construct
SEQUENCE: 98
EVQLLESGGG LVQPGGSLRL SCAASGFTFS SYYMEWVRQA PGKGLEWVAA SRNKANDYTT    60
EYADSVKGRF TISRDNSKNT LYLQMNSLRA EDTAVYYCAR DYYGSSYWYY DVWGQGTLVT   120
VSS                                                                 123
```

```
SEQ ID NO: 99          moltype = AA   length = 123
FEATURE                Location/Qualifiers
source                 1..123
                       mol_type = protein
                       organism = synthetic construct
SEQUENCE: 99
EVQLLESGGG LVQPGGSLRL SCAASGFTHS DFYMEWVRQA PGKGLEWVAA SRNKANGYTT    60
EYADSVKGRF TISRDNSKNT LYLQMNSLRA EDTAVYYCAR DYYGSSYWYF DSWGQGTLVT   120
VSS                                                                 123

SEQ ID NO: 100         moltype = AA   length = 123
FEATURE                Location/Qualifiers
source                 1..123
                       mol_type = protein
                       organism = synthetic construct
SEQUENCE: 100
EVQLLESGGG LVQPGGSLRL SCAASGFLFS DFYMEWVRQA PGKGLEWVAA SRNKANDYTT    60
TYADSVKGRF TISRDNSKNT LYLQMNSLRA EDTAVYYCAR DYYGSHYWYF DVWGQGTLVT   120
VSS                                                                 123

SEQ ID NO: 101         moltype = AA   length = 123
FEATURE                Location/Qualifiers
source                 1..123
                       mol_type = protein
                       organism = synthetic construct
SEQUENCE: 101
EVQLLESGGG LVQPGGSLRL SCAASGFTFS SYYMEWVRQA PGKGLEWVAA SRNKANEYTT    60
EYADSVKGRF TISRDNSKNT LYLQMNSLRA EDTAVYYCAR DYYGSSYWYF DVWGQGTLVT   120
VSS                                                                 123

SEQ ID NO: 102         moltype = AA   length = 123
FEATURE                Location/Qualifiers
source                 1..123
                       mol_type = protein
                       organism = synthetic construct
SEQUENCE: 102
EVQLLESGGG LVQPGGSLRL SCAASGFTFS DFYMEWVRQA PGKGLEWVAA SRNKNNDYTT    60
EYADSVKGRF TISRDNSKNT LYLQMNSLRA EDTAVYYCAR DYYGSSYWYF DVWGQGTLVT   120
VSS                                                                 123

SEQ ID NO: 103         moltype = AA   length = 123
FEATURE                Location/Qualifiers
source                 1..123
                       mol_type = protein
                       organism = synthetic construct
SEQUENCE: 103
EVQLLESGGG LVQPGGSLRL SCAASGFTFS SYYMEWVRQA PGKGLEWVAA SRNKANLYTT    60
EYADSVKGRF TISRDNSKNT LYLQMNSLRA EDTAVYYCAR DYYGSSTWYF DVWGQGTLVT   120
VSS                                                                 123

SEQ ID NO: 104         moltype = AA   length = 123
FEATURE                Location/Qualifiers
source                 1..123
                       mol_type = protein
                       organism = synthetic construct
SEQUENCE: 104
EVQLLESGGG LVQPGGSLRL SCAASGFTFS DHYMEWVRQA PGKGLEWVAA SRGKGNSYTT    60
AYADSVKGRF TISRDNSKNT LYLQMNSLRA EDTAVYYCAR DYYGSSYWYF DVWGQGTLVT   120
VSS                                                                 123

SEQ ID NO: 105         moltype = AA   length = 123
FEATURE                Location/Qualifiers
source                 1..123
                       mol_type = protein
                       organism = synthetic construct
SEQUENCE: 105
EVQLLESGGG LVQPGGSLRL SCAASGFTFS DFYMEWVRQA PGKGLEWVAA SRNKGNSYTT    60
AYADSVKGRF TISRDNSKNT LYLQMNSLRA EDTAVYYCAR DYYGSSYWYF DVWGQGTLVT   120
VSS                                                                 123

SEQ ID NO: 106         moltype = AA   length = 123
FEATURE                Location/Qualifiers
source                 1..123
                       mol_type = protein
                       organism = synthetic construct
SEQUENCE: 106
EVQLLESGGG LVQPGGSLRL SCAASGFTFS DHYMEWVRQA PGKGLEWVAA SRNKYNDYTT    60
EYADSVKGRF TISRDNSKNT LYLQMNSLRA EDTAVYYCAR DIYGSSYWYF DVWGQGTLVT   120
```

```
VSS                                                                             123

SEQ ID NO: 107          moltype = AA  length = 123
FEATURE                 Location/Qualifiers
source                  1..123
                        mol_type = protein
                        organism = synthetic construct
SEQUENCE: 107
EVQLLESGGG LVQPGGSLRL SCAASGFTFS DYYMEWVRQA PGKGLEWVAA SRNKANTYTT              60
EYADSVKGRF TISRDNSKNT LYLQMNSLRA EDTAVYYCAR DYYGSSYWYD DVWGQGTLVT             120
VSS                                                                          123

SEQ ID NO: 108          moltype = AA  length = 123
FEATURE                 Location/Qualifiers
source                  1..123
                        mol_type = protein
                        organism = synthetic construct
SEQUENCE: 108
EVQLLESGGG LVQPGGSLRL SCAASGFTFS DQYMEWVRQA PGKGLEWVAA SRNNANDYTT              60
EYADSVKGRF TISRDNSKNT LYLQMNSLRA EDTAVYYCAR DYYGSSYWYF DVWGQGTLVT             120
VSS                                                                          123

SEQ ID NO: 109          moltype = AA  length = 123
FEATURE                 Location/Qualifiers
source                  1..123
                        mol_type = protein
                        organism = synthetic construct
SEQUENCE: 109
EVQLLESGGG LVQPGGSLRL SCAASGFTNS DFYMEWVRQA PGKGLEWVAA SRNKFNDYTT              60
EYADSVKGRF TISRDNSKNT LYLQMNSLRA EDTAVYYCAR DYYGSSYWYF DVWGQGTLVT             120
VSS                                                                          123

SEQ ID NO: 110          moltype = AA  length = 123
FEATURE                 Location/Qualifiers
source                  1..123
                        mol_type = protein
                        organism = synthetic construct
SEQUENCE: 110
EVQLLESGGG LVQPGGSLRL SCAASGFTFS DYYMEWVRQA PGKGLEWVAA SRWKANDYTT              60
EYADSVKGRF TISRDNSKNT LYLQMNSLRA EDTAVYYCAR DYYGSSYWYF DVWGQGTLVT             120
VSS                                                                          123

SEQ ID NO: 111          moltype = AA  length = 123
FEATURE                 Location/Qualifiers
source                  1..123
                        mol_type = protein
                        organism = synthetic construct
SEQUENCE: 111
EVQLLESGGG LVQPGGSLRL SCAASGQTFS DFYMEWVRQA PGKGLEWVAA SRNKANGYTT              60
EYTDSVKGRF TISRDNSKNT LYLQMNSLRA EDTAVYYCAR DYYGSSYWYF DVWGQGTLVT             120
VSS                                                                          123

SEQ ID NO: 112          moltype = AA  length = 123
FEATURE                 Location/Qualifiers
source                  1..123
                        mol_type = protein
                        organism = synthetic construct
SEQUENCE: 112
EVQLLESGGG LVQPGGSLRL SCAASGFTAS DFYMEWVRQA PGKGLEWVAA SRNKANDYTT              60
EYADSVKGRF TISRDNSKNT LYLQMNSLRA EDTAVYYCAR DYYGSSYWYF DVWGQGTLVT             120
VSS                                                                          123

SEQ ID NO: 113          moltype = AA  length = 123
FEATURE                 Location/Qualifiers
source                  1..123
                        mol_type = protein
                        organism = synthetic construct
SEQUENCE: 113
EVQLLESGGG LVQPGGSLRL SCAASGFTFS DPYMEWVRQA PGKGLEWVAA SRNKANDYTT              60
EYADSVKGRF TISRDNSKNT LYLQMNSLRA EDTAVYYCAR DYYGSPYWYF DVWGQGTLVT             120
VSS                                                                          123

SEQ ID NO: 114          moltype = AA  length = 123
FEATURE                 Location/Qualifiers
source                  1..123
                        mol_type = protein
                        organism = synthetic construct
SEQUENCE: 114
EVQLLESGGG LVQPGGSLRL SCAASGFTFS DYYMEWVRQA PGKGLEWVAA SRNKANDYTT              60
```

```
EYADSVKGRF TISRDNSKNT LYLQMNSLRA EDTAVYYCAR DYYGSSYWYF DTWGQGTLVT    120
VSS                                                                 123

SEQ ID NO: 115          moltype = AA  length = 123
FEATURE                 Location/Qualifiers
source                  1..123
                        mol_type = protein
                        organism = synthetic construct
SEQUENCE: 115
EVQLLESGGG LVQPGGSLRL SCAASGFTQS DFYMEWVRQA PGKGLEWVAA SRNKANAYTT    60
EYADSVKGRF TISRDNSKNT LYLQMNSLRA EDTAVYYCAR DYYGYSYWYF DVWGQGTLVT    120
VSS                                                                 123

SEQ ID NO: 116          moltype = AA  length = 123
FEATURE                 Location/Qualifiers
source                  1..123
                        mol_type = protein
                        organism = synthetic construct
SEQUENCE: 116
EVQLLESGGG LVQPGGSLRL SCAASGFTFS DEYMEWVRQA PGKGLEWVAA SRNSGNSYTT    60
AYADSVKGRF TISRDNSKNT LYLQMNSLRA EDTAVYYCAR DYYGSSYWYF DVWGQGTLVT    120
VSS                                                                 123

SEQ ID NO: 117          moltype = AA  length = 123
FEATURE                 Location/Qualifiers
source                  1..123
                        mol_type = protein
                        organism = synthetic construct
SEQUENCE: 117
EVQLLESGGG LVQPGGSLRL SCAASGFTFS DYYMEWVRQA PGKGLEWVAA SRWKANDYTT    60
EYADSVKGRF TISRDNSKNT LYLQMNSLRA EDTAVYYCAR DYYGSSQWYF DVWGQGTLVT    120
VSS                                                                 123

SEQ ID NO: 118          moltype = AA  length = 123
FEATURE                 Location/Qualifiers
source                  1..123
                        mol_type = protein
                        organism = synthetic construct
SEQUENCE: 118
EVQLLESGGG LVQPGGSLRL SCAASGFTFS DDYMEWVRQA PGKGLEWVAA TRNKANDYTT    60
EYADSVKGRF TISRDNSKNT LYLQMNSLRA EDTAVYYCAR DYYGSSYWYF DSWGQGTLVT    120
VSS                                                                 123

SEQ ID NO: 119          moltype = AA  length = 123
FEATURE                 Location/Qualifiers
source                  1..123
                        mol_type = protein
                        organism = synthetic construct
SEQUENCE: 119
EVQLLESGGG LVQPGGSLRL SCAASGFTFS DQYMEWVRQA PGKGLEWVAA SRNKANDYTV    60
EYADSVKGRF TISRDNSKNT LYLQMNSLRA EDTAVYYCAR DYYGSSYWYF DVWGQGTLVT    120
VSS                                                                 123

SEQ ID NO: 120          moltype = AA  length = 123
FEATURE                 Location/Qualifiers
source                  1..123
                        mol_type = protein
                        organism = synthetic construct
SEQUENCE: 120
EVQLLESGGG LVQPGGSLRL SCAASGFGFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT    120
VSS                                                                 123

SEQ ID NO: 121          moltype = AA  length = 123
FEATURE                 Location/Qualifiers
source                  1..123
                        mol_type = protein
                        organism = synthetic construct
SEQUENCE: 121
EVQLLESGGG LVQPGGSLRL SCAASGFTGS DFYMEWVRQA PGKGLEWVAA SRNSGNSYTT    60
AYADSVKGRF TISRDNSKNT LYLQMNSLRA EDTAVYYCAR DYFGSSYWYF DVWGQGTLVT    120
VSS                                                                 123

SEQ ID NO: 122          moltype = AA  length = 123
FEATURE                 Location/Qualifiers
source                  1..123
                        mol_type = protein
                        organism = synthetic construct
SEQUENCE: 122
```

```
EVQLLESGGG LVQPGGSLRL SCAASGFTFS DEYMEWVRQA PGKGLEWVAA SRNKANDFTT    60
EYADSVKGRF TISRDNSKNT LYLQMNSLRA EDTAVYYCAR DFYGSSYWYF DVWGQGTLVT   120
VSS                                                                123

SEQ ID NO: 123           moltype = AA   length = 123
FEATURE                  Location/Qualifiers
source                   1..123
                         mol_type = protein
                         organism = synthetic construct
SEQUENCE: 123
EVQLLESGGG LVQPGGSLRL SCAASGFQFS DFYMEWVRQA PGKGLEWVAA SRNKGNSYTT    60
AYADSVKGRF TISRDNSKNT LYLQMNSLRA EDTAVYYCAR DYYGSSYWYF DVWGQGTLVT   120
VSS                                                                123

SEQ ID NO: 124           moltype = AA   length = 123
FEATURE                  Location/Qualifiers
source                   1..123
                         mol_type = protein
                         organism = synthetic construct
SEQUENCE: 124
EVQLLESGGG LVQPGGSLRL SCAASGTTFS DFYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                123

SEQ ID NO: 125           moltype = AA   length = 123
FEATURE                  Location/Qualifiers
source                   1..123
                         mol_type = protein
                         organism = synthetic construct
SEQUENCE: 125
EVQLLESGGG LVQPGGSLRL SCAASGFGFS DFYMEWVRQA PGKGLEWVAA SRNKANDYTT    60
EYADSVKGRF TISRDNSKNT LYLQMNSLRA EDTAVYYCAR DYYGSSYWYH DVWGQGTLVT   120
VSS                                                                123

SEQ ID NO: 126           moltype = AA   length = 123
FEATURE                  Location/Qualifiers
source                   1..123
                         mol_type = protein
                         organism = synthetic construct
SEQUENCE: 126
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DYYGSSHWYF DVWGQGTLVT   120
VSS                                                                123

SEQ ID NO: 127           moltype = AA   length = 123
FEATURE                  Location/Qualifiers
source                   1..123
                         mol_type = protein
                         organism = synthetic construct
SEQUENCE: 127
EVQLLESGGG LVQPGGSLRL SCAASGPTFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 128           moltype = AA   length = 123
FEATURE                  Location/Qualifiers
source                   1..123
                         mol_type = protein
                         organism = synthetic construct
SEQUENCE: 128
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DYYGSSYWYF DPWGQGTLVT   120
VSS                                                                123

SEQ ID NO: 129           moltype = AA   length = 123
FEATURE                  Location/Qualifiers
source                   1..123
                         mol_type = protein
                         organism = synthetic construct
SEQUENCE: 129
EVQLLESGGG LVQPGGSLRL SCAASGFTFS DAYMEWVRQA PGKGLEWVAA SRNKANDYTT    60
EYADSVKGRF TISRDNSKNT LYLQMNSLRA EDTAVYYCAR DYYGSHYWYF DVWGQGTLVT   120
VSS                                                                123

SEQ ID NO: 130           moltype = AA   length = 123
FEATURE                  Location/Qualifiers
source                   1..123
                         mol_type = protein
                         organism = synthetic construct
```

```
SEQUENCE: 130
EVQLLESGGG LVQPGGSLRL SCAASGFTFS SYYMEWVRQA PGKGLEWVAA SRNKANDYTY    60
EYADSVKGRF TISRDNSKNT LYLQMNSLRA EDTAVYYCAR DYYESSYWYF DVWGQGTLVT   120
VSS                                                                 123

SEQ ID NO: 131         moltype = AA   length = 123
FEATURE                Location/Qualifiers
source                 1..123
                       mol_type = protein
                       organism = synthetic construct
SEQUENCE: 131
EVQLLESGGG LVQPGGSLRL SCAASGDTFS DFYMEWVRQA PGKGLEWVAA SRNKANDYST    60
EYADSVKGRF TISRDNSKNT LYLQMNSLRA EDTAVYYCAR DYYGSSYWYF DVWGQGTLVT   120
VSS                                                                 123

SEQ ID NO: 132         moltype = AA   length = 123
FEATURE                Location/Qualifiers
source                 1..123
                       mol_type = protein
                       organism = synthetic construct
SEQUENCE: 132
EVQLLESGGG LVQPGGSLRL SCAASGFTFS EFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 133         moltype = AA   length = 123
FEATURE                Location/Qualifiers
source                 1..123
                       mol_type = protein
                       organism = synthetic construct
SEQUENCE: 133
EVQLLESGGG LVQPGGSLRL SCAASGFTFS SYYMEWVRQA PGKGLEWVAA SRSKANDYTT    60
EYADSVKGRF TISRDNSKNT LYLQMNSLRA EDTAVYYCAR DYYGSQYWYF DVWGQGTLVT   120
VSS                                                                 123

SEQ ID NO: 134         moltype = AA   length = 123
FEATURE                Location/Qualifiers
source                 1..123
                       mol_type = protein
                       organism = synthetic construct
SEQUENCE: 134
EVQLLESGGG LVQPGGSLRL SCAASGFHFS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 135         moltype = AA   length = 123
FEATURE                Location/Qualifiers
source                 1..123
                       mol_type = protein
                       organism = synthetic construct
SEQUENCE: 135
EVQLLESGGG LVQPGGSLRL SCAASGFTFS DGYMEWVRQA PGKGLEWVAA SRNKANDYTT    60
AYADSVKGRF TISRDNSKNT LYLQMNSLRA EDTAVYYCAR DYYGSSYWYF DVWGQGTLVT   120
VSS                                                                 123

SEQ ID NO: 136         moltype = AA   length = 123
FEATURE                Location/Qualifiers
source                 1..123
                       mol_type = protein
                       organism = synthetic construct
SEQUENCE: 136
EVQLLESGGG LVQPGGSLRL SCAASGFTFS SYYMEWVRQA PGKGLEWVAA SRNTANDYTT    60
EYADSVKGRF TISRDNSKNT LYLQMNSLRA EDTAVYYCAR DYYGSSYWYF DVWGQGTLVT   120
VSS                                                                 123

SEQ ID NO: 137         moltype = AA   length = 123
FEATURE                Location/Qualifiers
source                 1..123
                       mol_type = protein
                       organism = synthetic construct
SEQUENCE: 137
EVQLLESGGG LVQPGGSLRL SCAASGITFS DFYMEWVRQA PGKGLEWVAA SRNKYNDYTT    60
EYADSVKGRF TISRDNSKNT LYLQMNSLRA EDTAVYYCAR DYYGSSYWYF DVWGQGTLVT   120
VSS                                                                 123

SEQ ID NO: 138         moltype = AA   length = 123
FEATURE                Location/Qualifiers
source                 1..123
                       mol_type = protein
```

```
                       organism = synthetic construct
SEQUENCE: 138
EVQLLESGGG LVQPGGSLRL SCAASGFGFS DFYMEWVRQA PGKGLEWVAA SRNKANDYTT   60
EYADSVKGRF TISRDNSKNT LYLQMNSLRA EDTAVYYCAR DYYSSSYWYF DVWGQGTLVT  120
VSS                                                               123

SEQ ID NO: 139         moltype = AA  length = 123
FEATURE                Location/Qualifiers
source                 1..123
                       mol_type = protein
                       organism = synthetic construct
SEQUENCE: 139
EVQLLESGGG LVQPGGSLRL SCAASGFTFS DYYMEWVRQA PGKGLEWVAA SRNKANDYNT   60
EYADSVKGRF TISRDNSKNT LYLQMNSLRA EDTAVYYCAR DYYGSSYWYF DVWGQGTLVT  120
VSS                                                               123

SEQ ID NO: 140         moltype = AA  length = 123
FEATURE                Location/Qualifiers
source                 1..123
                       mol_type = protein
                       organism = synthetic construct
SEQUENCE: 140
EVQLLESGGG LVQPGGSLRL SCAASGFTFS DFYVEWVRQA PGKGLEWVAA SRNKANTYTT   60
EYADSVKGRF TISRDNSKNT LYLQMNSLRA EDTAVYYCAR DYYGSSYWYF DVWGQGTLVT  120
VSS                                                               123

SEQ ID NO: 141         moltype = AA  length = 123
FEATURE                Location/Qualifiers
source                 1..123
                       mol_type = protein
                       organism = synthetic construct
SEQUENCE: 141
EVQLLESGGG LVQPGGSLRL SCAASGFQFS DFYMEWVRQA PGKGLEWVAA SRWKANDYTT   60
EYADSVKGRF TISRDNSKNT LYLQMNSLRA EDTAVYYCAR DYYGSSYWYF DVWGQGTLVT  120
VSS                                                               123

SEQ ID NO: 142         moltype = AA  length = 123
FEATURE                Location/Qualifiers
source                 1..123
                       mol_type = protein
                       organism = synthetic construct
SEQUENCE: 142
EVQLLESGGG LVQPGGSLRL SCAASGFTFS DFYMEWVRQA PGKGLEWVAA SRNKANDYTT   60
EVADSVKGRF TISRDNSKNT LYLQMNSLRA EDTAVYYCAR DYYGSSNWYF DVWGQGTLVT  120
VSS                                                               123

SEQ ID NO: 143         moltype = AA  length = 123
FEATURE                Location/Qualifiers
source                 1..123
                       mol_type = protein
                       organism = synthetic construct
SEQUENCE: 143
EVQLLESGGG LVQPGGSLRL SCAASGFTFS DFYMEWVRQA PGKGLEWVAA SRNKANDYTT   60
EYADSVKGRF TISRDNSKNT LYLQMNSLRA EDTAVYYCAR DYYGSSYWYN DVWGQGTLVT  120
VSS                                                               123

SEQ ID NO: 144         moltype = AA  length = 123
FEATURE                Location/Qualifiers
source                 1..123
                       mol_type = protein
                       organism = synthetic construct
SEQUENCE: 144
EVQLLESGGG LVQPGGSLRL SCAASGSTFS DFYMEWVRQA PGKGLEWVAA SRNKANDFTT   60
EYADSVKGRF TISRDNSKNT LYLQMNSLRA EDTAVYYCAR DYYGSSYWYF DVWGQGTLVT  120
VSS                                                               123

SEQ ID NO: 145         moltype = AA  length = 123
FEATURE                Location/Qualifiers
source                 1..123
                       mol_type = protein
                       organism = synthetic construct
SEQUENCE: 145
EVQLLESGGG LVQPGGSLRL SCAASGFTFS DYYMEWVRQA PGKGLEWVAA SRNKANDYTT   60
EYADSVKGRF TISRDNSKNT LYLQMNSLRA EDTAVYYCAR DYYFSSYWYF DVWGQGTLVT  120
VSS                                                               123

SEQ ID NO: 146         moltype = AA  length = 123
FEATURE                Location/Qualifiers
source                 1..123
```

```
                        mol_type = protein
                        organism = synthetic construct
SEQUENCE: 146
EVQLLESGGG LVQPGGSLRL SCAASGFTTS DFYMEWVRQA PGKGLEWVAA SRNKANGYTT    60
EYADSVKGRF TISRDNSKNT LYLQMNSLRA EDTAVYYCAR DYYGSSYWYF DVWGQGTLVT   120
VSS                                                                 123

SEQ ID NO: 147          moltype = AA  length = 123
FEATURE                 Location/Qualifiers
source                  1..123
                        mol_type = protein
                        organism = synthetic construct
SEQUENCE: 147
EVQLLESGGG LVQPGGSLRL SCAASGFTNS DFYMEWVRQA PGKGLEWVAA SRNKANDYTT    60
ELADSVKGRF TISRDNSKNT LYLQMNSLRA EDTAVYYCAR DYYGSSYWYF DVWGQGTLVT   120
VSS                                                                 123

SEQ ID NO: 148          moltype = AA  length = 123
FEATURE                 Location/Qualifiers
source                  1..123
                        mol_type = protein
                        organism = synthetic construct
SEQUENCE: 148
EVQLLESGGG LVQPGGSLRL SCAASGETFS DFYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                 123

SEQ ID NO: 149          moltype = AA  length = 123
FEATURE                 Location/Qualifiers
source                  1..123
                        mol_type = protein
                        organism = synthetic construct
SEQUENCE: 149
EVQLLESGGG LVQPGGSLRL SCAASGFTFS SYYMEWVRQA PGKGLEWVAA SRNKANDYTT    60
EYADSVKGRF TISRDNSKNT LYLQMNSLRA EDTAVYYCAR DYYDSSYWYF DVWGQGTLVT   120
VSS                                                                 123

SEQ ID NO: 150          moltype = AA  length = 123
FEATURE                 Location/Qualifiers
source                  1..123
                        mol_type = protein
                        organism = synthetic construct
SEQUENCE: 150
EVQLLESGGG LVQPGGSLRL SCAASGFTFS DQYMEWVRQA PGKGLEWVAA SRNKNNDYTT    60
EYADSVKGRF TISRDNSKNT LYLQMNSLRA EDTAVYYCAR DYYGASYWYF DVWGQGTLVT   120
VSS                                                                 123

SEQ ID NO: 151          moltype = AA  length = 123
FEATURE                 Location/Qualifiers
source                  1..123
                        mol_type = protein
                        organism = synthetic construct
SEQUENCE: 151
EVQLLESGGG LVQPGGSLRL SCAASGFTFS DYYMEWVRQA PGKGLEWVAA SRNKGNDYTT    60
AYADSVKGRF TISRDNSKNT LYLQMNSLRA EDTAVYYCAR DYFGSSYWYF DVWGQGTLVT   120
VSS                                                                 123

SEQ ID NO: 152          moltype = AA  length = 123
FEATURE                 Location/Qualifiers
source                  1..123
                        mol_type = protein
                        organism = synthetic construct
SEQUENCE: 152
EVQLLESGGG LVQPGGSLRL SCAASGFTQS DFYMEWVRQA PGKGLEWVAA SRNKGNSYTT    60
AYADSVKGRF TISRDNSKNT LYLQMNSLRA EDTAVYYCAR DYYGSSYWYF DVWGQGTLVT   120
VSS                                                                 123

SEQ ID NO: 153          moltype = AA  length = 123
FEATURE                 Location/Qualifiers
source                  1..123
                        mol_type = protein
                        organism = synthetic construct
SEQUENCE: 153
EVQLLESGGG LVQPGGSLRL SCAASGFTFS DYYMEWVRQA PGKGLEWVAA SRNKANSYTT    60
AYADSVKGRF TISRDNSKNT LYLQMNSLRA EDTAVYYCAR DYYGSSYWYF DVWGQGTLVT   120
VSS                                                                 123

SEQ ID NO: 154          moltype = AA  length = 123
FEATURE                 Location/Qualifiers
```

```
source                  1..123
                        mol_type = protein
                        organism = synthetic construct
SEQUENCE: 154
EVQLLESGGG LVQPGGSLRL SCAASGFTFS DGYMEWVRQA PGKGLEWVAA SRNKANFYTT        60
EYADSVKGRF TISRDNSKNT LYLQMNSLRA EDTAVYYCAR DHYGSSYWYF DVWGQGTLVT       120
VSS                                                                    123

SEQ ID NO: 155          moltype = AA  length = 123
FEATURE                 Location/Qualifiers
source                  1..123
                        mol_type = protein
                        organism = synthetic construct
SEQUENCE: 155
EVQLLESGGG LVQPGGSLRL SCAASGFSFS DFYMEWVRQA PGKGLEWVAA SRNKWNDYTT        60
EYADSVKGRF TISRDNSKNT LYLQMNSLRA EDTAVYYCAR DYYGSSYWYF DVWGQGTLVT       120
VSS                                                                    123

SEQ ID NO: 156          moltype = AA  length = 123
FEATURE                 Location/Qualifiers
source                  1..123
                        mol_type = protein
                        organism = synthetic construct
SEQUENCE: 156
EVQLLESGGG LVQPGGSLRL SCAASGFTES DFYMEWVRQA PGKGLEWVAA SRNKYNDYTT        60
EYADSVKGRF TISRDNSKNT LYLQMNSLRA EDTAVYYCAR DYYGSSYWYF DVWGQGTLVT       120
VSS                                                                    123

SEQ ID NO: 157          moltype = AA  length = 123
FEATURE                 Location/Qualifiers
source                  1..123
                        mol_type = protein
                        organism = synthetic construct
SEQUENCE: 157
EVQLLESGGG LVQPGGSLRL SCAASGFTFD DFYMEWVRQA PGKGLEWVAA SRNEANDYTT        60
EYADSVKGRF TISRDNSKNT LYLQMNSLRA EDTAVYYCAR DYYGSSYWYF DVWGQGTLVT       120
VSS                                                                    123

SEQ ID NO: 158          moltype = AA  length = 123
FEATURE                 Location/Qualifiers
source                  1..123
                        mol_type = protein
                        organism = synthetic construct
SEQUENCE: 158
EVQLLESGGG LVQPGGSLRL SCAASGFTFS DFYMEWVRQA PGKGLEWVAA SRNKWNDYTT        60
EYADSVKGRF TISRDNSKNT LYLQMNSLRA EDTAVYYCAR DYYGSSYWYF DVWGQGTLVT       120
VSS                                                                    123

SEQ ID NO: 159          moltype = AA  length = 123
FEATURE                 Location/Qualifiers
source                  1..123
                        mol_type = protein
                        organism = synthetic construct
SEQUENCE: 159
EVQLLESGGG LVQPGGSLRL SCAASGFTFS DFYIEWVRQA PGKGLEWVAA SRNKANDYTT        60
EYADSVKGRF TISRDNSKNT LYLQMNSLRA EDTAVYYCAR DYYGSSYWYF DVWGQGTLVT       120
VSS                                                                    123

SEQ ID NO: 160          moltype = AA  length = 123
FEATURE                 Location/Qualifiers
source                  1..123
                        mol_type = protein
                        organism = synthetic construct
SEQUENCE: 160
EVQLLESGGG LVQPGGSLRL SCAASGFTQS DFYMEWVRQA PGKGLEWVAA SRNKANDYTT        60
EYADSVKGRF TISRDNSKNT LYLQMNSLRA EDTAVYYCAR DYYGESYWYF DVWGQGTLVT       120
VSS                                                                    123

SEQ ID NO: 161          moltype = AA  length = 123
FEATURE                 Location/Qualifiers
source                  1..123
                        mol_type = protein
                        organism = synthetic construct
SEQUENCE: 161
EVQLLESGGG LVQPGGSLRL SCAASGPTFS DFYMEWVRQA PGKGLEWVAA SRNKANGYTT        60
EYADSVKGRF TISRDNSKNT LYLQMNSLRA EDTAVYYCAR DYYGSSYWYF DVWGQGTLVT       120
VSS                                                                    123

SEQ ID NO: 162          moltype = AA  length = 123
```

```
FEATURE               Location/Qualifiers
source                1..123
                      mol_type = protein
                      organism = synthetic construct
SEQUENCE: 162
EVQLLESGGG LVQPGGSLRL SCAASGFTDS DFYMEWVRQA PGKGLEWVAA SRNKANGYTT    60
EYADSVKGRF TISRDNSKNT LYLQMNSLRA EDTAVYYCAR DYYGSSYWYF DVWGQGTLVT   120
VSS                                                                 123

SEQ ID NO: 163        moltype = AA  length = 123
FEATURE               Location/Qualifiers
source                1..123
                      mol_type = protein
                      organism = synthetic construct
SEQUENCE: 163
EVQLLESGGG LVQPGGSLRL SCAASGDTFS DFYMEWVRQA PGKGLEWVAA SRWKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 164        moltype = AA  length = 123
FEATURE               Location/Qualifiers
source                1..123
                      mol_type = protein
                      organism = synthetic construct
SEQUENCE: 164
EVQLLESGGG LVQPGGSLRL SCAASGFTFS SYYMEWVRQA PGKGLEWVAA SRNKANDYTT    60
EYADSVKGRF TISRDNSKNT LYLQMNSLRA EDTAVYYCAR DYYLSSYWYF DVWGQGTLVT   120
VSS                                                                 123

SEQ ID NO: 165        moltype = AA  length = 123
FEATURE               Location/Qualifiers
source                1..123
                      mol_type = protein
                      organism = synthetic construct
SEQUENCE: 165
EVQLLESGGG LVQPGGSLRL SCAASGFTFS DGYMEWVRQA PGKGLEWVAA IRNKANDYTT    60
EYADSVKGRF TISRDNSKNT LYLQMNSLRA EDTAVYYCAR DYYGSHYWYF DVWGQGTLVT   120
VSS                                                                 123

SEQ ID NO: 166        moltype = AA  length = 123
FEATURE               Location/Qualifiers
source                1..123
                      mol_type = protein
                      organism = synthetic construct
SEQUENCE: 166
EVQLLESGGG LVQPGGSLRL SCAASGFTFS DYYMEWVRQA PGKGLEWVAA SRNKGNDYTT    60
AYADSVKGRF TISRDNSKNT LYLQMNSLRA EDTAVYYCAR DYYGSSYWYF DVWGQGTLVT   120
VSS                                                                 123

SEQ ID NO: 167        moltype = AA  length = 123
FEATURE               Location/Qualifiers
source                1..123
                      mol_type = protein
                      organism = synthetic construct
SEQUENCE: 167
EVQLLESGGG LVQPGGSLRL SCAASGFTFS DYYMEWVRQA PGKGLEWVAA SRNVANDYTT    60
EYADSVKGRF TISRDNSKNT LYLQMNSLRA EDTAVYYCAR DYYGSSYWYF DVWGQGTLVT   120
VSS                                                                 123

SEQ ID NO: 168        moltype = AA  length = 123
FEATURE               Location/Qualifiers
source                1..123
                      mol_type = protein
                      organism = synthetic construct
SEQUENCE: 168
EVQLLESGGG LVQPGGSLRL SCAASGFTGS DFYMEWVRQA PGKGLEWVAA SRWKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 169        moltype = AA  length = 123
FEATURE               Location/Qualifiers
source                1..123
                      mol_type = protein
                      organism = synthetic construct
SEQUENCE: 169
EVQLLESGGG LVQPGGSLRL SCAASGFTFS DQYMEWVRQA PGKGLEWVAA SRNKANDWTT    60
EYADSVKGRF TISRDNSKNT LYLQMNSLRA EDTAVYYCAR DYYGSSYWYF DVWGQGTLVT   120
VSS                                                                 123
```

```
SEQ ID NO: 170          moltype = AA  length = 123
FEATURE                 Location/Qualifiers
source                  1..123
                        mol_type = protein
                        organism = synthetic construct
SEQUENCE: 170
EVQLLESGGG LVQPGGSLRL SCAASGNTFS DFYMEWVRQA PGKGLEWVAA SRNKANYYTT    60
EYADSVKGRF TISRDNSKNT LYLQMNSLRA EDTAVYYCAR DYYGSSYWYF DVWGQGTLVT   120
VSS                                                                123

SEQ ID NO: 171          moltype = AA  length = 123
FEATURE                 Location/Qualifiers
source                  1..123
                        mol_type = protein
                        organism = synthetic construct
SEQUENCE: 171
EVQLLESGGG LVQPGGSLRL SCAASGFTGS DFYMEWVRQA PGKGLEWVAA SRNKANDYTT    60
EYADSVKGRF TISRDNSKNT LYLQMNSLRA EDTAVYYCAR DYYGSPYWYF DVWGQGTLVT   120
VSS                                                                123

SEQ ID NO: 172          moltype = AA  length = 123
FEATURE                 Location/Qualifiers
source                  1..123
                        mol_type = protein
                        organism = synthetic construct
SEQUENCE: 172
EVQLLESGGG LVQPGGSLRL SCAASGFTSS DFYLEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                123

SEQ ID NO: 173          moltype = AA  length = 123
FEATURE                 Location/Qualifiers
source                  1..123
                        mol_type = protein
                        organism = synthetic construct
SEQUENCE: 173
EVQLLESGGG LVQPGGSLRL SCAASGFTFS PFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 174          moltype = AA  length = 123
FEATURE                 Location/Qualifiers
source                  1..123
                        mol_type = protein
                        organism = synthetic construct
SEQUENCE: 174
EVQLLESGGG LVQPGGSLRL SCAASGFTAS DFYMEWVRQA PGKGLEWVAA SRWKANDYTT    60
EYADSVKGRF TISRDNSKNT LYLQMNSLRA EDTAVYYCAR DIYGSSYWYF DVWGQGTLVT   120
VSS                                                                123

SEQ ID NO: 175          moltype = AA  length = 123
FEATURE                 Location/Qualifiers
source                  1..123
                        mol_type = protein
                        organism = synthetic construct
SEQUENCE: 175
EVQLLESGGG LVQPGGSLRL SCAASGFTFS DYYMEWVRQA PGKGLEWVAA SRNKWNDYTT    60
EYADSVKGRF TISRDNSKNT LYLQMNSLRA EDTAVYYCAR DYYLSSYWYF DVWGQGTLVT   120
VSS                                                                123

SEQ ID NO: 176          moltype = AA  length = 123
FEATURE                 Location/Qualifiers
source                  1..123
                        mol_type = protein
                        organism = synthetic construct
SEQUENCE: 176
EVQLLESGGG LVQPGGSLRL SCAASGFTTS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                123

SEQ ID NO: 177          moltype = AA  length = 123
FEATURE                 Location/Qualifiers
source                  1..123
                        mol_type = protein
                        organism = synthetic construct
SEQUENCE: 177
EVQLLESGGG LVQPGGSLRL SCAASGFTFS DFYMEWVRQA PGKGLEWVAA SRNKANDYTT    60
EYADSVKGRF TISRDNSKNT LYLQMNSLRA EDTAVYYCAR DFYGSSYWYF DVWGQGTLVT   120
VSS                                                                123
```

```
SEQ ID NO: 178           moltype = AA   length = 123
FEATURE                  Location/Qualifiers
source                   1..123
                         mol_type = protein
                         organism = synthetic construct
SEQUENCE: 178
EVQLLESGGG LVQPGGSLRL SCAASGFTGS DFYMEWVRQA PGKGLEWVAA SRNKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 179           moltype = AA   length = 123
FEATURE                  Location/Qualifiers
source                   1..123
                         mol_type = protein
                         organism = synthetic construct
SEQUENCE: 179
EVQLLESGGG LVQPGGSLRL SCAASGNTFS DFYMEWVRQA PGKGLEWVAA SRNKWNDYTT    60
EYADSVKGRF TISRDNSKNT LYLQMNSLRA EDTAVYYCAR DYYGSSYWYF DVWGQGTLVT   120
VSS                                                                 123

SEQ ID NO: 180           moltype = AA   length = 123
FEATURE                  Location/Qualifiers
source                   1..123
                         mol_type = protein
                         organism = synthetic construct
SEQUENCE: 180
EVQLLESGGG LVQPGGSLRL SCAASGFTFS DHYMEWVRQA PGKGLEWVAA SRWKANDYTT    60
EYADSVKGRF TISRDNSKNT LYLQMNSLRA EDTAVYYCAR DYYGSSYWYF DVWGQGTLVT   120
VSS                                                                 123

SEQ ID NO: 181           moltype = AA   length = 113
FEATURE                  Location/Qualifiers
source                   1..113
                         mol_type = protein
                         organism = synthetic construct
SEQUENCE: 181
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAEFYSY PLTFGGGTKV EIK          113

SEQ ID NO: 182           moltype = AA   length = 113
FEATURE                  Location/Qualifiers
source                   1..113
                         mol_type = protein
                         organism = synthetic construct
SEQUENCE: 182
DIQMTQSPSS LSASVGDRVT ITCTASESLY SSKHKVHYLA WYQQKPGKAP KLLIYGASNR    60
EIGVPSRFSG SGSGTDFTLT ISSLQPEDFA TYYCQQFYSY PLTFGGGTKV EIK          113

SEQ ID NO: 183           moltype = AA   length = 113
FEATURE                  Location/Qualifiers
source                   1..113
                         mol_type = protein
                         organism = synthetic construct
SEQUENCE: 183
DIQMTQSPSS LSASVGDRVT ITCTASESLY SSKHKVHYLA WYQQKPGKAP KLLIYGASHR    60
YIGVPSRFSG SGSGTDFTLT ISSLQPEDFA TYYCAQFYAY PLTFGGGTKV EIK          113

SEQ ID NO: 184           moltype = AA   length = 113
FEATURE                  Location/Qualifiers
source                   1..113
                         mol_type = protein
                         organism = synthetic construct
SEQUENCE: 184
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYSY PLTFGGGTKV EIK          113

SEQ ID NO: 185           moltype = AA   length = 113
FEATURE                  Location/Qualifiers
source                   1..113
                         mol_type = protein
                         organism = synthetic construct
SEQUENCE: 185
DIQMTQSPSS LSASVGDRVT ITCTASESLY SSKHKVHYLA WYQQKPGKAP KLLIYGASSL    60
QIGVPSRFSG SGSGTDFTLT ISSLQPEDFA TYYCAQFYSY PLTFGGGTKV EIK          113

SEQ ID NO: 186           moltype = AA   length = 113
FEATURE                  Location/Qualifiers
source                   1..113
```

```
                         mol_type = protein
                         organism = synthetic construct
SEQUENCE: 186
DIQMTQSPSS LSASVGDRVT ITCTASESLY SSKHKVHYLA WYQQKPGKAP KLLIYGASNR    60
YTGVPSRFSG SGSGTDFTLT ISSLQPEDFA TYYCAQFYHY PLTFGGGTKV EIK          113

SEQ ID NO: 187           moltype = AA   length = 113
FEATURE                  Location/Qualifiers
source                   1..113
                         mol_type = protein
                         organism = synthetic construct
SEQUENCE: 187
DIQMTQSPSS LSASVGDRVT ITCTASESLY SSKHKVHYLA WYQQKPGKAP KLLIYGASNR    60
YHGVPSRFSG SGSGTDFTLT ISSLQPEDFA TYYCAQFYSY PLTFGGGTKV EIK          113

SEQ ID NO: 188           moltype = AA   length = 113
FEATURE                  Location/Qualifiers
source                   1..113
                         mol_type = protein
                         organism = synthetic construct
SEQUENCE: 188
DIQMTQSPSS LSASVGDRVT ITCVASESLY SSKHKVHYLA WYQQKPGKAP KLLIYGASNR    60
YIGVPSRFSG SGSGTDFTLT ISSLQPEDFA TYYCAQFYSY PLTFGGGTKV EIK          113

SEQ ID NO: 189           moltype = AA   length = 113
FEATURE                  Location/Qualifiers
source                   1..113
                         mol_type = protein
                         organism = synthetic construct
SEQUENCE: 189
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYQY PLTFGGGTKV EIK          113

SEQ ID NO: 190           moltype = AA   length = 113
FEATURE                  Location/Qualifiers
source                   1..113
                         mol_type = protein
                         organism = synthetic construct
SEQUENCE: 190
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYYY PLTFGGGTKV EIK          113

SEQ ID NO: 191           moltype = AA   length = 113
FEATURE                  Location/Qualifiers
source                   1..113
                         mol_type = protein
                         organism = synthetic construct
SEQUENCE: 191
DIQMTQSPSS LSASVGDRVT ITCTASESLY SSKHKVHYLA WYQQKPGKAP KLLIYGSSNR    60
YIGVPSRFSG SGSGTDFTLT ISSLQPEDFA TYYCAQFYAY PLTFGGGTKV EIK          113

SEQ ID NO: 192           moltype = AA   length = 113
FEATURE                  Location/Qualifiers
source                   1..113
                         mol_type = protein
                         organism = synthetic construct
SEQUENCE: 192
DIQMTQSPSS LSASVGDRVT ITCTASESLY SSKHKVHYLA WYQQKPGKAP KLLIYGASNR    60
FIGVPSRFSG SGSGTDFTLT ISSLQPEDFA TYYCAQFYYY PLTFGGGTKV EIK          113

SEQ ID NO: 193           moltype = AA   length = 113
FEATURE                  Location/Qualifiers
source                   1..113
                         mol_type = protein
                         organism = synthetic construct
SEQUENCE: 193
DIQMTQSPSS LSASVGDRVT ITCRASESIS SSKNKVHYLA WYQQKPGKAP KLLIYGASNR    60
YYGVPSRFSG SGSGTDFTLT ISSLQPEDFA TYYCAQFYSY PLTFGGGTKV EIK          113

SEQ ID NO: 194           moltype = AA   length = 113
FEATURE                  Location/Qualifiers
source                   1..113
                         mol_type = protein
                         organism = synthetic construct
SEQUENCE: 194
DIQMTQSPSS LSASVGDRVT ITCTASESLY SSKHKVHYLA WYQQKPGKAP KLLIYGAANR    60
YIGVPSRFSG SGSGTDFTLT ISSLQPEDFA TYYCAQFYVY PLTFGGGTKV EIK          113

SEQ ID NO: 195           moltype = AA   length = 113
```

```
FEATURE                 Location/Qualifiers
source                  1..113
                        mol_type = protein
                        organism = synthetic construct
SEQUENCE: 195
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCGQFYSY PLTFGGGTKV EIK          113

SEQ ID NO: 196          moltype = AA  length = 113
FEATURE                 Location/Qualifiers
source                  1..113
                        mol_type = protein
                        organism = synthetic construct
SEQUENCE: 196
DIQMTQSPSS LSASVGDRVT ITCTASESLY SSKHKVHYLA WYQQKPGKAP KLLIYGASNR    60
YVGVPSRFSG SGSGTDFTLT ISSLQPEDFA TYYCAQFYSY PLTFGGGTKV EIK          113

SEQ ID NO: 197          moltype = AA  length = 113
FEATURE                 Location/Qualifiers
source                  1..113
                        mol_type = protein
                        organism = synthetic construct
SEQUENCE: 197
DIQMTQSPSS LSASVGDRVT ITCTASESLY SAKHKVHYLA WYQQKPGKAP KLLIYGSSNR    60
YIGVPSRFSG SGSGTDFTLT ISSLQPEDFA TYYCAQFYDY PLTFGGGTKV EIK          113

SEQ ID NO: 198          moltype = AA  length = 113
FEATURE                 Location/Qualifiers
source                  1..113
                        mol_type = protein
                        organism = synthetic construct
SEQUENCE: 198
DIQMTQSPSS LSASVGDRVT ITCTASESLY SSKHKVHYLA WYQQKPGKAP KLLIYGASNR    60
YDGVPSRFSG SGSGTDFTLT ISSLQPEDFA TYYCAQFYSY PLTFGGGTKV EIK          113

SEQ ID NO: 199          moltype = AA  length = 113
FEATURE                 Location/Qualifiers
source                  1..113
                        mol_type = protein
                        organism = synthetic construct
SEQUENCE: 199
DIQMTQSPSS LSASVGDRVT ITCTASESLY SSKHKVNYLA WYQQKPGKAP KLLIYGASNR    60
YIGVPSRFSG SGSGTDFTLT ISSLQPEDFA TYYCAQFYQY PLTFGGGTKV EIK          113

SEQ ID NO: 200          moltype = AA  length = 113
FEATURE                 Location/Qualifiers
source                  1..113
                        mol_type = protein
                        organism = synthetic construct
SEQUENCE: 200
DIQMTQSPSS LSASVGDRVT ITCTASESLY SSKHKVHYVA WYQQKPGKAP KLLIYGASNR    60
YIGVPSRFSG SGSGTDFTLT ISSLQPEDFA TYYCAQFYYY PLTFGGGTKV EIK          113

SEQ ID NO: 201          moltype = AA  length = 113
FEATURE                 Location/Qualifiers
source                  1..113
                        mol_type = protein
                        organism = synthetic construct
SEQUENCE: 201
DIQMTQSPSS LSASVGDRVT ITCTASFSLY SSKHKVHYLA WYQQKPGKAP KLLIYGASNR    60
YPGVPSRFSG SGSGTDFTLT ISSLQPEDFA TYYCAQFYYY PLTFGGGTKV EIK          113

SEQ ID NO: 202          moltype = AA  length = 113
FEATURE                 Location/Qualifiers
source                  1..113
                        mol_type = protein
                        organism = synthetic construct
SEQUENCE: 202
DIQMTQSPSS LSASVGDRVT ITCTASESLY SSKHKVHYLA WYQQKPGKAP KLLIYGAVNR    60
YIGVPSRFSG SGSGTDFTLT ISSLQPEDFA TYYCAQFYRY PLTFGGGTKV EIK          113

SEQ ID NO: 203          moltype = AA  length = 113
FEATURE                 Location/Qualifiers
source                  1..113
                        mol_type = protein
                        organism = synthetic construct
SEQUENCE: 203
DIQMTQSPSS LSASVGDRVT ITCTASESLY SSKHKVHYLA WYQQKPGKAP KLLIYGASNG    60
YIGVPSRFSG SGSGTDFTLT ISSLQPEDFA TYYCAQFYTY PLTFGGGTKV EIK          113
```

```
SEQ ID NO: 204          moltype = AA  length = 113
FEATURE                 Location/Qualifiers
source                  1..113
                        mol_type = protein
                        organism = synthetic construct
SEQUENCE: 204
DIQMTQSPSS LSASVGDRVT ITCTASESLY GSKHKVHYLA WYQQKPGKAP KLLIYGASNR   60
YSGVPSRFSG SGSGTDFTLT ISSLQPEDFA TYYCAQFYSY PLTFGGGTKV EIK         113

SEQ ID NO: 205          moltype = AA  length = 113
FEATURE                 Location/Qualifiers
source                  1..113
                        mol_type = protein
                        organism = synthetic construct
SEQUENCE: 205
DIQMTQSPSS LSASVGDRVT ITCTASESLY SSKHKVHYLA WYQQKPGKAP KLLIYGASNL   60
YSGVPSRFSG SGSGTDFTLT ISSLQPEDFA TYYCAQFYSY PLTFGGGTKV EIK         113

SEQ ID NO: 206          moltype = AA  length = 113
FEATURE                 Location/Qualifiers
source                  1..113
                        mol_type = protein
                        organism = synthetic construct
SEQUENCE: 206
DIQMTQSPSS LSASVGDRVT ITCTASESLY SSKHKVHYLA WYQQKPGKAP KLLIYGASNR   60
YFGVPSRFSG SGSGTDFTLT ISSLQPEDFA TYYCAQFYSY PLTFGGGTKV EIK         113

SEQ ID NO: 207          moltype = AA  length = 113
FEATURE                 Location/Qualifiers
source                  1..113
                        mol_type = protein
                        organism = synthetic construct
SEQUENCE: 207
DIQMTQSPSS LSASVGDRVT ITCTASESLY SSKHKVHYLA WYQQKPGKAP KLLIYGASNL   60
QSGVPSRFSG SGSGTDFTLT ISSLQPEDFA TYYCAQFYYY PLTFGGGTKV EIK         113

SEQ ID NO: 208          moltype = AA  length = 112
FEATURE                 Location/Qualifiers
source                  1..112
                        mol_type = protein
                        organism = synthetic construct
SEQUENCE: 208
DIQMTQSPSS LSASVGDRVT ITCRASESIS SSKHKHYLAW YQQKPGKAPK LLIYGASNRY   60
IGVPSRFSGS GSGTDFTLTI SSLQPEDFAT YYCAQFYVYP LTFGGGTKVE IK          112

SEQ ID NO: 209          moltype = AA  length = 113
FEATURE                 Location/Qualifiers
source                  1..113
                        mol_type = protein
                        organism = synthetic construct
SEQUENCE: 209
DIQMTQSPSS LSASVGDRVT ITCTASESLY SSKHKVHYLA WYQQKPGKAP KLLIYGASNR   60
YFGVPSRFSG SGSGTDFTLT ISSLQPEDFA TYYCAQFYQY PLTFGGGTKV EIK         113

SEQ ID NO: 210          moltype = AA  length = 113
FEATURE                 Location/Qualifiers
source                  1..113
                        mol_type = protein
                        organism = synthetic construct
SEQUENCE: 210
DIQMTQSPSS LSASVGDRVT ITCTASESLY SSKHKVHYLA WYQQKPGKAP KLLIYGLSNR   60
YIGVPSRFSG SGSGTDFTLT ISSLQPEDFA TYYCAQFYSY PLTFGGGTKV EIK         113

SEQ ID NO: 211          moltype = AA  length = 113
FEATURE                 Location/Qualifiers
source                  1..113
                        mol_type = protein
                        organism = synthetic construct
SEQUENCE: 211
DIQMTQSPSS LSASVGDRVT ITCTASESLY SSKHKVHYLA WYQQKPGKAP KLLIYGASNR   60
QSGVPSRFSG SGSGTDFTLT ISSLQPEDFA TYYCAQFYWY PLTFGGGTKV EIK         113

SEQ ID NO: 212          moltype = AA  length = 113
FEATURE                 Location/Qualifiers
source                  1..113
                        mol_type = protein
                        organism = synthetic construct
SEQUENCE: 212
```

```
DIQMTQSPSS LSASVGDRVT ITCTASESLY SSKHKVHYLA WYQQKPGKAP KLLIYGASNR    60
QSGVPSRFSG SGSGTDFTLT ISSLQPEDFA TYYCAQFYAY PLTFGGGTKV EIK          113

SEQ ID NO: 213            moltype = AA  length = 113
FEATURE                   Location/Qualifiers
source                    1..113
                          mol_type = protein
                          organism = synthetic construct
SEQUENCE: 213
DIQMTQSPSS LSASVGDRVT ITCTASESLY SSKHKVHYLA WYQQKPGKAP KLLIYGASNR    60
YHGVPSRFSG SGSGTDFTLT ISSLQPEDFA TYYCAQFYYY PLTFGGGTKV EIK          113

SEQ ID NO: 214            moltype = AA  length = 113
FEATURE                   Location/Qualifiers
source                    1..113
                          mol_type = protein
                          organism = synthetic construct
SEQUENCE: 214
DIQMTQSPSS LSASVGDRVT ITCTASESLY SSKHKVHYLA WYQQKPGKAP KLLIYGAFNR    60
YTGVPSRFSG SGSGTDFTLT ISSLQPEDFA TYYCAQFYTY PLTFGGGTKV EIK          113

SEQ ID NO: 215            moltype = AA  length = 113
FEATURE                   Location/Qualifiers
source                    1..113
                          mol_type = protein
                          organism = synthetic construct
SEQUENCE: 215
DIQMTQSPSS LSASVGDRVT ITCTASESLY SSKHKVHYLA WYQQKPGKAP KLLIYGASNR    60
LIGVPSRFSG SGSGTDFTLT ISSLQPEDFA TYYCAQFYWY PLTFGGGTKV EIK          113

SEQ ID NO: 216            moltype = AA  length = 113
FEATURE                   Location/Qualifiers
source                    1..113
                          mol_type = protein
                          organism = synthetic construct
SEQUENCE: 216
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCTQFYSY PLTFGGGTKV EIK          113

SEQ ID NO: 217            moltype = AA  length = 113
FEATURE                   Location/Qualifiers
source                    1..113
                          mol_type = protein
                          organism = synthetic construct
SEQUENCE: 217
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYVY PLTFGGGTKV EIK          113

SEQ ID NO: 218            moltype = AA  length = 113
FEATURE                   Location/Qualifiers
source                    1..113
                          mol_type = protein
                          organism = synthetic construct
SEQUENCE: 218
DIQMTQSPSS LSASVGDRVT ITCTASESLY SSKHKVHYLA WYQQKPGKAP KLLIYGQSNR    60
YIGVPSRFSG SGSGTDFTLT ISSLQPEDFA TYYCAQFYSY PLTFGGGTKV EIK          113

SEQ ID NO: 219            moltype = AA  length = 113
FEATURE                   Location/Qualifiers
source                    1..113
                          mol_type = protein
                          organism = synthetic construct
SEQUENCE: 219
DIQMTQSPSS LSASVGDRVT ITCTASEWLY SSKHKVHYLA WYQQKPGKAP KLLIYGASNR    60
NIGVPSRFSG SGSGTDFTLT ISSLQPEDFA TYYCAQFYYY PLTFGGGTKV EIK          113

SEQ ID NO: 220            moltype = AA  length = 113
FEATURE                   Location/Qualifiers
source                    1..113
                          mol_type = protein
                          organism = synthetic construct
SEQUENCE: 220
DIQMTQSPSS LSASVGDRVT ITCTASESLY SSKHKVHYLA WYQQKPGKAP KLLIYGAGNR    60
YIGVPSRFSG SGSGTDFTLT ISSLQPEDFA TYYCAQFYFY PLTFGGGTKV EIK          113

SEQ ID NO: 221            moltype = AA  length = 113
FEATURE                   Location/Qualifiers
source                    1..113
                          mol_type = protein
```

```
                        organism = synthetic construct
SEQUENCE: 221
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYWY PLTFGGGTKV EIK          113

SEQ ID NO: 222          moltype = AA  length = 113
FEATURE                 Location/Qualifiers
source                  1..113
                        mol_type = protein
                        organism = synthetic construct
SEQUENCE: 222
DIQMTQSPSS LSASVGDRVT ITCTASESLY SSKHKVHYLA WYQQKPGKAP KLLIYGASNR    60
YGGVPSRFSG SGSGTDFTLT ISSLQPEDFA TYYCAQFYEY PLTFGGGTKV EIK          113

SEQ ID NO: 223          moltype = AA  length = 113
FEATURE                 Location/Qualifiers
source                  1..113
                        mol_type = protein
                        organism = synthetic construct
SEQUENCE: 223
DIQMTQSPSS LSASVGDRVT ITCTATESLY SSKHKVHYLA WYQQKPGKAP KLLIYGASNR    60
YTGVPSRFSG SGSGTDFTLT ISSLQPEDFA TYYCAQFYSY PLTFGGGTKV EIK          113

SEQ ID NO: 224          moltype = AA  length = 113
FEATURE                 Location/Qualifiers
source                  1..113
                        mol_type = protein
                        organism = synthetic construct
SEQUENCE: 224
DIQMTQSPSS LSASVGDRVT ITCTASESLY SSKHKVHYLA WYQQKPGKAP KLLIYGASGR    60
YIGVPSRFSG SGSGTDFTLT ISSLQPEDFA TYYCAQFYSY PLTFGGGTKV EIK          113

SEQ ID NO: 225          moltype = AA  length = 113
FEATURE                 Location/Qualifiers
source                  1..113
                        mol_type = protein
                        organism = synthetic construct
SEQUENCE: 225
DIQMTQSPSS LSASVGDRVT ITCTASESLY SGKHKVHYLA WYQQKPGKAP KLLIYGASNL    60
QIGVPSRFSG SGSGTDFTLT ISSLQPEDFA TYYCAQFYYY PLTFGGGTKV EIK          113

SEQ ID NO: 226          moltype = AA  length = 113
FEATURE                 Location/Qualifiers
source                  1..113
                        mol_type = protein
                        organism = synthetic construct
SEQUENCE: 226
DIQMTQSPSS LSASVGDRVT ITCFASESLY SSKHKVHYLA WYQQKPGKAP KLLIYGASNR    60
GIGVPSRFSG SGSGTDFTLT ISSLQPEDFA TYYCAQFYSY PLTFGGGTKV EIK          113

SEQ ID NO: 227          moltype = AA  length = 113
FEATURE                 Location/Qualifiers
source                  1..113
                        mol_type = protein
                        organism = synthetic construct
SEQUENCE: 227
DIQMTQSPSS LSASVGDRVT ITCTASQSLY SSKNKVHYLA WYQQKPGKAP KLLIYGESNR    60
YIGVPSRFSG SGSGTDFTLT ISSLQPEDFA TYYCAQFYSY PLTFGGGTKV EIK          113

SEQ ID NO: 228          moltype = AA  length = 113
FEATURE                 Location/Qualifiers
source                  1..113
                        mol_type = protein
                        organism = synthetic construct
SEQUENCE: 228
DIQMTQSPSS LSASVGDRVT ITCEASESLY SSKHKVHYLA WYQQKPGKAP KLLIYGASNR    60
YPGVPSRFSG SGSGTDFTLT ISSLQPEDFA TYYCAQFYEY PLTFGGGTKV EIK          113

SEQ ID NO: 229          moltype = AA  length = 113
FEATURE                 Location/Qualifiers
source                  1..113
                        mol_type = protein
                        organism = synthetic construct
SEQUENCE: 229
DIQMTQSPSS LSASVGDRVT ITCTASESLY SSKHKVHYLA WYQQKPGKAP KLLIYGVSNR    60
YIGVPSRFSG SGSGTDFTLT ISSLQPEDFA TYYCAQFYSY PLTFGGGTKV EIK          113

SEQ ID NO: 230          moltype = AA  length = 113
FEATURE                 Location/Qualifiers
```

| source | 1..113 |
| | mol_type = protein |
| | organism = synthetic construct |

SEQUENCE: 230
DIQMTQSPSS LSASVGDRVT ITCTASESLY SSKHKVHYLA WYQQKPGKAP KLLIYGASNR  60
YGGVPSRFSG SGSGTDFTLT ISSLQPEDFA TYYCAQFYSY PLTFGGGTKV EIK         113

| SEQ ID NO: 231 | moltype = AA length = 113 |
| FEATURE | Location/Qualifiers |
| source | 1..113 |
| | mol_type = protein |
| | organism = synthetic construct |

SEQUENCE: 231
DIQMTQSPSS LSASVGDRVT ITCTASESLY SSKHKVHYLA WYQQKPGKAP KLLIYGASNR  60
PIGVPSRFSG SGSGTDFTLT ISSLQPEDFA TYYCAQFYSY PLTFGGGTKV EIK         113

| SEQ ID NO: 232 | moltype = AA length = 113 |
| FEATURE | Location/Qualifiers |
| source | 1..113 |
| | mol_type = protein |
| | organism = synthetic construct |

SEQUENCE: 232
DIQMTQSPSS LSASVGDRVT ITCTASESIS SSKHKVHYLA WYQQKPGKAP KLLIYGASNL  60
YSGVPSRFSG SGSGTDFTLT ISSLQPEDFA TYYCAHFYSY PLTFGGGTKV EIK         113

| SEQ ID NO: 233 | moltype = AA length = 113 |
| FEATURE | Location/Qualifiers |
| source | 1..113 |
| | mol_type = protein |
| | organism = synthetic construct |

SEQUENCE: 233
DIQMTQSPSS LSASVGDRVT ITCTASESLY SSKHKVHYLA WYQQKPGKAP KLLIYGAGNR  60
YIGVPSRFSG SGSGTDFTLT ISSLQPEDFA TYYCAQFYEY PLTFGGGTKV EIK         113

| SEQ ID NO: 234 | moltype = AA length = 113 |
| FEATURE | Location/Qualifiers |
| source | 1..113 |
| | mol_type = protein |
| | organism = synthetic construct |

SEQUENCE: 234
DIQMTQSPSS LSASVGDRVT ITCTASESLY SSKHKVHYLA WYQQKPGKAP KLLIYGASFR  60
YIGVPSRFSG SGSGTDFTLT ISSLQPEDFA TYYCAQFYSY PLTFGGGTKV EIK         113

| SEQ ID NO: 235 | moltype = AA length = 113 |
| FEATURE | Location/Qualifiers |
| source | 1..113 |
| | mol_type = protein |
| | organism = synthetic construct |

SEQUENCE: 235
DIQMTQSPSS LSASVGDRVT ITCTASESLY SSKHKVHYLA WYQQKPGKAP KLLIYGASNR  60
GIGVPSRFSG SGSGTDFTLT ISSLQPEDFA TYYCAQFYSY PLTFGGGTKV EIK         113

| SEQ ID NO: 236 | moltype = AA length = 113 |
| FEATURE | Location/Qualifiers |
| source | 1..113 |
| | mol_type = protein |
| | organism = synthetic construct |

SEQUENCE: 236
DIQMTQSPSS LSASVGDRVT ITCTASESLY SSKHKVHYLA WYQQKPGKAP KLLIYGADNR  60
YIGVPSRFSG SGSGTDFTLT ISSLQPEDFA TYYCAQFYHY PLTFGGGTKV EIK         113

| SEQ ID NO: 237 | moltype = AA length = 113 |
| FEATURE | Location/Qualifiers |
| source | 1..113 |
| | mol_type = protein |
| | organism = synthetic construct |

SEQUENCE: 237
DIQMTQSPSS LSASVGDRVT ITCTASESLY SSKHKVHYLA WYQQKPGKAP KLLIYGASNR  60
YDGVPSRFSG SGSGTDFTLT ISSLQPEDFA TYYCAQFYEY PLTFGGGTKV EIK         113

| SEQ ID NO: 238 | moltype = AA length = 113 |
| FEATURE | Location/Qualifiers |
| source | 1..113 |
| | mol_type = protein |
| | organism = synthetic construct |

SEQUENCE: 238
DIQMTQSPSS LSASVGDRVT ITCTASESLY SSKHKVHYLA WYQQKPGKAP KLLIYGASNR  60
QSGVPSRFSG SGSGTDFTLT ISSLQPEDFA TYYCAQFYVY PLTFGGGTKV EIK         113

```
SEQ ID NO: 239           moltype = AA  length = 113
FEATURE                  Location/Qualifiers
source                   1..113
                         mol_type = protein
                         organism = synthetic construct
SEQUENCE: 239
DIQMTQSPSS LSASVGDRVT ITCTASESLY SSKHKVHYLA WYQQKPGKAP KLLIYGASNR    60
YQGVPSRFSG SGSGTDFTLT ISSLQPEDFA TYYCAQFYFY PLTFGGGTKV EIK          113

SEQ ID NO: 240           moltype = AA  length = 113
FEATURE                  Location/Qualifiers
source                   1..113
                         mol_type = protein
                         organism = synthetic construct
SEQUENCE: 240
DIQMTQSPSS LSASVGDRVT ITCTASESLY SSKHKVHYLA WYQQKPGKAP KLLIYGASNR    60
YSGVPSRFSG SGSGTDFTLT ISSLQPEDFA TYYCAQFYKY PLTFGGGTKV EIK          113

SEQ ID NO: 241           moltype = AA  length = 113
FEATURE                  Location/Qualifiers
source                   1..113
                         mol_type = protein
                         organism = synthetic construct
SEQUENCE: 241
DIQMTQSPSS LSASVGDRVT ITCTASESLY SSKHKVHYLA WYQQKPGKAP KLLIYGASSR    60
YIGVPSRFSG SGSGTDFTLT ISSLQPEDFA TYYCAQFYEY PLTFGGGTKV EIK          113

SEQ ID NO: 242           moltype = AA  length = 113
FEATURE                  Location/Qualifiers
source                   1..113
                         mol_type = protein
                         organism = synthetic construct
SEQUENCE: 242
DIQMTQSPSS LSASVGDRVT ITCTASESLY SSKHKVHYLA WYQQKPGKAP KLLIYGTSNR    60
YIGVPSRFSG SGSGTDFTLT ISSLQPEDFA TYYCAQFYEY PLTFGGGTKV EIK          113

SEQ ID NO: 243           moltype = AA  length = 113
FEATURE                  Location/Qualifiers
source                   1..113
                         mol_type = protein
                         organism = synthetic construct
SEQUENCE: 243
DIQMTQSPSS LSASVGDRVT ITCTASESLY SQKHKVHYLA WYQQKPGKAP KLLIYGASNR    60
YIGVPSRFSG SGSGTDFTLT ISSLQPEDFA TYYCAQFYYY PLTFGGGTKV EIK          113

SEQ ID NO: 244           moltype = AA  length = 113
FEATURE                  Location/Qualifiers
source                   1..113
                         mol_type = protein
                         organism = synthetic construct
SEQUENCE: 244
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYFY PLTFGGGTKV EIK          113

SEQ ID NO: 245           moltype = AA  length = 113
FEATURE                  Location/Qualifiers
source                   1..113
                         mol_type = protein
                         organism = synthetic construct
SEQUENCE: 245
DIQMTQSPSS LSASVGDRVT ITCTASESLY SSKHKVHYLA WYQQKPGKAP KLLIYGASNR    60
QSGVPSRFSG SGSGTDFTLT ISSLQPEDFA TYYCAQFYSY PLTFGGGTKV EIK          113

SEQ ID NO: 246           moltype = AA  length = 113
FEATURE                  Location/Qualifiers
source                   1..113
                         mol_type = protein
                         organism = synthetic construct
SEQUENCE: 246
DIQMTQSPSS LSASVGDRVT ITCEASESLY SSKHKVHYLA WYQQKPGKAP KLLIYGASNR    60
LIGVPSRFSG SGSGTDFTLT ISSLQPEDFA TYYCAQFYEY PLTFGGGTKV EIK          113

SEQ ID NO: 247           moltype = AA  length = 113
FEATURE                  Location/Qualifiers
source                   1..113
                         mol_type = protein
                         organism = synthetic construct
SEQUENCE: 247
DIQMTQSPSS LSASVGDRVT ITCTASESLY SSKHSVHYLA WYQQKPGKAP KLLIYGASNR    60
```

```
FIGVPSRFSG SGSGTDFTLT ISSLQPEDFA TYYCAQFYSY PLTFGGGTKV EIK            113

SEQ ID NO: 248          moltype = AA   length = 113
FEATURE                 Location/Qualifiers
source                  1..113
                        mol_type = protein
                        organism = synthetic construct
SEQUENCE: 248
DIQMTQSPSS LSASVGDRVT ITCTASEELY SSKHKVHYLA WYQQKPGKAP KLLIYGASNR     60
YIGVPSRFSG SGSGTDFTLT ISSLQPEDFA TYYCAQFYSY PLTFGGGTKV EIK            113

SEQ ID NO: 249          moltype = AA   length = 113
FEATURE                 Location/Qualifiers
source                  1..113
                        mol_type = protein
                        organism = synthetic construct
SEQUENCE: 249
DIQMTQSPSS LSASVGDRVT ITCTASQSIS SSKHKVHYLA WYQQKPGKAP KLLIYGASNH     60
YIGVPSRFSG SGSGTDFTLT ISSLQPEDFA TYYCAQFYSY PLTFGGGTKV EIK            113

SEQ ID NO: 250          moltype = AA   length = 113
FEATURE                 Location/Qualifiers
source                  1..113
                        mol_type = protein
                        organism = synthetic construct
SEQUENCE: 250
DIQMTQSPSS LSASVGDRVT ITCTASESLY SSKHKVHYLA WYQQKPGKAP KLLIYGASNR     60
YIGVPSRFSG SGSGTDFTLT ISSLQPEDFA TYYCAQFYEY PLTFGGGTKV EIK            113

SEQ ID NO: 251          moltype = AA   length = 113
FEATURE                 Location/Qualifiers
source                  1..113
                        mol_type = protein
                        organism = synthetic construct
SEQUENCE: 251
DIQMTQSPSS LSASVGDRVT ITCTASESLY SSKHKVHYLA WYQQKPGKAP KLLIYGASNR     60
QIGVPSRFSG SGSGTDFTLT ISSLQPEDFA TYYCAQFYTY PLTFGGGTKV EIK            113

SEQ ID NO: 252          moltype = AA   length = 112
FEATURE                 Location/Qualifiers
source                  1..112
                        mol_type = protein
                        organism = synthetic construct
SEQUENCE: 252
DIQMTQSPSS LSASVGDRVT ITCTASESLS SSKHKHYLAW YQQKPGKAPK LLIYGASSRY     60
SGVPSRFSGS GSGTDFTLTI SSLQPEDFAT YYCAQFYSYP LTFGGGTKVE IK             112

SEQ ID NO: 253          moltype = AA   length = 113
FEATURE                 Location/Qualifiers
source                  1..113
                        mol_type = protein
                        organism = synthetic construct
SEQUENCE: 253
DIQMTQSPSS LSASVGDRVT ITCTASESLY SSKHKVHYLA WYQQKPGKAP KLLIYGASNR     60
DIGVPSRFSG SGSGTDFTLT ISSLQPEDFA TYYCGQFYSY PLTFGGGTKV EIK            113

SEQ ID NO: 254          moltype = AA   length = 113
FEATURE                 Location/Qualifiers
source                  1..113
                        mol_type = protein
                        organism = synthetic construct
SEQUENCE: 254
DIQMTQSPSS LSASVGDRVT ITCTASESLY SSKHKVHYLA WYQQKPGKAP KLLIYGSSNR     60
YIGVPSRFSG SGSGTDFTLT ISSLQPEDFA TYYCAQFYQY PLTFGGGTKV EIK            113

SEQ ID NO: 255          moltype = AA   length = 113
FEATURE                 Location/Qualifiers
source                  1..113
                        mol_type = protein
                        organism = synthetic construct
SEQUENCE: 255
DIQMTQSPSS LSASVGDRVT ITCTASESLY SSKHKVHYLA WYQQKPGKAP KLLIYGISNR     60
YIGVPSRFSG SGSGTDFTLT ISSLQPEDFA TYYCAQFYSY PLTFGGGTKV EIK            113

SEQ ID NO: 256          moltype = AA   length = 113
FEATURE                 Location/Qualifiers
source                  1..113
                        mol_type = protein
                        organism = synthetic construct
```

```
SEQUENCE: 256
DIQMTQSPSS LSASVGDRVT ITCTAEESLY SSKHKVHYLA WYQQKPGKAP KLLIYGASNL    60
YSGVPSRFSG SGSGTDFTLT ISSLQPEDFA TYYCAQFYSY PLTFGGGTKV EIK           113

SEQ ID NO: 257          moltype = AA   length = 113
FEATURE                 Location/Qualifiers
source                  1..113
                        mol_type = protein
                        organism = synthetic construct
SEQUENCE: 257
DIQMTQSPSS LSASVGDRVT ITCTASESLY SSKHKVHYLA WYQQKPGKAP KLLIYGASNR    60
QIGVPSRFSG SGSGTDFTLT ISSLQPEDFA TYYCAQFYSY PLTFGGGTKV EIK           113

SEQ ID NO: 258          moltype = AA   length = 113
FEATURE                 Location/Qualifiers
source                  1..113
                        mol_type = protein
                        organism = synthetic construct
SEQUENCE: 258
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYDY PLTFGGGTKV EIK           113

SEQ ID NO: 259          moltype = AA   length = 113
FEATURE                 Location/Qualifiers
source                  1..113
                        mol_type = protein
                        organism = synthetic construct
SEQUENCE: 259
DIQMTQSPSS LSASVGDRVT ITCTASESLY SSKHKVHYLA WYQQKPGKAP KLLIYGLSNR    60
YIGVPSRFSG SGSGTDFTLT ISSLQPEDFA TYYCAQFFSY PLTFGGGTKV EIK           113

SEQ ID NO: 260          moltype = AA   length = 113
FEATURE                 Location/Qualifiers
source                  1..113
                        mol_type = protein
                        organism = synthetic construct
SEQUENCE: 260
DIQMTQSPSS LSASVGDRVT ITCTASESLY SSKHKVHYLA WYQQKPGKAP KLLIYGASSL    60
YSGVPSRFSG SGSGTDFTLT ISSLQPEDFA TYYCAQFYEY PLTFGGGTKV EIK           113

SEQ ID NO: 261          moltype = AA   length = 113
FEATURE                 Location/Qualifiers
source                  1..113
                        mol_type = protein
                        organism = synthetic construct
SEQUENCE: 261
DIQMTQSPSS LSASVGDRVT ITCTASESLY SSKHGVHYLA WYQQKPGKAP KLLIYGASNR    60
YIGVPSRFSG SGSGTDFTLT ISSLQPEDFA TYYCAQFYQY PLTFGGGTKV EIK           113

SEQ ID NO: 262          moltype = AA   length = 113
FEATURE                 Location/Qualifiers
source                  1..113
                        mol_type = protein
                        organism = synthetic construct
SEQUENCE: 262
DIQMTQSPSS LSASVGDRVT ITCTASESLY SSKHKVHYLA WYQQKPGKAP KLLIYGASNR    60
AIGVPSRFSG SGSGTDFTLT ISSLQPEDFA TYYCAQFYTY PLTFGGGTKV EIK           113

SEQ ID NO: 263          moltype = AA   length = 113
FEATURE                 Location/Qualifiers
source                  1..113
                        mol_type = protein
                        organism = synthetic construct
SEQUENCE: 263
DIQMTQSPSS LSASVGDRVT ITCTASESLS SSKHKVHYLA WYQQKPGKAP KLLIYGASNR    60
YIGVPSRFSG SGSGTDFTLT ISSLQPEDFA TYYCAQFYSY PLTFGGGTKV EIK           113

SEQ ID NO: 264          moltype = AA   length = 113
FEATURE                 Location/Qualifiers
source                  1..113
                        mol_type = protein
                        organism = synthetic construct
SEQUENCE: 264
DIQMTQSPSS LSASVGDRVT ITCTASESLY SSKHKVHYLA WYQQKPGKAP KLLIYGASNR    60
YAGVPSRFSG SGSGTDFTLT ISSLQPEDFA TYYCGQFYSY PLTFGGGTKV EIK           113

SEQ ID NO: 265          moltype = AA   length = 113
FEATURE                 Location/Qualifiers
source                  1..113
```

-continued

```
                            mol_type = protein
                            organism = synthetic construct
SEQUENCE: 265
DIQMTQSPSS LSASVGDRVT ITCTASQSLY SSKHKVHYLA WYQQKPGKAP KLLIYGASNR    60
YIGVPSRFSG SGSGTDFTLT ISSLQPEDFA TYYCAQFYVY PLTFGGGTKV EIK          113

SEQ ID NO: 266              moltype = AA   length = 111
FEATURE                     Location/Qualifiers
source                      1..111
                            mol_type = protein
                            organism = synthetic construct
SEQUENCE: 266
DIQMTQSPSS LSASVGDRVT ITCRASESLY SSLHKYLAWY QQKPGKAPKL LIYGASNLQI    60
GVPSRFSGSG SGTDFTLTIS SLQPEDFATY YCAQFYSYPL TFGGGTKVEI K            111

SEQ ID NO: 267              moltype = AA   length = 113
FEATURE                     Location/Qualifiers
source                      1..113
                            mol_type = protein
                            organism = synthetic construct
SEQUENCE: 267
DIQMTQSPSS LSASVGDRVT ITCTASESLY SSKHKVHYLA WYQQKPGKAP KLLIYGASNR    60
VIGVPSRFSG SGSGTDFTLT ISSLQPEDFA TYYCAQFYSY PLTFGGGTKV EIK          113

SEQ ID NO: 268              moltype = AA   length = 113
FEATURE                     Location/Qualifiers
source                      1..113
                            mol_type = protein
                            organism = synthetic construct
SEQUENCE: 268
DIQMTQSPSS LSASVGDRVT ITCTASESLY SSKHKVHYLA WYQQKPGKAP KLLIYGPSNR    60
YIGVPSRFSG SGSGTDFTLT ISSLQPEDFA TYYCAQFYSY PLTFGGGTKV EIK          113

SEQ ID NO: 269              moltype = AA   length = 113
FEATURE                     Location/Qualifiers
source                      1..113
                            mol_type = protein
                            organism = synthetic construct
SEQUENCE: 269
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 270              moltype = AA   length = 113
FEATURE                     Location/Qualifiers
source                      1..113
                            mol_type = protein
                            organism = synthetic construct
SEQUENCE: 270
DIVMTQSPDS LAVSLGERAT INCTASESVY SSKNKKHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 271              moltype = AA   length = 113
FEATURE                     Location/Qualifiers
source                      1..113
                            mol_type = protein
                            organism = synthetic construct
SEQUENCE: 271
DIVMTQSPDS LAVSLGERAT INCTASESLY SSKGKVHYLA WYQQKPGQPP KLLIYGASNR    60
YIGVPDRFSG SGSGTDFTLT ISSLQAEDVA VYYCVQFYSY PLTFGGGTKV EIK          113

SEQ ID NO: 272              moltype = AA   length = 113
FEATURE                     Location/Qualifiers
source                      1..113
                            mol_type = protein
                            organism = synthetic construct
SEQUENCE: 272
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCGQFYSY PLTFGGGTKV EIK          113

SEQ ID NO: 273              moltype = AA   length = 113
FEATURE                     Location/Qualifiers
source                      1..113
                            mol_type = protein
                            organism = synthetic construct
SEQUENCE: 273
DIVMTQSPDS LAVSLGERAT INCTASESLY SSKHKVHYLA WYQQKPGQPP KLLIYGASNR    60
YDGVPDRFSG SGSGTDFTLT ISSLQAEDVA VYYCAQFYSY PLTFGGGTKV EIK          113

SEQ ID NO: 274              moltype = AA   length = 113
```

```
FEATURE                 Location/Qualifiers
source                  1..113
                        mol_type = protein
                        organism = synthetic construct
SEQUENCE: 274
DIVMTQSPDS LAVSLGERAT INCTASQSVY SSKNKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 275          moltype = AA  length = 113
FEATURE                 Location/Qualifiers
source                  1..113
                        mol_type = protein
                        organism = synthetic construct
SEQUENCE: 275
DIVMTQSPDS LAVSLGERAT INCTSSQSLL SSSHNKNYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 276          moltype = AA  length = 113
FEATURE                 Location/Qualifiers
source                  1..113
                        mol_type = protein
                        organism = synthetic construct
SEQUENCE: 276
DIVMTQSPDS LAVSLGERAT INCTASESLY SPKHKVHYLA WYQQKPGQPP KLLIYGASNR    60
YIGVPDRFSG SGSGTDFTLT ISSLQAEDVA VYYCAQFYIY PLTFGGGTKV EIK          113

SEQ ID NO: 277          moltype = AA  length = 113
FEATURE                 Location/Qualifiers
source                  1..113
                        mol_type = protein
                        organism = synthetic construct
SEQUENCE: 277
DIVMTQSPDS LAVSLGERAT INCTASESLW SSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 278          moltype = AA  length = 113
FEATURE                 Location/Qualifiers
source                  1..113
                        mol_type = protein
                        organism = synthetic construct
SEQUENCE: 278
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAQFYIY PLTFGGGTKV EIK          113

SEQ ID NO: 279          moltype = AA  length = 113
FEATURE                 Location/Qualifiers
source                  1..113
                        mol_type = protein
                        organism = synthetic construct
SEQUENCE: 279
DIVMTQSPDS LAVSLGERAT INCKASQSVL SSKNNVNYLA WYQQKPGQPP KLLIYGASNR    60
YSGVPDRFSG SGSGTDFTLT ISSLQAEDVA VYYCAQFYSY PLTFGGGTKV EIK          113

SEQ ID NO: 280          moltype = AA  length = 113
FEATURE                 Location/Qualifiers
source                  1..113
                        mol_type = protein
                        organism = synthetic construct
SEQUENCE: 280
DIVMTQSPDS LAVSLGERAT INCTASESLY SSKWKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 281          moltype = AA  length = 113
FEATURE                 Location/Qualifiers
source                  1..113
                        mol_type = protein
                        organism = synthetic construct
SEQUENCE: 281
DIVMTQSPDS LAVSLGERAT INCTASESLY SSKHKVHYLA WYQQKPGQPP KLLIYGASNR    60
VIGVPDRFSG SGSGTDFTLT ISSLQAEDVA VYYCANFYSY PLTFGGGTKV EIK          113

SEQ ID NO: 282          moltype = AA  length = 113
FEATURE                 Location/Qualifiers
source                  1..113
                        mol_type = protein
                        organism = synthetic construct
SEQUENCE: 282
DIVMTQSPDS LAVSLGERAT INCKSSESVY SSKHKKHYLA WYQQKPGQPP KLLIYGASNR    60
YIGVPDRFSG SGSGTDFTLT ISSLQAEDVA VYYCAQFYSY PLTFGGGTKV EIK          113
```

```
SEQ ID NO: 283          moltype = AA   length = 113
FEATURE                 Location/Qualifiers
source                  1..113
                        mol_type = protein
                        organism = synthetic construct
SEQUENCE: 283
DIVMTQSPDS LAVSLGERAT INCTASESLY SSKHKVDYLA WYQQKPGQPP KLLIYGASNR  60
YIGVPDRFSG SGSGTDFTLT ISSLQAEDVA VYYCAQFYSY PLTFGGGTKV EIK        113

SEQ ID NO: 284          moltype = AA   length = 113
FEATURE                 Location/Qualifiers
source                  1..113
                        mol_type = protein
                        organism = synthetic construct
SEQUENCE: 284
DIVMTQSPDS LAVSLGERAT INCTASESLY SSKHKVHYLA WYQQKPGQPP KLLIYGASNR  60
YIGVPDRFSG SGSGTDFTLT ISSLQAEDVA VYYCANFYSY PLTFGGGTKV EIK        113

SEQ ID NO: 285          moltype = AA   length = 113
FEATURE                 Location/Qualifiers
source                  1..113
                        mol_type = protein
                        organism = synthetic construct
SEQUENCE: 285
DIVMTQSPDS LAVSLGERAT INCTASESLY SPKHKVHYLA WYQQKPGQPP KLLIYGAFNR  60
YIGVPDRFSG SGSGTDFTLT ISSLQAEDVA VYYCAQFYSY PLTFGGGTKV EIK        113

SEQ ID NO: 286          moltype = AA   length = 113
FEATURE                 Location/Qualifiers
source                  1..113
                        mol_type = protein
                        organism = synthetic construct
SEQUENCE: 286
DIVMTQSPDS LAVSLGERAT INCTASESVY SSKNKKHYLA WYQQKPGQPP KLLIYGASNR  60
YIGVPDRFSG SGSGTDFTLT ISSLQAEDVA VYYCAQFYTY PLTFGGGTKV EIK        113

SEQ ID NO: 287          moltype = AA   length = 113
FEATURE                 Location/Qualifiers
source                  1..113
                        mol_type = protein
                        organism = synthetic construct
SEQUENCE: 287
DIVMTQSPDS LAVSLGERAT INCKSSQSLY YSSNKKNYLA WYQQKPGQPP KLLIYGASNR  60
YGGVPDRFSG SGSGTDFTLT ISSLQAEDVA VYYCAQFYRY PLTFGGGTKV EIK        113

SEQ ID NO: 288          moltype = AA   length = 113
FEATURE                 Location/Qualifiers
source                  1..113
                        mol_type = protein
                        organism = synthetic construct
SEQUENCE: 288
DIVMTQSPDS LAVSLGERAT INCTASESLY SSKHKVHYLA WYQQKPGQPP KLLIYGASNR  60
YIGVPDRFSG SGSGTDFTLT ISSLQAEDVA VYYCAHFYSY PLTFGGGTKV EIK        113

SEQ ID NO: 289          moltype = AA   length = 113
FEATURE                 Location/Qualifiers
source                  1..113
                        mol_type = protein
                        organism = synthetic construct
SEQUENCE: 289
DIVMTQSPDS LAVSLGERAT INCTASESLY SSKHKVHYLA WYQQKPGQPP KLLIYGASNR  60
YSGVPDRFSG SGSGTDFTLT ISSLQAEDVA VYYCAQFYSY PLTFGGGTKV EIK        113

SEQ ID NO: 290          moltype = AA   length = 113
FEATURE                 Location/Qualifiers
source                  1..113
                        mol_type = protein
                        organism = synthetic construct
SEQUENCE: 290
DIVMTQSPDS LAVSLGERAT INCTASESLY SSKHKVHYLA WYQQKPGQPP KLLIYGASNR  60
YVGVPDRFSG SGSGTDFTLT ISSLQAEDVA VYYCAQFYSY PLTFGGGTKV EIK        113

SEQ ID NO: 291          moltype = AA   length = 113
FEATURE                 Location/Qualifiers
source                  1..113
                        mol_type = protein
                        organism = synthetic construct
SEQUENCE: 291
```

```
DIVMTQSPDS LAVSLGERAT INCTASESLY SSKHKVHYLA WYQQKPGQPP KLLIYGASNR    60
EIGVPDRFSG SGSGTDFTLT ISSLQAEDVA VYYCAQFYFY PLTFGGGTKV EIK          113

SEQ ID NO: 292          moltype = AA  length = 113
FEATURE                 Location/Qualifiers
source                  1..113
                        mol_type = protein
                        organism = synthetic construct
SEQUENCE: 292
DIVMTQSPDS LAVSLGERAT INCTASTSLY SSKHKVHYLA WYQQKPGQPP KLLIYGASNR    60
YIGVPDRFSG SGSGTDFTLT ISSLQAEDVA VYYCAQFYTY PLTFGGGTKV EIK          113

SEQ ID NO: 293          moltype = AA  length = 113
FEATURE                 Location/Qualifiers
source                  1..113
                        mol_type = protein
                        organism = synthetic construct
SEQUENCE: 293
DIVMTQSPDS LAVSLGERAT INCTASESLY GSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 294          moltype = AA  length = 113
FEATURE                 Location/Qualifiers
source                  1..113
                        mol_type = protein
                        organism = synthetic construct
SEQUENCE: 294
DIVMTQSPDS LAVSLGERAT INCKASQSLY SSKHKKHYLA WYQQKPGQPP KLLIYGASNR    60
YPGVPDRFSG SGSGTDFTLT ISSLQAEDVA VYYCAQFYRY PLTFGGGTKV EIK          113

SEQ ID NO: 295          moltype = AA  length = 113
FEATURE                 Location/Qualifiers
source                  1..113
                        mol_type = protein
                        organism = synthetic construct
SEQUENCE: 295
DIVMTQSPDS LAVSLGERAT INCTASSSLY SSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 296          moltype = AA  length = 113
FEATURE                 Location/Qualifiers
source                  1..113
                        mol_type = protein
                        organism = synthetic construct
SEQUENCE: 296
DIVMTQSPDS LAVSLGERAT INCTASESLY SSKHKVHYLA WYQQKPGQPP KLLIYGAGNR    60
YIGVPDRFSG SGSGTDFTLT ISSLQAEDVA VYYCAQFYHY PLTFGGGTKV EIK          113

SEQ ID NO: 297          moltype = AA  length = 113
FEATURE                 Location/Qualifiers
source                  1..113
                        mol_type = protein
                        organism = synthetic construct
SEQUENCE: 297
DIVMTQSPDS LAVSLGERAT INCTASESLY SSKHKVHYLA WYQQKPGQPP KLLIYGASNR    60
YDGVPDRFSG SGSGTDFTLT ISSLQAEDVA VYYCANFYSY PLTFGGGTKV EIK          113

SEQ ID NO: 298          moltype = AA  length = 113
FEATURE                 Location/Qualifiers
source                  1..113
                        mol_type = protein
                        organism = synthetic construct
SEQUENCE: 298
DIVMTQSPDS LAVSLGERAT INCTASESLY SSKHKVHYLA WYQQKPGQPP KLLIYGAGNR    60
YIGVPDRFSG SGSGTDFTLT ISSLQAEDVA VYYCAQFYSY PLTFGGGTKV EIK          113

SEQ ID NO: 299          moltype = AA  length = 113
FEATURE                 Location/Qualifiers
source                  1..113
                        mol_type = protein
                        organism = synthetic construct
SEQUENCE: 299
DIVMTQSPDS LAVSLGERAT INCTASESLY SSKHKVHYLA WYQQKPGQPP KLLIYGASNR    60
QIGVPDRFSG SGSGTDFTLT ISSLQAEDVA VYYCAQFYHY PLTFGGGTKV EIK          113

SEQ ID NO: 300          moltype = AA  length = 113
FEATURE                 Location/Qualifiers
source                  1..113
                        mol_type = protein
```

```
                        organism = synthetic construct
SEQUENCE: 300
DIVMTQSPDS LAVSLGERAT INCTASESLY SVKHKVHYLA WYQQKPGQPP KLLIYGASNR     60
YIGVPDRFSG SGSGTDFTLT ISSLQAEDVA VYYCAQFYSY PLTFGGGTKV EIK           113

SEQ ID NO: 301          moltype = AA  length = 113
FEATURE                 Location/Qualifiers
source                  1..113
                        mol_type = protein
                        organism = synthetic construct
SEQUENCE: 301
DIVMTQSPDS LAVSLGERAT INCTASESLY SSKHKVHYLA WYQQKPGQPP KLLIYGASNR     60
YIGVPDRFSG SGSGTDFTLT ISSLQAEDVA VYYCAQFYVY PLTFGGGTKV EIK           113

SEQ ID NO: 302          moltype = AA  length = 113
FEATURE                 Location/Qualifiers
source                  1..113
                        mol_type = protein
                        organism = synthetic construct
SEQUENCE: 302
DIVMTQSPDS LAVSLGERAT INCTASESLY SSKHKVHYLA WYQQKPGQPP KLLIYGANNR     60
YIGVPDRFSG SGSGTDFTLT ISSLQAEDVA VYYCAQFYSY PLTFGGGTKV EIK           113

SEQ ID NO: 303          moltype = AA  length = 113
FEATURE                 Location/Qualifiers
source                  1..113
                        mol_type = protein
                        organism = synthetic construct
SEQUENCE: 303
DIVMTQSPDS LAVSLGERAT INCGASESLY SSKSKVHYLA WYQQKPGQPP KLLIYGASNR     60
YIGVPDRFSG SGSGTDFTLT ISSLQAEDVA VYYCAQFYSY PLTFGGGTKV EIK           113

SEQ ID NO: 304          moltype = AA  length = 113
FEATURE                 Location/Qualifiers
source                  1..113
                        mol_type = protein
                        organism = synthetic construct
SEQUENCE: 304
DIVMTQSPDS LAVSLGERAT INCTASESLY SSKHKVHYLA WYQQKPGQPP KLLIYGASNR     60
YIGVPDRFSG SGSGTDFTLT ISSLQAEDVA VYYCAQFYEY PLTFGGGTKV EIK           113

SEQ ID NO: 305          moltype = AA  length = 113
FEATURE                 Location/Qualifiers
source                  1..113
                        mol_type = protein
                        organism = synthetic construct
SEQUENCE: 305
DIVMTQSPDS LAVSLGERAT INCTASESLY SSKHKVHYLA WYQQKPGQPP KLLIYGAHNR     60
YIGVPDRFSG SGSGTDFTLT ISSLQAEDVA VYYCANFYSY PLTFGGGTKV EIK           113

SEQ ID NO: 306          moltype = AA  length = 113
FEATURE                 Location/Qualifiers
source                  1..113
                        mol_type = protein
                        organism = synthetic construct
SEQUENCE: 306
DIVMTQSPDS LAVSLGERAT INCTSSESVY SSSHKVHYLA WYQQKPGQPP KLLIYGASNR     60
YIGVPDRFSG SGSGTDFTLT ISSLQAEDVA VYYCAQFYYY PLTFGGGTKV EIK           113

SEQ ID NO: 307          moltype = AA  length = 113
FEATURE                 Location/Qualifiers
source                  1..113
                        mol_type = protein
                        organism = synthetic construct
SEQUENCE: 307
DIVMTQSPDS LAVSLGERAT INCTASESLY SSKHKVHYLA WYQQKPGQPP KLLIYGNSNR     60
YIGVPDRFSG SGSGTDFTLT ISSLQAEDVA VYYCGQFYSY PLTFGGGTKV EIK           113

SEQ ID NO: 308          moltype = AA  length = 113
FEATURE                 Location/Qualifiers
source                  1..113
                        mol_type = protein
                        organism = synthetic construct
SEQUENCE: 308
DIVMTQSPDS LAVSLGERAT INCTASESLY SSKHKKNYLA WYQQKPGQPP KLLIYGASWR     60
YIGVPDRFSG SGSGTDFTLT ISSLQAEDVA VYYCAQFYSY PLTFGGGTKV EIK           113

SEQ ID NO: 309          moltype = AA  length = 113
FEATURE                 Location/Qualifiers
```

```
source                  1..113
                        mol_type = protein
                        organism = synthetic construct
SEQUENCE: 309
DIVMTQSPDS LAVSLGERAT INCTASESLY SSKHKVHYLA WYQQKPGQPP KLLIYGASTR    60
YSGVPDRFSG SGSGTDFTLT ISSLQAEDVA VYYCAQFYTY PLTFGGGTKV EIK          113

SEQ ID NO: 310          moltype = AA   length = 113
FEATURE                 Location/Qualifiers
source                  1..113
                        mol_type = protein
                        organism = synthetic construct
SEQUENCE: 310
DIVMTQSPDS LAVSLGERAT INCKSSESLL YSKNNKNYLA WYQQKPGQPP KLLIYGASNR    60
YSGVPDRFSG SGSGTDFTLT ISSLQAEDVA VYYCAQFYSY PLTFGGGTKV EIK          113

SEQ ID NO: 311          moltype = AA   length = 113
FEATURE                 Location/Qualifiers
source                  1..113
                        mol_type = protein
                        organism = synthetic construct
SEQUENCE: 311
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAEFYSY PLTFGGGTKV EIK          113

SEQ ID NO: 312          moltype = AA   length = 113
FEATURE                 Location/Qualifiers
source                  1..113
                        mol_type = protein
                        organism = synthetic construct
SEQUENCE: 312
DIVMTQSPDS LAVSLGERAT INCTASESIY SSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 313          moltype = AA   length = 113
FEATURE                 Location/Qualifiers
source                  1..113
                        mol_type = protein
                        organism = synthetic construct
SEQUENCE: 313
DIVMTQSPDS LAVSLGERAT INCTSSQSVL SSKHNKNYLA WYQQKPGQPP KLLIYGASNR    60
YWGVPDRFSG SGSGTDFTLT ISSLQAEDVA VYYCAQFYSY PLTFGGGTKV EIK          113

SEQ ID NO: 314          moltype = AA   length = 113
FEATURE                 Location/Qualifiers
source                  1..113
                        mol_type = protein
                        organism = synthetic construct
SEQUENCE: 314
DIVMTQSPDS LAVSLGERAT INCTASESLY SSKHKVHYLA WYQQKPGQPP KLLIYGASNR    60
YPGVPDRFSG SGSGTDFTLT ISSLQAEDVA VYYCAQFYSY PLTFGGGTKV EIK          113

SEQ ID NO: 315          moltype = AA   length = 113
FEATURE                 Location/Qualifiers
source                  1..113
                        mol_type = protein
                        organism = synthetic construct
SEQUENCE: 315
DIVMTQSPDS LAVSLGERAT INCTASEDLY SSKHKVHYLA WYQQKPGQPP KLLIYGTSNR    60
YIGVPDRFSG SGSGTDFTLT ISSLQAEDVA VYYCAQYYSY PLTFGGGTKV EIK          113

SEQ ID NO: 316          moltype = AA   length = 113
FEATURE                 Location/Qualifiers
source                  1..113
                        mol_type = protein
                        organism = synthetic construct
SEQUENCE: 316
DIVMTQSPDS LAVSLGERAT INCKASQSVL YSKNKKHYLA WYQQKPGQPP KLLIYGASNR    60
QIGVPDRFSG SGSGTDFTLT ISSLQAEDVA VYYCAQFYVY PLTFGGGTKV EIK          113

SEQ ID NO: 317          moltype = AA   length = 113
FEATURE                 Location/Qualifiers
source                  1..113
                        mol_type = protein
                        organism = synthetic construct
SEQUENCE: 317
DIVMTQSPDS LAVSLGERAT INCTASESLY SSKHKLHYLA WYQQKPGQPP KLLIYGASNR    60
YIGVPDRFSG SGSGTDFTLT ISSLQAEDVA VYYCGQFYSY PLTFGGGTKV EIK          113
```

```
SEQ ID NO: 318           moltype = AA   length = 113
FEATURE                  Location/Qualifiers
source                   1..113
                         mol_type = protein
                         organism = synthetic construct
SEQUENCE: 318
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAQFYDY PLTFGGGTKV EIK          113

SEQ ID NO: 319           moltype = AA   length = 113
FEATURE                  Location/Qualifiers
source                   1..113
                         mol_type = protein
                         organism = synthetic construct
SEQUENCE: 319
DIVMTQSPDS LAVSLGERAT INCTASESLY SSKHKVVYLA WYQQKPGQPP KLLIYGASNR    60
YIGVPDRFSG SGSGTDFTLT ISSLQAEDVA VYYCAQFYFY PLTFGGGTKV EIK          113

SEQ ID NO: 320           moltype = AA   length = 113
FEATURE                  Location/Qualifiers
source                   1..113
                         mol_type = protein
                         organism = synthetic construct
SEQUENCE: 320
DIVMTQSPDS LAVSLGERAT INCTASESLY SSKHKVHYLA WYQQKPGQPP KLLIYGASNR    60
YLGVPDRFSG SGSGTDFTLT ISSLQAEDVA VYYCAQFYSY PLTFGGGTKV EIK          113

SEQ ID NO: 321           moltype = AA   length = 113
FEATURE                  Location/Qualifiers
source                   1..113
                         mol_type = protein
                         organism = synthetic construct
SEQUENCE: 321
DIVMTQSPDS LAVSLGERAT INCTSSESLY SSKNKVNYLA WYQQKPGQPP KLLIYGASNR    60
YIGVPDRFSG SGSGTDFTLT ISSLQAEDVA VYYCAQFYFY PLTFGGGTKV EIK          113

SEQ ID NO: 322           moltype = AA   length = 113
FEATURE                  Location/Qualifiers
source                   1..113
                         mol_type = protein
                         organism = synthetic construct
SEQUENCE: 322
DIVMTQSPDS LAVSLGERAT INCTASESLY SSKHKVHYLA WYQQKPGQPP KLLIYGASNR    60
YNGVPDRFSG SGSGTDFTLT ISSLQAEDVA VYYCAQFYTY PLTFGGGTKV EIK          113

SEQ ID NO: 323           moltype = AA   length = 113
FEATURE                  Location/Qualifiers
source                   1..113
                         mol_type = protein
                         organism = synthetic construct
SEQUENCE: 323
DIVMTQSPDS LAVSLGERAT INCTSSQSLY SSKHNKHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 324           moltype = AA   length = 113
FEATURE                  Location/Qualifiers
source                   1..113
                         mol_type = protein
                         organism = synthetic construct
SEQUENCE: 324
DIVMTQSPDS LAVSLGERAT INCEASESLY SSKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 325           moltype = AA   length = 113
FEATURE                  Location/Qualifiers
source                   1..113
                         mol_type = protein
                         organism = synthetic construct
SEQUENCE: 325
DIVMTQSPDS LAVSLGERAT INCTASESLY SSKHKVHYLA WYQQKPGQPP KLLIYGASNR    60
AIGVPDRFSG SGSGTDFTLT ISSLQAEDVA VYYCAQFYFY PLTFGGGTKV EIK          113

SEQ ID NO: 326           moltype = AA   length = 113
FEATURE                  Location/Qualifiers
source                   1..113
                         mol_type = protein
                         organism = synthetic construct
SEQUENCE: 326
DIVMTQSPDS LAVSLGERAT INCTASESLY SNKHKVHYLA WYQQKPGQPP KLLIYGASNR    60
```

```
YIGVPDRFSG SGSGTDFTLT ISSLQAEDVA VYYCAQFYSY PLTFGGGTKV EIK          113

SEQ ID NO: 327            moltype = AA   length = 113
FEATURE                   Location/Qualifiers
source                    1..113
                          mol_type = protein
                          organism = synthetic construct
SEQUENCE: 327
DIVMTQSPDS LAVSLGERAT INCTASENLY SSKHKVHYLA WYQQKPGQPP KLLIYGASNR    60
YSGVPDRFSG SGSGTDFTLT ISSLQAEDVA VYYCAQFYSY PLTFGGGTKV EIK          113

SEQ ID NO: 328            moltype = AA   length = 113
FEATURE                   Location/Qualifiers
source                    1..113
                          mol_type = protein
                          organism = synthetic construct
SEQUENCE: 328
DIVMTQSPDS LAVSLGERAT INCTASESLY SSKHKVHYLA WYQQKPGQPP KLLIYGASQR    60
YIGVPDRFSG SGSGTDFTLT ISSLQAEDVA VYYCAQFYLY PLTFGGGTKV EIK          113

SEQ ID NO: 329            moltype = AA   length = 113
FEATURE                   Location/Qualifiers
source                    1..113
                          mol_type = protein
                          organism = synthetic construct
SEQUENCE: 329
DIVMTQSPDS LAVSLGERAT INCTASESLY SSKHKVHYLA WYQQKPGQPP KLLIYGASNR    60
EIGVPDRFSG SGSGTDFTLT ISSLQAEDVA VYYCAQFYSY PLTFGGGTKV EIK          113

SEQ ID NO: 330            moltype = AA   length = 113
FEATURE                   Location/Qualifiers
source                    1..113
                          mol_type = protein
                          organism = synthetic construct
SEQUENCE: 330
DIVMTQSPDS LAVSLGERAT INCTASESLY SSKHKVHYLA WYQQKPGQPP KLLIYGASNR    60
YTGVPDRFSG SGSGTDFTLT ISSLQAEDVA VYYCAQFYSY PLTFGGGTKV EIK          113

SEQ ID NO: 331            moltype = AA   length = 113
FEATURE                   Location/Qualifiers
source                    1..113
                          mol_type = protein
                          organism = synthetic construct
SEQUENCE: 331
DIVMTQSPDS LAVSLGERAT INCTASESLY SSKHKVHYLA WYQQKPGQPP KLLIYGAANR    60
YIGVPDRFSG SGSGTDFTLT ISSLQAEDVA VYYCAQFYSY PLTFGGGTKV EIK          113

SEQ ID NO: 332            moltype = AA   length = 113
FEATURE                   Location/Qualifiers
source                    1..113
                          mol_type = protein
                          organism = synthetic construct
SEQUENCE: 332
DIVMTQSPDS LAVSLGERAT INCTASESLY SSKHKVHYLA WYQQKPGQPP KLLIYGAQNR    60
YIGVPDRFSG SGSGTDFTLT ISSLQAEDVA VYYCGQFYSY PLTFGGGTKV EIK          113

SEQ ID NO: 333            moltype = AA   length = 113
FEATURE                   Location/Qualifiers
source                    1..113
                          mol_type = protein
                          organism = synthetic construct
SEQUENCE: 333
DIVMTQSPDS LAVSLGERAT INCTASESLY SSKIKVHYLA WYQQKPGQPP KLLIYGAHNR    60
YIGVPDRFSG SGSGTDFTLT ISSLQAEDVA VYYCAQFYSY PLTFGGGTKV EIK          113

SEQ ID NO: 334            moltype = AA   length = 113
FEATURE                   Location/Qualifiers
source                    1..113
                          mol_type = protein
                          organism = synthetic construct
SEQUENCE: 334
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAQFYTY PLTFGGGTKV EIK          113

SEQ ID NO: 335            moltype = AA   length = 113
FEATURE                   Location/Qualifiers
source                    1..113
                          mol_type = protein
                          organism = synthetic construct
```

```
SEQUENCE: 335
DIVMTQSPDS LAVSLGERAT INCTASESLY SSKHKVHYLA WYQQKPGQPP KLLIYGASNR    60
YSGVPDRFSG SGSGTDFTLT ISSLQAEDVA VYYCAQFYHY PLTFGGGTKV EIK          113

SEQ ID NO: 336           moltype = AA   length = 113
FEATURE                  Location/Qualifiers
source                   1..113
                         mol_type = protein
                         organism = synthetic construct
SEQUENCE: 336
DIVMTQSPDS LAVSLGERAT INCTASESLY SSKHKVHYLA WYQQKPGQPP KLLIYGATNR    60
YIGVPDRFSG SGSGTDFTLT ISSLQAEDVA VYYCAEFYSY PLTFGGGTKV EIK          113

SEQ ID NO: 337           moltype = AA   length = 113
FEATURE                  Location/Qualifiers
source                   1..113
                         mol_type = protein
                         organism = synthetic construct
SEQUENCE: 337
DIVMTQSPDS LAVSLGERAT INCTASESLY SSKHKVHYLA WYQQKPGQPP KLLIYGASGR    60
YIGVPDRFSG SGSGTDFTLT ISSLQAEDVA VYYCAQFYSY PLTFGGGTKV EIK          113

SEQ ID NO: 338           moltype = AA   length = 113
FEATURE                  Location/Qualifiers
source                   1..113
                         mol_type = protein
                         organism = synthetic construct
SEQUENCE: 338
DIVMTQSPDS LAVSLGERAT INCKSSQSLL YSKNNVNYLA WYQQKPGQPP KLLIYGESNR    60
YIGVPDRFSG SGSGTDFTLT ISSLQAEDVA VYYCAQFYEY PLTFGGGTKV EIK          113

SEQ ID NO: 339           moltype = AA   length = 113
FEATURE                  Location/Qualifiers
source                   1..113
                         mol_type = protein
                         organism = synthetic construct
SEQUENCE: 339
DIVMTQSPDS LAVSLGERAT INCKSSESLY SSKNKVHYLA WYQQKPGQPP KLLIYGASNR    60
YIGVPDRFSG SGSGTDFTLT ISSLQAEDVA VYYCAQFYHY PLTFGGGTKV EIK          113

SEQ ID NO: 340           moltype = AA   length = 113
FEATURE                  Location/Qualifiers
source                   1..113
                         mol_type = protein
                         organism = synthetic construct
SEQUENCE: 340
DIVMTQSPDS LAVSLGERAT INCTASESLY SSKHKVNYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 341           moltype = AA   length = 113
FEATURE                  Location/Qualifiers
source                   1..113
                         mol_type = protein
                         organism = synthetic construct
SEQUENCE: 341
DIVMTQSPDS LAVSLGERAT INCTSSESLL SSKHKVHYLA WYQQKPGQPP KLLIYGASNR    60
YTGVPDRFSG SGSGTDFTLT ISSLQAEDVA VYYCAQFYSY PLTFGGGTKV EIK          113

SEQ ID NO: 342           moltype = AA   length = 113
FEATURE                  Location/Qualifiers
source                   1..113
                         mol_type = protein
                         organism = synthetic construct
SEQUENCE: 342
DIVMTQSPDS LAVSLGERAT INCTASQSVY SSKHKKHYLA WYQQKPGQPP KLLIYGANNR    60
YIGVPDRFSG SGSGTDFTLT ISSLQAEDVA VYYCGQFYSY PLTFGGGTKV EIK          113

SEQ ID NO: 343           moltype = AA   length = 113
FEATURE                  Location/Qualifiers
source                   1..113
                         mol_type = protein
                         organism = synthetic construct
SEQUENCE: 343
DIVMTQSPDS LAVSLGERAT INCTASQSVY SSKHNKHYLA WYQQKPGQPP KLLIYGASNP    60
YIGVPDRFSG SGSGTDFTLT ISSLQAEDVA VYYCAQFYSY PLTFGGGTKV EIK          113

SEQ ID NO: 344           moltype = AA   length = 113
FEATURE                  Location/Qualifiers
source                   1..113
```

```
                        mol_type = protein
                        organism = synthetic construct
SEQUENCE: 344
DIVMTQSPDS LAVSLGERAT INCTASESLY SGKHKVHYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 345          moltype = AA  length = 113
FEATURE                 Location/Qualifiers
source                  1..113
                        mol_type = protein
                        organism = synthetic construct
SEQUENCE: 345
DIVMTQSPDS LAVSLGERAT INCTSSQSLL YSSNKKHYLA WYQQKPGQPP KLLIYGASNR    60
YIGVPDRFSG SGSGTDFTLT ISSLQAEDVA VYYCAQFYEY PLTFGGGTKV EIK          113

SEQ ID NO: 346          moltype = AA  length = 113
FEATURE                 Location/Qualifiers
source                  1..113
                        mol_type = protein
                        organism = synthetic construct
SEQUENCE: 346
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCAQFYNY PLTFGGGTKV EIK          113

SEQ ID NO: 347          moltype = AA  length = 113
FEATURE                 Location/Qualifiers
source                  1..113
                        mol_type = protein
                        organism = synthetic construct
SEQUENCE: 347
DIVMTQSPDS LAVSLGERAT INCTASESLY SSKHKVHYLA WYQQKPGQPP KLLIYGASNR    60
YIGVPDRFSG SGSGTDFTLT ISSLQAEDVA VYYCASFYSY PLTFGGGTKV EIK          113

SEQ ID NO: 348          moltype = AA  length = 113
FEATURE                 Location/Qualifiers
source                  1..113
                        mol_type = protein
                        organism = synthetic construct
SEQUENCE: 348
DIVMTQSPDS LAVSLGERAT INCKSSQSVL SSKHKKNYLA WYQQKPGQPP KLLIYGASNR    60
YIGVPDRFSG SGSGTDFTLT ISSLQAEDVA VYYCAQFYSY PLTFGGGTKV EIK          113

SEQ ID NO: 349          moltype = AA  length = 113
FEATURE                 Location/Qualifiers
source                  1..113
                        mol_type = protein
                        organism = synthetic construct
SEQUENCE: 349
DIVMTQSPDS LAVSLGERAT INCTASESLY SSKHKVHYLA WYQQKPGQPP KLLIYGAQNR    60
YIGVPDRFSG SGSGTDFTLT ISSLQAEDVA VYYCAQFYSY PLTFGGGTKV EIK          113

SEQ ID NO: 350          moltype = AA  length = 113
FEATURE                 Location/Qualifiers
source                  1..113
                        mol_type = protein
                        organism = synthetic construct
SEQUENCE: 350
DIVMTQSPDS LAVSLGERAT INCTASQSVY SSKNKKHYLA WYQQKPGQPP KLLIYGASNR    60
YIGVPDRFSG SGSGTDFTLT ISSLQAEDVA VYYCAQFYRY PLTFGGGTKV EIK          113

SEQ ID NO: 351          moltype = AA  length = 113
FEATURE                 Location/Qualifiers
source                  1..113
                        mol_type = protein
                        organism = synthetic construct
SEQUENCE: 351
DIVMTQSPDS LAVSLGERAT INCTASESVL SSKHKKNYLA WYQQKPGQPP KLLIYGASTR    60
YIGVPDRFSG SGSGTDFTLT ISSLQAEDVA VYYCAQFYSY PLTFGGGTKV EIK          113

SEQ ID NO: 352          moltype = AA  length = 113
FEATURE                 Location/Qualifiers
source                  1..113
                        mol_type = protein
                        organism = synthetic construct
SEQUENCE: 352
DIVMTQSPDS LAVSLGERAT INCTASVSLY SSKHKVHYLA WYQQKPGQPP KLLIYGPSNR    60
YIGVPDRFSG SGSGTDFTLT ISSLQAEDVA VYYCAQFYSY PLTFGGGTKV EIK          113

SEQ ID NO: 353          moltype = AA  length = 113
```

```
FEATURE           Location/Qualifiers
source            1..113
                  mol_type = protein
                  organism = synthetic construct
SEQUENCE: 353
DIVMTQSPDS LAVSLGERAT INCTASESLY SSKHKVHYLA WYQQKPGQPP KLLIYGASNR  60
PIGVPDRFSG SGSGTDFTLT ISSLQAEDVA VYYCGQFYSY PLTFGGGTKV EIK        113

SEQ ID NO: 354       moltype = AA   length = 113
FEATURE              Location/Qualifiers
source               1..113
                     mol_type = protein
                     organism = synthetic construct
SEQUENCE: 354
DIVMTQSPDS LAVSLGERAT INCTASESLY SSKHKVHYLA WYQQKPGQPP KLLIYGASNR  60
YIGVPDRFSG SGSGTDFTLT ISSLQAEDVA VYYCAAFYSY PLTFGGGTKV EIK        113

SEQ ID NO: 355       moltype = AA   length = 113
FEATURE              Location/Qualifiers
source               1..113
                     mol_type = protein
                     organism = synthetic construct
SEQUENCE: 355
DIVMTQSPDS LAVSLGERAT INCTASESLY SPKHKVHYLA WYQQKPGQPP KLLIYGAENR  60
YIGVPDRFSG SGSGTDFTLT ISSLQAEDVA VYYCAQFYSY PLTFGGGTKV EIK        113

SEQ ID NO: 356       moltype = AA   length = 113
FEATURE              Location/Qualifiers
source               1..113
                     mol_type = protein
                     organism = synthetic construct
SEQUENCE: 356
DIVMTQSPDS LAVSLGERAT INCTASESLY SSKHKVHYLA WYQQKPGQPP KLLIYGASHR  60
QIGVPDRFSG SGSGTDFTLT ISSLQAEDVA VYYCAQFYSY PLTFGGGTKV EIK        113

SEQ ID NO: 357       moltype = AA   length = 113
FEATURE              Location/Qualifiers
source               1..113
                     mol_type = protein
                     organism = synthetic construct
SEQUENCE: 357
DIVMTQSPDS LAVSLGERAT INCTASESLY SSKHKVHYLA WYQQKPGQPP KLLIYGASQR  60
YIGVPDRFSG SGSGTDFTLT ISSLQAEDVA VYYCAQFYSY PLTFGGGTKV EIK        113

SEQ ID NO: 358       moltype = AA   length = 113
FEATURE              Location/Qualifiers
source               1..113
                     mol_type = protein
                     organism = synthetic construct
SEQUENCE: 358
DIVMTQSPDS LAVSLGERAT INCTASTSLY SSKHKVHYLA WYQQKPGQPP KLLIYGASNR  60
YIGVPDRFSG SGSGTDFTLT ISSLQAEDVA VYYCAQFYSY PLTFGGGTKV EIK        113

SEQ ID NO: 359       moltype = AA   length = 113
FEATURE              Location/Qualifiers
source               1..113
                     mol_type = protein
                     organism = synthetic construct
SEQUENCE: 359
DIVMTQSPDS LAVSLGERAT INCKSSESLY SSKNKVHYLA WYQQKPGQPP KLLIYGASNR  60
YSGVPDRFSG SGSGTDFTLT ISSLQAEDVA VYYCAQFYSY PLTFGGGTKV EIK        113

SEQ ID NO: 360       moltype = AA   length = 113
FEATURE              Location/Qualifiers
source               1..113
                     mol_type = protein
                     organism = synthetic construct
SEQUENCE: 360
DIVMTQSPDS LAVSLGERAT INCTASESLY STKHKVHYLA WYQQKPGQPP KLLIYGASHR  60
YIGVPDRFSG SGSGTDFTLT ISSLQAEDVA VYYCAQFYQY PLTFGGGTKV EIK        113

SEQ ID NO: 361       moltype = AA   length = 113
FEATURE              Location/Qualifiers
source               1..113
                     mol_type = protein
                     organism = synthetic construct
SEQUENCE: 361
DIVMTQSPDS LAVSLGERAT INCTASESLY SSKHKVHYLA WYQQKPGQPP KLLIYGVSNR  60
YIGVPDRFSG SGSGTDFTLT ISSLQAEDVA VYYCAQFYSY PLTFGGGTKV EIK        113
```

```
SEQ ID NO: 362          moltype = AA  length = 113
FEATURE                 Location/Qualifiers
source                  1..113
                        mol_type = protein
                        organism = synthetic construct
SEQUENCE: 362
DIVMTQSPDS LAVSLGERAT INCTASESLY SSKHKVHYLA WYQQKPGQPP KLLIYGASNR    60
VIGVPDRFSG SGSGTDFTLT ISSLQAEDVA VYYCAQFYIY PLTFGGGTKV EIK          113

SEQ ID NO: 363          moltype = AA  length = 113
FEATURE                 Location/Qualifiers
source                  1..113
                        mol_type = protein
                        organism = synthetic construct
SEQUENCE: 363
DIVMTQSPDS LAVSLGERAT INCTASESLY SSNHKVHYLA WYQQKPGQPP KLLIYGVSNR    60
YIGVPDRFSG SGSGTDFTLT ISSLQAEDVA VYYCAQFYSY PLTFGGGTKV EIK          113

SEQ ID NO: 364          moltype = AA  length = 113
FEATURE                 Location/Qualifiers
source                  1..113
                        mol_type = protein
                        organism = synthetic construct
SEQUENCE: 364
DIVMTQSPDS LAVSLGERAT INCKASQSVL SSKNNVNYLA WYQQKPGQPP KLLIYGASNR    60
YIGVPDRFSG SGSGTDFTLT ISSLQAEDVA VYYCAQFYQY PLTFGGGTKV EIK          113

SEQ ID NO: 365          moltype = AA  length = 113
FEATURE                 Location/Qualifiers
source                  1..113
                        mol_type = protein
                        organism = synthetic construct
SEQUENCE: 365
DIVMTQSPDS LAVSLGERAT INCTASESLY SSKHKVHYLA WYQQKPGQPP KLLIYGASNR    60
NIGVPDRFSG SGSGTDFTLT ISSLQAEDVA VYYCAHFYSY PLTFGGGTKV EIK          113

SEQ ID NO: 366          moltype = AA  length = 113
FEATURE                 Location/Qualifiers
source                  1..113
                        mol_type = protein
                        organism = synthetic construct
SEQUENCE: 366
DIVMTQSPDS LAVSLGERAT INCTASESLY SSKHKVHYLA WYQQKPGQPP KLLIYGASNR    60
YQGVPDRFSG SGSGTDFTLT ISSLQAEDVA VYYCAQFYWY PLTFGGGTKV EIK          113

SEQ ID NO: 367          moltype = AA  length = 113
FEATURE                 Location/Qualifiers
source                  1..113
                        mol_type = protein
                        organism = synthetic construct
SEQUENCE: 367
DIVMTQSPDS LAVSLGERAT INCTASESLY SSKHKVHYLA WYQQKPGQPP KLLIYGASNT    60
YIGVPDRFSG SGSGTDFTLT ISSLQAEDVA VYYCAQFYSY PLTFGGGTKV EIK          113

SEQ ID NO: 368          moltype = AA  length = 113
FEATURE                 Location/Qualifiers
source                  1..113
                        mol_type = protein
                        organism = synthetic construct
SEQUENCE: 368
DIVMTQSPDS LAVSLGERAT INCTASESLY SSKHKVHYLA WYQQKPGQPP KLLIYGASNR    60
YSGVPDRFSG SGSGTDFTLT ISSLQAEDVA VYYCAQFYNY PLTFGGGTKV EIK          113

SEQ ID NO: 369          moltype = AA  length = 9
FEATURE                 Location/Qualifiers
source                  1..9
                        mol_type = protein
                        organism = synthetic construct
SEQUENCE: 369
FTFSDYYME                                                             9

SEQ ID NO: 370          moltype = AA  length = 9
FEATURE                 Location/Qualifiers
source                  1..9
                        mol_type = protein
                        organism = synthetic construct
SEQUENCE: 370
FGFSDFYME                                                             9
```

| | | |
|---|---|---|
| SEQ ID NO: 371<br>FEATURE<br>source<br><br>SEQUENCE: 371<br>FTFSDQYIE | moltype = AA   length = 9<br>Location/Qualifiers<br>1..9<br>mol_type = protein<br>organism = synthetic construct | 9 |
| SEQ ID NO: 372<br>FEATURE<br>source<br><br>SEQUENCE: 372<br>FTFSDGYME | moltype = AA   length = 9<br>Location/Qualifiers<br>1..9<br>mol_type = protein<br>organism = synthetic construct | 9 |
| SEQ ID NO: 373<br>FEATURE<br>source<br><br>SEQUENCE: 373<br>FTASDFYME | moltype = AA   length = 9<br>Location/Qualifiers<br>1..9<br>mol_type = protein<br>organism = synthetic construct | 9 |
| SEQ ID NO: 374<br>FEATURE<br>source<br><br>SEQUENCE: 374<br>FTFSDSYME | moltype = AA   length = 9<br>Location/Qualifiers<br>1..9<br>mol_type = protein<br>organism = synthetic construct | 9 |
| SEQ ID NO: 375<br>FEATURE<br>source<br><br>SEQUENCE: 375<br>FTFEDFYME | moltype = AA   length = 9<br>Location/Qualifiers<br>1..9<br>mol_type = protein<br>organism = synthetic construct | 9 |
| SEQ ID NO: 376<br>FEATURE<br>source<br><br>SEQUENCE: 376<br>FTFSDFYME | moltype = AA   length = 9<br>Location/Qualifiers<br>1..9<br>mol_type = protein<br>organism = synthetic construct | 9 |
| SEQ ID NO: 377<br>FEATURE<br>source<br><br>SEQUENCE: 377<br>FTFSDQYME | moltype = AA   length = 9<br>Location/Qualifiers<br>1..9<br>mol_type = protein<br>organism = synthetic construct | 9 |
| SEQ ID NO: 378<br>FEATURE<br>source<br><br>SEQUENCE: 378<br>FQFSDFYME | moltype = AA   length = 9<br>Location/Qualifiers<br>1..9<br>mol_type = protein<br>organism = synthetic construct | 9 |
| SEQ ID NO: 379<br>FEATURE<br>source<br><br>SEQUENCE: 379<br>FEFSDNYME | moltype = AA   length = 9<br>Location/Qualifiers<br>1..9<br>mol_type = protein<br>organism = synthetic construct | 9 |
| SEQ ID NO: 380<br>FEATURE<br>source<br><br>SEQUENCE: 380 | moltype = AA   length = 9<br>Location/Qualifiers<br>1..9<br>mol_type = protein<br>organism = synthetic construct | |

FEFSDFYME                                                                    9

SEQ ID NO: 381          moltype = AA  length = 9
FEATURE                 Location/Qualifiers
source                  1..9
                        mol_type = protein
                        organism = synthetic construct
SEQUENCE: 381
FTFSDAYME                                                                    9

SEQ ID NO: 382          moltype = AA  length = 9
FEATURE                 Location/Qualifiers
source                  1..9
                        mol_type = protein
                        organism = synthetic construct
SEQUENCE: 382
FTESDFYME                                                                    9

SEQ ID NO: 383          moltype = AA  length = 9
FEATURE                 Location/Qualifiers
source                  1..9
                        mol_type = protein
                        organism = synthetic construct
SEQUENCE: 383
FTFSSYYME                                                                    9

SEQ ID NO: 384          moltype = AA  length = 9
FEATURE                 Location/Qualifiers
source                  1..9
                        mol_type = protein
                        organism = synthetic construct
SEQUENCE: 384
FTGSDFYME                                                                    9

SEQ ID NO: 385          moltype = AA  length = 9
FEATURE                 Location/Qualifiers
source                  1..9
                        mol_type = protein
                        organism = synthetic construct
SEQUENCE: 385
FAFSDFYME                                                                    9

SEQ ID NO: 386          moltype = AA  length = 9
FEATURE                 Location/Qualifiers
source                  1..9
                        mol_type = protein
                        organism = synthetic construct
SEQUENCE: 386
FTHSDFYME                                                                    9

SEQ ID NO: 387          moltype = AA  length = 9
FEATURE                 Location/Qualifiers
source                  1..9
                        mol_type = protein
                        organism = synthetic construct
SEQUENCE: 387
FTFSDTYME                                                                    9

SEQ ID NO: 388          moltype = AA  length = 9
FEATURE                 Location/Qualifiers
source                  1..9
                        mol_type = protein
                        organism = synthetic construct
SEQUENCE: 388
FTFSDDYME                                                                    9

SEQ ID NO: 389          moltype = AA  length = 9
FEATURE                 Location/Qualifiers
source                  1..9
                        mol_type = protein
                        organism = synthetic construct
SEQUENCE: 389
FTFSDNYME                                                                    9

SEQ ID NO: 390          moltype = AA  length = 9
FEATURE                 Location/Qualifiers
source                  1..9
                        mol_type = protein
                        organism = synthetic construct

```
SEQUENCE: 390
FTSSDFYME                                                                        9

SEQ ID NO: 391           moltype = AA  length = 9
FEATURE                  Location/Qualifiers
source                   1..9
                         mol_type = protein
                         organism = synthetic construct
SEQUENCE: 391
FTFSTFYME                                                                        9

SEQ ID NO: 392           moltype = AA  length = 9
FEATURE                  Location/Qualifiers
source                   1..9
                         mol_type = protein
                         organism = synthetic construct
SEQUENCE: 392
FTFSDEYME                                                                        9

SEQ ID NO: 393           moltype = AA  length = 9
FEATURE                  Location/Qualifiers
source                   1..9
                         mol_type = protein
                         organism = synthetic construct
SEQUENCE: 393
FWFSDFYME                                                                        9

SEQ ID NO: 394           moltype = AA  length = 9
FEATURE                  Location/Qualifiers
source                   1..9
                         mol_type = protein
                         organism = synthetic construct
SEQUENCE: 394
FTFSDVYME                                                                        9

SEQ ID NO: 395           moltype = AA  length = 9
FEATURE                  Location/Qualifiers
source                   1..9
                         mol_type = protein
                         organism = synthetic construct
SEQUENCE: 395
ATFSDFYME                                                                        9

SEQ ID NO: 396           moltype = AA  length = 9
FEATURE                  Location/Qualifiers
source                   1..9
                         mol_type = protein
                         organism = synthetic construct
SEQUENCE: 396
FDFSDFYME                                                                        9

SEQ ID NO: 397           moltype = AA  length = 9
FEATURE                  Location/Qualifiers
source                   1..9
                         mol_type = protein
                         organism = synthetic construct
SEQUENCE: 397
WTFSDFYME                                                                        9

SEQ ID NO: 398           moltype = AA  length = 9
FEATURE                  Location/Qualifiers
source                   1..9
                         mol_type = protein
                         organism = synthetic construct
SEQUENCE: 398
FTFSSFYME                                                                        9

SEQ ID NO: 399           moltype = AA  length = 9
FEATURE                  Location/Qualifiers
source                   1..9
                         mol_type = protein
                         organism = synthetic construct
SEQUENCE: 399
FTFNDFYME                                                                        9

SEQ ID NO: 400           moltype = AA  length = 9
FEATURE                  Location/Qualifiers
source                   1..9
                         mol_type = protein
```

-continued

```
                        organism = synthetic construct
SEQUENCE: 400
FTFSDHYME                                                            9

SEQ ID NO: 401          moltype = AA   length = 9
FEATURE                 Location/Qualifiers
source                  1..9
                        mol_type = protein
                        organism = synthetic construct
SEQUENCE: 401
FTFSDGYIE                                                            9

SEQ ID NO: 402          moltype = AA   length = 9
FEATURE                 Location/Qualifiers
source                  1..9
                        mol_type = protein
                        organism = synthetic construct
SEQUENCE: 402
GTFSDFYME                                                            9

SEQ ID NO: 403          moltype = AA   length = 9
FEATURE                 Location/Qualifiers
source                  1..9
                        mol_type = protein
                        organism = synthetic construct
SEQUENCE: 403
FTQSDFYME                                                            9

SEQ ID NO: 404          moltype = AA   length = 9
FEATURE                 Location/Qualifiers
source                  1..9
                        mol_type = protein
                        organism = synthetic construct
SEQUENCE: 404
DTFSDFYME                                                            9

SEQ ID NO: 405          moltype = AA   length = 9
FEATURE                 Location/Qualifiers
source                  1..9
                        mol_type = protein
                        organism = synthetic construct
SEQUENCE: 405
FTTSDFYME                                                            9

SEQ ID NO: 406          moltype = AA   length = 9
FEATURE                 Location/Qualifiers
source                  1..9
                        mol_type = protein
                        organism = synthetic construct
SEQUENCE: 406
ETFSDFYME                                                            9

SEQ ID NO: 407          moltype = AA   length = 9
FEATURE                 Location/Qualifiers
source                  1..9
                        mol_type = protein
                        organism = synthetic construct
SEQUENCE: 407
FPFSDFYME                                                            9

SEQ ID NO: 408          moltype = AA   length = 9
FEATURE                 Location/Qualifiers
source                  1..9
                        mol_type = protein
                        organism = synthetic construct
SEQUENCE: 408
ATFSDFYVE                                                            9

SEQ ID NO: 409          moltype = AA   length = 9
FEATURE                 Location/Qualifiers
source                  1..9
                        mol_type = protein
                        organism = synthetic construct
SEQUENCE: 409
FTDSDFYME                                                            9

SEQ ID NO: 410          moltype = AA   length = 9
FEATURE                 Location/Qualifiers
source                  1..9
```

```
                        mol_type = protein
                        organism = synthetic construct
SEQUENCE: 410
NTFSDFYME                                                              9

SEQ ID NO: 411          moltype = AA   length = 9
FEATURE                 Location/Qualifiers
source                  1..9
                        mol_type = protein
                        organism = synthetic construct
SEQUENCE: 411
DTFSDFYLE                                                              9

SEQ ID NO: 412          moltype = AA   length = 9
FEATURE                 Location/Qualifiers
source                  1..9
                        mol_type = protein
                        organism = synthetic construct
SEQUENCE: 412
FLFSDFYME                                                              9

SEQ ID NO: 413          moltype = AA   length = 9
FEATURE                 Location/Qualifiers
source                  1..9
                        mol_type = protein
                        organism = synthetic construct
SEQUENCE: 413
FTNSDFYME                                                              9

SEQ ID NO: 414          moltype = AA   length = 9
FEATURE                 Location/Qualifiers
source                  1..9
                        mol_type = protein
                        organism = synthetic construct
SEQUENCE: 414
QTFSDFYME                                                              9

SEQ ID NO: 415          moltype = AA   length = 9
FEATURE                 Location/Qualifiers
source                  1..9
                        mol_type = protein
                        organism = synthetic construct
SEQUENCE: 415
FTFSDPYME                                                              9

SEQ ID NO: 416          moltype = AA   length = 9
FEATURE                 Location/Qualifiers
source                  1..9
                        mol_type = protein
                        organism = synthetic construct
SEQUENCE: 416
TTFSDFYME                                                              9

SEQ ID NO: 417          moltype = AA   length = 9
FEATURE                 Location/Qualifiers
source                  1..9
                        mol_type = protein
                        organism = synthetic construct
SEQUENCE: 417
PTFSDFYME                                                              9

SEQ ID NO: 418          moltype = AA   length = 9
FEATURE                 Location/Qualifiers
source                  1..9
                        mol_type = protein
                        organism = synthetic construct
SEQUENCE: 418
FTFSEFYME                                                              9

SEQ ID NO: 419          moltype = AA   length = 9
FEATURE                 Location/Qualifiers
source                  1..9
                        mol_type = protein
                        organism = synthetic construct
SEQUENCE: 419
FHFSDFYME                                                              9

SEQ ID NO: 420          moltype = AA   length = 9
FEATURE                 Location/Qualifiers
```

```
source                          1..9
                                mol_type = protein
                                organism = synthetic construct
SEQUENCE: 420
ITFSDFYME                                                                    9

SEQ ID NO: 421                  moltype = AA   length = 9
FEATURE                         Location/Qualifiers
source                          1..9
                                mol_type = protein
                                organism = synthetic construct
SEQUENCE: 421
FTFSDFYVE                                                                    9

SEQ ID NO: 422                  moltype = AA   length = 9
FEATURE                         Location/Qualifiers
source                          1..9
                                mol_type = protein
                                organism = synthetic construct
SEQUENCE: 422
STFSDFYME                                                                    9

SEQ ID NO: 423                  moltype = AA   length = 9
FEATURE                         Location/Qualifiers
source                          1..9
                                mol_type = protein
                                organism = synthetic construct
SEQUENCE: 423
FSFSDFYME                                                                    9

SEQ ID NO: 424                  moltype = AA   length = 9
FEATURE                         Location/Qualifiers
source                          1..9
                                mol_type = protein
                                organism = synthetic construct
SEQUENCE: 424
FTFDDFYME                                                                    9

SEQ ID NO: 425                  moltype = AA   length = 9
FEATURE                         Location/Qualifiers
source                          1..9
                                mol_type = protein
                                organism = synthetic construct
SEQUENCE: 425
FTFSDFYIE                                                                    9

SEQ ID NO: 426                  moltype = AA   length = 9
FEATURE                         Location/Qualifiers
source                          1..9
                                mol_type = protein
                                organism = synthetic construct
SEQUENCE: 426
FTSSDFYLE                                                                    9

SEQ ID NO: 427                  moltype = AA   length = 9
FEATURE                         Location/Qualifiers
source                          1..9
                                mol_type = protein
                                organism = synthetic construct
SEQUENCE: 427
FTFSPFYME                                                                    9

SEQ ID NO: 428                  moltype = AA   length = 15
FEATURE                         Location/Qualifiers
source                          1..15
                                mol_type = protein
                                organism = synthetic construct
SEQUENCE: 428
AASRNKANDY TTEYA                                                            15

SEQ ID NO: 429                  moltype = AA   length = 15
FEATURE                         Location/Qualifiers
source                          1..15
                                mol_type = protein
                                organism = synthetic construct
SEQUENCE: 429
AASRNKWNDY TTEYA                                                            15

SEQ ID NO: 430                  moltype = AA   length = 15
```

```
FEATURE                 Location/Qualifiers
source                  1..15
                        mol_type = protein
                        organism = synthetic construct
SEQUENCE: 430
AASRNKANDY TTSYA                                                                15

SEQ ID NO: 431          moltype = AA  length = 15
FEATURE                 Location/Qualifiers
source                  1..15
                        mol_type = protein
                        organism = synthetic construct
SEQUENCE: 431
AASRNKANDY TTELA                                                                15

SEQ ID NO: 432          moltype = AA  length = 15
FEATURE                 Location/Qualifiers
source                  1..15
                        mol_type = protein
                        organism = synthetic construct
SEQUENCE: 432
AASRGKGNSY TTEYA                                                                15

SEQ ID NO: 433          moltype = AA  length = 15
FEATURE                 Location/Qualifiers
source                  1..15
                        mol_type = protein
                        organism = synthetic construct
SEQUENCE: 433
AASRNKANDY VTEYA                                                                15

SEQ ID NO: 434          moltype = AA  length = 15
FEATURE                 Location/Qualifiers
source                  1..15
                        mol_type = protein
                        organism = synthetic construct
SEQUENCE: 434
AASRNKYNDY TTEYA                                                                15

SEQ ID NO: 435          moltype = AA  length = 15
FEATURE                 Location/Qualifiers
source                  1..15
                        mol_type = protein
                        organism = synthetic construct
SEQUENCE: 435
AASRNKGNSY TTEYA                                                                15

SEQ ID NO: 436          moltype = AA  length = 15
FEATURE                 Location/Qualifiers
source                  1..15
                        mol_type = protein
                        organism = synthetic construct
SEQUENCE: 436
AASRNKANTY TTEYA                                                                15

SEQ ID NO: 437          moltype = AA  length = 15
FEATURE                 Location/Qualifiers
source                  1..15
                        mol_type = protein
                        organism = synthetic construct
SEQUENCE: 437
AASRNKNNDY TTEYA                                                                15

SEQ ID NO: 438          moltype = AA  length = 15
FEATURE                 Location/Qualifiers
source                  1..15
                        mol_type = protein
                        organism = synthetic construct
SEQUENCE: 438
AASRNIANDY TTEYA                                                                15

SEQ ID NO: 439          moltype = AA  length = 15
FEATURE                 Location/Qualifiers
source                  1..15
                        mol_type = protein
                        organism = synthetic construct
SEQUENCE: 439
AASRNSGNDY TTEYA                                                                15
```

```
SEQ ID NO: 440         moltype = AA  length = 15
FEATURE                Location/Qualifiers
source                 1..15
                       mol_type = protein
                       organism = synthetic construct
SEQUENCE: 440
AASRNKANDY TVEYA                                                      15

SEQ ID NO: 441         moltype = AA  length = 15
FEATURE                Location/Qualifiers
source                 1..15
                       mol_type = protein
                       organism = synthetic construct
SEQUENCE: 441
AASRNKANDY YTEYA                                                      15

SEQ ID NO: 442         moltype = AA  length = 15
FEATURE                Location/Qualifiers
source                 1..15
                       mol_type = protein
                       organism = synthetic construct
SEQUENCE: 442
AASRHKANDY TTEYA                                                      15

SEQ ID NO: 443         moltype = AA  length = 15
FEATURE                Location/Qualifiers
source                 1..15
                       mol_type = protein
                       organism = synthetic construct
SEQUENCE: 443
AASRNKANDY QTEYA                                                      15

SEQ ID NO: 444         moltype = AA  length = 15
FEATURE                Location/Qualifiers
source                 1..15
                       mol_type = protein
                       organism = synthetic construct
SEQUENCE: 444
AASRNQANDY TTEYA                                                      15

SEQ ID NO: 445         moltype = AA  length = 15
FEATURE                Location/Qualifiers
source                 1..15
                       mol_type = protein
                       organism = synthetic construct
SEQUENCE: 445
AASRNGANDY TTEYA                                                      15

SEQ ID NO: 446         moltype = AA  length = 15
FEATURE                Location/Qualifiers
source                 1..15
                       mol_type = protein
                       organism = synthetic construct
SEQUENCE: 446
AASRNKANDY TTDYA                                                      15

SEQ ID NO: 447         moltype = AA  length = 15
FEATURE                Location/Qualifiers
source                 1..15
                       mol_type = protein
                       organism = synthetic construct
SEQUENCE: 447
AASRNKANDY TNEYA                                                      15

SEQ ID NO: 448         moltype = AA  length = 15
FEATURE                Location/Qualifiers
source                 1..15
                       mol_type = protein
                       organism = synthetic construct
SEQUENCE: 448
AASRNAANDY TTEYA                                                      15

SEQ ID NO: 449         moltype = AA  length = 15
FEATURE                Location/Qualifiers
source                 1..15
                       mol_type = protein
                       organism = synthetic construct
SEQUENCE: 449
AASRNKANDQ TTEYA                                                      15
```

```
SEQ ID NO: 450          moltype = AA   length = 15
FEATURE                 Location/Qualifiers
source                  1..15
                        mol_type = protein
                        organism = synthetic construct
SEQUENCE: 450
AASRNSGNSY TTEYA                                                          15

SEQ ID NO: 451          moltype = AA   length = 15
FEATURE                 Location/Qualifiers
source                  1..15
                        mol_type = protein
                        organism = synthetic construct
SEQUENCE: 451
AASRNKANSY TTEYA                                                          15

SEQ ID NO: 452          moltype = AA   length = 15
FEATURE                 Location/Qualifiers
source                  1..15
                        mol_type = protein
                        organism = synthetic construct
SEQUENCE: 452
AASRWKANDY TTEYA                                                          15

SEQ ID NO: 453          moltype = AA   length = 15
FEATURE                 Location/Qualifiers
source                  1..15
                        mol_type = protein
                        organism = synthetic construct
SEQUENCE: 453
AAIRNKANSY TTEYA                                                          15

SEQ ID NO: 454          moltype = AA   length = 15
FEATURE                 Location/Qualifiers
source                  1..15
                        mol_type = protein
                        organism = synthetic construct
SEQUENCE: 454
AASRNKANSY TTAYA                                                          15

SEQ ID NO: 455          moltype = AA   length = 15
FEATURE                 Location/Qualifiers
source                  1..15
                        mol_type = protein
                        organism = synthetic construct
SEQUENCE: 455
AASRNKANDY TTTYA                                                          15

SEQ ID NO: 456          moltype = AA   length = 15
FEATURE                 Location/Qualifiers
source                  1..15
                        mol_type = protein
                        organism = synthetic construct
SEQUENCE: 456
AASRNKGNDY TTEYA                                                          15

SEQ ID NO: 457          moltype = AA   length = 15
FEATURE                 Location/Qualifiers
source                  1..15
                        mol_type = protein
                        organism = synthetic construct
SEQUENCE: 457
GASRNKHNDY TTEYA                                                          15

SEQ ID NO: 458          moltype = AA   length = 15
FEATURE                 Location/Qualifiers
source                  1..15
                        mol_type = protein
                        organism = synthetic construct
SEQUENCE: 458
AASRNKANAY TTEYA                                                          15

SEQ ID NO: 459          moltype = AA   length = 15
FEATURE                 Location/Qualifiers
source                  1..15
                        mol_type = protein
                        organism = synthetic construct
SEQUENCE: 459
```

AASRNKFNDY TTEYA                                                                15

SEQ ID NO: 460          moltype = AA  length = 15
FEATURE                 Location/Qualifiers
source                  1..15
                        mol_type = protein
                        organism = synthetic construct
SEQUENCE: 460
AASRNKANGY TTEYA                                                                15

SEQ ID NO: 461          moltype = AA  length = 15
FEATURE                 Location/Qualifiers
source                  1..15
                        mol_type = protein
                        organism = synthetic construct
SEQUENCE: 461
AASRNKANEY TTEYA                                                                15

SEQ ID NO: 462          moltype = AA  length = 15
FEATURE                 Location/Qualifiers
source                  1..15
                        mol_type = protein
                        organism = synthetic construct
SEQUENCE: 462
AASRNKANLY TTEYA                                                                15

SEQ ID NO: 463          moltype = AA  length = 15
FEATURE                 Location/Qualifiers
source                  1..15
                        mol_type = protein
                        organism = synthetic construct
SEQUENCE: 463
AASRGKGNSY TTAYA                                                                15

SEQ ID NO: 464          moltype = AA  length = 15
FEATURE                 Location/Qualifiers
source                  1..15
                        mol_type = protein
                        organism = synthetic construct
SEQUENCE: 464
AASRNKGNSY TTAYA                                                                15

SEQ ID NO: 465          moltype = AA  length = 15
FEATURE                 Location/Qualifiers
source                  1..15
                        mol_type = protein
                        organism = synthetic construct
SEQUENCE: 465
AASRNNANDY TTEYA                                                                15

SEQ ID NO: 466          moltype = AA  length = 15
FEATURE                 Location/Qualifiers
source                  1..15
                        mol_type = protein
                        organism = synthetic construct
SEQUENCE: 466
AASRNKANGY TTEYT                                                                15

SEQ ID NO: 467          moltype = AA  length = 15
FEATURE                 Location/Qualifiers
source                  1..15
                        mol_type = protein
                        organism = synthetic construct
SEQUENCE: 467
AASRNSGNSY TTAYA                                                                15

SEQ ID NO: 468          moltype = AA  length = 15
FEATURE                 Location/Qualifiers
source                  1..15
                        mol_type = protein
                        organism = synthetic construct
SEQUENCE: 468
AATRNKANDY TTEYA                                                                15

SEQ ID NO: 469          moltype = AA  length = 15
FEATURE                 Location/Qualifiers
source                  1..15
                        mol_type = protein
                        organism = synthetic construct

```
SEQUENCE: 469
AASRNKANDF TTEYA                                                            15

SEQ ID NO: 470         moltype = AA  length = 15
FEATURE                Location/Qualifiers
source                 1..15
                       mol_type = protein
                       organism = synthetic construct
SEQUENCE: 470
AASRNKANDY TYEYA                                                            15

SEQ ID NO: 471         moltype = AA  length = 15
FEATURE                Location/Qualifiers
source                 1..15
                       mol_type = protein
                       organism = synthetic construct
SEQUENCE: 471
AASRNKANDY STEYA                                                            15

SEQ ID NO: 472         moltype = AA  length = 15
FEATURE                Location/Qualifiers
source                 1..15
                       mol_type = protein
                       organism = synthetic construct
SEQUENCE: 472
AASRSKANDY TTEYA                                                            15

SEQ ID NO: 473         moltype = AA  length = 15
FEATURE                Location/Qualifiers
source                 1..15
                       mol_type = protein
                       organism = synthetic construct
SEQUENCE: 473
AASRNKANDY TTAYA                                                            15

SEQ ID NO: 474         moltype = AA  length = 15
FEATURE                Location/Qualifiers
source                 1..15
                       mol_type = protein
                       organism = synthetic construct
SEQUENCE: 474
AASRNTANDY TTEYA                                                            15

SEQ ID NO: 475         moltype = AA  length = 15
FEATURE                Location/Qualifiers
source                 1..15
                       mol_type = protein
                       organism = synthetic construct
SEQUENCE: 475
AASRNKANDY NTEYA                                                            15

SEQ ID NO: 476         moltype = AA  length = 15
FEATURE                Location/Qualifiers
source                 1..15
                       mol_type = protein
                       organism = synthetic construct
SEQUENCE: 476
AASRNKANDY TTEVA                                                            15

SEQ ID NO: 477         moltype = AA  length = 15
FEATURE                Location/Qualifiers
source                 1..15
                       mol_type = protein
                       organism = synthetic construct
SEQUENCE: 477
AASRNKGNDY TTAYA                                                            15

SEQ ID NO: 478         moltype = AA  length = 15
FEATURE                Location/Qualifiers
source                 1..15
                       mol_type = protein
                       organism = synthetic construct
SEQUENCE: 478
AASRNKANFY TTEYA                                                            15

SEQ ID NO: 479         moltype = AA  length = 15
FEATURE                Location/Qualifiers
source                 1..15
                       mol_type = protein
```

-continued

```
SEQUENCE: 479
AASRNEANDY TTEYA                                                    15

SEQ ID NO: 480          moltype = AA  length = 15
FEATURE                 Location/Qualifiers
source                  1..15
                        mol_type = protein
                        organism = synthetic construct
SEQUENCE: 480
AAIRNKANDY TTEYA                                                    15

SEQ ID NO: 481          moltype = AA  length = 15
FEATURE                 Location/Qualifiers
source                  1..15
                        mol_type = protein
                        organism = synthetic construct
SEQUENCE: 481
AASRNVANDY TTEYA                                                    15

SEQ ID NO: 482          moltype = AA  length = 15
FEATURE                 Location/Qualifiers
source                  1..15
                        mol_type = protein
                        organism = synthetic construct
SEQUENCE: 482
AASRNKANDW TTEYA                                                    15

SEQ ID NO: 483          moltype = AA  length = 15
FEATURE                 Location/Qualifiers
source                  1..15
                        mol_type = protein
                        organism = synthetic construct
SEQUENCE: 483
AASRNKANYY TTEYA                                                    15

SEQ ID NO: 484          moltype = AA  length = 16
FEATURE                 Location/Qualifiers
source                  1..16
                        mol_type = protein
                        organism = synthetic construct
SEQUENCE: 484
CARDYYGSSY WYFDVW                                                   16

SEQ ID NO: 485          moltype = AA  length = 16
FEATURE                 Location/Qualifiers
source                  1..16
                        mol_type = protein
                        organism = synthetic construct
SEQUENCE: 485
CARDYYGSSY WYYDVW                                                   16

SEQ ID NO: 486          moltype = AA  length = 16
FEATURE                 Location/Qualifiers
source                  1..16
                        mol_type = protein
                        organism = synthetic construct
SEQUENCE: 486
CARDYLGSSY WYFDVW                                                   16

SEQ ID NO: 487          moltype = AA  length = 16
FEATURE                 Location/Qualifiers
source                  1..16
                        mol_type = protein
                        organism = synthetic construct
SEQUENCE: 487
CARDYFGSSY WYFDVW                                                   16

SEQ ID NO: 488          moltype = AA  length = 16
FEATURE                 Location/Qualifiers
source                  1..16
                        mol_type = protein
                        organism = synthetic construct
SEQUENCE: 488
CARDYYASSY WYFDVW                                                   16

SEQ ID NO: 489          moltype = AA  length = 16
FEATURE                 Location/Qualifiers
source                  1..16
```

```
SEQUENCE: 489
CARDYYGSPY WYFDVW                                                 16

SEQ ID NO: 490         moltype = AA  length = 16
FEATURE                Location/Qualifiers
source                 1..16
                       mol_type = protein
                       organism = synthetic construct
SEQUENCE: 490
CARDYYGSSY WYFDSW                                                 16

SEQ ID NO: 491         moltype = AA  length = 16
FEATURE                Location/Qualifiers
source                 1..16
                       mol_type = protein
                       organism = synthetic construct
SEQUENCE: 491
CARDYYGSSY WYFDTW                                                 16

SEQ ID NO: 492         moltype = AA  length = 16
FEATURE                Location/Qualifiers
source                 1..16
                       mol_type = protein
                       organism = synthetic construct
SEQUENCE: 492
CARDYYGSSY WYFDLW                                                 16

SEQ ID NO: 493         moltype = AA  length = 16
FEATURE                Location/Qualifiers
source                 1..16
                       mol_type = protein
                       organism = synthetic construct
SEQUENCE: 493
CARDYYGSHY WYFDVW                                                 16

SEQ ID NO: 494         moltype = AA  length = 16
FEATURE                Location/Qualifiers
source                 1..16
                       mol_type = protein
                       organism = synthetic construct
SEQUENCE: 494
CARDYQGSSY WYFDVW                                                 16

SEQ ID NO: 495         moltype = AA  length = 16
FEATURE                Location/Qualifiers
source                 1..16
                       mol_type = protein
                       organism = synthetic construct
SEQUENCE: 495
CARDYYGHSY WYFDVW                                                 16

SEQ ID NO: 496         moltype = AA  length = 16
FEATURE                Location/Qualifiers
source                 1..16
                       mol_type = protein
                       organism = synthetic construct
SEQUENCE: 496
CARDYYGSSY WYLDVW                                                 16

SEQ ID NO: 497         moltype = AA  length = 16
FEATURE                Location/Qualifiers
source                 1..16
                       mol_type = protein
                       organism = synthetic construct
SEQUENCE: 497
CARDYYGNSY WYFDVW                                                 16

SEQ ID NO: 498         moltype = AA  length = 16
FEATURE                Location/Qualifiers
source                 1..16
                       mol_type = protein
                       organism = synthetic construct
SEQUENCE: 498
CARDYYGSAY WYFDVW                                                 16

SEQ ID NO: 499         moltype = AA  length = 16
FEATURE                Location/Qualifiers
```

```
source                  1..16
                        mol_type = protein
                        organism = synthetic construct
SEQUENCE: 499
CARDYYGQSY WYFDVW                                                      16

SEQ ID NO: 501          moltype = AA  length = 16
FEATURE                 Location/Qualifiers
source                  1..16
                        mol_type = protein
                        organism = synthetic construct
SEQUENCE: 500
CARDYYGSST WYFDVW                                                      16

SEQ ID NO: 501          moltype = AA  length = 16
FEATURE                 Location/Qualifiers
source                  1..16
                        mol_type = protein
                        organism = synthetic construct
SEQUENCE: 501
CARDYYESSY WYFDVW                                                      16

SEQ ID NO: 502          moltype = AA  length = 16
FEATURE                 Location/Qualifiers
source                  1..16
                        mol_type = protein
                        organism = synthetic construct
SEQUENCE: 502
CARDYYGSSH WYFDVW                                                      16

SEQ ID NO: 503          moltype = AA  length = 16
FEATURE                 Location/Qualifiers
source                  1..16
                        mol_type = protein
                        organism = synthetic construct
SEQUENCE: 503
CARDYYGDSY WYFDVW                                                      16

SEQ ID NO: 504          moltype = AA  length = 16
FEATURE                 Location/Qualifiers
source                  1..16
                        mol_type = protein
                        organism = synthetic construct
SEQUENCE: 504
CARDYYGSSY WYNDVW                                                      16

SEQ ID NO: 505          moltype = AA  length = 16
FEATURE                 Location/Qualifiers
source                  1..16
                        mol_type = protein
                        organism = synthetic construct
SEQUENCE: 505
CARDYYHSSY WYFDVW                                                      16

SEQ ID NO: 506          moltype = AA  length = 16
FEATURE                 Location/Qualifiers
source                  1..16
                        mol_type = protein
                        organism = synthetic construct
SEQUENCE: 506
CARDIYGSSY WYFDVW                                                      16

SEQ ID NO: 507          moltype = AA  length = 16
FEATURE                 Location/Qualifiers
source                  1..16
                        mol_type = protein
                        organism = synthetic construct
SEQUENCE: 507
CARDYYGSSY WYDDVW                                                      16

SEQ ID NO: 508          moltype = AA  length = 16
FEATURE                 Location/Qualifiers
source                  1..16
                        mol_type = protein
                        organism = synthetic construct
SEQUENCE: 508
CARDYYGYSY WYFDVW                                                      16

SEQ ID NO: 509          moltype = AA  length = 16
```

```
FEATURE                 Location/Qualifiers
source                  1..16
                        mol_type = protein
                        organism = synthetic construct
SEQUENCE: 509
CARDYYGSSQ WYFDVW                                                           16

SEQ ID NO: 510          moltype = AA  length = 16
FEATURE                 Location/Qualifiers
source                  1..16
                        mol_type = protein
                        organism = synthetic construct
SEQUENCE: 510
CARDFYGSSY WYFDVW                                                           16

SEQ ID NO: 511          moltype = AA  length = 16
FEATURE                 Location/Qualifiers
source                  1..16
                        mol_type = protein
                        organism = synthetic construct
SEQUENCE: 511
CARDYYGSSY WYHDVW                                                           16

SEQ ID NO: 512          moltype = AA  length = 16
FEATURE                 Location/Qualifiers
source                  1..16
                        mol_type = protein
                        organism = synthetic construct
SEQUENCE: 512
CARDYYGSSY WYFDPW                                                           16

SEQ ID NO: 513          moltype = AA  length = 16
FEATURE                 Location/Qualifiers
source                  1..16
                        mol_type = protein
                        organism = synthetic construct
SEQUENCE: 513
CARDYYGSQY WYFDVW                                                           16

SEQ ID NO: 514          moltype = AA  length = 16
FEATURE                 Location/Qualifiers
source                  1..16
                        mol_type = protein
                        organism = synthetic construct
SEQUENCE: 514
CARDYYSSSY WYFDVW                                                           16

SEQ ID NO: 515          moltype = AA  length = 16
FEATURE                 Location/Qualifiers
source                  1..16
                        mol_type = protein
                        organism = synthetic construct
SEQUENCE: 515
CARDYYGSSN WYFDVW                                                           16

SEQ ID NO: 516          moltype = AA  length = 16
FEATURE                 Location/Qualifiers
source                  1..16
                        mol_type = protein
                        organism = synthetic construct
SEQUENCE: 516
CARDYYFSSY WYFDVW                                                           16

SEQ ID NO: 517          moltype = AA  length = 16
FEATURE                 Location/Qualifiers
source                  1..16
                        mol_type = protein
                        organism = synthetic construct
SEQUENCE: 517
CARDYYDSSY WYFDVW                                                           16

SEQ ID NO: 518          moltype = AA  length = 16
FEATURE                 Location/Qualifiers
source                  1..16
                        mol_type = protein
                        organism = synthetic construct
SEQUENCE: 518
CARDYYGASY WYFDVW                                                           16
```

```
SEQ ID NO: 519          moltype = AA   length = 16
FEATURE                 Location/Qualifiers
source                  1..16
                        mol_type = protein
                        organism = synthetic construct
SEQUENCE: 519
CARDHYGSSY WYFDVW                                                          16

SEQ ID NO: 520          moltype = AA   length = 16
FEATURE                 Location/Qualifiers
source                  1..16
                        mol_type = protein
                        organism = synthetic construct
SEQUENCE: 520
CARDYYGESY WYFDVW                                                          16

SEQ ID NO: 521          moltype = AA   length = 16
FEATURE                 Location/Qualifiers
source                  1..16
                        mol_type = protein
                        organism = synthetic construct
SEQUENCE: 521
CARDYYLSSY WYFDVW                                                          16

SEQ ID NO: 522          moltype = AA   length = 16
FEATURE                 Location/Qualifiers
source                  1..16
                        mol_type = protein
                        organism = synthetic construct
SEQUENCE: 522
CARDYYGSSY WYFDYW                                                          16

SEQ ID NO: 523          moltype = AA   length = 17
FEATURE                 Location/Qualifiers
source                  1..17
                        mol_type = protein
                        organism = synthetic construct
SEQUENCE: 523
TASESLYSSK HKVHYLA                                                         17

SEQ ID NO: 524          moltype = AA   length = 17
FEATURE                 Location/Qualifiers
source                  1..17
                        mol_type = protein
                        organism = synthetic construct
SEQUENCE: 524
VASESLYSSK HKVHYLA                                                         17

SEQ ID NO: 525          moltype = AA   length = 17
FEATURE                 Location/Qualifiers
source                  1..17
                        mol_type = protein
                        organism = synthetic construct
SEQUENCE: 525
RASESISSSK NKVHYLA                                                         17

SEQ ID NO: 526          moltype = AA   length = 17
FEATURE                 Location/Qualifiers
source                  1..17
                        mol_type = protein
                        organism = synthetic construct
SEQUENCE: 526
TASESLYSAK HKVHYLA                                                         17

SEQ ID NO: 527          moltype = AA   length = 17
FEATURE                 Location/Qualifiers
source                  1..17
                        mol_type = protein
                        organism = synthetic construct
SEQUENCE: 527
TASESLYSSK HKVNYLA                                                         17

SEQ ID NO: 528          moltype = AA   length = 17
FEATURE                 Location/Qualifiers
source                  1..17
                        mol_type = protein
                        organism = synthetic construct
SEQUENCE: 528
TASESLYSSK HKVHYVA                                                         17
```

```
SEQ ID NO: 529          moltype = AA   length = 17
FEATURE                 Location/Qualifiers
source                  1..17
                        mol_type = protein
                        organism = synthetic construct
SEQUENCE: 529
TASFSLYSSK HKVHYLA                                                        17

SEQ ID NO: 530          moltype = AA   length = 17
FEATURE                 Location/Qualifiers
source                  1..17
                        mol_type = protein
                        organism = synthetic construct
SEQUENCE: 530
TASESLYGSK HKVHYLA                                                        17

SEQ ID NO: 531          moltype = AA   length = 16
FEATURE                 Location/Qualifiers
source                  1..16
                        mol_type = protein
                        organism = synthetic construct
SEQUENCE: 531
RASESISSSK HKHYLA                                                         16

SEQ ID NO: 532          moltype = AA   length = 17
FEATURE                 Location/Qualifiers
source                  1..17
                        mol_type = protein
                        organism = synthetic construct
SEQUENCE: 532
TASEWLYSSK HKVHYLA                                                        17

SEQ ID NO: 533          moltype = AA   length = 17
FEATURE                 Location/Qualifiers
source                  1..17
                        mol_type = protein
                        organism = synthetic construct
SEQUENCE: 533
TATESLYSSK HKVHYLA                                                        17

SEQ ID NO: 534          moltype = AA   length = 17
FEATURE                 Location/Qualifiers
source                  1..17
                        mol_type = protein
                        organism = synthetic construct
SEQUENCE: 534
TASESLYSGK HKVHYLA                                                        17

SEQ ID NO: 535          moltype = AA   length = 17
FEATURE                 Location/Qualifiers
source                  1..17
                        mol_type = protein
                        organism = synthetic construct
SEQUENCE: 535
FASESLYSSK HKVHYLA                                                        17

SEQ ID NO: 536          moltype = AA   length = 17
FEATURE                 Location/Qualifiers
source                  1..17
                        mol_type = protein
                        organism = synthetic construct
SEQUENCE: 536
TASQSLYSSK NKVHYLA                                                        17

SEQ ID NO: 537          moltype = AA   length = 17
FEATURE                 Location/Qualifiers
source                  1..17
                        mol_type = protein
                        organism = synthetic construct
SEQUENCE: 537
EASESLYSSK HKVHYLA                                                        17

SEQ ID NO: 538          moltype = AA   length = 17
FEATURE                 Location/Qualifiers
source                  1..17
                        mol_type = protein
                        organism = synthetic construct
SEQUENCE: 538
```

TASESISSSK HKVHYLA                                                              17

SEQ ID NO: 539          moltype = AA   length = 17
FEATURE                 Location/Qualifiers
source                  1..17
                        mol_type = protein
                        organism = synthetic construct SEQUENCE: 539
TASESLYSQK HKVHYLA                                                              17

SEQ ID NO: 540          moltype = AA   length = 17
FEATURE                 Location/Qualifiers
source                  1..17
                        mol_type = protein
                        organism = synthetic construct SEQUENCE: 540
TASESLYSSK HSVHYLA                                                              17

SEQ ID NO: 541          moltype = AA   length = 17
FEATURE                 Location/Qualifiers
source                  1..17
                        mol_type = protein
                        organism = synthetic construct SEQUENCE: 541
TASEELYSSK HKVHYLA                                                              17

SEQ ID NO: 542          moltype = AA   length = 17
FEATURE                 Location/Qualifiers
source                  1..17
                        mol_type = protein
                        organism = synthetic construct SEQUENCE: 542
TASQSISSSK HKVHYLA                                                              17

SEQ ID NO: 543          moltype = AA   length = 16
FEATURE                 Location/Qualifiers
source                  1..16
                        mol_type = protein
                        organism = synthetic construct SEQUENCE: 543
TASESLSSSK HKHYLA                                                               16

SEQ ID NO: 544          moltype = AA   length = 17
FEATURE                 Location/Qualifiers
source                  1..17
                        mol_type = protein
                        organism = synthetic construct SEQUENCE: 544
TAEESLYSSK HKVHYLA                                                              17

SEQ ID NO: 545          moltype = AA   length = 17
FEATURE                 Location/Qualifiers
source                  1..17
                        mol_type = protein
                        organism = synthetic construct SEQUENCE: 545
TASESLYSSK HGVHYLA                                                              17

SEQ ID NO: 546          moltype = AA   length = 17
FEATURE                 Location/Qualifiers
source                  1..17
                        mol_type = protein
                        organism = synthetic construct SEQUENCE: 546
TASESLSSSK HKVHYLA                                                              17

SEQ ID NO: 547          moltype = AA   length = 17
FEATURE                 Location/Qualifiers
source                  1..17
                        mol_type = protein
                        organism = synthetic construct SEQUENCE: 547
TASQSLYSSK HKVHYLA                                                              17

SEQ ID NO: 548          moltype = AA   length = 15
FEATURE                 Location/Qualifiers
source                  1..15
                        mol_type = protein
                        organism = synthetic construct

```
SEQUENCE: 548
RASESLYSSL HKYLA                                                        15

SEQ ID NO: 549          moltype = AA  length = 17
FEATURE                 Location/Qualifiers
source                  1..17
                        mol_type = protein
                        organism = synthetic construct
SEQUENCE: 549
TASESVYSSK NKKHYLA                                                      17

SEQ ID NO: 550          moltype = AA  length = 17
FEATURE                 Location/Qualifiers
source                  1..17
                        mol_type = protein
                        organism = synthetic construct
SEQUENCE: 550
TASESLYSSK GKVHYLA                                                      17

SEQ ID NO: 551          moltype = AA  length = 17
FEATURE                 Location/Qualifiers
source                  1..17
                        mol_type = protein
                        organism = synthetic construct
SEQUENCE: 551
TASQSVYSSK NKVHYLA                                                      17

SEQ ID NO: 552          moltype = AA  length = 17
FEATURE                 Location/Qualifiers
source                  1..17
                        mol_type = protein
                        organism = synthetic construct
SEQUENCE: 552
TSSQSLLSSS HNKNYLA                                                      17

SEQ ID NO: 553          moltype = AA  length = 17
FEATURE                 Location/Qualifiers
source                  1..17
                        mol_type = protein
                        organism = synthetic construct
SEQUENCE: 553
TASESLYSPK HKVHYLA                                                      17

SEQ ID NO: 554          moltype = AA  length = 17
FEATURE                 Location/Qualifiers
source                  1..17
                        mol_type = protein
                        organism = synthetic construct
SEQUENCE: 554
TASESLWSSK HKVHYLA                                                      17

SEQ ID NO: 555          moltype = AA  length = 17
FEATURE                 Location/Qualifiers
source                  1..17
                        mol_type = protein
                        organism = synthetic construct
SEQUENCE: 555
KASQSVLSSK NNVNYLA                                                      17

SEQ ID NO: 556          moltype = AA  length = 17
FEATURE                 Location/Qualifiers
source                  1..17
                        mol_type = protein
                        organism = synthetic construct
SEQUENCE: 556
TASESLYSSK WKVHYLA                                                      17

SEQ ID NO: 557          moltype = AA  length = 17
FEATURE                 Location/Qualifiers
source                  1..17
                        mol_type = protein
                        organism = synthetic construct
SEQUENCE: 557
KSSESVYSSK HKKHYLA                                                      17

SEQ ID NO: 558          moltype = AA  length = 17
FEATURE                 Location/Qualifiers
source                  1..17
                        mol_type = protein
```

```
                        organism = synthetic construct
SEQUENCE: 558
TASESLYSSK HKVDYLA                                                      17

SEQ ID NO: 559          moltype = AA   length = 17
FEATURE                 Location/Qualifiers
source                  1..17
                        mol_type = protein
                        organism = synthetic construct
SEQUENCE: 559
KSSQSLYYSS NKKNYLA                                                      17

SEQ ID NO: 560          moltype = AA   length = 17
FEATURE                 Location/Qualifiers
source                  1..17
                        mol_type = protein
                        organism = synthetic construct
SEQUENCE: 560
TASTSLYSSK HKVHYLA                                                      17

SEQ ID NO: 561          moltype = AA   length = 17
FEATURE                 Location/Qualifiers
source                  1..17
                        mol_type = protein
                        organism = synthetic construct
SEQUENCE: 561
KASQSLYSSK HKKHYLA                                                      17

SEQ ID NO: 562          moltype = AA   length = 17
FEATURE                 Location/Qualifiers
source                  1..17
                        mol_type = protein
                        organism = synthetic construct
SEQUENCE: 562
TASSSLYSSK HKVHYLA                                                      17

SEQ ID NO: 563          moltype = AA   length = 17
FEATURE                 Location/Qualifiers
source                  1..17
                        mol_type = protein
                        organism = synthetic construct
SEQUENCE: 563
TASESLYSVK HKVHYLA                                                      17

SEQ ID NO: 564          moltype = AA   length = 17
FEATURE                 Location/Qualifiers
source                  1..17
                        mol_type = protein
                        organism = synthetic construct
SEQUENCE: 564
GASESLYSSK SKVHYLA                                                      17

SEQ ID NO: 565          moltype = AA   length = 17
FEATURE                 Location/Qualifiers
source                  1..17
                        mol_type = protein
                        organism = synthetic construct
SEQUENCE: 565
TSSESVYSSS HKVHYLA                                                      17

SEQ ID NO: 566          moltype = AA   length = 17
FEATURE                 Location/Qualifiers
source                  1..17
                        mol_type = protein
                        organism = synthetic construct
SEQUENCE: 566
TASESLYSSK HKKNYLA                                                      17

SEQ ID NO: 567          moltype = AA   length = 17
FEATURE                 Location/Qualifiers
source                  1..17
                        mol_type = protein
                        organism = synthetic construct
SEQUENCE: 567
KSSESLLYSK NNKNYLA                                                      17

SEQ ID NO: 568          moltype = AA   length = 17
FEATURE                 Location/Qualifiers
source                  1..17
```

```
SEQUENCE: 568
TASESIYSSK HKVHYLA                                                  17

SEQ ID NO: 569         moltype = AA  length = 17
FEATURE                Location/Qualifiers
source                 1..17
                       mol_type = protein
                       organism = synthetic construct
SEQUENCE: 569
TSSQSVLSSK HKNNYLA                                                  17

SEQ ID NO: 570         moltype = AA  length = 17
FEATURE                Location/Qualifiers
source                 1..17
                       mol_type = protein
                       organism = synthetic construct
SEQUENCE: 570
TASEDLYSSK HKVHYLA                                                  17

SEQ ID NO: 571         moltype = AA  length = 17
FEATURE                Location/Qualifiers
source                 1..17
                       mol_type = protein
                       organism = synthetic construct
SEQUENCE: 571
KASQSVLYSK NKKHYLA                                                  17

SEQ ID NO: 572         moltype = AA  length = 17
FEATURE                Location/Qualifiers
source                 1..17
                       mol_type = protein
                       organism = synthetic construct
SEQUENCE: 572
TASESLYSSK HKLHYLA                                                  17

SEQ ID NO: 573         moltype = AA  length = 17
FEATURE                Location/Qualifiers
source                 1..17
                       mol_type = protein
                       organism = synthetic construct
SEQUENCE: 573
TASESLYSSK HKVVYLA                                                  17

SEQ ID NO: 574         moltype = AA  length = 17
FEATURE                Location/Qualifiers
source                 1..17
                       mol_type = protein
                       organism = synthetic construct
SEQUENCE: 574
TSSESLYSSK NKVNYLA                                                  17

SEQ ID NO: 575         moltype = AA  length = 17
FEATURE                Location/Qualifiers
source                 1..17
                       mol_type = protein
                       organism = synthetic construct
SEQUENCE: 575
TSSQSLYSSK HNKHYLA                                                  17

SEQ ID NO: 576         moltype = AA  length = 17
FEATURE                Location/Qualifiers
source                 1..17
                       mol_type = protein
                       organism = synthetic construct
SEQUENCE: 576
TASESLYSNK HKVHYLA                                                  17

SEQ ID NO: 577         moltype = AA  length = 17
FEATURE                Location/Qualifiers
source                 1..17
                       mol_type = protein
                       organism = synthetic construct
SEQUENCE: 577
TASENLYSSK HKVHYLA                                                  17

SEQ ID NO: 578         moltype = AA  length = 17
FEATURE                Location/Qualifiers
```

```
source                   1..17
                         mol_type = protein
                         organism = synthetic construct
SEQUENCE: 578
TASESLYSSK IKVHYLA                                                          17

SEQ ID NO: 579           moltype = AA   length = 17
FEATURE                  Location/Qualifiers
source                   1..17
                         mol_type = protein
                         organism = synthetic construct
SEQUENCE: 579
KSSQSLLYSK NNVNYLA                                                          17

SEQ ID NO: 580           moltype = AA   length = 17
FEATURE                  Location/Qualifiers
source                   1..17
                         mol_type = protein
                         organism = synthetic construct
SEQUENCE: 580
KSSESLYSSK NKVHYLA                                                          17

SEQ ID NO: 581           moltype = AA   length = 17
FEATURE                  Location/Qualifiers
source                   1..17
                         mol_type = protein
                         organism = synthetic construct
SEQUENCE: 581
TSSESLLSSK HKVHYLA                                                          17

SEQ ID NO: 582           moltype = AA   length = 17
FEATURE                  Location/Qualifiers
source                   1..17
                         mol_type = protein
                         organism = synthetic construct
SEQUENCE: 582
TASQSVYSSK HKKHYLA                                                          17

SEQ ID NO: 583           moltype = AA   length = 17
FEATURE                  Location/Qualifiers
source                   1..17
                         mol_type = protein
                         organism = synthetic construct
SEQUENCE: 583
TASQSVYSSK HNKHYLA                                                          17

SEQ ID NO: 584           moltype = AA   length = 17
FEATURE                  Location/Qualifiers
source                   1..17
                         mol_type = protein
                         organism = synthetic construct
SEQUENCE: 584
TSSQSLLYSS NKKHYLA                                                          17

SEQ ID NO: 585           moltype = AA   length = 17
FEATURE                  Location/Qualifiers
source                   1..17
                         mol_type = protein
                         organism = synthetic construct
SEQUENCE: 585
KSSQSVLSSK HKKNYLA                                                          17

SEQ ID NO: 586           moltype = AA   length = 17
FEATURE                  Location/Qualifiers
source                   1..17
                         mol_type = protein
                         organism = synthetic construct
SEQUENCE: 586
TASQSVYSSK NKKHYLA                                                          17

SEQ ID NO: 587           moltype = AA   length = 17
FEATURE                  Location/Qualifiers
source                   1..17
                         mol_type = protein
                         organism = synthetic construct
SEQUENCE: 587
TASESVLSSK HKKNYLA                                                          17

SEQ ID NO: 588           moltype = AA   length = 17
```

```
FEATURE                 Location/Qualifiers
source                  1..17
                        mol_type = protein
                        organism = synthetic construct
SEQUENCE: 588
TASVSLYSSK HKVHYLA                                                          17

SEQ ID NO: 589          moltype = AA  length = 17
FEATURE                 Location/Qualifiers
source                  1..17
                        mol_type = protein
                        organism = synthetic construct
SEQUENCE: 589
TASESLYSTK HKVHYLA                                                          17

SEQ ID NO: 590          moltype = AA  length = 17
FEATURE                 Location/Qualifiers
source                  1..17
                        mol_type = protein
                        organism = synthetic construct
SEQUENCE: 590
TASESLYSSN HKVHYLA                                                          17

SEQ ID NO: 591          moltype = AA  length = 7
FEATURE                 Location/Qualifiers
source                  1..7
                        mol_type = protein
                        organism = synthetic construct
SEQUENCE: 591
GASNRYI                                                                     7

SEQ ID NO: 592          moltype = AA  length = 7
FEATURE                 Location/Qualifiers
source                  1..7
                        mol_type = protein
                        organism = synthetic construct
SEQUENCE: 592
GASNREI                                                                     7

SEQ ID NO: 593          moltype = AA  length = 7
FEATURE                 Location/Qualifiers
source                  1..7
                        mol_type = protein
                        organism = synthetic construct
SEQUENCE: 593
GASHRYI                                                                     7

SEQ ID NO: 594          moltype = AA  length = 7
FEATURE                 Location/Qualifiers
source                  1..7
                        mol_type = protein
                        organism = synthetic construct
SEQUENCE: 594
GASSLQI                                                                     7

SEQ ID NO: 595          moltype = AA  length = 7
FEATURE                 Location/Qualifiers
source                  1..7
                        mol_type = protein
                        organism = synthetic construct
SEQUENCE: 595
GASNRYT                                                                     7

SEQ ID NO: 596          moltype = AA  length = 7
FEATURE                 Location/Qualifiers
source                  1..7
                        mol_type = protein
                        organism = synthetic construct
SEQUENCE: 596
GASNRYH                                                                     7

SEQ ID NO: 597          moltype = AA  length = 7
FEATURE                 Location/Qualifiers
source                  1..7
                        mol_type = protein
                        organism = synthetic construct
SEQUENCE: 597
GSSNRYI                                                                     7
```

-continued

| | | |
|---|---|---|
| SEQ ID NO: 598<br>FEATURE<br>source | moltype = AA   length = 7<br>Location/Qualifiers<br>1..7<br>mol_type = protein<br>organism = synthetic construct | |
| SEQUENCE: 598<br>GASNRFI | | 7 |
| SEQ ID NO: 599<br>FEATURE<br>source | moltype = AA   length = 7<br>Location/Qualifiers<br>1..7<br>mol_type = protein<br>organism = synthetic construct | |
| SEQUENCE: 599<br>GASNRYY | | 7 |
| SEQ ID NO: 600<br>FEATURE<br>source | moltype = AA   length = 7<br>Location/Qualifiers<br>1..7<br>mol_type = protein<br>organism = synthetic construct | |
| SEQUENCE: 600<br>GAANRYI | | 7 |
| SEQ ID NO: 601<br>FEATURE<br>source | moltype = AA   length = 7<br>Location/Qualifiers<br>1..7<br>mol_type = protein<br>organism = synthetic construct | |
| SEQUENCE: 601<br>GASNRYV | | 7 |
| SEQ ID NO: 602<br>FEATURE<br>source | moltype = AA   length = 7<br>Location/Qualifiers<br>1..7<br>mol_type = protein<br>organism = synthetic construct | |
| SEQUENCE: 602<br>GASNRYD | | 7 |
| SEQ ID NO: 603<br>FEATURE<br>source | moltype = AA   length = 7<br>Location/Qualifiers<br>1..7<br>mol_type = protein<br>organism = synthetic construct | |
| SEQUENCE: 603<br>GASNRYP | | 7 |
| SEQ ID NO: 604<br>FEATURE<br>source | moltype = AA   length = 7<br>Location/Qualifiers<br>1..7<br>mol_type = protein<br>organism = synthetic construct | |
| SEQUENCE: 604<br>GAVNRYI | | 7 |
| SEQ ID NO: 605<br>FEATURE<br>source | moltype = AA   length = 7<br>Location/Qualifiers<br>1..7<br>mol_type = protein<br>organism = synthetic construct | |
| SEQUENCE: 605<br>GASNGYI | | 7 |
| SEQ ID NO: 606<br>FEATURE<br>source | moltype = AA   length = 7<br>Location/Qualifiers<br>1..7<br>mol_type = protein<br>organism = synthetic construct | |
| SEQUENCE: 606<br>GASNRYS | | 7 |
| SEQ ID NO: 607<br>FEATURE<br>source | moltype = AA   length = 7<br>Location/Qualifiers<br>1..7<br>mol_type = protein<br>organism = synthetic construct | |
| SEQUENCE: 607<br>GASNLYS | | 7 |

```
SEQ ID NO: 608           moltype = AA  length = 7
FEATURE                  Location/Qualifiers
source                   1..7
                         mol_type = protein
                         organism = synthetic construct
SEQUENCE: 608
GASNRYF                                                                   7

SEQ ID NO: 609           moltype = AA  length = 7
FEATURE                  Location/Qualifiers
source                   1..7
                         mol_type = protein
                         organism = synthetic construct
SEQUENCE: 609
GASNLQS                                                                   7

SEQ ID NO: 610           moltype = AA  length = 7
FEATURE                  Location/Qualifiers
source                   1..7
                         mol_type = protein
                         organism = synthetic construct
SEQUENCE: 610
GLSNRYI                                                                   7

SEQ ID NO: 611           moltype = AA  length = 7
FEATURE                  Location/Qualifiers
source                   1..7
                         mol_type = protein
                         organism = synthetic construct
SEQUENCE: 611
GASNRQS                                                                   7

SEQ ID NO: 612           moltype = AA  length = 7
FEATURE                  Location/Qualifiers
source                   1..7
                         mol_type = protein
                         organism = synthetic construct
SEQUENCE: 612
GAFNRYT                                                                   7

SEQ ID NO: 613           moltype = AA  length = 7
FEATURE                  Location/Qualifiers
source                   1..7
                         mol_type = protein
                         organism = synthetic construct
SEQUENCE: 613
GASNRLI                                                                   7

SEQ ID NO: 614           moltype = AA  length = 7
FEATURE                  Location/Qualifiers
source                   1..7
                         mol_type = protein
                         organism = synthetic construct
SEQUENCE: 614
GQSNRYI                                                                   7

SEQ ID NO: 615           moltype = AA  length = 7
FEATURE                  Location/Qualifiers
source                   1..7
                         mol_type = protein
                         organism = synthetic construct
SEQUENCE: 615
GASNRNI                                                                   7

SEQ ID NO: 616           moltype = AA  length = 7
FEATURE                  Location/Qualifiers
source                   1..7
                         mol_type = protein
                         organism = synthetic construct
SEQUENCE: 616
GAGNRYI                                                                   7

SEQ ID NO: 617           moltype = AA  length = 7
FEATURE                  Location/Qualifiers
source                   1..7
                         mol_type = protein
                         organism = synthetic construct
SEQUENCE: 617
```

```
GASNRYG                                                                          7

SEQ ID NO: 618          moltype = AA  length = 7
FEATURE                 Location/Qualifiers
source                  1..7
                        mol_type = protein
                        organism = synthetic construct SEQUENCE: 618
GASGRYI                                                                          7

SEQ ID NO: 619          moltype = AA  length = 7
FEATURE                 Location/Qualifiers
source                  1..7
                        mol_type = protein
                        organism = synthetic construct SEQUENCE: 619
GASNLQI                                                                          7

SEQ ID NO: 620          moltype = AA  length = 7
FEATURE                 Location/Qualifiers
source                  1..7
                        mol_type = protein
                        organism = synthetic construct SEQUENCE: 620
GASNRGI                                                                          7

SEQ ID NO: 621          moltype = AA  length = 7
FEATURE                 Location/Qualifiers
source                  1..7
                        mol_type = protein
                        organism = synthetic construct SEQUENCE: 621
GESNRYI                                                                          7

SEQ ID NO: 622          moltype = AA  length = 7
FEATURE                 Location/Qualifiers
source                  1..7
                        mol_type = protein
                        organism = synthetic construct SEQUENCE: 622
GVSNRYI                                                                          7

SEQ ID NO: 623          moltype = AA  length = 7
FEATURE                 Location/Qualifiers
source                  1..7
                        mol_type = protein
                        organism = synthetic construct SEQUENCE: 623
GASNRPI                                                                          7

SEQ ID NO: 624          moltype = AA  length = 7
FEATURE                 Location/Qualifiers
source                  1..7
                        mol_type = protein
                        organism = synthetic construct SEQUENCE: 624
GASFRYI                                                                          7

SEQ ID NO: 625          moltype = AA  length = 7
FEATURE                 Location/Qualifiers
source                  1..7
                        mol_type = protein
                        organism = synthetic construct SEQUENCE: 625
GADNRYI                                                                          7

SEQ ID NO: 626          moltype = AA  length = 7
FEATURE                 Location/Qualifiers
source                  1..7
                        mol_type = protein
                        organism = synthetic construct SEQUENCE: 626
GASNRYQ                                                                          7

SEQ ID NO: 627          moltype = AA  length = 7
FEATURE                 Location/Qualifiers
source                  1..7
                        mol_type = protein
                        organism = synthetic construct
```

-continued

```
SEQUENCE: 627
GASSRYI                                                                          7

SEQ ID NO: 628          moltype = AA  length = 7
FEATURE                 Location/Qualifiers
source                  1..7
                        mol_type = protein
                        organism = synthetic construct
SEQUENCE: 628
GTSNRYI                                                                          7

SEQ ID NO: 629          moltype = AA  length = 7
FEATURE                 Location/Qualifiers
source                  1..7
                        mol_type = protein
                        organism = synthetic construct
SEQUENCE: 629
GASNHYI                                                                          7

SEQ ID NO: 630          moltype = AA  length = 7
FEATURE                 Location/Qualifiers
source                  1..7
                        mol_type = protein
                        organism = synthetic construct
SEQUENCE: 630
GASNRQI                                                                          7

SEQ ID NO: 631          moltype = AA  length = 7
FEATURE                 Location/Qualifiers
source                  1..7
                        mol_type = protein
                        organism = synthetic construct
SEQUENCE: 631
GASSRYS                                                                          7

SEQ ID NO: 632          moltype = AA  length = 7
FEATURE                 Location/Qualifiers
source                  1..7
                        mol_type = protein
                        organism = synthetic construct
SEQUENCE: 632
GASNRDI                                                                          7

SEQ ID NO: 633          moltype = AA  length = 7
FEATURE                 Location/Qualifiers
source                  1..7
                        mol_type = protein
                        organism = synthetic construct
SEQUENCE: 633
GISNRYI                                                                          7

SEQ ID NO: 634          moltype = AA  length = 7
FEATURE                 Location/Qualifiers
source                  1..7
                        mol_type = protein
                        organism = synthetic construct
SEQUENCE: 634
GASSLYS                                                                          7

SEQ ID NO: 635          moltype = AA  length = 7
FEATURE                 Location/Qualifiers
source                  1..7
                        mol_type = protein
                        organism = synthetic construct
SEQUENCE: 635
GASNRAI                                                                          7

SEQ ID NO: 636          moltype = AA  length = 7
FEATURE                 Location/Qualifiers
source                  1..7
                        mol_type = protein
                        organism = synthetic construct
SEQUENCE: 636
GASNRYA                                                                          7

SEQ ID NO: 637          moltype = AA  length = 7
FEATURE                 Location/Qualifiers
source                  1..7
                        mol_type = protein
```

```
                        organism = synthetic construct
SEQUENCE: 637
GASNRVI                                                                 7

SEQ ID NO: 638          moltype = AA  length = 7
FEATURE                 Location/Qualifiers
source                  1..7
                        mol_type = protein
                        organism = synthetic construct
SEQUENCE: 638
GPSNRYI                                                                 7

SEQ ID NO: 639          moltype = AA  length = 7
FEATURE                 Location/Qualifiers
source                  1..7
                        mol_type = protein
                        organism = synthetic construct
SEQUENCE: 639
GAFNRYI                                                                 7

SEQ ID NO: 640          moltype = AA  length = 7
FEATURE                 Location/Qualifiers
source                  1..7
                        mol_type = protein
                        organism = synthetic construct
SEQUENCE: 640
GANNRYI                                                                 7

SEQ ID NO: 641          moltype = AA  length = 7
FEATURE                 Location/Qualifiers
source                  1..7
                        mol_type = protein
                        organism = synthetic construct
SEQUENCE: 641
GAHNRYI                                                                 7

SEQ ID NO: 642          moltype = AA  length = 7
FEATURE                 Location/Qualifiers
source                  1..7
                        mol_type = protein
                        organism = synthetic construct
SEQUENCE: 642
GNSNRYI                                                                 7

SEQ ID NO: 643          moltype = AA  length = 7
FEATURE                 Location/Qualifiers
source                  1..7
                        mol_type = protein
                        organism = synthetic construct
SEQUENCE: 643
GASWRYI                                                                 7

SEQ ID NO: 644          moltype = AA  length = 7
FEATURE                 Location/Qualifiers
source                  1..7
                        mol_type = protein
                        organism = synthetic construct
SEQUENCE: 644
GASTRYS                                                                 7

SEQ ID NO: 645          moltype = AA  length = 7
FEATURE                 Location/Qualifiers
source                  1..7
                        mol_type = protein
                        organism = synthetic construct
SEQUENCE: 645
GASNRYW                                                                 7

SEQ ID NO: 646          moltype = AA  length = 7
FEATURE                 Location/Qualifiers
source                  1..7
                        mol_type = protein
                        organism = synthetic construct
SEQUENCE: 646
GASNRYL                                                                 7

SEQ ID NO: 647          moltype = AA  length = 7
FEATURE                 Location/Qualifiers
source                  1..7
```

```
SEQUENCE: 647
GASNRYN                                                             7

SEQ ID NO: 648              moltype = AA  length = 7
FEATURE                     Location/Qualifiers
source                      1..7
                            mol_type = protein
                            organism = synthetic construct
SEQUENCE: 648
GASQRYI                                                             7

SEQ ID NO: 649              moltype = AA  length = 7
FEATURE                     Location/Qualifiers
source                      1..7
                            mol_type = protein
                            organism = synthetic construct
SEQUENCE: 649
GAQNRYI                                                             7

SEQ ID NO: 650              moltype = AA  length = 7
FEATURE                     Location/Qualifiers
source                      1..7
                            mol_type = protein
                            organism = synthetic construct
SEQUENCE: 650
GATNRYI                                                             7

SEQ ID NO: 651              moltype = AA  length = 7
FEATURE                     Location/Qualifiers
source                      1..7
                            mol_type = protein
                            organism = synthetic construct
SEQUENCE: 651
GASNPYI                                                             7

SEQ ID NO: 652              moltype = AA  length = 7
FEATURE                     Location/Qualifiers
source                      1..7
                            mol_type = protein
                            organism = synthetic construct
SEQUENCE: 652
GASTRYI                                                             7

SEQ ID NO: 653              moltype = AA  length = 7
FEATURE                     Location/Qualifiers
source                      1..7
                            mol_type = protein
                            organism = synthetic construct
SEQUENCE: 653
GAENRYI                                                             7

SEQ ID NO: 654              moltype = AA  length = 7
FEATURE                     Location/Qualifiers
source                      1..7
                            mol_type = protein
                            organism = synthetic construct
SEQUENCE: 654
GASHRQI                                                             7

SEQ ID NO: 655              moltype = AA  length = 7
FEATURE                     Location/Qualifiers
source                      1..7
                            mol_type = protein
                            organism = synthetic construct
SEQUENCE: 655
GASNTYI                                                             7

SEQ ID NO: 656              moltype = AA  length = 11
FEATURE                     Location/Qualifiers
source                      1..11
                            mol_type = protein
                            organism = synthetic construct
SEQUENCE: 656
CAEFYSYPLT F                                                       11

SEQ ID NO: 657              moltype = AA  length = 11
FEATURE                     Location/Qualifiers
```

```
source                     1..11
                           mol_type = protein
                           organism = synthetic construct
SEQUENCE: 657
CQQFYSYPLT F                                                              11

SEQ ID NO: 658             moltype = AA  length = 11
FEATURE                    Location/Qualifiers
source                     1..11
                           mol_type = protein
                           organism = synthetic construct
SEQUENCE: 658
CAQFYAYPLT F                                                              11

SEQ ID NO: 659             moltype = AA  length = 11
FEATURE                    Location/Qualifiers
source                     1..11
                           mol_type = protein
                           organism = synthetic construct
SEQUENCE: 659
CAQFYSYPLT F                                                              11

SEQ ID NO: 660             moltype = AA  length = 11
FEATURE                    Location/Qualifiers
source                     1..11
                           mol_type = protein
                           organism = synthetic construct
SEQUENCE: 660
CAQFYHYPLT F                                                              11

SEQ ID NO: 661             moltype = AA  length = 11
FEATURE                    Location/Qualifiers
source                     1..11
                           mol_type = protein
                           organism = synthetic construct
SEQUENCE: 661
CAQFYQYPLT F                                                              11

SEQ ID NO: 662             moltype = AA  length = 11
FEATURE                    Location/Qualifiers
source                     1..11
                           mol_type = protein
                           organism = synthetic construct
SEQUENCE: 662
CAQFYYYPLT F                                                              11

SEQ ID NO: 663             moltype = AA  length = 11
FEATURE                    Location/Qualifiers
source                     1..11
                           mol_type = protein
                           organism = synthetic construct
SEQUENCE: 663
CAQFYVYPLT F                                                              11

SEQ ID NO: 664             moltype = AA  length = 11
FEATURE                    Location/Qualifiers
source                     1..11
                           mol_type = protein
                           organism = synthetic construct
SEQUENCE: 664
CGQFYSYPLT F                                                              11

SEQ ID NO: 665             moltype = AA  length = 11
FEATURE                    Location/Qualifiers
source                     1..11
                           mol_type = protein
                           organism = synthetic construct
SEQUENCE: 665
CAQFYDYPLT F                                                              11

SEQ ID NO: 666             moltype = AA  length = 11
FEATURE                    Location/Qualifiers
source                     1..11
                           mol_type = protein
                           organism = synthetic construct
SEQUENCE: 666
CAQFYRYPLT F                                                              11

SEQ ID NO: 667             moltype = AA  length = 11
```

```
                            -continued

FEATURE                 Location/Qualifiers
source                  1..11
                        mol_type = protein
                        organism = synthetic construct
SEQUENCE: 667
CAQFYTYPLT F                                                                    11

SEQ ID NO: 668          moltype = AA   length = 11
FEATURE                 Location/Qualifiers
source                  1..11
                        mol_type = protein
                        organism = synthetic construct
SEQUENCE: 668
CAQFYWYPLT F                                                                    11

SEQ ID NO: 669          moltype = AA   length = 11
FEATURE                 Location/Qualifiers
source                  1..11
                        mol_type = protein
                        organism = synthetic construct
SEQUENCE: 669
CTQFYSYPLT F                                                                    11

SEQ ID NO: 670          moltype = AA   length = 11
FEATURE                 Location/Qualifiers
source                  1..11
                        mol_type = protein
                        organism = synthetic construct
SEQUENCE: 670
CAQFYFYPLT F                                                                    11

SEQ ID NO: 671          moltype = AA   length = 11
FEATURE                 Location/Qualifiers
source                  1..11
                        mol_type = protein
                        organism = synthetic construct
SEQUENCE: 671
CAQFYEYPLT F                                                                    11

SEQ ID NO: 672          moltype = AA   length = 11
FEATURE                 Location/Qualifiers
source                  1..11
                        mol_type = protein
                        organism = synthetic construct
SEQUENCE: 672
CAHFYSYPLT F                                                                    11

SEQ ID NO: 673          moltype = AA   length = 11
FEATURE                 Location/Qualifiers
source                  1..11
                        mol_type = protein
                        organism = synthetic construct
SEQUENCE: 673
CAQFYKYPLT F                                                                    11

SEQ ID NO: 674          moltype = AA   length = 11
FEATURE                 Location/Qualifiers
source                  1..11
                        mol_type = protein
                        organism = synthetic construct
SEQUENCE: 674
CAQFFSYPLT F                                                                    11

SEQ ID NO: 675          moltype = AA   length = 11
FEATURE                 Location/Qualifiers
source                  1..11
                        mol_type = protein
                        organism = synthetic construct
SEQUENCE: 675
CVQFYSYPLT F                                                                    11

SEQ ID NO: 676          moltype = AA   length = 11
FEATURE                 Location/Qualifiers
source                  1..11
                        mol_type = protein
                        organism = synthetic construct
SEQUENCE: 676
CAQFYIYPLT F                                                                    11
```

```
SEQ ID NO: 677          moltype = AA   length = 11
FEATURE                 Location/Qualifiers
source                  1..11
                        mol_type = protein
                        organism = synthetic construct
SEQUENCE: 677
CANFYSYPLT F                                                              11

SEQ ID NO: 678          moltype = AA   length = 11
FEATURE                 Location/Qualifiers
source                  1..11
                        mol_type = protein
                        organism = synthetic construct
SEQUENCE: 678
CAQYYSYPLT F                                                              11

SEQ ID NO: 679          moltype = AA   length = 11
FEATURE                 Location/Qualifiers
source                  1..11
                        mol_type = protein
                        organism = synthetic construct
SEQUENCE: 679
CAQFYLYPLT F                                                              11

SEQ ID NO: 680          moltype = AA   length = 11
FEATURE                 Location/Qualifiers
source                  1..11
                        mol_type = protein
                        organism = synthetic construct
SEQUENCE: 680
CAQFYNYPLT F                                                              11

SEQ ID NO: 681          moltype = AA   length = 11
FEATURE                 Location/Qualifiers
source                  1..11
                        mol_type = protein
                        organism = synthetic construct
SEQUENCE: 681
CASFYSYPLT F                                                              11

SEQ ID NO: 682          moltype = AA   length = 11
FEATURE                 Location/Qualifiers
source                  1..11
                        mol_type = protein
                        organism = synthetic construct
SEQUENCE: 682
CAAFYSYPLT F                                                              11

SEQ ID NO: 683          moltype = AA   length = 329
FEATURE                 Location/Qualifiers
source                  1..329
                        mol_type = protein
                        organism = synthetic construct
SEQUENCE: 683
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 684          moltype = AA   length = 326
FEATURE                 Location/Qualifiers
source                  1..326
                        mol_type = protein
                        organism = synthetic construct
SEQUENCE: 684
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 685          moltype = AA   length = 113
FEATURE                 Location/Qualifiers
source                  1..113
                        mol_type = protein
                        organism = synthetic construct
```

```
SEQUENCE: 685
DIQMTQSPSS LSASVGDRVT ITCTASESLY SSKHKVHYLA WYQQKPGKAP KLLIYGASNR    60
YIGVPSRFSG SGSGTDFTLT ISSLQPEDFA TYYCAQFYSY PLTFGQGTKV EIK          113

SEQ ID NO: 686          moltype = AA   length = 19
FEATURE                 Location/Qualifiers
source                  1..19
                        mol_type = protein
                        organism = synthetic construct
SEQUENCE: 686
AGGGGSGGGG SGGGGSAAA                                                 19

SEQ ID NO: 687          moltype = AA   length = 24
FEATURE                 Location/Qualifiers
source                  1..24
                        mol_type = protein
                        organism = synthetic construct
SEQUENCE: 687
AEAAAKEAAA KEAAAKEAAA KAAA                                           24

SEQ ID NO: 688          moltype = AA   length = 107
FEATURE                 Location/Qualifiers
source                  1..107
                        mol_type = protein
                        organism = synthetic construct
SEQUENCE: 688
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                  107

SEQ ID NO: 689          moltype = AA   length = 106
FEATURE                 Location/Qualifiers
source                  1..106
                        mol_type = protein
                        organism = synthetic construct
SEQUENCE: 689
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTECS                   106

SEQ ID NO: 690          moltype = AA   length = 106
FEATURE                 Location/Qualifiers
source                  1..106
                        mol_type = protein
                        organism = synthetic construct
SEQUENCE: 690
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                   106

SEQ ID NO: 691          moltype = AA   length = 106
FEATURE                 Location/Qualifiers
source                  1..106
                        mol_type = protein
                        organism = synthetic construct
SEQUENCE: 691
GQPKAAPSVT LFPPSSEELQ ANKATLVCLI SDFYPGAVTV AWKADSSPVK AGVETTTPSK    60
QSNNKYAASS YLSLTPEQWK SHKSYSCQVT HEGSTVEKTV APTECS                   106

SEQ ID NO: 692          moltype = AA   length = 106
FEATURE                 Location/Qualifiers
source                  1..106
                        mol_type = protein
                        organism = synthetic construct
SEQUENCE: 692
GQPKAAPSVT LFPPSSEELQ ANKATLVCLI SDFYPGAVKV AWKADGSPVN TGVETTTPSK    60
QSNNKYAASS YLSLTPEQWK SHRSYSCQVT HEGSTVEKTV APAECS                   106

SEQ ID NO: 693          moltype = AA   length = 106
FEATURE                 Location/Qualifiers
source                  1..106
                        mol_type = protein
                        organism = synthetic construct
SEQUENCE: 693
GQPKAAPSVT LFPPSSEELQ ANKATLVCLV SDFNPGAVTV AWKADGSPVK VGVETTKPSK    60
QSNNKYAASS YLSLTPEQWK SHRSYSCRVT HEGSTVEKTV APAECS                   106
```